US007183415B2

(12) United States Patent
Ishihara et al.

(10) Patent No.: US 7,183,415 B2
(45) Date of Patent: Feb. 27, 2007

(54) QUINOLINE COMPOUND

(75) Inventors: Yuji Ishihara, Hyogo (JP); Makoto Kamata, Osaka (JP); Shiro Takekawa, Hyogo (JP); Nobuhiro Suzuki, Osaka (JP); Koki Kato, Hyogo (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 10/493,427

(22) PCT Filed: Oct. 24, 2002

(86) PCT No.: PCT/JP02/11045

§ 371 (c)(1),
(2), (4) Date: Apr. 23, 2004

(87) PCT Pub. No.: WO03/035624

PCT Pub. Date: May 1, 2003

(65) Prior Publication Data

US 2005/0209213 A1 Sep. 22, 2005

(30) Foreign Application Priority Data

Oct. 25, 2001 (JP) ............................ 2001-327924
Jun. 4, 2002 (JP) ............................ 2002-163239

(51) Int. Cl.
*C07D 215/38* (2006.01)
*C07D 215/14* (2006.01)

(52) U.S. Cl. ...................................... 546/171; 546/174

(58) Field of Classification Search ................ 514/312, 514/314; 546/171, 174
See application file for complete search history.

(56) References Cited

U.S. PATENT DOCUMENTS

2003/0212070 A1 11/2003 Schwink et al.

FOREIGN PATENT DOCUMENTS

| | | | |
|---|---|---|---|
| DE | 2 502 588 A1 | | 7/1976 |
| EP | 0 325 247 A1 | | 7/1989 |
| EP | 1 099 701 A1 | | 5/2001 |
| EP | 1099442 A2 | * | 5/2001 |
| JP | 59-051287 A | | 3/1984 |
| WO | WO 95/32967 | | 12/1995 |
| WO | WO 00/35924 A1 | | 6/2000 |
| WO | WO 01/21577 A2 | | 3/2001 |
| WO | WO 01/82925 A1 | | 11/2001 |

* cited by examiner

*Primary Examiner*—D. Margaret Seaman
(74) *Attorney, Agent, or Firm*—Foley & Lardner LLP

(57) ABSTRACT

A compound, which has a melanin-concentrating hormone antagonistic action and useful as an agent for preventing or treating obesity, and which is represented by the formula:

(I)

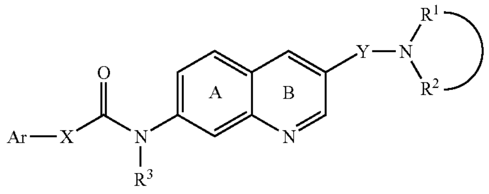

wherein

Ar is a cyclic group optionally having substituent(s);

X is a bond or a spacer having a main chain of 1 to 6 atoms;

$R^1$ and $R^2$ are the same or different and each is a hydrogen atom or a hydrocarbon group optionally having substituent(s), or $R^1$ and $R^2$ may form, together with the adjacent nitrogen atom, a nitrogen-containing heterocycle optionally having substituent(s);

Y is a divalent hydrocarbon group optionally having substituent(s) (except CO);

$R^3$ is a hydrogen atom or a hydrocarbon group optionally having substituent(s); and ring A and ring B may further have substituents, and when ring B further has a substituent, the substituent may be linked to $R^1$ to form a ring, or a salt thereof, or a prodrug thereof, is provided.

15 Claims, No Drawings

SEQUENCE LISTING

<160> NUMBER OF SEQ ID NOS: 16

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic polynucleotide sequence

<400> SEQUENCE: 1
gtcgacatgg atctgcaaac ctcgttgctg tg 32

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic polynucleotide sequence

<400> SEQUENCE: 2
actagttcag gtgcctttgc tttctgtcct ct 32

<210> SEQ ID NO 3
<211> LENGTH: 353
<212> TYPE: PRT
<213> ORGANISM: Rattus sp.

<400> SEQUENCE: 3

```
Met Asp Leu Gln Thr Ser Leu Leu Ser Thr Gly Pro Asn Ala Ser Asn
  1               5                  10                  15

Ile Ser Asp Gly Gln Asp Asn Leu Thr Leu Pro Gly Ser Pro Pro Arg
             20                  25                  30

Thr Gly Ser Val Ser Tyr Ile Asn Ile Ile Met Pro Ser Val Phe Gly
         35                  40                  45

Thr Ile Cys Leu Leu Gly Ile Val Gly Asn Ser Thr Val Ile Phe Ala
     50                  55                  60

Val Val Lys Lys Ser Lys Leu His Trp Cys Ser Asn Val Pro Asp Ile
 65                  70                  75                  80

Phe Ile Ile Asn Leu Ser Val Val Asp Leu Leu Phe Leu Leu Gly Met
                 85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Thr Ile Asp Arg Tyr Leu Ala
    130                 135                 140

Thr Val His Pro Ile Ser Ser Thr Lys Phe Arg Lys Pro Ser Met Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220
```

```
Thr Ala Ala Tyr Val Lys Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
        275                 280                 285

Phe Val Tyr Leu Tyr Asn Ala Ala Ile Ser Leu Gly Tyr Ala Asn Ser
    290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Thr
                325                 330                 335

Val Ser Asn Ala Gln Thr Ala Asp Glu Glu Arg Thr Glu Ser Lys Gly
            340                 345                 350

Thr

<210> SEQ ID NO 4
<211> LENGTH: 1074
<212> TYPE: DNA
<213> ORGANISM: Rattus sp.

<400> SEQUENCE: 4

gtcgacatgg atctgcaaac ctcgttgctg tccactggcc ccaatgccag caacatctcc     60

gatggccagg ataatctcac attgccgggg tcacctcctc gcacagggag tgtctcctac    120

atcaacatca ttatgccttc cgtgtttggt accatctgtc tcctgggcat cgtgggaaac    180

tccacggtca tctttgctgt ggtgaagaag tccaagctac actggtgcag caacgtcccc    240

gacatcttca tcatcaacct ctctgtggtg gatctgctct tcctgctggg catgcctttc    300

atgatccacc agctcatggg gaacggcgtc tggcactttg ggggaaaccat gtgcaccctc    360

atcacagcca tggacgccaa cagtcagttc actagcacct acatcctgac tgccatgacc    420

attgaccgct acttggccac cgtccacccc atctcctcca ccaagttccg gaagccctcc    480

atggccaccc tggtgatctg cctcctgtgg gcgctctcct tcatcagtat cacccctgtg    540

tggctctacg ccaggctcat tcccttccca gggggtgctg tgggctgtgg catccgcctg    600

ccaaacccgg acactgacct ctactggttc actctgtacc agtttttcct ggcctttgcc    660

cttccgtttg tggtcattac cgccgcatac gtgaaaatac tacagcgcat gacgtcttcg    720

gtggccccag cctcccaacg cagcatccgg cttcggacaa agagggtgac ccgcacggcc    780

attgccatct gtctggtctt ctttgtgtgc tgggcaccct actatgtgct gcagctgacc    840

cagctgtcca tcagccgccc gaccctcacg tttgtctact tgtacaacgc ggccatcagc    900

ttgggctatg ctaacagctg cctgaacccc tttgtgtaca tagtgctctg tgagaccttt    960

cgaaaacgct tggtgttgtc agtgaagcct gcagcccagg ggcagctccg cacggtcagc   1020

aacgctcaga cagctgatga ggagaggaca gaaagcaaag gcacctgaac tagt         1074

<210> SEQ ID NO 5
<211> LENGTH: 262
<212> TYPE: RNA
<213> ORGANISM: Rattus sp.

<400> SEQUENCE: 5
```

-continued

```
gcgaauuggg uaccgggccc ccccucgagg ucgacgguau cgauaagcuu gauaucgaau     60

uccugcagcc cgggggaucc gcccacuagu ucaggugccu uugcuuucug uccucuccuc    120

aucagcuguc ugagcguugc ugaccgugcg gagcugcccc ugggcugcag gcuucacuga    180

caacaccaag cguuuucgaa aggucucaca gagcacuaug uacacaaagg gguucaggca    240

gcuguuagca uagcccaagc ug                                             262
```

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic polynucleotide sequence

<400> SEQUENCE: 6

```
caacagctgc ctcaaccc                                                   18
```

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic polynucleotide sequence

<400> SEQUENCE: 7

```
cctggtgatc tgcctcct                                                   18
```

<210> SEQ ID NO 8
<211> LENGTH: 1275
<212> TYPE: DNA
<213> ORGANISM: Homo sapiens

<400> SEQUENCE: 8

```
taggtgatgt cagtgggagc catgaagaag ggagtgggga gggcagttgg gcttggaggc     60

ggcagcggct gccaggctac ggaggaagac ccccttccca actgcggggc ttgcgctccg    120

ggacaaggtg gcaggcgctg gaggctgccg cagcctgcgt gggtggaggg gagctcagct    180

cggttgtggg agcaggcgac cggcactggc tggatggacc tggaagcctc gctgctgccc    240

actggtccca acgccagcaa cacctctgat ggccccgata acctcacttc ggcaggatca    300

cctcctcgca cggggagcat ctcctacatc aacatcatca tgccttcggt gttcggcacc    360

atctgcctcc tgggcatcat cgggaactcc acggtcatct tcgcggtcgt gaagaagtcc    420

aagctgcact ggtgcaacaa cgtccccgac atcttcatca tcaacctctc ggtagtagat    480

ctcctctttc tcctgggcat gcccttcatg atccaccagc tcatgggcaa tggggtgtgg    540

cactttgggg agaccatgtg caccctcatc acggccatgg atgccaatag tcagttcacc    600

agcacctaca tcctgaccgc catggccatt gaccgctacc tggccactgt ccaccccatc    660

tcttccacga agttccggaa gccctctgtg gccaccctgg tgatctgcct cctgtgggcc    720

ctctccttca tcagcatcac ccctgtgtgg ctgtatgcca gactcatccc cttcccagga    780

ggtgcagtgg gctgcggcat acgcctgccc aacccagaca ctgacctcta ctggttcacc    840

ctgtaccagt ttttcctggc ctttgccctg ccttttgtgg tcatcacagc cgcatacgtg    900

aggatcctgc agcgcatgac gtcctcagtg gccccccgcct cccagcgcag catccggctg    960

cggacaaaga gggtgacccg cacagccatc gccatctgtc tggtcttctt tgtgtgctgg   1020

gcaccctact atgtgctaca gctgacccag ttgtccatca gccgcccgac cctcaccttt   1080
```

gtctacttat acaatgcggc catcagcttg ggctatgcca acagctgcct caaccccttt 1140
gtgtacatcg tgctctgtga gacgttccgc aaacgcttgg tcctgtcggt gaagcctgca 1200
gcccaggggc agcttcgcgc tgtcagcaac gctcagacgg ctgacgagga gaggacagaa 1260
agcaaaggca cctga 1275

<210> SEQ ID NO 9
<211> LENGTH: 422
<212> TYPE: PRT
<213> ORGANISM: Homo sapiens

<400> SEQUENCE: 9

Met Ser Val Gly Ala Met Lys Lys Gly Val Gly Arg Ala Val Gly Leu
1 5 10 15

Gly Gly Gly Ser Gly Cys Gln Ala Thr Glu Glu Asp Pro Leu Pro Asn
20 25 30

Cys Gly Ala Cys Ala Pro Gly Gln Gly Gly Arg Arg Trp Arg Leu Pro
35 40 45

Gln Pro Ala Trp Val Glu Gly Ser Ser Ala Arg Leu Trp Glu Gln Ala
50 55 60

Thr Gly Thr Gly Trp Met Asp Leu Glu Ala Ser Leu Leu Pro Thr Gly
65 70 75 80

Pro Asn Ala Ser Asn Thr Ser Asp Gly Pro Asp Asn Leu Thr Ser Ala
85 90 95

Gly Ser Pro Pro Arg Thr Gly Ser Ile Ser Tyr Ile Asn Ile Ile Met
100 105 110

Pro Ser Val Phe Gly Thr Ile Cys Leu Leu Gly Ile Ile Gly Asn Ser
115 120 125

Thr Val Ile Phe Ala Val Val Lys Lys Ser Lys Leu His Trp Cys Asn
130 135 140

Asn Val Pro Asp Ile Phe Ile Ile Asn Leu Ser Val Val Asp Leu Leu
145 150 155 160

Phe Leu Leu Gly Met Pro Phe Met Ile His Gln Leu Met Gly Asn Gly
165 170 175

Val Trp His Phe Gly Glu Thr Met Cys Thr Leu Ile Thr Ala Met Asp
180 185 190

Ala Asn Ser Gln Phe Thr Ser Thr Tyr Ile Leu Thr Ala Met Ala Ile
195 200 205

Asp Arg Tyr Leu Ala Thr Val His Pro Ile Ser Ser Thr Lys Phe Arg
210 215 220

Lys Pro Ser Val Ala Thr Leu Val Ile Cys Leu Leu Trp Ala Leu Ser
225 230 235 240

Phe Ile Ser Ile Thr Pro Val Trp Leu Tyr Ala Arg Leu Ile Pro Phe
245 250 255

Pro Gly Gly Ala Val Gly Cys Gly Ile Arg Leu Pro Asn Pro Asp Thr
260 265 270

Asp Leu Tyr Trp Phe Thr Leu Tyr Gln Phe Phe Leu Ala Phe Ala Leu
275 280 285

Pro Phe Val Val Ile Thr Ala Ala Tyr Val Arg Ile Leu Gln Arg Met
290 295 300

Thr Ser Ser Val Ala Pro Ala Ser Gln Arg Ser Ile Arg Leu Arg Thr
305 310 315 320

Lys Arg Val Thr Arg Thr Ala Ile Ala Ile Cys Leu Val Phe Phe Val
325 330 335

-continued

```
Cys Trp Ala Pro Tyr Tyr Val Leu Gln Leu Thr Gln Leu Ser Ile Ser
            340                 345                 350

Arg Pro Thr Leu Thr Phe Val Tyr Leu Tyr Asn Ala Ala Ile Ser Leu
        355                 360                 365

Gly Tyr Ala Asn Ser Cys Leu Asn Pro Phe Val Tyr Ile Val Leu Cys
    370                 375                 380

Glu Thr Phe Arg Lys Arg Leu Val Leu Ser Val Lys Pro Ala Ala Gln
385                 390                 395                 400

Gly Gln Leu Arg Ala Val Ser Asn Ala Gln Thr Ala Asp Glu Glu Arg
                405                 410                 415

Thr Glu Ser Lys Gly Thr
            420


<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 10

gtcgacatgg acctggaagc ctcgctgctg c                                31


<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 11

actagttcag gtgcctttgc tttctgtcct c                                31


<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 12

agtcgacatg tcagtgggag ccatgaagaa ggg                              33


<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 13

aactagttca ggtgcctttg ctttctgtcc tct                              33


<210> SEQ ID NO 14
<211> LENGTH: 1074
<212> TYPE: DNA
<213> ORGANISM: Homo sapiens

<400> SEQUENCE: 14
```

-continued

```
gtcgacatgg acctggaagc ctcgctgctg cccactggtc ccaacgccag caacacctct     60
gatggccccg ataacctcac ttcggcagga tcacctcctc gcacggggag catctcctac    120
atcaacatca tcatgccttc ggtgttcggc accatctgcc tcctgggcat catcgggaac    180
tccacggtca tcttcgcggt cgtgaagaag tccaagctgc actggtgcaa caacgtcccc    240
gacatcttca tcatcaacct ctcggtagta gatctcctct ttctcctggg catgcccttc    300
atgatccacc agctcatggg caatggggtg tggcactttg ggagaccat gtgcaccctc     360
atcacggcca tggatgccaa tagtcagttc accagcacct acatcctgac cgccatggcc    420
attgaccgct acctggccac tgtccacccc atctcttcca cgaagttccg gaagccctct    480
gtggccaccc tggtgatctg cctcctgtgg gccctctcct tcatcagcat cacccctgtg    540
tggctgtatg ccagactcat ccccttccca ggaggtgcag tgggctgcgg catacgcctg    600
cccaacccag acactgacct ctactggttc accctgtacc agtttttcct ggcctttgcc    660
ctgccttttg tggtcatcac agccgcatac gtgaggatcc tgcagcgcat gacgtcctca    720
gtggcccccg cctcccagcg cagcatccgg ctgcggacaa agagggtgac ccgcacagcc    780
atcgccatct gtctggtctt ctttgtgtgc tgggcaccct actatgtgct acagctgacc    840
cagttgtcca tcagccgccc gaccctcacc tttgtctact tatacaatgc ggccatcagc    900
ttgggctatg ccaacagctg cctcaacccc tttgtgtaca tcgtgctctg tgagacgttc    960
cgcaaacgct tggtcctgtc ggtgaagcct gcagcccagg ggcagcttcg cgctgtcagc   1020
aacgctcaga cggctgacga ggagaggaca gaaagcaaag gcacctgaac tagt         1074
```

<210> SEQ ID NO 15
<211> LENGTH: 1283
<212> TYPE: DNA
<213> ORGANISM: Homo sapiens

<400> SEQUENCE: 15

```
agtcgacatg tcagtgggag ccatgaagaa gggagtgggg agggcagttg ggcttggagg     60
cggcagcggc tgccaggcta cggaggaaga ccccccttccc aactgcgggg cttgcgctcc    120
gggacaaggt ggcaggcgct ggaggctgcc gcagcctgcg tgggtggagg ggagctcagc    180
tcggttgtgg gagcaggcga ccggcactgg ctggatggac ctggaagcct cgctgctgcc    240
cactggtccc aacgccagca acacctctga tggccccgat aacctcactt cggcaggatc    300
acctcctcgc acggggagca tctcctacat caacatcatc atgccttcgg tgttcggcac    360
catctgcctc ctgggcatca tcgggaactc cacggtcatc ttcgcggtcg tgaagaagtc    420
caagctgcac tggtgcaaca acgtccccga catcttcatc atcaacctct cggtagtaga    480
tctcctcttt ctcctgggca tgcccttcat gatccaccag ctcatgggca atggggtgtg    540
gcactttggg gagaccatgt gcaccctcat cacggccatg gatgccaata gtcagttcac    600
cagcacctac atcctgaccg ccatggccat tgaccgctac ctggccactg tccaccccat    660
ctcttccacg aagttccgga agccctctgt ggccaccctg gtgatctgcc tcctgtgggc    720
cctctccttc atcagcatca cccctgtgtg gctgtatgcc agactcatcc ccttcccagg    780
aggtgcagtg ggctgcggca tacgcctgcc caacccagac actgacctct actggttcac    840
cctgtaccag tttttcctgg cctttgccct gccttttgtg gtcatcacag ccgcatacgt    900
gaggatcctg cagcgcatga cgtcctcagt ggcccccgcc tcccagcgca gcatccggct    960
gcggacaaag agggtgaccc gcacagccat cgccatctgt ctggtcttct ttgtgtgctg   1020
ggcaccctac tatgtgctac agctgaccca gttgtccatc agccgcccga ccctcacctt   1080
```

-continued

```
tgtctactta tacaatgcgg ccatcagctt gggctatgcc aacagctgcc tcaacccctt   1140

tgtgtacatc gtgctctgtg agacgttccg caaacgcttg gtcctgtcgg tgaagcctgc   1200

agcccagggg cagcttcgcg ctgtcagcaa cgctcagacg gctgacgagg agaggacaga   1260

aagcaaaggc acctgaacta gtt                                           1283


<210> SEQ ID NO 16
<211> LENGTH: 420
<212> TYPE: RNA
<213> ORGANISM: Homo sapiens

<400> SEQUENCE: 16

caaaagcugg agcuccaccg cgguggcggc cgcucuagcc cacuaguuca ggugccuuug     60

cuuucugucc ucuccucguc agccgucuga gcguugcuga cagcgcgaag cugccccugg    120

gcugcaggcu ucaccgacag gaccaagcgu uugcggaacg ucucacagag cacgauguac    180

acaaaggggu ugaggcagcu guuggcauag cccaagcuga uggccgcauu guauaaguag    240

acaaagguga gggucgggcg gcugauggac aacuggguca gcuguagcac auaguagggu    300

gcccagcaca caaagaagac cagacagaug gcgauggcug ugcgggucac ccucuuuguc    360

cgcagccgga ugcugcgcug ggaggcgggg gccacugagg acgucaugcg cugcaggauc    420
```

QUINOLINE COMPOUND

TECHNICAL FIELD

The present invention relates to a quinoline compound having a melanin-concentrating hormone (hereinafter sometimes to be abbreviated as MCH) antagonistic action and useful as an agent for preventing or treating obesity and the like.

BACKGROUND ART

Feeding behavior is an indispensable action for many organisms including human. An abnormality in feeding behavior causes deviation from normal life support activities, which in most cases results in diseases. Along with the recent changes in feeding environments, obesity is becoming a social problem. It is widely known that obesity is not only a serious risk factor of life-style related diseases, such as diabetes, hypertension, arteriosclerosis and the like, but also causes arthritis and pain resulting from an excessive burden on joints of knee etc. due to increased body weight. In addition, the dieting boom and the like have increased the potential population that desires weight loss. There are many reports on eating disorders, such as hyperphagia and the like, due to neuropathy and the like, which are genetic or caused by stress.

Consequently, the development and investigation of agents for preventing or treating obesity or feeding deterrents started some time ago, and mazindol has been on the market as a centrally acting anorectic agent.

Along therewith, a number of appetite-regulating factors represented by leptin have been found in recent years, and new anti-obesity agents and anorectic agents that suppress the activity of such appetite-regulating factors have been developed. Among others, melanin-concentrating hormone is a hormone derived from hypothalamus and known to have an appetite stimulating action. Furthermore, MCH knockout mouse has been reported to show significantly decreased food intake and be lean, as compared to normal mouse, though normal in daily behavior [*Nature*, vol. 396, p. 670, 1998]. From the foregoing, an MCH antagonist, once completed, is expected to be a superior anorectic agent or anti-obesity agent.

On the other hand, the following compounds are known as fused heterocyclic compounds.

1) WO95/32967 describes a compound of the formula:

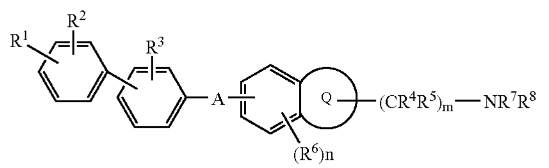

wherein A is CONR, in which R is hydrogen or $C_{1-6}$ alkyl; Q is an optionally substituted 5- to 7-membered heterocycle containing 1 to 3 hetero atoms selected from oxygen, nitrogen and sulfur; $R^1$ is hydrogen, halogen, etc.; $R^2$ and $R^3$ are independently hydrogen, halogen, etc.; $R_4$ and $R_5$ are independently hydrogen or $C_{1-6}$ alkyl; $R^6$ is halogen, hydroxy, etc.; $R^7$ and $R^8$ are independently hydrogen, $C_{1-6}$ alkyls, etc.; m is 0 to 4; n is 0, 1 or 2; or its salt, which has 5HT1D antagonist activity and is expected to ameliorate anorexia.

2) JP-A-2001/139555 describes a compound of the formula:

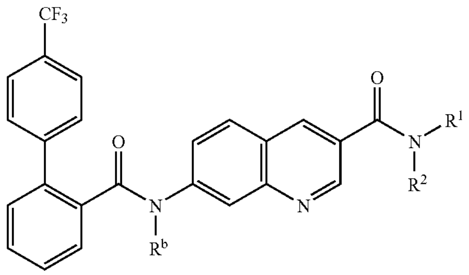

wherein $R^b$ is hydrogen or $C_1$–$C_8$ alkyl and $R^1$ and $R^2$ are hydrogen, $C_1$–$C_8$ alkyl and the like, that inhibits secretion of apoprotein B and is useful for treating atherosclerosis and the like.

DISCLOSURE OF THE INVENTION

There has been a great desire for the development of a compound having a melanin-concentrating hormone antagonistic action and useful as an agent for preventing or treating obesity and the like.

As a result of the intensive studies of compounds having an MCH antagonistic action, the present inventors have found that a compound represented by the formula:

(I)

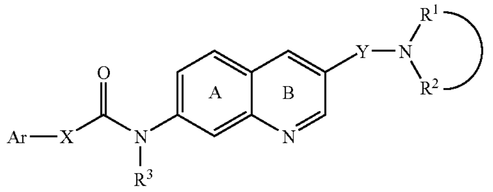

wherein

Ar is a cyclic group optionally having substituent(s);

X is a bond or a spacer having a main chain of 1 to 6 atoms;

$R^1$ and $R^2$ are the same or different and each is a hydrogen atom or a hydrocarbon group optionally having substituent(s), or $R^1$ and $R^2$ may form, together with the adjacent nitrogen atom, a nitrogen-containing heterocycle optionally having substituent(s);

Y is a divalent hydrocarbon group optionally having substituent(s) (except CO);

$R^3$ is a hydrogen atom or a hydrocarbon group optionally having substituent(s); and ring A and ring B may further have substituent(s), and when ring B further has a substituent, the substituent may be linked to $R^1$ to form a ring;

which has a specific substituent at the 3-position and the 7-position of a quinoline ring represented by the formula:

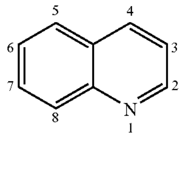

or a salt thereof [hereinafter sometimes to be abbreviated as compound (I)] has a superior MCH antagonistic action, which resulted in the completion of the present invention.

Accordingly, the present invention relates to 1) the compound (I) or a prodrug thereof;
2) the compound (I) wherein X is a bond and the substituent that ring B may further have is not linked to $R^1$;
3) the compound (I) wherein Ar is a group represented by the formula: $Ar^2$—$Ar^1$— wherein $Ar^1$ is a cyclic group optionally having substituent(s) and $Ar^2$ is an aromatic ring group optionally having substituent(s);
4) the compound of the aforementioned 3) wherein the cyclic group for $Ar^1$ is a phenyl, a 5- or 6-membered aromatic heterocyclic group or a 5- to 8-membered monocyclic non-aromatic heterocyclic group;
5) the compound of the aforementioned 3) wherein the aromatic ring group for $Ar^2$ is a phenyl or a 5- or 6-membered aromatic heterocyclic group;
6) the compound (I) wherein X is a bond;
7) the compound (I) wherein $R^1$ and $R^2$ form, together with the adjacent nitrogen atom, a nitrogen-containing heterocycle optionally having substituent(s);
8) the compound of the aforementioned 7) wherein the nitrogen-containing heterocycle is azetidine, morpholine, piperidine, piperazine, pyrrolidine, hexamethyleneimine, 1,3-thiazolidine, 1H-imidazole, 4,5-dihydro-1H-imidazole, 2,3-dihydroindole, 1,2,3,4-tetrahydroquinoline or 1,2,3,4-tetrahydroisoquinoline;
9) the compound (I) wherein Y is a $C_{1-3}$ alkylene;
10) the compound (I) wherein $R^3$ is a hydrogen atom;
11) the compound (I) wherein the substituent that the ring A and the ring B may further have is a halogen atom, an optionally halogenated $C_{1-6}$ alkyl or an optionally halogenated $C_{1-6}$ alkoxy;
12) the compound (I) which is 4'-fluoro-N-[8-methyl-3-(1-pyrrolidinylmethyl)-7-quinolinyl][1,1'-biphenyl]-4-carboxamide;

N-[6-fluoro-3-(1-pyrrolidinylmethyl)-7-quinolinyl]-4'-methoxy[1,1'-biphenyl]-4-carboxamide;

6-(4-methoxyphenyl)-N-[8-methyl-3-(1-pyrrolidinylmethyl)-7-quinolinyl]nicotinamide;

3-fluoro-4'-methoxy-N-[8-methyl-3-(1-pyrrolidinylmethyl)-7-quinolinyl][1,1'-biphenyl]-4-carboxamide;

4-(cyclopropylmethoxy)-N-[8-methyl-3-(1-pyrrolidinylmethyl)-7-quinolinyl]benzamide;

N-[3-(1-azepanylmethyl)-8-methyl-7-quinolinyl]-4-(2-oxopentyl)benzamide; or a salt thereof;

13) a pharmaceutical composition comprising compound (I);
14) the composition of the aforementioned 13), which is a melanin-concentrating hormone antagonist;
15) the composition of the aforementioned 13), which is an agent for preventing or treating a disease caused by a melanin-concentrating hormone;
16) the composition of the aforementioned 13), which is an agent for preventing or treating obesity;
17) the composition of the aforementioned 13), which is a feeding deterrent;
18) the composition of the aforementioned 13), which is an agent for preventing or treating depression;
19) the composition of the aforementioned 13), which is an agent for preventing or treating anxiety;
20) a pharmaceutical agent comprising compound (I) and at least one kind selected from an antidiabetic agent, an agent for treating hyperlipidemia, an agent for treating arthritis, an anti-anxiety agent and an antidepressant in combination;
21) use of compound (I) or a salt thereof or a prodrug thereof for the production of a melanin-concentrating hormone antagonist;
22) a method for antagonizing a melanin-concentrating hormone receptor in a mammal, which comprises administering an effective amount of compound (I) or a salt thereof or a prodrug thereof to the mammal;
23) use of compound (I) or a salt thereof or a prodrug thereof for the production of an agent for preventing or treating a disease caused by a melanin-concentrating hormone;
24) a method for preventing or treating a disease caused by a melanin-concentrating hormone in a mammal, which comprises administering an effective amount of compound (I) or a salt thereof or a prodrug thereof to the mammal;
25) use of compound (I) or a salt thereof or a prodrug thereof for the production of an agent for preventing or treating obesity;
26) a method for preventing or treating obesity in a mammal, which comprises administering an effective amount of compound (I) or a salt thereof or a prodrug thereof to the mammal;
27) use of compound (I) or a salt thereof or a prodrug thereof for the production of a feeding deterrent;
28) a method for suppressing food intake of a mammal, which comprises administering an effective amount of compound (I) or a salt thereof or a prodrug thereof to the mammal;
29) use of compound (I) or a salt thereof or a prodrug thereof for the production of an agent for preventing or treating depression;
30) a method for preventing or treating depression in a mammal, which comprises administering an effective amount of compound (I) or a salt thereof or a prodrug thereof to the mammal;
31) use of compound (I) or a salt thereof or a prodrug thereof for the production of an agent for preventing or treating anxiety;
32) a method for preventing or treating anxiety in a mammal, which comprises administering an effective amount of compound (I) or a salt thereof or a prodrug thereof to the mammal;
33) a method for producing compound (I) or a salt thereof or a prodrug thereof, which comprises reacting a compound represented by the formula: Ar—X—COOH wherein Ar and X are as defined in the aforementioned 1), or a salt thereof or a reactive derivative thereof with a compound represented by the formula:

(III)

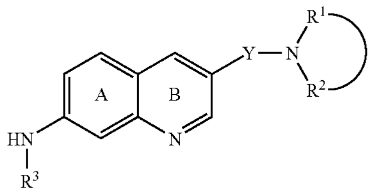

wherein the symbols in the formula are as defined in the aforementioned 1), or a salt thereof;

34) a compound represented by the formula (III)

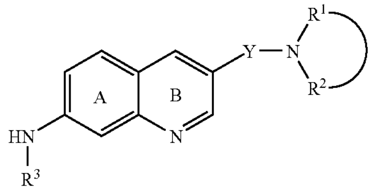

wherein the symbols in the formula are as defined in the aforementioned 1), or a salt thereof; and the like.

Examples of the "cyclic group" of the "cyclic group optionally having substituent(s)" for Ar include an aromatic group, a non-aromatic cyclic hydrocarbon group, a non-aromatic heterocyclic group and the like.

Here, examples of the "aromatic group" include a monocyclic aromatic group and a condensed polycyclic aromatic group.

Examples of the monocyclic aromatic group include phenyl and a 5- or 6-membered aromatic heterocyclic group.

Examples of the "5- or 6-membered aromatic heterocyclic group" include a 5- or 6-membered aromatic heterocyclic group containing one or more (e.g., 1 to 3) hetero atoms selected from nitrogen atom, sulfur atom and oxygen atom in addition to carbon atom, and the like. Concretely, thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, oxadiazolyl, thiadiazolyl, furazanyl, etc. can be mentioned.

Concrete examples of the "monocyclic aromatic groups" include phenyl, 2- or 3-thienyl, 2-, 3-, or 4-pyridyl, 2- or 3-furyl, 2-, 4- or 5-thiazolyl, 2-, 4- or 5-oxazolyl, 1-, 3- or 4-pyrazolyl, 2-pyrazinyl, 2-, 4- or 5-pyrimidinyl, 1-, 2- or 3-pyrrolyl, 1-, 2- or 4-imidazolyl, 3- or 4-pyridazinyl, 3-isothiazolyl, 3-isoxazolyl, 1,2,4-oxadiazol-5-yl, 1,2,4-oxadiazol-3-yl and the like.

The "condensed polycyclic aromatic group" is preferably bicyclic to tetracyclic, more preferably bicyclic or tricyclic, aromatic group. Examples of the "condensed polycyclic aromatic group" include condensed polycyclic aromatic hydrocarbon groups, condensed polycyclic aromatic heterocyclic groups and the like.

Examples of the "condensed polycyclic aromatic hydrocarbon groups" include $C_{9-14}$ condensed polycyclic (bicyclic or tricyclic) aromatic hydrocarbon groups (e.g., naphthalenyl, indenyl, fluorenyl, anthracenyl, etc.) and the like.

Examples of the "condensed polycyclic aromatic heterocyclic groups" include 9- to 14-membered, preferably, 9- or 10-membered, condensed polycyclic aromatic heterocyclic groups containing one or more (for instance, 1 to 4 atoms) hetero atoms selected from nitrogen atom, sulfur atom and oxygen atom in addition to carbon atoms, and the like. The "condensed polycyclic aromatic heterocyclic groups" is more preferably a 10-membered condensed polycyclic aromatic heterocyclic group.

Concrete examples of the "condensed polycyclic aromatic heterocyclic groups" include benzothienyl, benzofuranyl, benzimidazolyl, benzoxazolyl, benzothiazolyl, benzisothiazolyl, naphtho[2,3-b]thiophenyl, isoquinolyl, quinolyl, indolyl, quinoxalinyl, phenanthridinyl, phenothiazinyl, phenoxazinyl, phthalazinyl, naphthyridinyl, quinazolinyl, cinnolinyl, carbazolyl, β-carbolinyl, acridinyl, phenazinyl, phthalimido, thioxanthenyl and the like.

Concrete examples of the "condensed polycyclic aromatic group" include 1-naphthyl; 2-naphthyl; 2-, 3-, 4-, 5- or 8-quinolyl; 1-, 3-, 4-, 5-, 6-, 7- or 8-isoquinolyl; 1-, 2-, 3-, 4-, 5-, 6- or 7-indolyl; 1-, 2-, 4- or 5-isoindolyl; 1-, 5- or 6-phthalazinyl; 2-, 3- or 5-quinoxalinyl; 2-, 3-, 4-, 5- or 6-benzothienyl; 2-, 3-, 4-, 5- or 6-benzofuranyl; 2-, 4-, 5- or 6-benzothiazolyl; and 1-, 2-, 4-, 5- or 6-benzimidazolyl; and the like.

Examples of the "non-aromatic cyclic hydrocarbon group" include $C_{3-8}$ cycloalkyl, $C_{3-8}$ cycloalkenyl and the like.

Here, concrete examples of the $C_{3-8}$ cycloalkyl include cyclopropyl, cyclobutyl, cyclopentyl, cyclohexyl, cycloheptyl, cyclooctyl and the like.

Concrete examples of the $C_{3-8}$ cycloalkenyl include cyclopropenyl, cyclobutenyl, cyclopentenyl, cyclohexenyl, cycloheptenyl, cyclooctenyl and the like.

Examples of the "non-aromatic heterocyclic group" include monocyclic non-aromatic heterocyclic groups, condensed polycyclic non-aromatic heterocyclic groups and the like.

Examples of the "monocyclic non-aromatic heterocyclic groups" include 5- to 8-membered monocyclic non-aromatic heterocyclic groups containing one or more (e.g., 1 to 3) hetero atoms selected from nitrogen atom, sulfur atom and oxygen atom in addition to carbon atom and the like. Concretely, tetrahydrothiophenyl, tetrahydrofuranyl, pyrrolidinyl, imidazolinyl, imidazolidinyl, pyrazolinyl, pyrazolidinyl, tetrahydrothiazolyl, tetrahydroisothiazolyl, tetrohydrooxazolyl, tetrahydroisoxazolyl, piperidinyl, tetrahydropyridyl, dihydropyridyl, piperazinyl, morpholinyl, thiomorpholinyl, tetrahydropyrimidinyl, tetrahydropyridazinyl, hexamethyleneiminyl, dioxanyl, etc. can be mentioned.

The "condensed polycyclic non-aromatic heterocyclic groups" is preferably bicyclic to tetracyclic, more preferably bicyclic or tricyclic non-aromatic heterocyclic group. Examples of the "condensed polycyclic non-aromatic heterocyclic groups" include 9- to 14-membered, preferably 9- or 10-membered condensed polycyclic non-aromatic heterocyclic groups which contain one or more (e.g., 1 to 4) hetero atoms selected from nitrogen atom, sulfur atom and oxygen atom in addition to carbon atoms, and the like. Concretely, dihydrobenzofuranyl, dihydrobenzimidazolyl, dihydrobenzoxazolyl, dihydrobenzothiazolyl, dihydrobenzisothiazolyl, dihydronaphtho[2,3-b]thiophenyl, tetrahydroisoquinolyl, tetrahydroquinolyl, indolinyl, isoindolinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacridinyl, tetrahydrophenazinyl, tetrahydrothioxantenyl, dihydrobenzopyranyl, tetrahydrobenzoxepinyl, etc., can be mentioned.

The "cyclic group" for Ar is preferably phenyl, a 5- or 6-membered aromatic heterocyclic group, a 5- to 8-membered monocyclic non-aromatic heterocyclic group and the like, more preferably phenyl, pyridyl, piperidinyl and the like.

Examples of the "substituent(s)" of the "cyclic group optionally having substituent(s)" for Ar include halogen atoms (e.g., fluorine, chlorine, bromine, iodine, etc.), $C_{1-3}$ alkylenedioxy (e.g., methylenedioxy, ethylenedioxy, etc.), nitro, cyano, optionally halogenated $C_{1-10}$ alkyl, hydroxy-$C_{1-10}$ alkyl (e.g., hydroxymethyl, hydroxyethyl), $C_{6-14}$ aryloxy-$C_{1-6}$ alkyl (e.g., phenoxymethyl, etc.), $C_{1-6}$ alkyl-$C_{6-14}$ aryl-$C_{2-6}$ alkenyl (e.g., methylphenylethenyl, etc.), optionally halogenated $C_{1-10}$ alkoxy, optionally halogenated $C_{1-10}$ alkylthio, $C_{7-19}$ aralkyl optionally having substituent(s), hydroxy, $C_{6-14}$ aryloxy optionally having substituent(s), $C_{7-19}$ aralkyloxy optionally having substituent(s), amino, amino-$C_{1-10}$ alkyl (e.g., aminomethyl, aminoethyl, aminopropyl, aminobutyl, etc.), mono- or d-$C_{1-10}$ alkylamino (e.g., methylamino, ethylamino, propylamino, isopropylamino, butylamino, dimethylamino, diethylamino, dipropylamino, dibutylamino, ethylmethylamino, etc.), mono- or di- $C_{1-10}$ alkylamino-$C_{1-6}$ alkyl (e.g., methylaminomethyl, ethylaminomethyl, propylaminomethyl, isopropylaminoethyl, butylaminoethyl, dimethylaminomethyl, diethylaminomethyl, dipropylaminomethyl, diisopropylaminoethyl, dibutylaminoethyl, etc.), aromatic ring group optionally having substituent(s), non-aromatic ring group optionally having substituent(s), $C_{3-6}$ cycloalkyl-$C_{1-6}$ alkyl optionally having substituent(s), $C_{3-6}$ cycloalkyl-$C_{1-6}$ alkoxy optionally having substituent(s), $C_{1-6}$ alkoxy-$C_{1-6}$ alkoxy, acyl, acylamino, acyloxy, acyl-$C_{1-6}$ alkyl, acylamino-$C_{1-6}$ alkyl, acyloxy-$C_{1-6}$ alkyl and the like.

The "cyclic group" for Ar may have 1 to 5, preferably 1 to 3, of the above-mentioned substituents at substitutable position(s) on the cyclic group. When the number of substituents is 2 or more, respective substituents can be the same or different.

Examples of the above "optionally halogenated $C_{1-10}$ alkyl" include $C_{1-10}$ alkyl (e.g., methyl, ethyl, propyl, isopropyl, butyl, isobutyl, sec-butyl, tert-butyl, pentyl, hexyl, heptyl, octyl, nonyl, decyl, etc.) which may have 1 to 5, preferably 1 to 3, halogen atoms (e.g., fluorine, chlorine, bromine, iodine, etc.). Concrete examples include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, heptyl, octyl, nonyl, decyl and the like.

Examples of the above "optionally halogenated $C_{1-10}$ alkoxy" include $C_{1-10}$ alkoxy (e.g., methoxy, ethoxy, propoxy, butoxy, pentyloxy, hexyloxy, heptyloxy, octyloxy, nonyloxy, decyloxy, etc.) which may have 1 to 5, preferably 1 to 3, halogen atoms (e.g., fluorine, chlorine, bromine, iodine, etc.). Concrete examples include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, isopentyloxy, hexyloxy, heptyloxy, octyloxy, nonyloxy, decyloxy and the like.

Examples of the above "optionally halogenated $C_{1-10}$ alkylthio" include $C_{1-10}$ alkylthio (e.g., methylthio, ethylthio, propylthio, isopropylthio, butylthio, sec-butylthio, tert-butylthio, pentylthio, hexylthio, heptylthio, octylthio, nonylthio, decylthio etc.) which may have 1 to 5, preferably 1 to 3, halogen atoms (e.g., fluorine, chlorine, bromine, iodine, etc.). Concrete examples include methylthio, difluoromethylthio, trifluoromethylthio, ethylthio, propylthio, isopropylthio, butylthio, 4,4,4-trifluorobutylthio, pentylthio, hexylthio, heptylthio, octylthio, nonylthio, decylthio and the like.

Examples of the "$C_{7-19}$ aralkyl" of the above "$C_{7-19}$ aralkyl optionally having substituent(s)" include benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl and the like.

As the "$C_{6-14}$ aryloxy" of the above "$C_{6-14}$ aryloxy optionally having substituent(s)", for example, phenyloxy, 1-naphthyloxy, 2-naphthyloxy and the like can be mentioned.

As the $C_{7-19}$ aralkyloxy" of the above "$C_{7-19}$ aralkyloxy optionally having substituent(s)", for example, benzyloxy, phenethyloxy, diphenylmethyloxy, triphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy and the like can be mentioned.

As the "aromatic ring group" of the above "aromatic ring group optionally having substituent(s)", the above "aromatic group" exemplified for Ar can be mentioned. The "aromatic ring group" is preferably phenyl, naphthyl, 5- or 6-membered aromatic heterocyclic group, 9- or 10-membered condensed polycyclic aromatic heterocyclic group and the like, more preferably phenyl, 5- or 6-membered aromatic heterocyclic group and the like. Of these, phenyl, pyridyl and the like are preferable.

As the "non-aromatic ring group" of the above "non-aromatic ring group optionally having substituent(s)", the above "non-aromatic cyclic hydrocarbon group" and "non-aromatic heterocyclic group" exemplified for Ar can be mentioned. The "non-aromatic ring group" is preferably $C_{3-8}$ cycloalkyl, 5- to 8-membered monocyclic non-aromatic heterocyclic group and the like, more preferably cyclohexyl and the like.

As the "$C_{3-6}$ cycloalkyl-$C_{1-6}$ alkyl" of the above "$C_{3-6}$ cycloalkyl-$C_{1-6}$ alkyl optionally having substituent(s)", for example, cyclopropylmethyl, cyclopropylethyl, cyclobutylmethyl, cyclobutylethyl, cyclopentylmethyl, cyclopentylethyl, cyclohexylmethyl, cyclohexylethyl, cyclohexylpropyl and the like can be mentioned.

As the "$C_{3-6}$ cycloalkyl-$C_{1-6}$ alkoxy" of the above "$C_{3-6}$ cycloalkyl-$C_{1-6}$ alkoxy optionally having substituent(s)", for example, cyclopropylmethoxy, cyclopropylethoxy, cyclobutylmethoxy, cyclobutylethoxy, cyclopentylmethoxy, cyclopentylethoxy, cyclohexylmethoxy, cyclohexylethoxy, cyclohexylpropoxy and the like can be mentioned.

As the above "$C_{1-6}$ alkoxy-$C_{1-6}$ alkoxy", for example, methoxymethoxy, methoxyethoxy, ethoxymethoxy, ethoxyethoxy and the like can be mentioned.

As the "substituent(s)" of the above "$C_{7-19}$ aralkyl optionally having substituent(s)", "$C_{6-14}$ aryloxy optionally having substituent(s)", "$C_{7-19}$ aralkyloxy optionally having substituent(s)", "aromatic ring group optionally having substituent(s)", "non-aromatic ring group optionally having substituent(s)", "$C_{3-6}$ cycloalkyl-$C_{1-6}$ alkyl optionally having substituent(s)" and "$C_{3-6}$ cycloalkyl-$C_{1-6}$ alkoxy optionally having substituent(s)", for example, halogen atoms (e.g., fluorine, chlorine, bromine, iodine, etc.), $C_{1-3}$ alkylenedioxy (e.g., methylenedioxy, ethylenedioxy, etc.), nitro, cyano, optionally halogenated $C_{1-10}$ alkyl, hydroxy-$C_{1-10}$ alkyl (e.g., hydroxymethyl, hydroxyethyl), optionally halogenated $C_{3-6}$ cycloalkyl, optionally halogenated $C_{1-10}$ alkoxy, optionally halogenated $C_{1-10}$ alkylthio, hydroxy, amino, mono- or di-$C_{1-10}$ alkylamino (e.g., methylamino, ethylamino, propylamino, isopropylamino, butylamino, dimethylamino, diethylamino, dipropylamino, dibutylamino, ethylmethylamino, etc.), amino-$C_{1-10}$ alkyl (e.g., aminomethyl, aminoethyl, aminopropyl, aminobutyl, etc.), mono- or di-$C_{1-10}$ alkylamino-$C_{1-6}$ alkyl (e.g., methylaminomethyl, ethylaminomethyl, propylaminomethyl, isopropylaminoethyl, butylaminoethyl, dimethylaminomethyl, diethylaminomethyl, dipropylaminomethyl, diisopropylaminoethyl, dibutylaminoethyl, etc.), formyl, carboxy, carbamoyl, thiocarbamoyl, optionally halogenated $C_{1-6}$ alkyl-carbonyl, $C_{1-6}$ alkoxy-carbonyl (e.g., methoxycarbonyl, ethoxycarbonyl, propoxycarbonyl, tert-butoxycarbonyl, etc.), 5- or 6-membered heterocyclylcarbonyl, mono- or di-$C_{1-6}$ alkyl-carbamoyl (e.g., methylcarbamoyl, ethylcarbamoyl, dimethylcarbamoyl, diethylcarbamoyl, ethylmethylcarbamoyl, etc.), 5- or 6-membered heterocyclylcarbamoyl, carbamoyl-$C_{1-6}$ alkyl (e.g., carbamoylmethyl, carbamoylethyl, carbamoylpropyl, etc.), mono- or di-$C_{1-6}$ alkyl-carbamoyl-$C_{1-6}$ alkyl (e.g., methylcarbamoylmethyl, methylcarbamoylethyl, methylcarbamoylpropyl, dimethylcarbamoylmethyl, dimethylcarbamoylethyl, dimethylcarbamoylpropyl, ethylcarbamoylmethyl, ethylcarbamoylethyl, ethylcarbamoylpropyl, diethylcarbamoylmethyl, diethylcarbamoylethyl, diethylcarbamoylpropyl, etc.), 5- or 6-membered heterocyclylcarbonyl-$C_{1-6}$ alkyl, 5- or 6-membered heterocyclylcarbamoyl-$C_{1-6}$ alkyl, optionally halogenated $C_{1-6}$ alkylsulfonyl, formylamino, optionally halogenated $C_{1-6}$ alkyl-carboxamido, $C_{1-6}$ alkoxy-carboxamido (e.g., methoxycarboxamido, ethoxycarboxamido, propoxycarboxamido, butoxycarboxamido, etc.), $C_{1-6}$ alkylsulfonylamino (e.g., methylsulfonylamino, ethylsulfonylamino, etc.), $C_{1-6}$ alkyl-carbonyloxy (e.g., acetoxy, propanoyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono- or di-$C_{1-6}$ alkyl-carbamoyloxy (e.g., methylcarbamoyloxy, ethylcarbamoyloxy, dimethylcarbamoyloxy, diethylcarbamoyloxy, etc.), mono- or di-$C_{1-6}$ alkyl-carbamoyl-$C_{1-6}$ alkoxy (e.g., methylcarbamoylmethoxy, ethylcarbamoylmethoxy, dimethylcarbamoylmethoxy, diethylcarbamoylmethoxy, etc.), 5- or 6-membered non-aromatic heterocyclic group (e.g., pyrrolidinyl, piperidinyl, etc.) and the like can be mentioned. The number of substituents is, for instance, 1 to 5, preferably 1 to 3. When the number of substituents is 2 or more, respective substituents can be the same or different.

Here, as the "optionally halogenated $C_{1-10}$ alkyl", "optionally halogenated $C_{1-10}$ alkoxy" and "optionally halogenated $C_{1-10}$ alkylthio", those exemplified as "substituent(s)" of the above "cyclic group optionally having substituent(s)" for Ar can be used respectively.

As the above "optionally halogenated $C_{3-6}$ cycloalkyl", for example, $C_{3-6}$ cycloalkyl (e.g., cyclopropyl, cyclobutyl, cyclopentyl, cyclohexyl, etc.) optionally having 1 to 5, preferably 1 to 3, halogen atoms (e.g., fluorine, chlorine, bromine, iodine, etc.) and the like can be mentioned. Concrete examples include cyclopropyl, cyclobutyl, cyclopentyl, cyclohexyl, 4,4-dichlorocyclohexyl, 2,2,3,3-tetrafluorocyclopentyl, 4-chlorocyclohexyl and the like.

Examples of the above "optionally halogenated $C_{1-6}$ alkyl-carbonyl" include $C_{1-6}$ alkyl-carbonyl (e.g., acetyl, propanoyl, 2-methylpropanoyl, butanoyl, 3-methylbutanoyl, pentanoyl, hexanoyl, etc.) which may have 1 to 5, preferably 1 to 3, halogen atoms (e.g., fluorine, chlorine, bromine, iodine, etc.). Concrete examples include acetyl, monochloroacetyl, trifluoroacetyl, trichloroacetyl, propanoyl, 2-methylpropanoyl, butanoyl, 3-methylbutanoyl, pentanoyl, hexanoyl and the like.

As the "5- or 6-membered heterocyclylcarbonyl" of the above "5- or 6-membered heterocyclylcarbonyl" and "5- or 6-membered heterocyclylcarbonyl-$C_{1-6}$ alkyl", for example, nicotinoyl, isonicotinoyl, 2-thenoyl, 3-thenoyl, 2-furoyl, 3-furoyl, morpholinocarbonyl, piperidinocarbonyl, 1-pyrrolidinylcarbonyl and the like can be mentioned.

As the "5- or 6-membered heterocyclylcarbonyl-$C_{1-6}$ alkyl", for example, morpholinocarbonylmethyl, morpholinocarbonylethyl, morpholinocarbonylpropyl, piperidinocarbonylmethyl, piperidinocarbonylethyl, piperidinocarbonylpropyl, 1-pyrrolidinylcarbonylmethyl, 1-pyrrolidinylcarbonylethyl, 1-pyrrolidinylcarbonylpropyl and the like can be mentioned.

As the "5- or 6-membered heterocyclylcarbamoyl" of the above "5- or 6-membered heterocyclylcarbamoyl" and "5- or 6-membered heterocyclylcarbamoyl-$C_{1-6}$ alkyl", for example, morpholinocarbamoyl, piperidinocarbamoyl, 1-pyrrolidinylcarbamoyl, 2-pyridylcarbamoyl, 3-pyridylcarbamoyl, 4-pyridylcarbamoyl, 2-thienylcarbamoyl, 3-thienylcarbamoyl and the like can be mentioned.

As the "5- or 6-membered heterocyclylcarbamoyl-$C_{1-6}$ alkyl", for example, morpholinocarbamoylmethyl, morpholinocarbamoylethyl, morpholinocarbamoylpropyl, piperidinocarbamoylmethyl, piperidinocarbamoylethyl, piperidinocarbamoylpropyl, 1-pyrrolidinylcarbamoylmethyl, 1-pyrrolidinylcarbamoylethyl, 1-pyrrolidinylcarbamoylpropyl and the like can be mentioned.

Examples of the above "optionally halogenated $C_{1-6}$ alkylsulfonyl" include $C_{1-6}$ alkylsulfonyl (e.g., methylsulfonyl, ethylsulfonyl, propylsulfonyl, isopropylsulfonyl, butylsulfonyl, sec-butylsulfonyl, tert-butylsulfonyl, etc.) which may have 1 to 5, preferably 1 to 3, halogen atoms (e.g., fluorine, chlorine, bromine, iodine, etc.) and the like. Concrete examples include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl, hexylsulfonyl and the like.

Examples of the above "optionally halogenated $C_{1-6}$ alkyl-carboxamido" include $C_{1-6}$ alkyl-carboxamido (e.g., acetamido, propanamido, butanamido, etc.) which may have 1 to 5, preferably 1 to 3, halogen atoms (e.g., fluorine, chlorine, bromine, iodine, etc.) and the like. Concrete examples include acetamido, trifluoroacetamido, propanamido and butanamido.

Examples of the above "acyl" include acyl of the formula: $—CO—R^4$, $—CO—OR^4$, $—CO—NR^4R^5$, $—CS—NR^4R^5$, $—SO_2—R^{4a}$, $—SO—R^{4a}$, $—PO(—OR^4)—OR^5$ or $—PO_2—R^{4a}$ wherein $R^4$ is (i) hydrogen atom, (ii) hydrocarbon group optionally having substituent(s) or (iii) heterocyclic group optionally having substituent(s); $R^{4a}$ is (i) hydrocarbon group optionally having substituent(s) or (ii) heterocyclic group optionally having substituent(s); $R^5$ is hydrogen atom or $C_{1-6}$ alkyl; $R^4$ and $R^5$, together with the adjacent nitrogen atom, can form a nitrogen-containing heterocycle optionally having substituent(s), and the like.

Examples of the "hydrocarbon group" of the "hydrocarbon group optionally having substituent(s)" for $R^4$ or $R^{4a}$ include straight-chain or cyclic hydrocarbon groups (e.g., alkyl, alkenyl, alkynyl, cycloalkyl, aryl, aralkyl, cycloalkyl-alkyl, etc.), and the like. Of these, $C_{1-19}$ straight-chain or cyclic hydrocarbon groups as shown below are preferable. In addition, the cycloalkyl in the above cycloalkyl and cycloalkyl-alkyl may be condensed with a benzene ring.

a) $C_{1-6}$ alkyl (e.g., methyl, ethyl, propyl, isopropyl, butyl, isobutyl, sec-butyl, tert-butyl, pentyl, hexyl, etc.);

b) $C_{2-6}$ alkenyl (e.g., vinyl, allyl, isopropenyl, 2-butenyl, etc.);

c) $C_{2-6}$ alkynyl (e.g., ethynyl, propargyl, 2-butynyl, etc.);

d) $C_{3-6}$ cycloalkyl optionally condensed with benzene ring (e.g., cyclopropyl, cyclobutyl, cyclopentyl, cyclohexyl, etc.);

e) $C_{6-14}$ aryl (e.g., phenyl, 1-naphthyl, 2-naphthyl, 2-indenyl, 2-anthryl, etc.);

f) $C_{7-19}$ aralkyl (e.g., benzyl, phenethyl, diphenylmethyl, triphenylmethyl, 1-naphthylmethyl, 2-naphthylmethyl, 2,3-diphenylethyl, 3-phenylpropyl, 4-phenylbutyl, 5-phenylpentyl, etc.);

g) ($C_{3-6}$ cycloalkyl optionally condensed with a benzene ring)-$C_{1-6}$ alkyl (e.g., cyclopropylmethyl, cyclopropylethyl, cyclobutylmethyl, cyclopentylmethyl, cyclopentylethyl, cyclohexylpropyl and the like).

The "hydrocarbon group" is preferably $C_{1-6}$ alkyl, $C_{6-14}$ aryl, $C_{7-19}$ aralkyl, $C_{3-6}$ cycloalkyl optionally condensed with a benzene ring, ($C_{3-6}$ cycloalkyl optionally condensed with a benzene ring)-$C_{1-6}$ alkyl, and the like.

Examples of the "substituent(s)" of the "hydrocarbon group optionally having substituent(s)" include halogen atom (e.g., fluorine, chlorine, bromine, iodine, etc.), $C_{1-3}$ alkylenedioxy (e.g., methylenedioxy, ethylenedioxy, etc.), nitro, cyano, optionally halogenated $C_{1-10}$ alkoxy, optionally halogenated $C_{1-10}$ alkylthio, hydroxy, amino, mono- or di-$C_{1-10}$ alkylamino (e.g., methylamino, ethylamino, propylamino, isopropylamino, butylamino, dimethylamino, diethylamino, dipropylamino, dibutylamino, ethylmethylamino, etc.), formyl, carboxy, carbamoyl, thiocarbamoyl, optionally halogenated $C_{1-6}$ alkyl-carbonyl, $C_{1-6}$ alkoxy-carbonyl (e.g., methoxycarbonyl, ethoxycarbonyl, propoxycarbonyl, tert-butoxycarbonyl, etc.), 5- to 10-membered aromatic heterocyclic group optionally having substituent(s), $C_{6-14}$ aryl-carbonyl optionally having substituent(s), $C_{6-14}$ aryloxy-carbonyl optionally having substituent(s), $C_{7-19}$ aralkyloxy-carbonyl optionally having substituent(s), 5- or 6-membered heterocyclylcarbonyl optionally having substituent(s), mono- or di-$C_{1-6}$ alkyl-carbamoyl (e.g., methylcarbamoyl, ethylcarbamoyl, dimethylcarbamoyl, diethylcarbamoyl, ethylmethylcarbamoyl, etc.), $C_{6-14}$ aryl-carbamoyl optionally having substituent(s), 5- or 6-membered heterocyclylcarbamoyl optionally having substituent(s), optionally halogenated $C_{1-6}$ alkylsulfonyl, $C_{6-14}$ arylsulfonyl optionally having substituent(s), formylamino, $C_{1-6}$ alkyl-carbonyloxy (e.g., acetoxy, propanoyloxy, etc.), $C_{6-14}$ aryl-carbonyloxy optionally having substituent(s), $C_{1-6}$ alkoxy-carbonyloxy (e.g., methoxycarbonyloxy, ethoxycarbonyloxy, propoxycarbonyloxy, butoxycarbonyloxy, etc.), mono- or di-$C_{1-6}$ alkyl-carbamoyloxy (e.g., methylcarbamoyloxy, ethylcarbamoyloxy, dimethylcarbamoyloxy, diethylcarbamoyloxy, etc.), $C_{6-14}$ aryl-carbamoyloxy optionally having substituent(s), 5- or 6-membered heterocyclylcarbonyloxy optionally having substituent(s) and the like. The number of substituents is, for example, 1 to 5, preferably 1 to 3. When the number of substituents is 2 or more, respective substituents can be the same or different.

Here, as the "optionally halogenated $C_{1-10}$ alkoxy", and "optionally halogenated $C_{1-10}$ alkylthio", those exemplified for the "substituent(s)" of the above "cyclic group optionally having substituent(s)" for Ar can be used, respectively.

As the above "optionally halogenated $C_{1-6}$ alkyl-carbonyl" and "optionally halogenated $C_{1-6}$ alkylsulfonyl", those exemplified for the "substituent(s)" of the above "$C_{7-19}$ aralkyl optionally having substituent(s)" can be used, respectively.

As the "5- to 10-membered aromatic heterocyclic group" of the above "5- to 10-membered aromatic heterocyclic group optionally having substituent(s)", for example, 5- to 10-membered monocyclic or bicyclic aromatic heterocyclic group containing 1 to 4 heteroatoms selected from nitrogen atom, sulfur atom and oxygen atom in addition to carbon atoms can be mentioned. Specifically, for example, 2- or 3-thienyl; 2-, 3- or 4-pyridyl; 2- or 3-furyl; 2-, 4- or 5-thiazolyl; 2-, 4- or 5-oxazolyl; 1-, 3- or 4-pyrazolyl; 2-pyrazinyl; 2-, 4- or 5-pyrimidinyl; 1-, 2- or 3-pyrrolyl; 1-, 2- or 4-imidazolyl; 3- or 4-pyridazinyl; 3-isothiazolyl; 3-isoxazolyl; 1,2,4-oxadiazol-5-yl; 1,2,4-oxadiazol-3-yl; 2-, 3-, 4-, 5- or 8-quinolyl; 1-, 3-, 4-, 5-, 6-, 7- or 8-isoquinolyl; 1-, 2-, 3-, 4-, 5-, 6- or 7-indolyl; 1-, 2-, 4- or 5-isoindolyl; 1-, 5- or 6-phthalazinyl; 2-, 3- or 5-quinoxalinyl; 2-, 3-, 4-, 5- or 6-benzofuranyl; 2-, 4-, 5- or 6-benzothiazolyl; 1-, 2-, 4-, 5- or 6-benzimidazolyl and the like can be mentioned.

Examples of the "$C_{6-14}$ aryl-carbonyl" of the above "$C_{6-14}$ aryl-carbonyl optionally having substituent(s)" include benzoyl, 1-naphthoyl, 2-naphthoyl and the like.

As the "$C_{6-14}$ aryloxy-carbonyl" of the above "$C_{6-14}$ aryloxy-carbonyl optionally having substituent(s)", for example, phenyloxycarbonyl, 1-naphthyloxycarbonyl, 2-naphthyloxycarbonyl and the like can be mentioned.

As the "$C_{7-19}$ aralkyloxy-carbonyl" of the above "$C_{7-19}$ aralkyloxy-carbonyl optionally having substituent(s)", for example, benzyloxycarbonyl, phenethyloxycarbonyl, diphenylmethyloxycarbonyl, triphenylmethyloxycarbonyl, 1-naphthylmethyloxycarbonyl, 2-naphthylmethyloxycarbonyl, 2,2-diphenylethyloxycarbonyl, 3-phenylpropyloxycarbonyl, 4-phenylbutyloxycarbonyl, 5-phenylpentyloxycarbonyl and the like can be mentioned.

As the "5- or 6-membered heterocyclylcarbonyl" of the above "5- or 6-membered heterocyclylcarbonyl optionally having substituent(s)", those exemplified for the "substituent(s)" of the above "$C_{7-19}$ aralkyl optionally having substituent(s)" can be used.

As the "$C_{6-14}$ aryl-carbamoyl" of the above "$C_{6-14}$ aryl-carbamoyl optionally having substituent(s)", for example, phenylcarbamoyl, 1-naphthylcarbamoyl, 2-naphthylcarbamoyl and the like can be mentioned.

As the "5- or 6-membered heterocyclylcarbamoyl" of the above "5- or 6-membered heterocyclylcarbamoyl optionally having substituent(s)", those exemplified for the "substituent(s)" of the above "$C_{7-19}$ aralkyl optionally having substituent(s)" can be used.

As the "$C_{6-14}$ arylsulfonyl" of the above "$C_{6-14}$ arylsulfonyl optionally having substituent(s)", for example, phenylsulfonyl, 1-naphthylsulfonyl, 2-naphthylsulfonyl and the like can be mentioned.

As the "$C_{6-14}$ aryl-carbonyloxy" of the above "$C_{6-14}$ aryl-carbonyloxy optionally having substituent(s)", for example, benzoyloxy, 1-naphthoyloxy, 2-naphthoyloxy and the like can be mentioned.

As the "$C_{6-14}$ aryl-carbamoyloxy" of the above "$C_{6-14}$ aryl-carbamoyloxy optionally having substituent(s)", for example, phenylcarbamoyloxy, naphthylcarbamoyloxy and the like can be mentioned.

As the "5- or 6-membered heterocyclylcarbonyloxy" of the above "5- or 6-membered heterocyclylcarbonyloxy optionally having substituent(s)", for example, nicotinoyloxy, isonicotinoyloxy, 2-thenoyloxy, 3-thenoyloxy, 2-furoyloxy, 3-furoyloxy, morpholinocarbonyloxy, piperidinocarbonyloxy, pyrrolidin-1-ylcarbonyloxy and the like can be mentioned.

As the "substituent(s)" of the above "5- to 10-membered aromatic heterocyclic group optionally having substituent(s)", "$C_{6-14}$ aryl-carbonyl optionally having substituent(s)", "$C_{6-14}$ aryloxy-carbonyl optionally having substituent(s)", "$C_{7-19}$ aralkyloxy-carbonyl optionally having substituent(s)", "5- or 6-membered heterocyclylcarbonyl optionally having substituent(s)", "$C_{6-14}$ aryl-carbamoyl optionally having substituent(s)", "5- or 6-membered heterocyclylcarbamoyl optionally having substituent(s)", "$C_{6-14}$ arylsulfonyl optionally having substituent(s)", "$C_{6-14}$ aryl-carbonyloxy optionally having substituent(s)", "$C_{6-14}$ aryl-carbamoyloxy optionally having substituent(s)" and "5- or 6-membered heterocyclylcarbonyloxy optionally having substituent(s)", those exemplified for the "substituent(s)" of the above "$C_{7-19}$ aralkyl optionally having substituent(s)" can be mentioned. The number of the substituents is, for example, 1 to 5, preferably 1 to 3. When the number of substituents is 2 or more, respective substituents can be the same or different.

Examples of the "heterocyclic group" of the "heterocyclic group optionally having substituent(s)" for $R^4$ or $R^{4a}$ include 5- to 14-membered (monocyclic, bicyclic or tricyclic) heterocyclic groups containing 1 to 4 hetero atoms selected from nitrogen atom, sulfur atom and oxygen atom in addition to carbon atom. Preferably, (i) an aromatic heterocyclic group, (ii) a 5- to 10-membered non-aromatic heterocyclic group, (iii) a 7- to 10-membered cross-linked heterocyclic group and the like can be mentioned.

Here, examples of the "aromatic heterocyclic group" include a 5- to 14-membered, preferably 5- to 10-membered, aromatic heterocyclic group containing one or more hetero atoms (e.g., 1 to 4) selected from nitrogen atom, sulfur atom and oxygen atom in addition to carbon atoms, and the like. Concrete examples include aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, oxadiazolyl, thiadiazolyl, furazanyl, benzothienyl, benzofuranyl, benzimidazolyl, benzoxazolyl, benzothiazolyl, benzisothiazolyl, naphtho[2,3-b] thiophenyl, phenoxathiinyl, indolyl, isoindolyl, 1H-indazolyl, purinyl, 4H-quinolidinyl, isoquinolinyl, quinolyl, phthalazinyl, naphthyridinyl, quinoxalinyl, quinazolinyl, cinnolinyl, carbazolyl, β-carbolinyl, phenanthridinyl, acridinyl, phenazinephenothiazinyl, phenoxazinyl, phthalimido, etc.; or a group formed by condensing these groups with one to multiple (preferably 1 or 2) aromatic rings (e.g., benzene ring, etc.).

Examples of the "5- to 10-membered non-aromatic heterocyclic group" include 2- or 3-pyrrolyl, pyrrolidinyl, 2- or 3-imidazolinyl, 2-oxazolinyl, oxazolidinyl, 2- or 3-pyrazolinyl, pyrazolidinyl, 2-thiazolinyl, piperidinyl, piperazinyl, hexamethyleneiminyl, morpholinyl, thiomorpholinyl, tetrahydrofuranyl and the like.

Examples of the "7- to 10-membered cross-linked heterocyclic group" include quinuclidinyl, 7-azabicyclo[2.2.1] heptanyl and the like.

The "heterocyclic group" is preferably 5- to 10-membered (monocyclic or bicyclic) heterocyclic groups containing 1 to 4 hetero atoms selected from nitrogen atom, sulfur atom and oxygen atom in addition to carbon atom. Concrete examples include aromatic heterocyclic groups such as 2- or 3-thienyl; 2-, 3- or 4-pyridyl; 2- or 3-furyl; 2-, 4- or 5-thiazolyl; 2-, 4- or 5-oxazolyl; 1-, 3- or 4-pyrazolyl; 2-pyrazinyl; 2-, 4- or 5-pyrimidinyl; 1-, 2- or 3-pyrrolyl; 1-, 2- or 4-imidazolyl; 3- or 4-pyridazinyl; 3-isothiazolyl; 3-isoxazolyl; 1,2,4-oxadiazol-5-yl; 1,2,4-oxadiazol-3-yl; 2-, 3-, 4-, 5- or 8-quinolyl; 1-, 3-, 4-, 5-, 6-, 7- or 8-isoquinolyl; 1-, 2-, 3-, 4-, 5-, 6- or 7-indolyl; 1-, 2-, 4- or 5-isoindolyl; 1-, 5- or 6-phthalazinyl; 2-, 3- or 5-quinoxalinyl; 2-, 3-, 4-, 5- or 6-benzofuranyl; 2-, 3-, 4-, 5- or 6-benzothienyl; 2-, 4-, 5- or 6-benzothiazolyl; 1-, 2-, 4-, 5- or 6-benzimidazolyl, etc.; and non-aromatic heterocyclic groups such as 1-, 2- or 3-pyrrolidinyl; 1-, 2-, 4- or 5-imidazolidinyl; 2- or 4-imidazolinyl; 2-, 3- or 4-pyrazolidinyl; piperidino; 2-, 3- or 4-piperidyl; 1- or 2-piperazinyl; morpholino, etc. and the like.

As the "substituent(s)" of the "heterocyclic group optionally having substituent(s)", those exemplified for the "substituent(s)" of the above "$C_{7-19}$ aralkyl optionally having substituent(s)" can be used. The number of substituents is, for example, 1 to 5, preferably 1 to 3. When the number of substituents is 2 or more, respective substituents can be the same or different.

As the "$C_{1-6}$ alkyl" for $R^5$, for example, methyl, ethyl, propyl, isopropyl, butyl, isobutyl, sec-butyl, tert-butyl, pentyl, hexyl and the like can be mentioned.

As the "nitrogen-containing heterocycle" of the "nitrogen-containing heterocycle optionally having substituent(s)" formed by $R^4$ and $R^5$ together with the adjacent nitrogen atom, for example, a 5- or 7-membered nitrogen-containing heterocycle containing at least one nitrogen atom and optionally containing 1 to 3 heteroatoms selected from nitrogen atom, sulfur atom and oxygen atom in addition to carbon atoms, and the like can be mentioned. The "nitrogen-containing heterocycle" is preferably piperidine, morpholine, thiomorpholine, piperazine, pyrrolidine and the like.

As the "substituent(s)" of the "nitrogen-containing heterocycle optionally having substituent(s)", those exemplified for the "substituent(s)" of the above "$C_{7-19}$ aralkyl optionally having substituent(s)" are used. The number of substituents is, for example, 1 to 5, preferably 1 to 3. When the number of substituents is 2 or more, respective substituents can be the same or different.

The "acyl" is preferably formyl, carboxy, carbamoyl, optionally halogenated $C_{1-6}$ alkyl-carbonyl (e.g., acetyl, propanoyl, 2-methylpropanoyl, butanoyl, 3-methylbutanoyl, pentanoyl, hexanoyl, etc.), $C_{1-6}$ alkoxy-carbonyl (e.g., methoxycarbonyl, ethoxycarbonyl, propoxycarbonyl, tert-butoxycarbonyl, etc.), $C_{6-14}$ aryl-carbonyl optionally having substituent(s) (e.g., benzoyl, 1-naphthoyl, 2-naphthoyl, etc.), $C_{6-14}$ aryloxy-carbonyl optionally having substituent(s) (e.g., phenyloxycarbonyl, 1-naphthyloxycarbonyl, 2-naphthyloxycarbonyl, etc.), $C_{7-19}$ aralkyloxy-carbonyl optionally having substituent(s) (e.g., benzyloxycarbonyl, phenethyloxycarbonyl, etc.), a 5- to 6-membered heterocyclylcarbonyl optionally having substituent(s) (e.g., nicotinoyl, tetrahydrofuroyl, etc.), mono- or di-$C_{1-6}$ alkyl-carbamoyl (e.g., ethylcarbamoyl, ethylcarbamoyl, dimethylcarbamoyl, diethylcarbamoyl, ethylmethylcarbamoyl, etc.), $C_{6-14}$ aryl-carbamoyl optionally having substituent(s) (e.g., phenylcarbamoyl, 4-methoxyphenylcarbamoyl, 3,4-dimethoxyphenylcarbamoyl, etc.), 5- or 6-membered heterocyclylcarbamoyl optionally having substituent(s) (e.g., pyridylcarbamoyl, etc.), optionally halogenated $C_{1-6}$ alkylsulfonyl (e.g., methylsulfonyl, propylsulfonyl, butylsulfonyl, etc.), $C_{6-14}$ arylsulfonyl optionally having substituent(s) (e.g., phenylsulfonyl, etc.), $C_{3-6}$ cycloalkyl-carbonyl optionally having substituent(s) (e.g., cyclopropylcarbonyl, cyclohexylcarbonyl, etc.), $C_{3-6}$ cycloalkyl-$C_{1-6}$ alkyl-carbonyl optionally having substituent(s) (e.g., cyclopropylmethylcarbonyl, cyclopropylethylcarbonyl, cyclopentylmethylcarbonyl, cyclohexylmethylcarbonyl, etc.) and the like.

Here, as the "optionally halogenated $C_{1-6}$ alkyl-carbonyl" and "optionally halogenated $C_{1-6}$ alkylsulfonyl", those exemplified for the "substituent(s)" of the above "$C_{7-19}$ aralkyl optionally having substituent(s)" can be used.

As the "$C_{6-14}$ aryl-carbonyl optionally having substituent(s)", "$C_{6-14}$ aryloxy-carbonyl optionally having substituent(s)", "$C_{7-19}$ aralkyloxy-carbonyl optionally having substituent(s)", "5- or 6-membered heterocyclylcarbonyl optionally having substituent(s)", "$C_{6-14}$ aryl-carbamoyl optionally having substituent(s)", "5- or 6-membered heterocyclylcarbamoyl optionally having substituent(s)" and "$C_{6-14}$ arylsulfonyl optionally having substituent(s)", those exemplified as "substituent(s)" of the above "hydrocarbon group optionally having substituent(s)" for $R^4$ can be used.

As the substituent of the "$C_{3-6}$ cycloalkyl-carbonyl optionally having substituent(s)" and "$C_{3-6}$ cycloalkyl-$C_{1-6}$ alkyl-carbonyl optionally having substituent(s)", those exemplified for the "substituent(s)" of the above "$C_{7-19}$ aralkyl optionally having substituent(s)" can be used. The number of substituents is, for example, 1 to 3. When the number of substituents is 2 or more, respective substituents can be the same or different.

As the above "acylamino", for example, amino substituted with one or two from the above "acyl" can be mentioned. Preferably, acylamino represented by the formula: $—NR^6—COR^7$, $—NR^6—COOR^{7a}$, $—NR^6—SO_2R^{7a}$, $—NR^6—CONR^{7a}R^{7b}$, $—NR^6—PO(—OR^7)—OR^{7b}$ or $—NR^6—PO_2—R^7$ wherein $R^6$ is hydrogen atom or $C_{1-6}$ alkyl; $R^7$ is as defined for the above $R^4$; $R^{7a}$ is as defined for the above $R^{4a}$; $R^{7b}$ is as defined for $R^5$, and the like can be mentioned.

As the "$C_{1-6}$ alkyl" for $R^6$, those exemplified for the above $R^5$ can be mentioned.

The "acylamino" is preferably formylamino, optionally halogenated $C_{1-6}$ alkyl-carboxamido (e.g., methylcarboxamido, trifluoromethylcarboxamido, propylcarboxamido, isopropylcarboxamido, butylcarboxamido etc.), $C_{6-14}$ arylcarboxamido optionally having substituent(s) (e.g., phenylcarboxamido, 2-methoxyphenylcarboxamido, 4-methoxyphenylcarboxamido, propanoylmethylphenylcarboxamido etc.), N—($C_{6-14}$ aryl-carbonyl optionally having substituent(s))-N—$C_{1-6}$ alkylamino (e.g., N-4-methoxybenzoyl-N-methylamino etc.), $C_{7-19}$ aralkyl-carboxamido optionally having substituent(s) (e.g., benzylcarboxamido etc.), aromatic heterocycle-carboxamido optionally having substituent(s) (e.g., benzothiophen-2-ylcarboxamido), optionally halogenated $C_{1-6}$ alkoxy-carboxamido (e.g., methoxycarboxamido, ethoxycarboxamido, propoxycarboxamido, butoxycarboxamido etc.), $C_{6-14}$ arylamino-carbonylamino optionally having substituent(s) (e.g., phenylaminocarbonylamino etc.), optionally halogenated $C_{1-6}$ alkylsulfonylamino (e.g., methylsulfonylamino, trifluoromethylsulfonylamino, ethylsulfonylamino etc.), $C_{6-14}$ arylsulfonylamino optionally having substituent(s) (e.g., 4-methoxyphenylsulfonylamino etc.) and the like.

Here, as the "substituent(s)" of the "$C_{6-14}$ aryl-carboxamide optionally having substituent(s)", "N—($C_{6-14}$ aryl-carbonyl optionally having substituent(s))-N—$C_{1-6}$ alkylamino", "$C_{7-19}$ aralkyl-carboxamido optionally having substituent(s)", "aromatic heterocycle-carboxamido optionally having substituent(s)", "$C_{6-14}$ arylamino-carbonylamino optionally having substituent(s)" and "$C_{6-14}$ arylsulfonylamino optionally having substituent(s)", those exemplified for the "substituent(s)" of the above "$C_{7-19}$ aralkyl optionally having substituent(s)" can be mentioned. The number of substituents is, for example, 1 to 5, preferably 1 to 3. When the number of substituents is 2 or more, respective substituents can be the same or different.

As the above "acyloxy", for example, oxy substituted with one from the above "acyl" can be mentioned. Preferably, acyloxy represented by the formula: $—O—COR^8$, $—O—COOR^8$, $—O—CONHR^8$, $—O—PO(OH)—OR^8$ or $—O—PO^2—R^8$ wherein $R^8$ is as defined for the above $R^4$, and the like can be mentioned.

The "acyloxy" is preferably optionally halogenated $C_{1-6}$ alkyl-carbonyloxy (e.g., acetoxy, propanoyloxy, butanoyloxy, etc.), $C_{6-14}$ aryl-carbonyloxy optionally having substituent(s) (e.g., benzoyloxy, 4-methoxybenzoyloxy, etc.), optionally halogenated $C_{1-6}$ alkoxy-carbonyloxy (e.g., methoxycarbonyloxy, trifluoromethoxycarbonyloxy, ethoxycarbonyloxy, propoxycarbonyloxy, butoxycarbonyloxy, etc.), mono- or di-$C_{1-6}$ alkyl-carbamoyloxy (e.g., methylcarbamoyloxy, ethylcarbamoyloxy, dimethylcarbamoyloxy, diethylcarbamoyloxy, etc.), $C_{6-14}$ aryl-carbamoyloxy optionally having substituent(s) (e.g., phenylcarbamoyloxy, naphthylcarbamoyloxy, etc.), nicotinoyloxy and the like.

As the "substituent(s)" of the "$C_{6-14}$ aryl-carbonyloxy optionally having substituent(s)" or "$C_{6-14}$ aryl-carbamoyloxy optionally having substituent(s)", those exemplified for the "substituent(s)" of the above "$C_{7-19}$ aralkyl optionally having substituent(s)" can be mentioned. The number of substituents is, for example, 1 to 5, preferably 1 to 3. When the number of substituents is 2 or more, respective substituents can be the same or different.

As the above "acyl-$C_{1-6}$ alkyl", "acylamino-$C_{1-6}$ alkyl" and "acyloxy-$C_{1-6}$ alkyl", $C_{1-6}$ alkyl (e.g., methyl, ethyl, propyl, isopropyl, butyl, isobutyl, sec-butyl, tert-butyl, pentyl, hexyl, etc.) substituted with the above "acyl", "acylamino" or "acyloxy" can be mentioned, respectively.

The "substituent(s)" of the "cyclic group optionally having substituent(s)" for Ar is preferably halogen atom (e.g., fluorine, chlorine, bromine, iodine, etc.), $C_{1-3}$ alkylenedioxy (e.g., methylenedioxy, ethylenedioxy, etc.), nitro, cyano, optionally halogenated $C_{1-10}$ alkyl, aromatic ring group optionally having substituent(s), non-aromatic ring group optionally having substituent(s), optionally halogenated $C_{1-10}$ alkoxy, $C_{6-14}$ aryloxy optionally having substituent(s), $C_{7-19}$ aralkyloxy optionally having substituent(s), $C_{3-6}$ cycloalkyl-$C_{1-6}$ alkyl, $C_{3-6}$ cycloalkyl-$C_{1-6}$ alkoxy optionally having substituent(s), acyl, acyl-$C_{1-6}$ alkyl, hydroxy, $C_{1-6}$ alkoxy-$C_{1-6}$ alkoxy, optionally halogenated $C_{1-10}$ alkylthio, acylamino, acyloxy and the like.

The "substituent(s)" of the "cyclic group optionally having substituent(s)" for Ar is more preferably halogen atom (e.g., fluorine, chlorine, bromine, iodine, etc.), $C_{1-3}$ alkylenedioxy (e.g., methylenedioxy, ethylenedioxy, etc.), nitro, cyano, optionally halogenated $C_{1-10}$ alkyl, aromatic ring group optionally having substituent(s), non-aromatic ring group optionally having substituent(s), optionally halogenated $C_{1-10}$ alkoxy, $C_{6-14}$ aryloxy optionally having substituent(s), $C_{7-19}$ aralkyloxy optionally having substituent(s), $C_{3-6}$ cycloalkyl-$C_{1-6}$ alkoxy optionally having substituent(s), acyl, acyl-$C_{1-6}$ alkyl and the like.

Ar is preferably a group represented by the formula: $Ar^2—Ar^1—$ wherein $Ar^3$ is a cyclic group optionally having substituent(s), $Ar^2$ is an aromatic ring group optionally having substituent(s).

Here, as the "cyclic group" of the "cyclic group optionally having substituent(s)" for $Ar^1$, the above "aromatic group", "non-aromatic cyclic hydrocarbon group" and "non-aromatic heterocyclic group" exemplified for Ar can be mentioned. The "cyclic group" is preferably phenyl, 5- or 6-membered aromatic heterocyclic group, 5- to 8-membered monocyclic non-aromatic heterocyclic group and the like, more preferably phenyl, pyridyl, piperidinyl and the like.

As the "substituent(s)" of the "cyclic group optionally having substituent(s)" for $Ar^1$, those exemplified as "substituent(s)" for the above Ar can be mentioned. The number of substituent is, for example, 1 to 4, preferably 1 to 3. When the number of substituents is 2 or more, respective substituents can be the same or different. The substituent is preferably halogen atom (preferably, fluorine, chlorine, etc.), optionally halogenated $C_{1-6}$ alkyl (preferably, methyl, trifluoromethyl, ethyl, etc.) and the like.

As the "aromatic ring group optionally having substituent(s)" for $Ar^2$, those exemplified as "substituent(s)" of the above "cyclic group optionally having substituent(s)" for Ar can be mentioned. The "aromatic ring group" is preferably phenyl, naphthyl, 5- or 6-membered aromatic heterocyclic group, 9- or 10-membered condensed polycyclic aromatic heterocyclic group and the like, more preferably, phenyl, 5- or 6-membered aromatic heterocyclic group and the like. Of these, phenyl, pyridyl and the like are preferable. The "aromatic ring group" optionally has, for example, 1 to 4, preferably 1 to 3, substituents, at substitutable position(s). As such substituent, halogen atom (preferably fluorine, chlorine, etc.), optionally halogenated $C_{1-6}$ alkyl (preferably methyl, trifluoromethyl, ethyl, etc.), optionally halogenated $C_{1-6}$ alkoxy (preferably methoxy, trifluoromethoxy, etc.), optionally halogenated $C_{1-6}$ alkylthio (preferably methylthio, etc.), $C_{1-3}$ alkylenedioxy (preferably methylenedioxy, ethylenedioxy, etc.), optionally halogenated $C_{1-6}$ alkyl-carbonyl (preferably acetyl, etc.), optionally halogenated $C_{1-6}$ alkyl-carboxamido (preferably isopropylcarboxamido, etc.) and the like are preferable.

As concrete examples of the above group represented by the formula: $Ar^2$—$Ar^1$— (wherein the symbols in the formula are as defined above), 2-,3- or 4-biphenylyl; 3-(1-naphthyl)-1,2,4-oxadiazol-5-yl; 3-(2-naphthyl)-1,2,4-oxadiazol-5-yl; 3-(2-benzofuranyl)-1,2,4-oxadiazol-5-yl; 3-phenyl-1,2,4-oxadiazol-5-yl; 3-(2-benzoxazolyl)-1,2,4-oxadiazol-5-yl; 3-(3-indolyl)-1,2,4-oxadiazol-5-yl; 3-(2-indolyl)-1,2,4-oxadiazol-5-yl; 4-phenylthiazol-2-yl; 4-(2-benzofuranyl)thiazol-2-yl; 4-phenyl-1,3-oxazol-5-yl; 5-phenylisothiazol-4-yl; 5-phenyloxazol-2-yl; 4-(2-thienyl)phenyl; 4-(3-thienyl)phenyl; 3-(3-pyridyl)phenyl; 4-(3-pyridyl)phenyl; 6-phenyl-3-pyridyl; 5-phenyl-1,3,4-oxadiazol-2-yl; 4-(2-naphthyl)phenyl; 4-(2-benzofuranyl)phenyl; 4,4'-terphenyl; 5-phenyl-2-pyridyl; 2-phenyl-5-pyrimidinyl; 4-(4-pyridyl)phenyl; 2-phenyl-1,3-oxazol-5-yl; 2,4-diphenyl-1,3-oxazol-5-yl; 3-phenyl-isoxazol-5-yl; 5-phenyl-2-furyl; 4-(2-furyl)phenyl; 4-(3-furyl)phenyl; 4-(2-benzothienyl)phenyl; 4-phenyl-1-pyrrolidinyl and the like, each of which may have 1 to 3 substituents, can be mentioned. Of these, 2-, 3- or 4-biphenylyl; 4-(2-thienyl)phenyl; 4-(3-thienyl)phenyl; 4-(2-furyl)phenyl; 4-(3-furyl)phenyl; 6-phenyl-3-pyridyl; 5-phenyl-2-pyridyl; 4-(2-naphthyl)phenyl; 4-(2-benzofuranyl)phenyl; 4-(2-benzothienyl)phenyl and the like are preferable.

Here, as the preferable examples of substituent, halogen atom (preferably fluorine, chlorine, etc.), optionally halogenated $C_{1-6}$ alkyl (preferably methyl, trifluoromethyl, ethyl, etc.), optionally halogenated $C_{1-6}$ alkoxy (preferably methoxy, trifluoromethoxy, etc.), optionally halogenated $C_{1-6}$ alkylthio (preferably methylthio, etc.), $C_{1-3}$ alkylenedioxy (preferably methylenedioxy, ethylenedioxy, etc.), optionally halogenated $C_{1-6}$ alkyl-carbonyl (preferably acetyl, etc.), optionally halogenated $C_{1-6}$ alkyl-carboxamido (preferably isopropylcarboxamido, etc.) and the like can be mentioned.

Of these substituents, halogen atom (preferably fluorine, chlorine, etc.), optionally halogenated $C_{1-6}$ alkyl (preferably methyl, trifluoromethyl, ethyl, etc.), optionally halogenated $C_{1-6}$ alkoxy (preferably methoxy, trifluoromethoxy, etc.), optionally halogenated $C_{1-6}$ alkylthio (preferably methylthio, etc.), $C_{1-3}$ alkylenedioxy (preferably methylenedioxy, ethylenedioxy, etc.), optionally halogenated $C_{1-6}$ alkyl-carbonyl (preferably acetyl, etc.) and the like are preferable.

As the preferable examples of Ar, phenyl, 5- or 6-membered aromatic heterocyclic group, or 5- to 8-membered monocyclic non-aromatic heterocyclic group (preferably phenyl, pyridyl, piperidinyl), each optionally having 1 to 3 substituents selected from halogen atom (e.g., fluorine, chlorine, bromine, iodine, etc.), $C_{1-3}$ alkylenedioxy (e.g., methylenedioxy, ethylenedioxy, etc.), nitro, cyano, optionally halogenated $C_{1-10}$ alkyl (e.g., methyl, ethyl, propyl, butyl, pentyl), optionally halogenated $C_{1-10}$ alkoxy (e.g., methoxy, ethoxy, propoxy, butoxy, isobutoxy, pentyloxy, isopentyloxy, etc.), $C_{6-14}$ aryloxy optionally having substituent(s) (preferably phenoxy), $C_{7-19}$ aralkyloxy (preferably benzyloxy) optionally having substituent(s) (preferably halogen atom, optionally halogenated $C_{1-10}$ alkyl, optionally halogenated $C_{1-10}$ alkoxy, etc.), $C_{3-6}$ cycloalkyl-$C_{1-6}$ alkyl (preferably cyclopropylmethyl), $C_{3-6}$ cycloalkyl-$C_{1-6}$ alkoxy (preferably cyclopropylmethoxy) optionally having substituent(s), acyl [preferably optionally halogenated $C_{1-6}$ alkyl-carbonyl (e.g., pentanoyl, hexanoyl, etc.), optionally halogenated $C_{1-6}$ alkylsulfonyl (e.g., butylsulfonyl, etc) and the like], acyl-$C_{1-6}$ alkyl [preferably optionally halogenated $C^{1-6}$ alkyl-carbonyl-$C_{1-6}$ alkyl (e.g., propanoylmethyl, propanoylethyl, 2-methylpropanoylmethyl, butanoylmethyl, 3-methylbutanoylmethyl, pentanoylmethyl, etc.), optionally halogenated $C_{1-6}$ alkylsulfonyl-$C_{1-6}$ alkyl (e.g., propylsulfonylmethyl, butylsulfonylmethyl, etc), $C_{6-14}$ aryl-carbonyl-$C_{1-6}$ alkyl (e.g., benzoylmethyl, etc.), $C_{3-6}$ cycloalkyl-carbonyl-$C_{1-6}$ alkyl (e.g., cyclopropylcarbonylmethyl, cyclobutylcarbonylmethyl, etc.), 5- or 6-membered heterocyclylcarbonyl-$C_{1-6}$ alkyl (e.g., tetrahydrofuroylmethyl, etc.) and the like], hydroxy, $C_{1-6}$ alkoxy-$C_{1-6}$ alkoxy (preferably methoxymethoxy, ethoxyethoxy), optionally halogenated $C_{1-10}$ alkylthio (preferably methylthio, butylthio, etc.), acylamino [preferably optionally halogenated $C_{1-6}$ alkyl-carboxamido (e.g., propylcarboxamido, isopropylcarboxamido, butylcarboxamido, etc.), $C_{6-14}$ aryl-carboxamido (preferably phenylcarboxamido, propanoylmethylphenyl-carboxamido, etc.) optionally having substituent(s) (preferably $C_{1-6}$ alkyl-carbonyl-$C_{1-6}$ alkyl), etc.], acyloxy [preferably $C_{1-6}$ alkyl-carbonyloxy (e.g., propanoyloxy, butanoyloxy, etc.)] and the like can also be mentioned.

Of the above-mentioned substituents, halogen atom (e.g., fluorine, chlorine, bromine, iodine, etc.), $C_{1-3}$ alkylenedioxy (e.g., methylenedioxy, ethylenedioxy, etc.), nitro, cyano, optionally halogenated $C_{1-10}$ alkyl, optionally halogenated $C_{1-10}$ alkoxy, $C_{6-14}$ aryloxy optionally having substituent(s), $C_{7-19}$ aralkyloxy optionally having substituent(s), $C_{3-6}$ cycloalkyl-$C_{1-6}$ alkoxy optionally having substituent(s), acyl, acyl-$C_{1-6}$ alkyl and the like are preferable.

The "spacer having a main chain of 1 to 6 atoms" for X means an interval of 1 to 6 atoms linked in the main chain. Here, "the number of atoms in the main chain" is counted so that the number of atoms in the main chain is minimum. For example, the number of atoms of 1,2-cyclopentylene is counted as 2, the number of atoms of 1,3-cyclopentylene is counted as 3.

As the "spacer having a main chain of 1 to 6 atoms", for example, a divalent group comprising 1 to 3 selected from —O—, —S—, —CO—, —SO—, —$SO_2$—, —$NR^{10}$— ($R^{10}$ is hydrogen atom, optionally halogenated $C_{1-10}$ alkyl, optionally halogenated $C_{1-6}$ alkyl-carbonyl, optionally halogenated $C_{1-6}$ alkylsulfonyl) and optionally halogenated divalent $C_{1-6}$ acyclic hydrocarbon group, and the like can be mentioned.

Here, as the "optionally halogenated $C_{1-10}$ alkyl", those exemplified for the "substituent(s)" of the above "cyclic group optionally having substituent(s)" for Ar can be used.

As the "optionally halogenated $C_{1-6}$ alkyl-carbonyl" and "optionally halogenated $C_{1-6}$ alkylsulfonyl", those exemplified for the "substituent(s)" of the above "$C_{7-19}$ aralkyl optionally having substituent(s)" can be used, respectively.

As the "divalent $C_{1-6}$ acyclic hydrocarbon group" of the "optionally halogenated divalent $C_{1-6}$ acyclic hydrocarbon group", those exemplified for Y mentioned below can be used. The "divalent $C_{1-6}$ acyclic hydrocarbon group" may have 1 to 5, preferably 1 to 3, halogen atoms (e.g., fluorine, chlorine, bromine, iodine, etc).

As preferable examples of the "spacer having a main chain of 1 to 6 atoms", (1) $C_{1-6}$ alkylene (e.g., $—CH_2—$, $—(CH_2)_2—$, $—(CH_2)_3—$, $—(CH_2)_4—$, $—(CH_2)_5—$, $—(CH_2)_6—$, $—CHCH_3—$, $—C(CH_3)_2—$, $—(CH(CH_3))_2—$, $—(CF_2)_2—$, $—(CH_2)_2C(CH_3)_2—$, $—(CH_2)_3C(CH_3)_2—$ etc);

(2) $C_{2-6}$ alkenylene (e.g., $—CH=CH—$, $—CH_2—CH=CH—$, $—C(CH_3)_2—CH=CH—$, $—CH_2—CH=CH—CH_2—$, $—CH_2—CH_2—CH=CH—$, $—CH=CH—CH=CH—$, $—CH=CH—CH_2—CH_2—CH_2—$ etc);

(3) $C_{2-6}$ alkynylene (e.g., $—C≡C—$, $—CH_2—C≡C—$, $—CH_2—C≡C—CH_2—CH_2—$ etc);

(4) $—(CH_2)_{w1}O(CH_2)_{w2}—$, $—(CH_2)_{w1}S(CH_2)_{w2}—$, $—(CH_2)_{w1}CO_2(CH_2)_{w2}—$, $—(CH_2)_{w1}SO(CH_2)_{w2}—$, $—(CH_2)_{w1}SO_2(CH_2)_{w2}—$, $—(CH_2)_{w1}NR^{10}(CH_2)_{w2}—$;

($R^{10}$ is as defined above; w1 and w2 are each an integer of 0 to 5 and w1+w2 is 0 to 5) and the like can be mentioned.

The "spacer having a main chain of 1 to 6 atoms" for X is preferably $C_{1-6}$ alkylene (e.g., $—CH_2—$, $—(CH_2)_2—$, $—(CH_2)_3—$, $—(CH_2)_4—$ etc), $—(CH_2)_{w1}CO(CH_2)_{w2}—$ and the like.

X is preferably a bond.

As the "divalent hydrocarbon group" of the "divalent hydrocarbon group optionally having substituent(s) (except CO)" for Y, for example, divalent $C_{1-6}$ acyclic hydrocarbon group, divalent $C_{5-8}$ monocyclic non-aromatic hydrocarbon group, phenylene group and the like can be mentioned.

As the "divalent $C_{1-6}$ acyclic hydrocarbon group", for example, (1) $C_{1-6}$ alkylene (e.g., $—CH_2—$, $—(CH_2)_2—$, $—(CH_2)_3—$, $—(CH_2)_4—$, $—(CH_2)_5—$, $—(CH_2)_6—$, $—CH(CH_3)—$, $—CH(C_2H_5)—$, $—C(CH_3)$ 2—, $—(CH(CH_3))_2—$, $—(CH_2)_2$ $C(CH_3)_2—$, $—(CH_2)_3C(CH_3)_2—$ etc);

(2) $C_{2-6}$ alkenylene (e.g., $—CH=CH—$, $—CH_2—CH=CH—$, $—C(CH_3)_2—CH=CH—$, $—CH_2—CH=CH—CH_2—$, $—CH_2—CH_2—CH=CH—$, $—CH=CH—CH=CH—$, $—CH=CH—CH_2—CH_2—CH_2—$ etc);

(3) $C_{2-6}$ alkynylene (e.g., $—C≡C—$, $—CH_2—C≡C—$, $—CH_2—C≡C—CH_2—CH_2—$ etc) and the like can be mentioned.

As the "divalent $C_{5-8}$ monocyclic non-aromatic hydrocarbon group", for example, a divalent group produced by removing any two hydrogen atoms from $C_{5-8}$ cycloalkane or $C_{5-8}$ cycloalkene can be mentioned. As concrete examples, for example, 1,2-cyclopentylene; 1,3-cyclopentylene; 1,2-cyclohexylene; 1,3-cyclohexylene; 1,4-cyclohexylene; 1,2-cycloheptylene; 1,3-cycloheptylene; 1,4-cycloheptylene; 3-cyclohexen-1,4-ylene; 3-cyclohexen-1,2-ylene; 2,5-cyclohexadien-1,4-ylene and the like can be mentioned. Of these, $C_{5-8}$ cycloalkylene is preferable.

As the "divalent hydrocarbon group", $C_{1-6}$ alkylene, $C_{2-6}$ alkenylene and the like, each substituted with phenyl, can also be mentioned.

As the "substituent(s)" of the "divalent hydrocarbon group optionally having substituent(s) (except CO)" for Y, for example, halogen atom (e.g., fluorine, chlorine, bromine, iodine and the like), $C_{1-3}$ alkylenedioxy (e.g., methylenedioxy, ethylenedioxy and the like), nitro, cyano, optionally halogenated $C_{1-10}$ alkoxy, optionally halogenated $C_{1-10}$ alkylthio, hydroxy, amino, mono- or di-$C_{1-10}$ alkylamino, formyl, carboxy, carbamoyl, thiocarbamoyl, optionally halogenated $C_{1-6}$ alkyl-carbonyl, $C_{1-6}$ alkoxy-carbonyl, mono- or di-$C_{1-6}$ alkyl-carbamoyl, optionally halogenated $C_{1-6}$ alkylsulfonyl, formylamino, optionally halogenated $C_{1-6}$ alkyl-carboxamido, $C_{1-6}$ alkoxy-carboxamido, $C_{1-6}$ alkylsulfonylamino, $C_{1-6}$ alkyl-carbonyloxy, $C_{3-6}$ alkoxy-carbonyloxy, mono- or di-$C_{1-6}$ alkyl-carbamoyloxy and the like can be mentioned. As such substituents, those similar to the "substituent(s)" of the above "$C_{7-19}$ aralkyl optionally having substituent(s)" can be used.

The number of substituents is, for example, 1 to 5, preferably 1 to 3. When the number of substituents is 2 or more, respective substituents can be the same or different.

Y is preferably $C_{1-6}$ alkylene, more preferably $C_{1-3}$ alkylene. Of these, $—CH_2—$, $—CH(CH_3)—$ and $—CH(C_2H_5)—$ are preferable.

As the "hydrocarbon group optionally having substituent(s)" for $R^3$, those exemplified for the above $R^4$ can be used.

The "hydrocarbon group optionally having substituent(s)" is preferably "$C_{1-6}$ alkyl optionally having substituent(s)".

Here, as the "$C_{1-6}$ alkyl" of "$C_{1-6}$ alkyl optionally having substituent(s)", for example, methyl, ethyl, propyl, isopropyl, butyl, isobutyl, sec-butyl, tert-butyl, pentyl, hexyl and the like can be mentioned. Of these, methyl, ethyl, propyl, isopropyl and the like are preferable.

In addition, as the "substituent(s)" of the "$C_{1-6}$ alkyl optionally having substituent(s)", for example, halogen atom (e.g., fluorine, chlorine, bromine, iodine, etc.), $C_{1-3}$ alkylenedioxy (e.g., methylenedioxy, ethylenedioxy, etc.), nitro, cyano, optionally halogenated $C_{3-6}$ cycloalkyl, optionally halogenated $C_{1-10}$ alkoxy, optionally halogenated $C_{1-10}$ alkylthio, hydroxy, amino, mono- or di-$C_{1-10}$ alkylamino (e.g., methylamino, ethylamino, propylamino, isopropylamino, butylamino, dimethylamino, diethylamino, dipropylamino, dibutylamino, ethylmethylamino, etc.), formyl, carboxy, carbamoyl, thiocarbamoyl, optionally halogenated $C_{1-6}$ alkyl-carbonyl, $C_{1-6}$ alkoxy-carbonyl (e.g., methoxycarbonyl, ethoxycarbonyl, propoxycarbonyl, tert-butoxycarbonyl, etc.), mono- or di-$C_{1-6}$ alkyl-carbamoyl (e.g., methylcarbamoyl, ethylcarbamoyl, dimethylcarbamoyl, diethylcarbamoyl, ethylmethylcarbamoyl, etc.), optionally halogenated $C_{1-6}$ alkylsulfonyl, formylamino, optionally halogenated $C_{1-6}$ alkyl-carboxamide, $C_{1-6}$ alkoxy-carboxamide (e.g., methoxycarboxamide, ethoxycarboxamide, propoxycarboxamide, butoxycarboxamide, etc.), $C_{1-6}$ alkylsulfonylamino (e.g., methylsulfonylamino, ethylsulfonylamino, etc.), $C_{1-6}$ alkyl-carbonyloxy (e.g., acetoxy, propanoyloxy, etc.), $C_{1-6}$ alkoxy-carbonyloxy (e.g., methoxycarbonyloxy, ethoxycarbonyloxy, propoxycarbonyloxy, butoxycarbonyloxy, etc.), mono- or di-$C_{1-6}$ alkyl-carbamoyloxy (e.g., methylcarbamoyloxy, ethylcarbamoyloxy, dimethylcarbamoyloxy, diethylcarbamoyloxy, etc.), aromatic ring group optionally having substituent(s) and the like can be mentioned. The number of substituents is, for example, 1 to 5, preferably 1 to 3. When the number of substituents is 2 or more, respective substituents can be the same or different.

Here, as the "optionally halogenated $C_{1-10}$ alkoxy" and "optionally halogenated $C_{1-10}$ alkylthio", those exemplified for the "substituent(s)" of the above "cyclic group optionally having substituent(s)" for Ar can be used.

As the "optionally halogenated $C_{3-6}$ cycloalkyl", "optionally halogenated $C_{1-6}$ alkyl-carbonyl", "optionally halogenated $C_{1-6}$ alkylsulfonyl" and "optionally halogenated $C_{1-6}$ alkyl-carboxamido", those exemplified for the "substituent(s)" of the above "$C_{7-19}$ aralkyl optionally having substituent(s)" can be used.

As the "aromatic ring group optionally having substituent(s)", those exemplified for the substituent of the above "cyclic group optionally having substituent(s)" for Ar can be used.

The "hydrocarbon group optionally having substituent(s)" for $R^3$ is more preferably $C_{1-6}$ alkyl. Of these, methyl, ethyl, isopropyl and the like are preferable.

$R^3$ is preferably hydrogen atom.

Ring A and ring B each may further have substituent(s) besides a group represented by the formula:

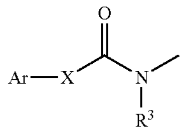

wherein the symbols in the formula are as defined above, and a group represented by the formula:

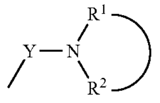

wherein the symbols in the formula are as defined above, respectively. As such "substituent(s)", those similar to the "substituent(s)" of the above "$C_{7-19}$ aralkyl optionally having substituent(s)" can be used.

The number of substituents is, for example, 1 to 3, preferably 1 to 2. When the number of substituents is 2 or more, respective substituents can be the same or different.

The substituent is preferably halogen atom (preferably fluorine, chlorine, bromine, etc.), optionally halogenated $C_{1-10}$ alkyl (preferably methyl, ethyl, propyl, trifluoromethyl, etc.), optionally halogenated $C_{1-10}$ alkoxy (preferably methoxy, ethoxy, etc.), optionally halogenated $C_{1-10}$ alkylthio (preferably methylthio, etc.), hydroxy, amino, mono- or di-$C_{1-10}$ alkylamino (preferably methylamino, dimethylamino, etc.), formyl, carboxy, $C_{1-6}$ alkoxy-carbonyl (preferably methoxycarbonyl, ethoxycarbonyl, etc.), optionally halogenated $C_{1-6}$ alkyl-carboxamido (preferably methylcarboxamido, trifluoromethylcarboxamido, etc.), 5- or 6-membered non-aromatic heterocyclic group (preferably pyrrolidinyl, etc.) and the like, more preferably halogen atom (preferably fluorine, chlorine, bromine, etc.), optionally halogenated $C_{1-6}$ alkyl (preferably methyl, ethyl, propyl, trifluoromethyl, etc.), optionally halogenated $C_{1-6}$ alkoxy (preferably methoxy, ethoxy, etc.) and the like.

As the substitution position of the above-mentioned substituent, the 6-position or 8-position of the quinoline ring represented by the formula:

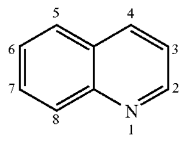

is preferable.

When ring B further has a substituent, the substituent may be linked to $R^1$ to form a ring. As such ring, for example, 5- to 7-membered nitrogen-containing heterocycle containing at least one nitrogen atom and optionally containing 1 to 3 heteroatoms selected from nitrogen atom, sulfur atom and oxygen atom in addition to carbon atoms, and the like can be mentioned. The ring formed by the bond of substituent on ring B and $R^1$ is preferably piperidine, morpholine, thiomorpholine, piperazine, pyrrolidine and the like.

As the "hydrocarbon group optionally having substituent(s)" for $R^1$ and $R^2$, those exemplified for the above $R^4$ can be used. The "hydrocarbon group optionally having substituent(s)" is preferably "$C_{1-6}$ alkyl optionally having substituent(s)" or "$C_{7-19}$ aralkyl optionally having substituent(s)". Here, as the "$C_{1-6}$ alkyl optionally having substituent(s)", those exemplified for the above $R^3$ can be used, and as the "$C_{7-19}$ aralkyl optionally having substituent(s)", those exemplified for the substituent of the above "cyclic group optionally having substituent(s)" for Ar can be used.

The "hydrocarbon group optionally having substituent(s)" for $R^1$ and $R^2$ is more preferably $C_{1-6}$ alkyl; or $C_{7-19}$ aralkyl (preferably benzyl, phenethyl, etc.) optionally having 1 to 3 substituents selected from halogen atom (preferably fluorine, chlorine, etc.), optionally halogenated $C_{1-6}$ alkyl (preferably methyl, etc.) and optionally halogenated $C_{1-6}$ alkoxy (preferably methoxy, etc.), and the like. Of these, $C_{1-6}$ alkyl (preferably methyl, ethyl, propyl, isopropyl) is preferable.

As the "nitrogen-containing heterocycle" of the "nitrogen-containing heterocycle optionally having substituent(s)" formed by $R^1$ and $R^2$ together with the adjacent nitrogen atom, for example, 3 to 10-membered (preferably 3 to 8-membered) nitrogen-containing heterocycle containing, besides carbon atom, at least one nitrogen atom and optionally 1 to 3 heteroatoms selected from nitrogen atom, sulfur atom and oxygen atom, which may be condensed with a benzene ring, can be mentioned. Concrete examples include aziridine, azetidine, morpholine, thiomorpholine, piperidine, piperazine, pyrrolidine, hexamethyleneimine (azepane), heptamethyleneimine, hexahydropyrimidine, 1,4-diazepane, thiazolidine, imidazolidine, heptahydroindole, decahydroquinoline, decahydroisoquinoline and an unsaturated cyclic amine thereof (e.g., 1,2,5,6-tetrahydropyridine, 1H-imidazole, 4,5-dihydro-1H-imidazole, 2,3-dihydroindole, 1,2,3,4-tetrahydroquinoline, 1,2,3,4-tetrahydroisoquinoline, etc.) and the like. Of these, azetidine, morpholine, piperidine, piperazine, pyrrolidine, hexamethyleneimine (azepane), 1,3-thiazolidine, 1H-imidazole, 4,5-dihydro-1H-imidazole, 2,3-dihydroindole, 1,2,3,4-tetrahydroquinoline, 1,2,3,4-tetrahydroisoquinoline and the like are preferable, and particularly, piperidine, piperazine, pyrrolidine, hexamethyleneimine (azepane), morpholine, thiomorpholine and the like are preferable.

As the "substituent(s)" of the "nitrogen-containing heterocycle optionally having substituent(s)", for example, in addition to those exemplified for the "substituent(s)" of the above "$C_{7-19}$ aralkyl optionally having substituent(s)", the "$C_{7-19}$ aralkyl optionally having substituent(s)" and the "aromatic ring group optionally having substituent(s)", exemplified for the "substituent(s)" of the "cyclic group optionally having substituent(s) for Ar can be used. The number of substituents is, for example, 1 to 5, preferably 1 to 3. When the number of substituents is 2 or more, respective substituents can be the same or different.

The substituent is preferably optionally halogenated $C_{1-10}$ alkyl (preferably methyl, ethyl, propyl, butyl, isobutyl, etc.); optionally halogenated $C_{3-6}$ cycloalkyl (preferably cyclohexyl, etc.); carbamoyl; mono- or di-$C_{1-6}$ alkyl-carbamoyl (preferably methylcarbamoyl, ethylcarbamoyl, dimethylcarbamoyl, diethylcarbamoyl, etc.); 5- or 6-membered heterocyclylcarbonyl (preferably morpholinocarbonyl, piperidinocarbonyl, 1-pyrrolidinylcarbonyl, etc.); optionally halogenated $C_{1-6}$ alkyl-carboxamido (preferably acetamido, etc.); hydroxy-$C_{1-6}$ alkyl (preferably hydroxymethyl, hydroxyethyl, etc.); carbamoyl-$C_{1-6}$ alkyl (preferably carbamoylmethyl, carbamoylethyl, carbamoylpropyl, etc.); mono- or di-$C_{1-6}$ alkyl-carbamoyl-$C_{1-6}$ alkyl (preferably methylcarbamoylmethyl, methylcarbamoylethyl, methylcarbamoylpropyl, dimethylcarbamoylmethyl, dimethylcarbamoylethyl, dimethylcarbamoylpropyl, ethylcarbamoylmethyl, ethylcarbamoylethyl, ethylcarbamoylpropyl, diethylcarbamoylmethyl, diethylcarbamoylethyl, diethylcarbamoylpropyl, etc.); 5- or 6-membered heterocyclylcarbonyl-$C_{1-6}$ alkyl (preferably morpholinocarbonylmethyl, morpholinocarbonylethyl, morpholinocarbonylpropyl, piperidinocarbonylmethyl, piperidinocarbonylethyl, piperidinocarbonylpropyl, 1-pyrrolidinylcarbonylmethyl, 1-pyrrolidinylcarbonylethyl, 1-pyrrolidinylcarbonylpropyl, etc.); mono- or di-$C_{1-6}$ alkyl-carbamoyl-$C_{1-6}$ alkoxy (preferably ethylcarbamoylmethoxy, etc.); $C_{7-19}$ aralkyl optionally having substituent(s) (preferably benzyl, etc.); aromatic ring group optionally having substituent(s) (preferably phenyl, etc.) and the like.

As the substituent of the "$C_{7-19}$ aralkyl optionally having substituent(s)" and "aromatic ring group optionally having substituent(s)", halogen atom (preferably fluorine, chlorine, etc.), optionally halogenated $C_{1-6}$ alkyl (preferably methyl, etc.) and optionally halogenated $C_{1-6}$ alkoxy (preferably methoxy, etc.) and the like are preferable. The number of substituents is, for example, 1 to 3, preferably 1 or 2. When the number of substituents is 2 or more, respective substituents can be the same or different.

The above "5- or 6-membered heterocyclylcarbonyl" and 15- or 6-membered heterocyclylcarbonyl-$C_{1-6}$ alkyl" may have 1 to 3 substituents selected from halogen atom (preferably fluorine, chlorine, etc.), optionally halogenated $C_{1-6}$ alkyl (preferably methyl, etc.), optionally halogenated $C_{1-6}$ alkoxy (preferably methoxy, etc.) and the like.

The "nitrogen-containing heterocycle optionally having substituent(s)", formed by $R^1$ and $R^2$ together with the adjacent nitrogen atom, is preferably 3 to 8-membered nitrogen-containing heterocycle (preferably piperidine, piperazine, pyrrolidine, hexamethyleneimine (azepane), morpholine or thiomorpholine) optionally having 1 to 3 substituents selected from optionally halogenated $C_{1-10}$ alkyl (preferably methyl, ethyl, propyl, butyl, isobutyl, etc.); optionally halogenated $C_{3-6}$ cycloalkyl (preferably cyclohexyl, etc.); carbamoyl; mono- or di-$C_{1-6}$ alkyl-carbamoyl (preferably methylcarbamoyl, ethylcarbamoyl, dimethylcarbamoyl, diethylcarbamoyl, etc.); 5- or 6-membered heterocyclylcarbonyl (e.g., morpholinocarbonyl, piperidinocarbonyl, 1-pyrrolidinylcarbonyl, etc.); optionally halogenated $C_{1-6}$ alkyl-carboxamido (preferably acetamido, etc.); hydroxy-$C_{1-6}$ alkyl (preferably hydroxymethyl, hydroxyethyl, etc.); carbamoyl-$C_{1-6}$ alkyl (preferably carbamoylmethyl, carbamoylethyl, carbamoylpropyl, etc.); mono- or di-$C_{1-6}$ alkyl-carbamoyl-$C_{1-6}$ alkyl (preferably methylcarbamoylmethyl, methylcarbamoylethyl, methylcarbamoylpropyl, dimethylcarbamoylmethyl, dimethylcarbamoylethyl, dimethylcarbamoylpropyl, ethylcarbamoylmethyl, ethylcarbamoylethyl, ethylcarbamoylpropyl, diethylcarbamoylmethyl, diethylcarbamoylethyl, diethylcarbamoylpropyl, etc.); 5- or 6-membered heterocyclylcarbonyl-$C_{1-6}$ alkyl (preferably morpholinocarbonylmethyl, morpholinocarbonylethyl, morpholinocarbonylpropyl, piperidinocarbonylmethyl, piperidinocarbonylethyl, piperidinocarbonylpropyl, 1-pyrrolidinylcarbonylmethyl, 1-pyrrolidinylcarbonylethyl, 1-pyrrolidinylcarbonylpropyl, etc.); mono- or di-$C_{1-6}$ alkyl-carbamoyl-$C_{1-6}$ alkoxy (preferably ethylcarbamoylmethoxy, etc.); $C_{7-19}$ aralkyl (preferably benzyl, etc.) optionally having 1 to 3 substituents selected from halogen atom (preferably, fluorine, chlorine, etc.), optionally halogenated $C_{1-6}$ alkyl (preferably methyl, etc.) and optionally halogenated $C_{1-6}$ alkoxy (preferably methoxy, etc.); aromatic ring group (preferably phenyl) optionally having 1 to 3 substituents selected from halogen atom (preferably fluorine, chlorine, etc.), optionally halogenated $C_{1-6}$ alkyl (preferably methyl, etc.) and optionally halogenated $C_{1-6}$ alkoxy (preferably methoxy, etc.).

$R^1$ and $R^2$ preferably form, together with the adjacent nitrogen atom, 3- to 8-membered nitrogen-containing heterocycle (preferably piperidine, piperazine, pyrrolidine, hexamethyleneimine (azepane), morpholine, thiomorpholine) each optionally having 1 to 3 substituents selected from optionally halogenated $C_{1-10}$ alkyl (preferably methyl, ethyl, propyl, butyl, isobutyl, etc.); optionally halogenated $C_{3-6}$ cycloalkyl (preferably, cyclohexyl, etc.); carbamoyl; mono- or di-$C_{1-6}$ alkyl-carbamoyl (preferably methylcarbamoyl, ethylcarbamoyl, dimethylcarbamoyl, diethylcarbamoyl, etc.); 5- or 6-membered heterocyclylcarbonyl (e.g., morpholinocarbonyl, piperidinocarbonyl, 1-pyrrolidinylcarbonyl, etc.); optionally halogenated $C_{1-6}$ alkyl-carboxamido (preferably acetamido, etc.); hydroxy-$C_{1-6}$ alkyl (preferably hydroxymethyl, hydroxyethyl, etc.); carbamoyl-$C_{1-6}$ alkyl (preferably carbamoylmethyl, carbamoylethyl, carbamoylpropyl, etc.); mono- or di-$C_{1-6}$ alkyl-carbamoyl-$C_{1-6}$ alkyl (preferably methylcarbamoylmethyl, methylcarbamoylethyl, methylcarbamoylpropyl, dimethylcarbamoylmethyl, dimethylcarbamoylethyl, dimethylcarbamoylpropyl, ethylcarbamoylmethyl, ethylcarbamoylethyl, ethylcarbamoylpropyl, diethylcarbamoylmethyl, diethylcarbamoylethyl, diethylcarbamoylpropyl, etc.); 5- or 6-membered heterocyclylcarbonyl-$C_{1-6}$ alkyl (preferably morpholinocarbonylmethyl, morpholinocarbonylethyl, morpholinocarbonylpropyl, piperidinocarbonylmethyl, piperidinocarbonylethyl, piperidinocarbonylpropyl, 1-pyrrolidinylcarbonylmethyl, 1-pyrrolidinylcarbonylethyl, 1-pyrrolidinylcarbonylpropyl, etc.); mono- or di-$C_{1-6}$ alkyl-carbamoyl-$C_{1-6}$ alkoxy (preferably ethylcarbamoylmethoxy, etc.); $C_{7-19}$ aralkyl (preferably benzyl, etc.) optionally having 1 to 3 substituents selected from halogen atom (preferably fluorine, chlorine, etc.), optionally halogenated $C_{1-6}$ alkyl (preferably methyl, etc.) and optionally halogenated $C_{1-6}$ alkoxy (preferably methoxy, etc.); aromatic ring group (preferably phenyl) optionally having 1 to 3 substituents selected from halogen atom (preferably fluorine, chlorine, etc.), optionally halogenated $C_{1-6}$ alkyl (preferably methyl, etc.) and optionally halogenated $C_{1-6}$ alkoxy (preferably methoxy, etc.).

As preferable examples of the compound (I), the following compounds can be mentioned.

1) A compound wherein Ar is a group represented by the formula: $Ar^2$-$Ar^1$—

$Ar^1$ is phenyl, 5- or 6-membered aromatic heterocyclic group or 5- to 8-membered monocyclic non-aromatic heterocyclic group (preferably phenyl, pyridyl, piperidinyl) and $Ar^2$ is phenyl or 5- or 6-membered aromatic heterocyclic group (preferably phenyl, pyridyl, etc.), each optionally having 1 to 3 substituents selected from halogen atom (preferably fluorine, chlorine, etc.), optionally halogenated $C_{1-6}$ alkyl (preferably methyl, trifluoromethyl, ethyl, etc.), optionally halogenated $C_{1-6}$ alkoxy (preferably methoxy, trifluoromethoxy, etc.), optionally halogenated $C_{1-6}$ alkylthio (preferably methylthio, etc.), $C_{1-3}$ alkylenedioxy (preferably methylenedioxy, ethylenedioxy, etc.) and optionally halogenated $C_{1-6}$ alkyl-carbonyl (preferably acetyl, etc.) [$Ar^2$ is preferably phenyl or 5- or 6-membered aromatic heterocyclic group (preferably phenyl, pyridyl, etc.), each optionally having 1 to 3 substituents selected from halogen atom (preferably fluorine, chlorine, etc.), optionally halogenated $C_{1-6}$ alkyl (preferably methyl, etc.) and optionally halogenated $C_{1-6}$ alkoxy (preferably methoxy, etc.)];

X is a bond;

$R^1$ and $R^2$ are the same or different and each is hydrogen atom; $C_{1-6}$ alkyl (preferably methyl, ethyl, propyl, isopropyl); or $C_{7-19}$ aralkyl (preferably benzyl, etc.) optionally having 1 to 3 substituents selected from halogen atom (preferably fluorine, chlorine, etc.), optionally halogenated $C_{1-6}$ alkyl (preferably methyl, etc.) and optionally halogenated $C_{1-6}$ alkoxy (preferably methoxy, etc.);

Y is $C_{1-6}$ alkylene (preferably $—CH_2—$, $—CH(CH_3)—$, $—CH(C_2H_5)—$);

$R^3$ is hydrogen atom; and ring A and ring B may further have 1 to 3 substituents selected from halogen atom (preferably fluorine, chlorine, bromine, etc.), optionally halogenated $C_{1-6}$ alkyl (preferably methyl, ethyl, propyl, trifluoromethyl, etc.) and optionally halogenated $C_{1-6}$ alkoxy (preferably methoxy, ethoxy, etc.).

2) A compound wherein Ar is a group represented by the formula: $Ar^2—Ar^1—$, $Ar^1$ is phenyl, 5- or 6-membered aromatic heterocyclic group or 5- to 8-membered monocyclic non-aromatic heterocyclic group (preferably phenyl, pyridyl, piperidinyl) and $Ar^2$ is phenyl or 5- or 6-membered aromatic heterocyclic group (preferably phenyl, pyridyl, etc.), each optionally having 1 to 3 substituents selected from halogen atom (preferably fluorine, chlorine, etc.) optionally halogenated $C_{1-6}$ alkyl (preferably methyl, trifluoromethyl, ethyl, etc.), optionally halogenated $C_{1-6}$ alkoxy (preferably methoxy, trifluoromethoxy, etc.), optionally halogenated $C_{1-6}$ alkylthio (preferably methylthio, etc.), $C_{1-3}$ alkylenedioxy (preferably methylenedioxy, ethylenedioxy, etc.) and optionally halogenated $C_{1-6}$ alkyl-carbonyl (preferably acetyl, etc.) [$Ar^2$ is preferably phenyl or 5- or 6-membered aromatic heterocyclic group (preferably phenyl, pyridyl, etc.), each optionally having 1 to 3 substituents selected from halogen atom (preferably fluorine, chlorine, etc.), optionally halogenated $C_{1-6}$ alkyl (preferably methyl, etc.) and optionally halogenated $C_{1-6}$ alkoxy (preferably methoxy, etc.)];

X is a bond;

$R^1$ and $R^2$ form, together with the adjacent nitrogen atom, 3- to 8-membered nitrogen-containing heterocycle (preferably piperidine, piperazine, pyrrolidine, hexamethyleneimine, morpholine, thiomorpholine) optionally having 1 to 3 substituents selected from optionally halogenated $C_{1-10}$ alkyl (preferably methyl, ethyl, propyl, butyl, isobutyl, etc.); optionally halogenated $C_{3-6}$ cycloalkyl (preferably cyclohexyl, etc.); carbamoyl; mono- or di-$C_{1-6}$ alkyl-carbamoyl (preferably methylcarbamoyl, ethylcarbamoyl, dimethylcarbamoyl, diethylcarbamoyl, etc.); 5- or 6-membered heterocyclylcarbonyl (e.g., morpholinocarbonyl, piperidinocarbonyl, 1-pyrrolidinylcarbonyl, etc.); optionally halogenated $C_{1-6}$ alkyl-carboxamido (preferably, acetamido, etc.); hydroxy-$C_{1-6}$ alkyl (preferably hydroxymethyl, hydroxyethyl, etc.); carbamoyl-$C_{1-6}$ alkyl (preferably carbamoylmethyl, carbamoylethyl, carbamoylpropyl, etc.); mono- or di-$C_{1-6}$ alkyl-carbamoyl-$C_{1-6}$ alkyl (preferably methylcarbamoylmethyl, methylcarbamoylethyl, methylcarbamoylpropyl, dimethylcarbamoylmethyl, dimethylcarbamoylethyl, dimethylcarbamoylpropyl, ethylcarbamoylmethyl, ethylcarbamoylethyl, ethylcarbamoylpropyl, diethylcarbamoylmethyl, diethylcarbamoylethyl, diethylcarbamoylpropyl, etc.); 5- or 6-membered heterocyclylcarbonyl-$C_{1-6}$ alkyl (preferably morpholinocarbonylmethyl, morpholinocarbonylethyl, morpholinocarbonylpropyl, piperidinocarbonylmethyl, piperidinocarbonylethyl, piperidinocarbonylpropyl, 1-pyrrolidinylcarbonylmethyl, 1-pyrrolidinylcarbonylethyl, 1-pyrrolidinylcarbonylpropyl, etc.); mono- or di-$C_{1-6}$ alkyl-carbamoyl-$C_{1-6}$ alkoxy (preferably ethylcarbamoylmethoxy, etc.); $C_{7-19}$ aralkyl (preferably benzyl, etc.) optionally having 1 to 3 substituents selected from halogen atom (preferably fluorine, chlorine, etc.), optionally halogenated $C_{1-6}$ alkyl (preferably methyl, etc.) and optionally halogenated $C_{1-6}$ alkoxy (preferably methoxy, etc.); and aromatic ring group (preferably phenyl) optionally having 1 to 3 substituents selected from halogen atom (preferably fluorine, chlorine, etc.), optionally halogenated $C_{1-6}$ alkyl (preferably methyl, etc.) and optionally halogenated $C_{1-6}$ alkoxy (preferably methoxy, etc.);

Y is $C_{1-6}$ alkylene (preferably $—CH_2—$, $—CH(CH_3)—$, $—CH(C_2H_5)—$);

$R^3$ is hydrogen atom; and ring A and ring B may further have 1 to 3 substituents selected from halogen atom (preferably fluorine, chlorine, bromine, etc.), optionally halogenated $C_{1-6}$ alkyl (preferably methyl, ethyl, propyl, trifluoromethyl, etc.) and optionally halogenated $C_{1-6}$ alkoxy (preferably methoxy, ethoxy, etc.).

3) A compound wherein Ar is phenyl or 5- or 6-membered aromatic heterocyclic group or 5- to 8-membered monocyclic non-aromatic heterocyclic group (preferably phenyl, pyridyl, piperidinyl), each optionally having 1 to 3 substituents selected from halogen atom (e.g., fluorine, chlorine, bromine, iodine, etc.), $C_{1-3}$ alkylenedioxy (e.g., methylenedioxy, ethylenedioxy, etc.), nitro, cyano, optionally halogenated $C_{1-10}$ alkyl, optionally halogenated $C_{1-10}$ alkoxy, $C_{6-14}$ aryloxy optionally having substituent(s), $C_{7-19}$ aralkyloxy optionally having substituent(s), $C_{3-6}$ cycloalkyl-$C_{1-6}$ alkoxy optionally having substituent(s), acyl, acyl-$C_{1-6}$ alkyl and the like;

X is a bond;

$R^1$ and $R^2$ form, together with the adjacent nitrogen atom, 3- to 8-membered nitrogen-containing heterocycle (preferably piperidine, piperazine, pyrrolidine, hexamethyleneimine, morpholine, thiomorpholine) optionally having 1 to 3 substituents selected from optionally halogenated $C_{1-10}$ alkyl (preferably methyl, ethyl, propyl, butyl, isobutyl, etc.); optionally halogenated $C_{3-6}$ cycloalkyl (preferably cyclohexyl, etc.); carbamoyl; mono- or di-$C_{1-6}$ alkyl-carbamoyl (preferably methylcarbamoyl, ethylcarbamoyl, dimethylcarbamoyl, diethylcarbamoyl, etc.); 5- or 6-membered heterocyclylcarbonyl (e.g., morpholinocarbonyl, piperidinocarbonyl, 1-pyrrolidinylcarbonyl, etc.); optionally halogenated $C_{1-6}$ alkyl-carboxamido (preferably acetamido, etc.); hydroxy-$C_{1-6}$ alkyl (preferably hydroxymethyl, hydroxyethyl, etc.); carbamoyl-$C_{1-6}$ alkyl (preferably carbamoylmethyl, carbamoylethyl, carbamoylpropyl, etc.); mono- or di-$C_{1-6}$ alkyl-carbamoyl-$C_{1-6}$ alkyl (preferably methylcarbamoylmethyl, methylcarbamoylethyl, methylcarbamoylpropyl, dimethylcarbamoylmethyl, dimethylcarbamoylethyl, dimethylcarbamoylpropyl, ethylcarbamoylmethyl, ethylcarbamoylethyl, ethylcarbamoylpropyl, diethylcarbamoylmethyl, diethylcarbamoylethyl, diethylcarbamoylpropyl, etc.); 5- or 6-membered heterocyclylcarbonyl-$C_{1-6}$ alkyl (preferably morpholinocarbonylmethyl, morpholinocarbonylethyl, morpholinocarbonylpropyl, piperidinocarbonylmethyl, piperidinocarbonylethyl, piperidinocarbonylpropyl, 1-pyrrolidinylcarbonylmethyl, 1-pyrrolidinylcarbonylethyl, 1-pyrrolidinylcarbonylpropyl, etc.); mono- or di-$C_{1-6}$ alkyl-carbamoyl-$C_{1-6}$ alkoxy (preferably ethylcarbamoylmethoxy, etc.); $C_{7-19}$ aralkyl (preferably benzyl, etc.) optionally having 1 to 3 substituents selected from halogen atom (preferably fluorine, chlorine, etc.), optionally halogenated $C_{1-6}$ alkyl (preferably methyl, etc.) and optionally halogenated $C_{1-6}$ alkoxy (preferably methoxy, etc.); aromatic ring group (preferably phenyl) optionally having 1 to 3 substituents selected from halogen atom (preferably fluorine, chlorine, etc.), optionally halogenated $C_{1-6}$ alkyl (preferably methyl, etc.) and optionally halogenated $C_{1-6}$ alkoxy (preferably methoxy, etc.);

Y is $C_{1-6}$ alkylene (preferably $—CH_2—$, $—CH(CH_3)—$, $—CH(C_2H_5)—$);

$R^3$ is hydrogen atom; and ring A and ring B may further have 1 to 3 substituents selected from halogen atom (preferably fluorine, chlorine, bromine, etc.), optionally halogenated $C_{1-6}$ alkyl (preferably methyl, ethyl, propyl, trifluoromethyl, etc.) and optionally halogenated $C_{1-6}$ alkoxy (preferably methoxy, ethoxy, etc.).

2A) A compound wherein Ar is a group represented by the formula: $Ar^2—Ar^1—$, $Ar^1$ is phenyl, 5- or 6-membered aromatic heterocyclic group (preferably pyridyl) or 5- to 8-membered monocyclic non-aromatic heterocyclic group (preferably piperidinyl), each optionally having 1 to 3 substituents selected from halogen atom (preferably fluorine, chlorine, etc.) and optionally halogenated $C_{1-6}$ alkyl (preferably methyl, trifluoromethyl, ethyl, etc.), and $Ar^2$ is phenyl, naphthyl, 5- or 6-membered aromatic heterocyclic group (preferably thienyl, furyl, pyridyl) or 9- or 10-membered condensed polycyclic aromatic heterocyclic group (preferably benzothienyl, benzofuranyl), each optionally having 1 to 3 substituents selected from halogen atom (preferably fluorine, chlorine, etc.), optionally halogenated $C_{1-6}$ alkyl (preferably methyl, trifluoromethyl, ethyl, etc.), optionally halogenated $C_{1-6}$ alkoxy (preferably methoxy, trifluoromethoxy, etc.), optionally halogenated $C_{1-6}$ alkylthio (preferably methylthio, etc.), $C_{1-3}$ alkylenedioxy (preferably methylenedioxy, ethylenedioxy, etc.), optionally halogenated $C_{1-6}$ alkyl-carbonyl (preferably acetyl, etc.) and optionally halogenated $C_{1-6}$ alkyl-carboxamido (preferably isopropylcarboxamido, etc.);

X is a bond;

$R^1$ and $R^2$ form, together with the adjacent nitrogen atom, 3- to 8-membered nitrogen-containing heterocycle (preferably piperidine, piperazine, pyrrolidine, hexamethyleneimine (azepane), morpholine, thiomorpholine) optionally having 1 to 3 substituents selected from optionally halogenated $C_{1-10}$ alkyl (preferably methyl, ethyl, propyl, butyl, isobutyl, etc.); optionally halogenated $C_{3-6}$ cycloalkyl (preferably cyclohexyl, etc.); carbamoyl; mono- or di-$C_{1-6}$ alkyl-carbamoyl (preferably methylcarbamoyl, ethylcarbamoyl, dimethylcarbamoyl, diethylcarbamoyl, etc.); 5- or 6-membered heterocyclylcarbonyl (e.g., morpholinocarbonyl, piperidinocarbonyl, 1-pyrrolidinylcarbonyl, etc.); optionally halogenated $C_{1-6}$ alkyl-carboxamido (preferably acetamido, etc.); hydroxy-$C_{1-6}$ alkyl (preferably hydroxymethyl, hydroxyethyl, etc.); carbamoyl-$C_{1-6}$ alkyl (preferably carbamoylmethyl, carbamoylethyl, carbamoylpropyl, etc.); mono- or di-$C_{1-6}$ alkyl-carbamoyl-$C_{1-6}$ alkyl (preferably methylcarbamoylmethyl, ethylcarbamoylethyl, methylcarbamoylpropyl, dimethylcarbamoylmethyl, dimethylcarbamoylethyl, dimethylcarbamoylpropyl, ethylcarbamoylmethyl, ethylcarbamoylethyl, ethylcarbamoylpropyl, diethylcarbamoylmethyl, diethylcarbamoylethyl, diethylcarbamoylpropyl, etc.); 5- or 6-membered heterocyclylcarbonyl-$C_{1-6}$ alkyl (preferably morpholinocarbonylmethyl, morpholinocarbonylethyl, morpholinocarbonylpropyl, piperidinocarbonylmethyl, piperidinocarbonylethyl, piperidinocarbonylpropyl, 1-pyrrolidinylcarbonylmethyl, 1-pyrrolidinylcarbonylethyl, 1-pyrrolidinylcarbonylpropyl, etc.); mono- or di-$C_{1-6}$ alkyl-carbamoyl-$C_{1-6}$ alkoxy (preferably ethylcarbamoylmethoxy, etc.); $C_{7-19}$ aralkyl (preferably benzyl, etc.) optionally having 1 to 3 substituents selected from halogen atom (preferably fluorine, chlorine, etc.), optionally halogenated $C_{1-6}$ alkyl(preferably, methyl, etc.) and optionally halogenated $C_{1-6}$ alkoxy (preferably methoxy, etc.); aromatic ring group (preferably phenyl) optionally having 1 to 3 substituents selected from halogen atom (preferably fluorine, chlorine, etc.), optionally halogenated $C_{1-6}$ alkyl (preferably methyl, etc.) and optionally halogenated $C_{1-6}$ alkoxy (preferably methoxy, etc.);

Y is $C_{1-6}$ alkylene (preferably $—CH_2—$, $—CH(CH_3)—$, $—CH(C_2H_5)—$);

$R^3$ is hydrogen atom; and ring A and ring B may further have 1 to 3 substituents selected from halogen atom (preferably fluorine, chlorine, bromine, etc.), optionally halogenated $C_{1-6}$ alkyl-(preferably methyl, ethyl, propyl, trifluoromethyl, etc.) and optionally halogenated $C_{1-6}$ alkoxy (preferably methoxy, ethoxy, etc.).

3A) A compound wherein Ar is phenyl, 5- or 6-membered aromatic heterocyclic group (preferably pyridyl), or 5- to 8-membered monocyclic non-aromatic heterocyclic group (preferably piperidinyl), each optionally having 1 to 3 substituents selected from halogen atom (e.g., fluorine, chlorine, bromine, iodine, etc.), $C_{1-3}$ alkylenedioxy (e.g., methylenedioxy, ethylenedioxy, etc.), nitro, cyano, optionally halogenated $C_{1-10}$ alkyl (e.g., methyl, ethyl, propyl, butyl, pentyl), optionally halogenated $C_{1-10}$ alkoxy (e.g., methoxy, ethoxy, propoxy, butoxy, isobutoxy, pentyloxy, isopentyloxy, etc.), $C_{6-14}$ aryloxy optionally having substituent(s) (preferably phenoxy), $C_{7-19}$ aralkyloxy (preferably benzyloxy) optionally having substituent(s) (preferably halogen atom, optionally halogenated $C_{1-10}$ alkyl, optionally halogenated $C_{1-10}$ alkoxy, etc.), $C_{3-6}$ cycloalkyl-$C_{1-6}$ alkyl (preferably cyclopropylmethyl), $C_{3-6}$ cycloalkyl-$C_{1-6}$ alkoxy (preferably cyclopropylmethoxy) optionally having substituent(s), acyl [preferably optionally halogenated $C_{1-6}$ alkyl-carbonyl (e.g., pentanoyl, hexanoyl, etc.), optionally halogenated $C_{1-6}$ alkylsulfonyl (e.g., butylsulfonyl, etc.) and the like], acyl-$C_{1-6}$ alkyl [preferably optionally halogenated $C_{1-6}$ alkyl-carbonyl-$C_{1-6}$ alkyl (e.g., propanoylmethyl, propanoylethyl, 2-methylpropanoylmethyl, butanoylmethyl, 3-methylbutanoylmethyl, pentanoylmethyl, etc.), optionally halogenated $C_{1-6}$ alkylsulfonyl-$C_{1-6}$ alkyl (e.g., propylsulfonylmethyl, butylsulfonylmethyl, etc.), $C_{6-14}$ aryl-carbonyl-$C_{1-6}$ alkyl (e.g., benzoylmethyl, etc.), $C_{3-6}$ cycloalkyl-carbonyl-$C_{1-6}$ alkyl (e.g., cyclopropylcarbonylmethyl, cyclobutylcarbonylmethyl, etc.), 5- or 6-membered heterocyclylcarbonyl-$C_{1-6}$ alkyl (e.g., tetrahydrofuroylmethyl, etc.) and the like], hydroxy, $C_{1-6}$ alkoxy-$C_{1-6}$ alkoxy (preferably methoxymethoxy, ethoxyethoxy), optionally halogenated $C_{1-10}$ alkylthio (preferably methylthio, butylthio, etc.), acylamino [preferably optionally halogenated $C_{1-6}$ alkyl-carboxamido (e.g., propylcarboxamido, isopropylcarboxamido, butylcarboxamido, etc.), $C_{6-14}$ aryl-carboxamido (preferably phenylcarboxamido, propanoylmethylphenylcarboxamido, etc.) optionally having substituent(s) (preferably $C_{1-6}$ alkyl-carbonyl-$C_{1-6}$ alkyl) and the like] and acyloxy [preferably $C_{1-6}$ alkyl-carbonyloxy (e.g., propanoyloxy, butanoyloxy, etc.)];

X is a bond, $C_{1-6}$ alkylene or $—(CH_2)_{w1}CO(CH_2)_{w2}—$ (w1 and w2 is an integer of 0 to 5 and w1+w2 is 0 to 5);

$R^1$ and $R^2$ form, together with the adjacent nitrogen atom, 3- to 8-membered nitrogen-containing heterocycle (preferably piperidine, piperazine, pyrrolidine, hexamethyleneimine (azepane), morpholine, thiomorpholine) optionally having 1 to 3 substituents selected from optionally halogenated $C_{1-10}$ alkyl (preferably methyl, ethyl, propyl, butyl, isobutyl, etc.); optionally halogenated $C_{3-6}$ cycloalkyl (preferably cyclohexyl, etc.); carbamoyl; mono- or di-$C_{1-6}$ alkyl-carbamoyl (preferably methylcarbamoyl, ethylcarbamoyl, dimethylcarbamoyl, diethylcarbamoyl, etc.); 5- or 6-membered heterocyclylcarbonyl (e.g., morpholinocarbonyl, piperidinocarbonyl, 1-pyrrolidinylcarbonyl, etc.); optionally halogenated $C_{1-6}$ alkyl-carboxamido (preferably acetamido, etc.); hydroxy-$C_{1-6}$ alkyl (preferably hydroxymethyl, hydroxyethyl, etc.); carbamoyl-$C_{1-6}$ alkyl (preferably carbamoylmethyl, carbamoylethyl, carbamoylpropyl, etc.); mono- or di-$C_{1-6}$ alkyl-carbamoyl-$C_{1-6}$ alkyl (preferably methylcarbamoylmethyl, methylcarbamoylethyl, methylcarbamoylpropyl, dimethylcarbamoylmethyl, dimethylcarbamoylethyl, dimethylcarbamoylpropyl, ethylcarbamoylmethyl, ethylcarbamoylethyl, ethylcarbamoylpropyl, diethylcarbamoylmethyl, diethylcarbamoylethyl, diethylcarbamoylpropyl, etc.); 5- or 6-membered heterocyclylcarbonyl-$C_{1-6}$ alkyl (preferably morpholinocarbonylmethyl, morpholinocarbonylethyl, morpholinocarbonylpropyl, piperidinocarbonylmethyl, piperidinocarbonylethyl, piperidinocarbonylpropyl, 1-pyrrolidinylcarbonylmethyl, 1-pyrrolidinylcarbonylethyl, 1-pyrrolidinylcarbonylpropyl, etc.); mono- or di-$C_{1-6}$ alkyl-carbamoyl-$C_{1-6}$ alkoxy (preferably ethylcarbamoylmethoxy, etc.); $C_{7-19}$ aralkyl (preferably benzyl, etc.) optionally having 1 to 3 substituents selected from halogen atom (preferably fluorine, chlorine, etc.), optionally halogenated $C_{1-6}$ alkyl (preferably methyl, etc.) and optionally halogenated $C_{1-6}$ alkoxy (preferably methoxy, etc.); aromatic ring group (preferably phenyl) optionally having 1 to 3 substituents selected from halogen atom (preferably fluorine, chlorine, etc.), optionally halogenated $C_{1-6}$ alkyl (preferably methyl, etc.) and optionally halogenated $C_{1-6}$ alkoxy (preferably methoxy, etc.);

Y is $C_{1-6}$ alkylene (preferably —$CH_2$—, —$CH(CH_3)$—, —$CH(C_2H_5)$—);

$R^3$ is hydrogen atom; and ring A and ring B may further have 1 to 3 substituents selected from halogen atom (preferably fluorine, chlorine, bromine, etc.), optionally halogenated $C_{1-6}$ alkyl (preferably methyl, ethyl, propyl, trifluoromethyl, etc.) and optionally halogenated $C_{1-6}$ alkoxy (preferably methoxy, ethoxy, etc.).

4) 4'-fluoro-N-[8-methyl-3-(1-pyrrolidinylmethyl)-7-quinolinyl][1,1'-biphenyl]-4-carboxamide (Example number: 19);

N-[6-fluoro-3-(1-pyrrolidinylmethyl)-7-quinolinyl]-4'-methoxy[1,1'-biphenyl]-4-carboxamide (Example number: 53);

6-(4-methoxyphenyl)-N-[8-methyl-3-(1-pyrrolidinylmethyl)-7-quinolinyl]nicotinamide (Example number: 96);

3-fluoro-4'-methoxy-N-[8-methyl-3-(1-pyrrolidinylmethyl)-7-quinolinyl][1,1'-biphenyl]-4-carboxamide (Example number: 147);

4-(cyclopropylmethoxy)-N-[8-methyl-3-(1-pyrrolidinylmethyl)-7-quinolinyl]benzamide (Example number: 297);

N-[3-(1-azepanylmethyl)-8-methyl-7-quinolinyl]-4-(2-oxopentyl)benzamide (Example number: 315); or a salt thereof.

When the compound (I) is in the form of a salt, concrete examples thereof include salts with inorganic bases, ammonium salts, salts with organic bases, salts with inorganic acids, salts with organic acids, salts with basic or acidic amino acids and the like.

Preferable examples of the salts with inorganic bases include alkali metal salts such as sodium salt, potassium salt, and the like; alkaline earth metal salts such as calcium salts, magnesium salts, barium salts, and the like; aluminum salts, and the like.

Preferable examples of the salts with organic bases include salts with trimethylamine, triethylamine, pyridine, picoline, ethanolamine, diethanolamine, triethanolamine, dicyclohexylamine, N,N-dibenzylethylenediamine, and the like.

Preferable examples of the salts with inorganic acids include salts with hydrochloric acid, hydrobromic acid, nitric acid, sulfuric acid, phosphoric acid, and the like.

Preferable examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like.

Preferable examples of the salts with basic amino acids include salts with arginine, lysine, ornithine, and the like.

Preferable examples of the salts with acidic amino acids include salts with aspartic acid, glutamic acid, and the like.

Of these, pharmaceutically acceptable salts are preferable.

Preferable examples when compound (I) has an acidic functional group include inorganic salts such as alkali metal salts (e.g., sodium salt, potassium salt, etc.), alkaline earth metal salts (e.g., calcium salt, magnesium salt, barium salt, etc.) and the like, ammonium salts, etc.; and when compound (I) has a basic functional group, inorganic salts such as hydrochloride, sulfate, phosphate and hydrobromide; or organic salts such as acetate, maleate, fumarate, succinate, methanesulfonate, p-toluenesulfonate, citrate and tartrate.

The compound (I) may be an anhydrate or a hydrate. When it is a hydrate, it may contain 0.5 to 3 water molecules.

Furthermore, compound (I) may be labeled with an isotope (e.g., $^{3}H$, $^{14}C$, $^{35}S$, etc.).

Where compound (I) includes optical isomers, stereo isomers, regio isomers and rotational isomers, these are within the scope of compound (I), and can be isolated as their single compound through synthesis or separation known per se. For example, where optical isomers of compound (I) exist, those resolved from their mixtures through optical resolution are within the scope of compound (I).

Said optical isomers can be produced by methods known per se. Concretely, optically active synthetic intermediates may be used, or mixtures of racemate of the final product are subjected to ordinary optical resolution to give the corresponding optical isomers.

As the optical resolution method, methods known per se such as fractional recrystallization method, chiral column method, diastereomer method which are described in detail below and the like are employed.

1) Fractional Recrystallization Method

The method which comprises allowing a racemate to react with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) to give a salt, which is then isolated through fractional recrystallization method, followed by, when desired, subjecting the isolated compound to neutralization to obtain free optical isomers.

2) Chiral Column Method

The method of separating a racemate or a salt thereof, which comprises utilizing a column for fractionating optical isomers (chiral column). In the case of liquid chromatography, for example, a mixture of optical isomers is applied to a chiral column, such as ENANTIO-OVM (manufactured by Tosoh Corp.), CHIRAL SERIES (manufactured by Daicel Co.), and the like, which is then eluted with water, various buffers (e.g., phosphate buffer) and organic solvents (e.g., ethanol, methanol, isopropanol, acetonitrile, trifluoroacetic acid, diethylamine, etc.), singly or as a suitable mixture of them, to isolate the individual optical isomers. In the case of gas chromatography, for example, a chiral column such as CP-Chirasil-DeX CB (manufactured by GL Science Co.), and the like is used for isolation.

3) Diastereomer Method

A racemic mixture is chemically reacted with an optically-active reagent to give a mixture of diastereomer, which is subjected to ordinary separation means (e.g., fractional recrystallization, chromatography, etc.) to give single compounds. The thus-isolated single compounds are then chemically processed, for example, through hydrolysis to thereby remove the optically-active reagent site from the compounds to obtain optical isomers. For example, where compound (I) has a hydroxy group or a primary or secondary amino group in the molecule, it is condensed with an optically-active organic acid (e.g., MTPA [α-methoxy-α-(trifluoromethyl) phenyl-acetic acid], (−)-menthoxyacetic acid, etc.) or the like to give the corresponding ester-type or amide-type diastereomer. On the other hand, where compound (I) has a carboxylic acid group, it is condensed with an optically active amine or alcohol reagent to give the corresponding amide-type or ester-type diastereomer, respectively. The thus-isolated diastereomer is then subjected to acidic or basic hydrolysis, through which it is converted into the optical isomer of the original compound.

The prodrug of the compound (I) means a compound capable of being converted to the compound (I) in vivo by the action of an enzyme or gastric juice and the like under physiological conditions, namely a compound capable of being converted to the compound (I) upon enzymatic oxidation, reduction or hydrolysis and the like, or a compound capable of being converted to the compound (I) upon hydrolysis and the like by gastric juice and the like. As the prodrug of the compound (I), compounds derived by acylation, alkylation or phosphorylation of the amino group of the compound (I) (e.g., compounds derived by eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation of the amino group of the compound (I) etc.); compounds derived by acylation, alkylation, phosphorylation or boration of the hydroxy group of the compound (I) (e.g., compounds derived by acetylation, palmitoylation, propanoylation, pivaloylation, succinylation, fumarylation, alanylation or dimethylaminomethylcarbonylation of the hydroxy group of the compound (I), etc.); and compounds derived by esterification or amidation of the carboxyl group of the compound (I) (e.g., compounds derived by ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, or methylamidation of the carboxyl group of the compound (I) etc.), and the like can be mentioned. These compounds can be produced from the compound (I) by methods known per se.

The prodrug of the compound (I) may be one capable of being converted to the compound (I) under physiological conditions, as described in "*Iyakuhin no Kaihatsu* (*Development of Drugs*)", vol. 7, Molecular Designing, published by Hirokawa Shoten, 1990, pages 163–198.

The compound (I) can be produced by [production method 1] to [production method 4] which are described in detail below, or an analogous method thereto.

The compounds for the starting material compound may be used in the form of a salt, respectively. As such salt, those exemplified for the salt of the aforementioned compound (I) can be used.

In the following [production method 1] to [production method 4], when alkylation reaction, hydrolysis reaction, amination reaction, esterification reaction, amidation reaction, esterification reaction, etherification reaction, oxidation reaction, reduction reaction etc. are to be conducted, these reactions are carried out according to methods known per se, for example, those described in *Organic Functional Group Preparations,* 2nd Ed., Academic Press Inc., 1989*; Comprehensive Organic Transformations*, VCH Publishers Inc., 1989; and the like.

Of the following compounds, compounds (I), (Ia), (Ib), (Ic), (III), (IIIa), (IIIb), (IIIh) and (IIIj) are novel compounds.

[Production Method 1]

The compound (I) is produced by, for example, the following amidation reaction.

(Amidation Reaction)

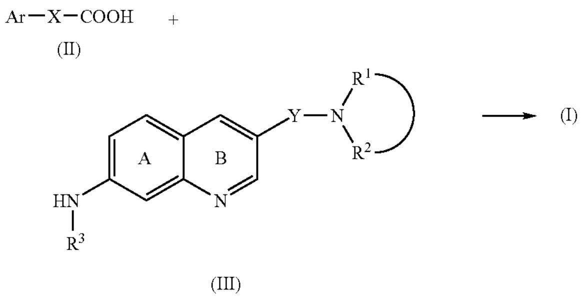

wherein the symbols in the formula are as defined above.

The "amidation reaction" includes "a method using a dehydration condensing agent" and "a method using a reactive derivative of carboxy" described below.

i) Method Using a Dehydration Condensing Agent

Compound (III), 1 to 5 equivalent amount of compound (II) and 1 to 2 equivalent amount of dehydration condensing agent are reacted in an inert solvent. Where necessary, reaction may be carried out in the co-presence of 1 to 1.5 equivalent amount of 1-hydroxybenzotriazole (HOBT) and/or catalytic amount to 5 equivalent amount of a base.

As the "dehydration condensing agent", for example, dicyclohexylcarbodiimide (DCC), 1-ethyl-3-(3-dimethylaminopropyl)carbodiimide hydrochloride (WSC) and the like can be mentioned. Of these, WSC is preferable.

As the "inert solvent", for example, nitrile solvent (preferably acetonitrile), amide solvent (preferably DMF), halogenated hydrocarbon solvent (preferably dichloromethane), ether solvent (preferably THF) and the like can be mentioned. Two or more kinds of these can be mixed in an appropriate ratio and used.

Said "base" includes, for example;

1) strong bases such as alkali metal or alkaline earth metal hydrides (e.g., lithium hydride, sodium hydride, potassium hydride, calcium hydride, etc.), alkali metal or alkaline earth metal amides (e.g., lithium amide, sodium amide, lithium diisopropylamide, lithium dicyclohexylamide, lithium hexamethyldisilazide, sodium hexamethyldisilazide, potassium hexamethyldisilazide, etc.), alkali metal or alkaline earth metal lower-alkoxides (e.g., sodium methoxide, sodium ethoxide, potassium tert-butoxide, etc.), and the like;

2) inorganic bases such as alkali metal or alkaline earth metal hydroxides (e.g., sodium hydroxide, potassium hydroxide, lithium hydroxide, barium hydroxide, etc), alkali metal or alkaline earth metal carbonates (e.g., sodium carbonate, potassium carbonate, cesium carbonate, etc), alkali metal or alkaline earth metal hydrogen carbonates (e.g., sodium hydrogen carbonate, potassium hydrogen carbonate, etc.) and the like; and 3) organic bases such as amines exemplified by triethylamine, diisopropylethylamine, N-methylmorpholine, dimethylaminopyridine, DBU (1,8-diazabicyclo[5.4.0]undec-7-ene), DBN (1,5-diazabicyclo[4.3.0]non-5-ene) and the like, basic heterocyclic compounds exemplified by pyridine, imidazole, 2,6-lutidine and the like. Of the above-mentioned bases, preferred are triethylamine and 4-dimethylaminopyridine, and the like.

The reaction temperature is generally room temperature (0 to 30° C., hereinafter the same). The reaction time is, for example, 10 hours to 24 hours.

ii) Method Using a Reactive Derivative of Carboxy

The reactive derivative of Compound (II) and 1 to 5 equivalents (preferably 1 to 3 equivalents) amount of Compound (III) are reacted in an inert solvent. Where necessary, the reaction may be carried out in the co-presence of 1 to 10 equivalents, preferably 1 to 3 equivalents, of a base.

The "reactive derivative" of Compound (II) include, for example, acid halide (e.g., acid chloride, acid bromide, etc.), mixed acid anhydride (e.g., anhydride with $C_{1-6}$ alkyl carboxylic acid, $C_{6-10}$ aryl carboxylic acid or $C_{1-6}$ alkyl carbonic acid, etc.), activated ester (e.g., ester with phenol optionally having substituent(s), 1-hydroxybenzotriazole or N-hydroxysuccinimide, etc.) and the like.

The "substituent(s)" of the "phenol optionally having substituent(s)" includes, for example, halogen atom (e.g., fluorine, chlorine, bromine, iodine, etc.), nitro, optionally halogenated $C_{1-6}$ alkyl and optionally halogenated $C_{1-6}$ alkoxy. The number of the substituents is, for example, 1 to 5.

As the "optionally halogenated $C_{1-6}$ alkyl" and "optionally halogenated $C_{1-6}$ alkoxy", those exemplified for the "substituent(s)" of the above "cyclic group optionally having substituent(s)" for Ar can be used.

Concrete examples of the "phenol optionally having substituent(s)" include phenol, pentachlorophenol, pentafluorophenol, p-nitrophenol and the like. The reactive derivative is preferably acid halide.

The "inert solvent" includes, for example, ether solvent, halogenated hydrocarbon solvent, aromatic solvent, nitrile solvent, amide solvent, ketone solvent, sulfoxide solvent, water and the like. These may be used on mixing two or more kinds at a suitable proportion. Of these, preferred are acetonitrile, THF, dichloromethane, chloroform, and the like.

As the "base", those similar to the aforementioned can be used. The base is preferably sodium hydride, potassium carbonate, sodium carbonate, sodium hydroxide, potassium hydroxide, sodium hydrogen carbonate, potassium hydrogen carbonate, triethylamine, pyridine and the like.

The reaction temperature is generally −20° C. to 50° C., preferably room temperature. The reaction time is generally 5 min to 40 hrs., preferably 1 to 18 hrs.

The aforementioned compound (II) can be produced by methods known per se.

For example, the compound (II) can be produced by hydrolyzing, by methods known per se, an ester compound produced according to the methods described in *J. Org. Lett*, vol. 2, p. 879 (2000); *Tetrahedron*, vol. 56, p. 8661 (2000); EP-A0006735; JP-B-1-30820 and the like, or analogous methods thereto.

The aforementioned compound (III) can be produced, for example, subjecting a compound represented by the formula:

(IIIa)

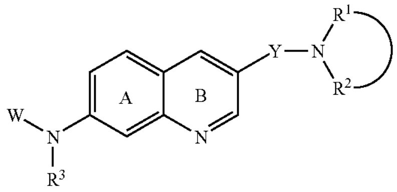

wherein W is an amino protecting group and other symbols are as defined above, to deprotection reaction to remove W.

Examples of the amino protecting group for W include formyl, $C_{1-6}$ alkyl-carbonyl (e.g., acetyl, propionyl, etc.), $C_{1-6}$ alkoxy-carbonyl (e.g., methoxycarbonyl, ethoxycarbonyl, tert-butoxycarbonyl, etc.), benzoyl, $C_{7-10}$ aralkyl-carbonyl (e.g., benzylcarbonyl, etc.), $C_{7-14}$ aralkyloxy-carbonyl (e.g., benzyloxycarbonyl, 9-fluorenylmethoxycarbonyl, etc.), trityl, phthaloyl, N,N-dimethylaminomethylene, silyl (e.g., trimethylsilyl, triethylsilyl, dimethylphenylsilyl, tert-butyldimethylsilyl, tert-butyldiethylsilyl, etc.), $C_{2-6}$ alkenyl (e.g., 1-allyl, etc.) and the like. These groups may be substituted by 1 to 3 of halogen atom (e.g., fluorine, chlorine, bromine, iodine, etc.), $C_{1-6}$ alkoxy (e.g., methoxy, ethoxy, propoxy, etc.), nitro and the like.

Deprotection reaction is carried out, for example, by maintaining compound (IIIa) in an aqueous solution of an acid such as mineral acid (e.g., hydrochloric acid, sulfuric acid, hydrobromic acid, iodic acid, periodic acid, etc.) and the like or a base such as alkali metal hydroxide (e.g., sodium hydroxide, potassium hydroxide, lithium hydroxide) and the like, preferably at 20° C. to 140° C. The amount to be used of acid and base is generally 1 to 100 equivalent amount, preferably 1 to 40 equivalent amount, per compound (IIIa). The strength of acid or base is generally 0.1N to 18N, preferably 1N to 12N.

The reaction time is generally 0.5 hr to 48 hrs., preferably 1 hr. to 24 hrs.

When W is tert-butoxycarbonyl group and the like, deprotection reaction is also carried out by maintaing compound (IIIa) after dissolving in an organic acid (e.g., trifluoroacetic acid, formic acid, acetic acid, methanesulfonic acid, benzenesulfonic acid, trifluoromethanesulfonic acid, etc.), at generally −20° C. to 200° C., preferably 0° C. to 100° C. The amount to be used of organic acid is generally 1 to 100 equivalent amount, preferably 1 to 40 equivalent amount, per compound (IIIa).

In addition, deprotection reaction is carried out by subjecting compound (IIIa) to catalytic hydrogenation reaction with palladium, palladium-carbon, Raney-nickel, Raney cobalt, platinum oxide and the like as a catalyst, for example, in a solvent of an alcohol solvent such as ethanol and the like or acetic acid and the like at a normal pressure or under pressure where necessary.

The aforementioned compound (IIIa) can be produced, for example, by reacting a compound represented by the formula:

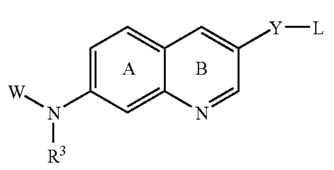

(IIIb)

wherein L is a leaving group and other symbols are as defined above, with a compound represented by the formula:

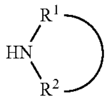

(IV)

wherein the symbols in the formula are as defined above.

As the "leaving group" for L, for example, halogen atom (e.g., chlorine, bromine, iodine, etc.), optionally halogenated $C_{1-6}$ alkylsulfonyloxy (e.g., methanesulfonyloxy, ethanesulfonyloxy, trifluoromethanesulfonyloxy, etc.), $C_{6-10}$ arylsulfonyloxy optionally having substituent(s), hydroxy and the like can be mentioned.

As the "substituent(s)" of the "$C_{6-10}$ arylsulfonyloxy optionally having substituent(s)", for example, halogen atom (e.g., chlorine, bromine, iodine, etc.), optionally halogenated $C_{1-6}$ alkyl, $C_{1-6}$ alkoxy and the like can be mentioned. The number of substituent is, for example, 1 to 3. As concrete examples of the "$C_{6-10}$ arylsulfonyloxy optionally having substituent(s)", benzenesulfonyloxy, p-toluenesulfonyloxy, 1-naphthalenesulfonyloxy, 2-naphthalenesulfonyloxy and the like can be mentioned.

The "leaving group" is preferably halogen atom (e.g., chlorine, bromine, iodine, etc.), methanesulfonyloxy, trifluoromethanesulfonyloxy, p-toluenesulfonyloxy and the like.

The reaction is generally carried out in an inert solvent.

As the "inert solvent", for example, alcohol solvent, ether solvent, halogenated hydrocarbon solvent, aromatic solvent, nitrile solvent, amide solvent, ketone solvent, sulfoxide solvent, water and the like can be mentioned. These may be used in an appropriate combination of two or more thereof. Of these, acetonitrile, N,N-dimethylformamide (DMF), acetone, ethanol, pyridine and the like are preferable.

The amount to be used of compound (IV) is generally 1 equivalent amount to 100 equivalent amount per compound (IIIb). An excess amount of compound (IV) may also be used as a reaction solvent.

The reaction temperature is generally about −20° C. to 200° C., preferably room temperature to 100° C. The reaction time is, for example, about 0.5 hr. to 1 day.

The reaction may also be carried out in the presence of a base. As the base, those exemplified for the aforementioned "method using a dehydration condensing agent" can be used. The base is preferably sodium hydride, potassium carbonate, sodium carbonate, sodium hydroxide, potassium hydroxide, sodium hydrogen carbonate, potassium hydrogen carbonate, triethylamine, pyridine and the like. The amount to be used of the base is generally 0.1 to 100 equivalent amount, preferably 1 to 10 equivalent amount, per compound (IIIb).

Compound (IIIb) in which L is optionally halogenated $C_{1-6}$ alkylsulfonyloxy, $C_{6-10}$ arylsulfonyloxy optionally having substituent(s) or halogen atom, can be produced, for example, from a compound represented by the formula:

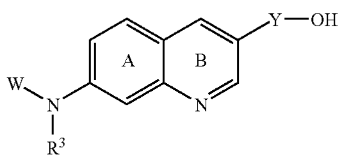

(IIIh)

wherein the symbols in the formula are as defined above.

Compound (IIIb) in which L is optionally halogenated $C_{1-6}$ alkylsulfonyloxy or $C_{6-10}$ arylsulfonyloxy optionally having substituent(s) can be produced, for example, by reacting compound (IIIh) with 1 to 5 equivalent amount of corresponding sulfonyl halide in an inert solvent in the presence of a base.

As the "base", those exemplified for the aforementioned "method using a dehydration condensing agent" can be used. The base is preferably potassium carbonate, sodium hydrogen carbonate, triethylamine, N-methylmorpholine, pyridine and the like. The amount to be used of the base is preferably 1 to 10 equivalent amount.

As the "inert solvent", for example, ether solvent, halogenated hydrocarbon solvent, aromatic solvent, nitrile solvent, amide solvent, ketone solvent, sulfoxide solvent and the like can be mentioned.

The reaction temperature is generally −20° C. to 200° C., preferably 0° C. to 100° C. The reaction time is generally 0.1 hr. to 48 hrs., preferably 1 to 24 hrs.

Compound (IIIb) in which L is halogen atom can be produced by subjecting compound (IIIh) to known halogenation reaction.

This reaction is carried out, for example, by using a halogenating agent. As the halogenating agent., for example, halogenated inorganic acid such as thionyl chloride, thionyl bromide, phosphorus trichloride, phosphorus pentachloride, phosphorus oxychloride and the like; hydrogen halide such as hydrogen chloride, hydrogen bromide and the like can be mentioned. This reaction is carried out in the presence or absence of a solvent. As the solvent, for example, "inert solvent" used in the above-mentioned reaction of the compound (IIIh) and sulfonyl halide, and the like can be mentioned.

The reaction temperature is generally −20° C. to 200° C., preferably 0° C. to 100° C. The reaction time is generally 0.1 hr. to 48 hrs., preferably 1 to 24 hrs.

Compound (IIIh) can be produced by reducing, according to a known reduction method, aldehyde compound (IIIc) in which $R^9$ is a hydrogen atom, or ester compound (IIId) both of which are mentioned below. As the reduction method, for example, a method using a reducing agent (e.g., borohydride reagent such as sodium borohydride, aluminum hydride reagent such as lithium aluminum hydride and the like, etc.), a catalytic hydrogenation method using a transition metal catalyst (e.g., platinum catalyst, palladium catalyst, rhodium catalyst, ruthenium catalyst, nickel catalyst, etc.), a microorganism reduction method using pan-yeast and the like, and the like can be mentioned.

The aforementioned compound (IV) can be produced by a method known per se.

The aforementioned compound (IIIa) can be also produced by reacting a compound represented by the formula:

(IIIc)

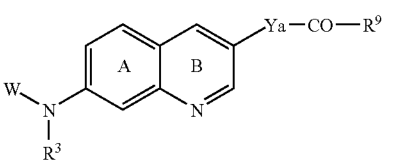

wherein Ya is a bond or an optionally halogenated divalent $C_{1-5}$ acyclic hydrocarbon group, $R^9$ is a hydrogen atom or an optionally halogenated $C_{1-5}$ alkyl group, and other symbols are as defined above, with the afore-mentioned compound (IV).

Here, as the "divalent $C_{1-5}$ acyclic hydrocarbon group" of the "optionally halogenated divalent $C_{1-5}$ acyclic hydrocarbon group" for Ya, those having 1 to 5 carbon atoms of the above "divalent $C_{1-6}$ acyclic hydrocarbon group" exemplified for Y, can be mentioned. This "divalent $C_{1-5}$ acyclic hydrocarbon group" is optionally substituted by 1 to 5 halogen atoms (e.g., fluorine, chlorine, bromine, iodine, etc.). As the "optionally halogenated $C_{1-5}$ alkyl group", those having 1 to 5 carbon atoms of the "optionally halogenated $C_{1-6}$ alkyl group" exemplified for the substituent of the above "cyclic group optionally having substituent(s)" for Ar can be mentioned.

This reaction can be carried out, for example, by reacting compound (IIIc) and generally 1 to 20 equivalent amount, preferably 1 to 5 equivalent amount of compound (IV) with a reducing agent in an inert solvent.

As the "inert solvent", for example, alcohol solvent, ether solvent, halogenated hydrocarbon solvent, aromatic solvent, nitrile solvent, amide solvent, organic acid solvent and the like can be mentioned. These may be used in an appropriate combination of two or more thereof. Of these, methanol, ethanol, acetic acid and the like are preferable.

As the reducing agent, for example, sodium borohydride, triacetoxy sodium borohydride, sodium cyano borohydride and the like are used. The amount to be used of the reducing agent is generally 1 to 20 equivalent amount, preferably 1 to 5 equivalent amount.

The reaction temperature is generally −20° C. to 150° C., preferably 20 to 100° C. The reaction time is generally 5 min. to 40 hrs., preferably 1 to 24 hrs.

This reaction can be also carried out in the presence of an acid. As the acid to be used, for example, organic acids such as acetic acid, methanesulfonic acid and the like; inorganic acids such as hydrochloric acid, sulfuric acid and the like, and the like can be mentioned. The amount to be used of the acid is, in the case of inorganic acid, generally 0.01 equivalent amount to 0.1 equivalent amount, and in the case of organic acid, generally 0.01 equivalent amount to 100 equivalent amount. When using organic acid, an excess amount of organic acid may be used as a reaction solvent.

The aforementioned compound (IIIc) can be produced by a method known per se. For example, N-(3-formyl-7-quinolinyl)acetamide contained in compound (IIIc) can be produced by the method described in *Synthesis*, p. 1351(2001), and the like.

Compound (IIIc) can be also produced by subjecting the aforementioned compound (IIIh) to a known oxidation reaction. The oxidation reaction is carried out, for example, using an oxidant. For the oxidant, for example, manganese dioxide, chromic acid, lead tetraacetate, silver oxide, copper oxide, acid halide, oxidation (Swern oxidation) using dimethyl sulfoxide, organic peracid, oxygen, electrode-oxidation and the like are employed.

Compound (IIIc) can be also produced from ester compound (IIId) mentioned below by a known method using an organic metal reagent such as Grignard reagent, dialkyl copper lithium and the like.

Compound (IIIa) can be also produced by subjecting the compound represented by the formula:

(IIId)

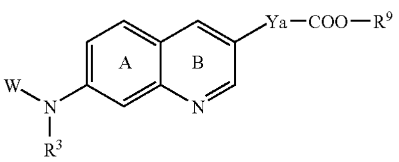

wherein each symbol in the formula is as defined above, with compound (IV) to a known condensation reaction (e.g., the aforementioned method using a dehydration condensing agent or a reactive derivative of carboxy) and subjecting the resulting amide compound to a known reduction reaction. This reduction reaction is generally carried out by using a reducing agent. As the reducing agent, for example, borohydride reagent such as diborane, sodium borohydride and the like, aluminum hydride reagent such as lithium aluminum hydride and the like, and the like can be used.

The compound (IIId) can be produced by a method known per se. For example, compound (IIId) in which Ya is a bond can be produced by protecting the amino group of ethyl 7-amino-3-quinolinecarboxylate, produced by the method described in JP-A-2001-139555 and the like, with W. The protecting group can be introduced by a method known per se, for example, the method described in *Protective Groups in Organic Synthesis*, John Wiley and Sons (1980), and the like.

[Production Method 2]

Compound (I) can be also produced, for example, reacting compound (IIIj) with compound (IV).

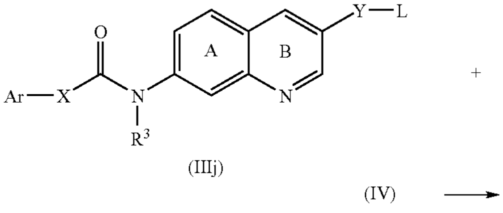

(IIIj)

(IV)

(I)

wherein the symbols in the formula are as defined above.

This reaction is carried out in the same manner as the reaction of the compound (IIIb) and compound (IV) mentioned above.

[Production Method 3]

Compound (Ia) in which Ar is non-aromatic cyclic amino group optionally having substituent(s) and X is a bond is also produced, for example, by the following urea reaction.

(Urea reaction)

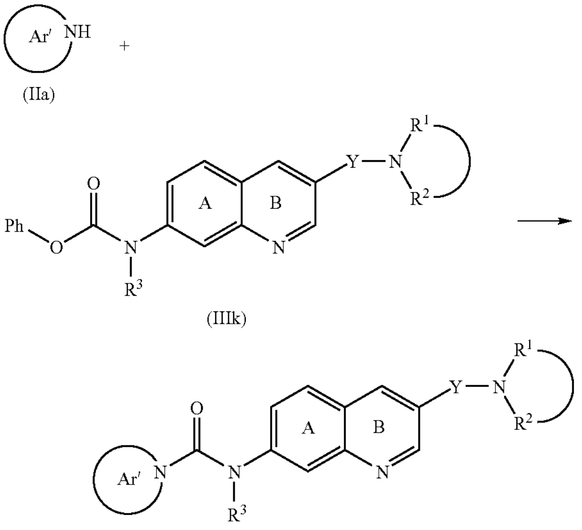

(IIa) (IIIk) (Ia)

wherein Ar' is non-aromatic cyclic amino group optionally having substituent(s), Ph is phenyl group and other symbols are as defined above.

As the "non-aromatic cyclic amino group optionally having substituent(s)" for Ar', the above "cyclic group optionally having substituent(s)" exemplified for Ar in which the cyclic group is a non-aromatic cyclic amino group can be used. Here, as concrete examples of the non-aromatic cyclic amino group, pyrrolidinyl, piperidinyl, piperazinyl, morpholinyl, thiomorpholinyl and the like can be mentioned. This reaction is carried out by reacting compound (IIIk) with 1 to 5 equivalent amount (preferably 1 to 1.5 equivalent amount) of compound (IIa) in an inert solvent in the copresence of a base.

As the "base", those exemplified in the aforementioned "method using a dehydration condensing agent" can be used. The base is preferably potassium carbonate, sodium carbonate, sodium hydroxide, potassium hydroxide, sodium hydrogen carbonate, potassium hydrogen carbonate, triethylamine, pyridine and the like.

As the "inert solvent", for example, alcohol solvent, ether solvent, halogenated hydrocarbon solvent, aromatic solvent, nitrile solvent, amide solvent, ketone solvent, sulfoxide solvent, water and the like can be mentioned. These may be used on mixing two or more kinds at a suitable proportion. Of these, acetonitrile, DMF, acetone, ethanol, pyridine and the like are preferable.

The reaction temperature is generally about −20° C. to 100° C., preferably room temperature to 80° C. The reaction time is, for example, about 0.5 hr. to 1 day.

The aforementioned compound (IIa) and compound (IIIk) can be produced by a method known per se.

[Production Method 4]

Compound (Ib) in which Ar in the formula (I) is a group represented by the formula: $Ar^2$—$Ar^{1a}$—, wherein $Ar^{1a}$ is aromatic group optionally having substituent(s) and $Ar^2$ is as defined above, can be also produced, for example, by the following aryl coupling reaction.

(Aryl coupling reaction)

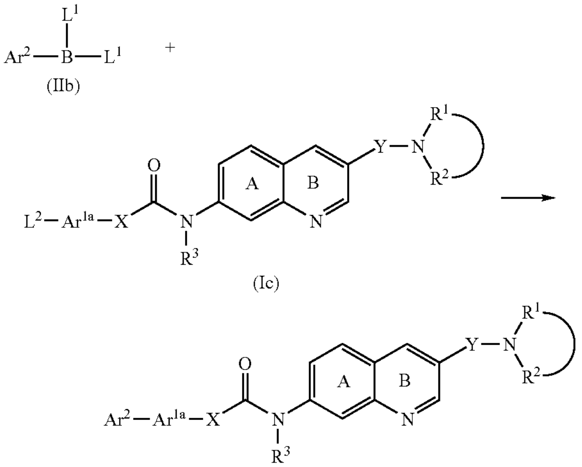

(IIb) (Ic) (Ib)

wherein $L^1$ is hydroxy or $C_{1-6}$ alkoxy; $L^2$ is halogen (preferably chlorine, bromine) or trifluoromethanesulfonyloxy; and other symbols are as defined above.

As the "aromatic group optionally having substituent(s)" for $Ar^{1a}$, the above "cyclic group optionally having substituent(s)" for Ar in which the cyclic group is aromatic group can be mentioned.

Compound (Ib), in which both $Ar^2$ and $Ar^{1a}$ is phenyl optionally having substituent(s) and $Ar^2$—$Ar^{1a}$— is biphenylyl optionally having substituent(s), is particularly preferable.

As the $C_{1-6}$ alkoxy for $L^1$, for example, methoxy, ethoxy, propoxy and the like can be mentioned.

The aryl coupling reaction can be carried out by a method known per se, for example, the method described in *Acta. Chemica Scandinavia*, pp. 221–230, (1993) and the like or an analogous method thereto.

This reaction is carried out, for example, reacting compound (IIb) with 1 to 3 equivalent amount (preferably 1 to 1.5 equivalent amount) of compound (Ic) in an inert solvent in the presence of a base and a transition metal catalyst.

As the "base", those exemplified in the above "method using a dehydration condensing agent" can be used. The base is preferably sodium carbonate, sodium hydrogen carbonate and the like.

The amount to be use of the "base" is, for example, generally about 1 to 10 equivalent amount per compound (Ic).

As the "transition metal catalyst", for example, palladium catalyst, nickel catalyst and the like can be mentioned. As the "palladium catalyst", for example, tetrakis(triphenylphosphine) palladium(0), palladium acetate, bis(triphenylphosphine)palladium(II) chloride, palladium-carbon and the like can be mentioned.

As the "nickel catalyst", for example, tetrakis(triphenylphosphine) nickel(0) and the like can be mentioned.

The amount to be used of the "transition metal catalyst" is generally about 0.01 to 1 equivalent amount, preferably about 0.01 to 0.5 equivalent amount, per compound (Ic).

The reaction temperature is generally room temperature to 150° C., preferably about 80° C. to 150° C. The reaction time is, for example about 1 to 48 hrs.

As the "inert solvent", for example, water, alcohol solvent, aromatic solvent and the like can be mentioned. These may be used in an appropriate combination of two or more thereof. Of these, water, ethanol, toluene and the like alone or a mixed solvent of two or more of these is preferable.

The aforementioned compound (IIb) can be produced by a method known per se.

The aforementioned compound (Ic) is included in compound (I) and can be produced, for example, by the aforementioned [production method 1] and the like.

As the aforementioned "alcohol solvent", for example, methanol, ethanol, isopropanol, tert-butanol and the like can be used.

As the aforementioned "ether solvent", for example, diethylether, tetrahydrofuran (THF), 1,4-dioxane, 1,2-dimethoxyethane and the like can be used.

As the aforementioned "halogenated hydrocarbon solvent", for example, dichloromethane, chloroform, 1,2-dichloroethane, carbon tetrachloride and the like can be used.

As the aforementioned "aromatic solvent", for example, benzene, toluene, xylene, pyridine and the like can be used.

As the aforementioned "hydrocarbon solvent", for example, hexane, pentane, cyclohexane and the like can be used.

As the aforementioned "amide solvent", for example, N,N-dimethylformamide (DMF), N,N-dimethylacetamide, N-methylpyrrolidone and the like can be used.

As the aforementioned "ketone solvent", for example, acetone, methyl ethyl ketone and the like can be used.

As the aforementioned "sulfoxide solvent", for example, dimethyl sulfoxide (DMSO) and the like can be used.

As the aforementioned "nitrile solvent", for example, acetonitrile, propionitrile and the like can be used.

In the compound (I) thus obtained, the functional group in a molecule can be also converted to the object functional group by combining chemical reactions known per se. As the examples of such chemical reaction, oxidation reaction, reduction reaction, alkylation reaction, hydrolysis reaction, amination reaction, esterification reaction, aryl coupling reaction, deprotection reaction and the like can be mentioned.

In each of the aforementioned reactions, when the starting material compound has an amino group, carboxy group, hydroxy group or carbonyl group as a substituent, a protecting group generally used in peptide chemical and the like may be introduced and an object compound can be obtained by removing the protecting group after the reaction where necessary.

As the amino protecting group, those exemplified for the aforementioned W can be used.

Examples of the protecting group for carboxy group include $C_{1-6}$ alkyl (e.g., methyl, ethyl, propyl, isopropyl, butyl, tert-butyl, etc.), $C_{7-11}$ aralkyl (e.g., benzyl, etc.), phenyl, trityl, silyl (e.g., trimethylsilyl, triethylsilyl, dimethylphenylsilyl, tert-butyldimethylsilyl, tert-butyldiethylsilyl, etc.), $C_{2-6}$ alkenyl (e.g., 1-allyl, etc.) and the like. These groups may be substituted by 1 to 3 halogen atoms (e.g., fluorine, chlorine, bromine, iodine, etc.), $C_{1-6}$ alkoxy (e.g., methoxy, ethoxy, propoxy, etc.) or nitro etc. Examples of the protective group for hydroxy group include $C_{1-6}$ alkyl (e.g., methyl, ethyl, propyl, isopropyl, butyl, tert-butyl, etc.), phenyl, trityl, $C_{7-10}$ aralkyl (e.g., benzyl, etc.)., formyl, $C_{1-6}$ alkyl-carbonyl (e.g., acetyl, propionyl, etc.), benzoyl, $C_{7-10}$ aralkyl-carbonyl (e.g., benzylcarbonyl, etc.), 2-tetrahydropyranyl, 2-tetrahydrofuranyl, silyl (e.g., trimethylsilyl, triethylsilyl, dimethylphenylsilyl, tert-butyldimethylsilyl, tert-butyldiethylsilyl, etc.), $C_{2-6}$ alkenyl (e.g., 1-allyl, etc.) and the like. These groups may be substituted by 1 to 3 of halogen atom (e.g., fluorine, chlorine, bromine, iodine, etc.), $C_{1-6}$ alkyl (e.g., methyl, ethyl, n-propyl, etc.), $C_{1-6}$ alkoxy (e.g., methoxy, ethoxy, propoxy, etc.) or nitro etc.

Examples of the protecting group for carbonyl group include cyclic acetal (e.g., 1,3-dioxane, etc.), and acyclic acetal (e.g., di-$C_{1-6}$ alkylacetal, etc.) and the like.

Removal of the above protecting groups can be carried out in accordance with methods known per se such as those described in *Protective Groups in Organic Synthesis*, published by John Wiley and Sons (1980) and the like. For instance, the methods using acid, base, ultraviolet light, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide, etc.) and the like, a reduction method and the like can be used.

Compound (I) can be isolated and purified by methods known per se such as solvent extraction, changing of liquid properties, transdissolution, crystallization, recrystallization, chromatography, and the like. It is also possible to isolate and purify the starting material compounds of a compound (I), or their salts using the same known methods as above, but they can be also used as starting materials in the next process as a reaction mixture without being isolated.

Inasmuch as the compound (I) and a prodrug thereof (hereinafter abbreviated as the compound of the present invention) has a superior MCH receptor antagonistic action, it is useful as an agent for preventing or treating diseases caused by MCH. In addition, the compound of the present invention shows low toxicity, and superior oral absorption performance and transfer into the brain.

Accordingly, the compound of the present invention is safely administered as an agent for preventing or treating diseases caused by MCH to mammals (e.g., rat, mouse, guinea pig, rabbit, sheep, horse, pig, cow, monkey, human, etc.).

The diseases caused by MCH include, for example, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity and the like], hyperphagia, emotional disorder, sexual dysfunction, depression, anxiety and the like.

The compound of the present invention is also useful as an agent for preventing or treating life-style related diseases such as diabetes, diabetic complications (e.g., diabetic retinopathy, diabetic neuropathy, diabetic nephropathy, etc.), arteriosclerosis, gonarthritis and the like.

Furthermore, the compound of the present invention is also useful as a feeding deterrent.

The compound of the present invention can be also concurrently used with diet therapy (e.g., diet therapy for diabetes, etc.), or an exercise therapy.

The compound of the present invention can be used for preventing or treating pigmentation disorder based on abnormality of melanin or melanocyte. Here, as the pigmentation disorder, pigment proliferation, pigment decrease and the like can be mentioned. As the pigment proliferation, drug pigmentation caused by antitumor agent and the like; chromatosis and incompetence of pigment associated with diseases such as endocrine metabolism disorder (e.g., Addison's disease), genetic diseases, chronic hepatopathy, kidney failure, acanthosis nigricans, systemic scleroderma and the like; and the like can be mentioned. As the pigment decrease, phenylketonuria, systemic or localized albinism, foliaceous leukoderma or leukoderma vulgaris associated with tuberous sclerosis; depigmentation associated with systemic scleroderma and the like can be mentioned.

The compound of the present invention can be used for preventing or treating depigmentation due to chloasma, ephelides, sunburn and the like; and further, hyperpigmentation or hypopigmentation for cosmetic purposes.

The pharmaceutical composition of the present invention can be produced by formulating the compound of the present invention as it is or along with a pharmacologically acceptable carrier according to a method known per se.

As the pharmacologically acceptable carrier, various organic or inorganic carrier substance conventionally used as a material for preparation, such as excipient, lubricant, binder, disintegrant for solid preparation; solvent, dissolution aids, suspending agent, isotonicity agent, buffer, soothing agent and the like for liquid preparation are mentioned. In formulating a preparation, additives such as preservative, antioxidant, coloring agent, sweetening agent, absorbent, moistening agent and the like can be also added as necessary.

Examples of the excipient include lactose, saccharose, D-mannitol, starch, cornstarch, crystalline cellulose, light silicic anhydride and the like.

Examples of the lubricant include magnesium stearate, calcium stearate, talc, colloidal silica and the like.

Examples of the binder include crystalline cellulose, saccharose, D-mannitol, dextrin, hydroxypropyl cellulose, hydroxypropylmethyl cellulose, polyvinylpyrrolidone, starch, sucrose, gelatin, methyl cellulose, carboxymethyl cellulose sodium and the like.

Examples of the disintegrant include starch, carboxymethyl cellulose, carboxymethyl cellulose calcium, crosscarmellose sodium, carboxymethyl starch sodium, low substituted hydroxypropyl cellulose (L-HPC) and the like.

Examples of the solvent include water for injection, alcohol, propylene glycol, macrogol, sesame oil, corn oil and the like.

Examples of the dissolution aids include polyethylene glycol, propylene glycol, D-mannitol, benzyl benzoate, ethanol, tris-aminomethane, cholesterol, triethanolamine, sodium carbonate, sodium citrate and the like.

Examples of the suspending agent include surfactant such as stearyl triethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, carboxymethyl cellulose sodium, methyl cellulose, hydroxymethyl cellulose, hydroxyethyl cellulose, hydroxypropyl cellulose and the like, and the like.

Examples of the isotonicity agent include glucose, D-sorbitol, sodium chloride, glycerine, D-mannitol and the like.

Examples of the buffer include buffers such as phosphate, acetate, carbonate, citrate and the like and the like.

Examples of the soothing agent include benzyl alcohol and the like.

Examples of the preservative include p-oxybenzoic acid esters, chlorobutanol, benzyl alcohol, phenethyl alcohol, dehydroacetic acid, sorbic acid and the like.

Examples of the antioxidant include sulfite, ascorbic acid and the like.

Examples of the dosage form of a pharmaceutical composition of the present invention include oral preparations such as tablet (inclusive of sugar-coated tablet and firm coated tablet), powder, granule, capsule (inclusive of soft capsule), liquid and the like; parenteral preparations such as injection (e.g., subcutaneous injection, intravenous injection, intramuscular injection, intraperitoneal injection, etc.), external preparation (e.g., transnasal administration preparation, percutaneous preparation, ointment, etc.), suppository (e.g., rectal suppository, pessary, etc.), sustained-release preparation (e.g., sustained-release microcapsule, etc.), pellet, drops and the like; and the like, and can be safely administered orally or parenterally (e.g., topical, rectal, intravenous administration, etc.).

The content of the compound of the present invention in the pharmaceutical composition of the present invention is, for example, about 0.1 to 100 wt % of the whole amount of pharmaceutical composition.

The dose of the compound of the present invention is appropriately determined according to the administration subject, administration route, disease and the like.

For example, when the compound of the present invention is orally administered to adult patients (body weight about 60 kg) with obesity, the daily dose is about 0.1 to about 500 mg, preferably about 1 to about 100 mg, more preferably about 5 to about 100 mg, which dose is administered once or divided in several times a day.

With the aim of, for example, "enhancement of treatment effect against obesity", "enhancement of treatment effect against depression or anxiety", "reduction of the amount of MCH antagonist to be used" and the like, the compound of the present invention may be used along with a combination drug, which does not exert an adverse influence on the compound of the present invention. As such combination drug, for example, "antidiabetic agent", "agent for treating diabetic complication", "anti-obesity agent other than MCH antagonist", "agent for treating hypertension", "agent for treating hyperlipidemia (agent for treating arteriosclerosis), "agent for treating arthritis", "anti-anxiety agent", antidepressant" and the like are mentioned. These combination drugs may be used in a combination of two or more thereof in an appropriate proportion.

As the above-mentioned "antidiabetic agent", for example, insulin sensitizer, insulin secretagogue, biguanide agent, insulin, α-glucosidase inhibitor, β3 adrenergic receptor agonist and the like are mentioned.

As the insulin sensitizer, for example, pioglitazone or a salt thereof (preferably hydrochloride), troglitazone, rosiglitazone or a salt thereof (preferably maleate), Reglixane (JTT-501), GI-262570, Netoglitazone (MCC-555), YM-440, DRF-2593, BM-13-1258, KRP-297, R-119702, CS-011, FK-614, compounds described in WO99/58510 (e.g., (E)-4-[4-(5-methyl-2-phenyl-4-oxazolylmethoxy)benzyloxyimino]-4-phenylbutanoic acid), Tesaglitazar (AZ-242), Ragaglitazar (NN-622), BMS-298585, ONO-5816, BM-13-1258, LM-4156, MBX-102, LY-519818, MX-6054, LY-510929 and the like are mentioned.

As the insulin secretagogue, for example, sulfonylurea agent is mentioned. Examples of the sulfonylurea agent include tolbutamide, chlorpropamide, tolazamide, acetohexamide, glyclopyramide and ammonium salt thereof, glibenclamide, gliclazide, glimepiride and the like.

In addition to the above, insulin secretagogue includes, for example, repaglinide, nateglinide, mitiglinide (KAD-1229), JTT-608 and the like.

As the biguanide agent, for example, metformin, buformin, phenformin and the like are mentioned.

As the insulin, for example, animal insulin extracted from pancreas of cow and swine; semi-synthetic human insulin enzymatically synthesized from insulin extracted from pancreas of swine; human insulin genetically synthesized using *Escherichia coli* or yeast; and the like are mentioned. As insulin, insulin zinc containing 0.45 to 0.9 (w/w) % of zinc; protamine insulin zinc produced from zinc chloride, protamine sulfate and insulin, and the like can be also used. Moreover, insulin can be a fragment or derivative thereof (e.g., INS-1, etc.).

While insulin includes various types such as very rapid acting type, short-acting type, biphasic type, intermediate-acting type, extended type and the like, which can be determined depending on the disease state of patients.

As the α-glucosidase inhibitor, for example, acarbose, voglibose, miglitol, emiglitate and the like are mentioned.

As the β3 adrenergic receptor agonist, for example, AJ-9677, BMS-196085, SB-226552, AZ40140, CP-331684 and the like are mentioned.

In addition to the above, the "antidiabetic agent" includes, for example, ergoset, pramlintide, leptin, BAY-27-9955 and the like.

As the above-mentioned "agent for treating diabetes complication", for example, aldose reductase inhibitor, glycation inhibitor, protein kinase C inhibitor and the like are mentioned.

As the aldose reductase inhibitor, for example, tolrestat; epalrestat; imirestat; zenarestat; SNK-860; zopolrestat; ARI-509; AS-3201 and the like are mentioned.

As the glycation inhibitor, for example, pimagedine and the like are mentioned.

As the protein kinase C inhibitor, for example, NGF, LY-333531 and the like are mentioned.

In addition to the above, the "agent for treating diabetes complication" includes, for example, alprostadil, tiapride hydrochloride, cilostazol, mexiletine hydrochloride, ethyl icosapentate, memantine, pimagedline (ALT-711), neurotrophic factor and enhancer thereof (e.g., NGF, NT-3, BDNF, neurotrophin production/secretion promoters (e.g., 4-(4-chlorophenyl)-2-(2-methyl-1-imidazolyl)-5-[3-(2-methylphenoxy)propyl]oxazole, etc.) described in WO01/14372 and the like), neuranagenesis accelerating drug (e.g., Y-128, etc.) and the like.

As the above-mentioned "anti-obesity agent other than MCH antagonist", for example, lipase inhibitor, anorectic agent, β3 adrenergic receptor agonist and the like are mentioned.

As the lipase inhibitor, for example, orlistat, ATL-962 and the like are mentioned.

As the anorectic agent, for example, mazindol, dexfenfluramine, fluoxetine, sibutramine, biamine and the like are mentioned.

As the β3 adrenergic receptor agonist, "β3 adrenergic receptor agonist" exemplified for the above-mentioned "antidiabetic agent" can be mentioned.

In addition to the above, the "anti-obesity agent other than MCH antagonist" includes, for example, lipstatin and the like.

As the above-mentioned "agent for treating hypertension", for example, angiotensin converting enzyme inhibitor, calcium antagonist, potassium channel opener, angiotensin II antagonist and the like are mentioned.

As the angiotensin converting enzyme inhibitor, for example, captoril, enalapril, alacepril, delapril (hydrochrolide), lisinopril, imidapril, benazepril, cilazapril, temocapril, trandolapril, manidipine (hydrochrolide) and the like are mentioned.

As the calcium antagonist, for example, nifedipine, amlodipine, efonidipine, nicardipine and the like are mentioned.

As the potassium channel opener, for example, levcromakalim, L-27152, AL 0671, NIP-121 and the like are mentioned.

As the angiotensin II antagonist, for example, losartan, candesartan cilexetil, valsartan, irbesartan, CS-866, E4177 and the like are mentioned.

As the above-mentioned "agent for treating hyperlipidemia (agent for treating arteriosclerosis)", for example, HMG-CoA reductase inhibitor, fibrate compound and the like are mentioned.

As the HMG-CoA reductase inhibitor, for example, pravastatin, simvatatin, lovastatin, atorvastatin, fluvastatin, lipantil, cerivastatin, itavastatin, ZD-4522 or salts thereof (e.g., sodium salt, etc.) and the like are mentioned.

As the fibrate compound, for example, bezafibrate, clinofibrate, clofibrate, simfibrate and the like are mentioned.

As the above-mentioned "agent for treating arthritis", for example, ibuprofen and the like are mentioned.

As the above-mentioned "anti-anxiety agent", for example, chlordiazepoxide, diazepam, oxazolam, medazepam, cloxazolam, bromazepam, lorazepam, alprazolam, fludiazepam and the like are mentioned.

As the above-mentioned "antidepressant", for example, fluoxetine, fluvoxamine, imipramine, paroxetine, sertraline and the like are mentioned.

The time of administration of the aforementioned combination drug is not limited. The compound of the present invention and a combination drug may be simultaneously administered to an administration subject or administered in a staggered manner. The dose of the combination drug can be determined according to the dose clinically employed, and can be determined as appropriate depending on the administration subject, administration route, disease, combination and the like.

The mode of administration of the combination drug is not particularly limited, and may be any as long as the compound of the present invention and combination drug are combined on administration. Such administration mode is exemplified by 1) administration of a single preparation obtained by simultaneously formulating the compound of the present invention and combination drug(s), 2) simultaneous administration by the same administration route of two kinds of preparations obtained by separately formulating the compound of the present invention and combination drug(s), 3) staggered administration by the same administration route of two kinds of preparations obtained by separately formulating the compound of the present invention and combination drug, 4) simultaneous administration by different administration routes of two kinds of preparations obtained by separately formulating the compound of the present invention and combination drug, 5) staggered administration by different administration routes of two kinds of preparations obtained by separately formulating the compound of the present invention and combination drug (e.g., administration of compound of the present invention and combination drug in this order, and administration in the reversed order) and the like.

The admixing ratio of the compound of the present invention and combination drug can be appropriately determined depending on the administration subject, administration route, disease and the like.

The present invention is described in detail by way of the following Reference Examples, Examples, Formulation Examples and Experimental Examples. These are not intended to restrict the present invention, and may be modified within the range not deviating from the scope of this invention.

The "room temperature" in the following Reference Examples and Examples means a temperature of 0° C. to 30° C. For drying an organic layer, anhydrous magnesium sulfate or anhydrous sodium sulfate was employed. Unless otherwise specifically indicated, "%" means percent by weight.

The infrared spectrum was measured using Fourier transform infrared spectrophotometer by Diffuse Reflectance method.

FABMS(pos) is mass spectrum measured by the (+) method in the Fast Atom Bombardment Mass Spectrometry.

Other definitions used in the specification mean as follows.

s: singlet
d: doublet
t: triplet
q: quartet
m: multiplet
br: broad
J: coupling constant
Hz: Hertz
$CDCl_3$: deuterated chloroform
DMSO-d: deuterated dimethyl sulfoxide
THF: tetrahydrofuran
DMF: N,N-dimethylformamide
DMSO: dimethyl sulfoxide
WSCD: 1-ethyl-3-(3-dimethylaminopropyl)carbodiimide
WSC: 1-ethyl-3-(3-dimethylaminopropyl)carbodiimide hydrochloride
$^1$H-NMR: proton nuclear magnetic resonance (free compound is generally used for measurement in $CDCl_3$)
IR: infrared spectrum
Me: methyl
Et: ethyl
HOBt 1-hydroxy-1H-benzotriazole
IPE: diisopropyl ether
DMAP 4-dimethylaminopyridine In the present specification, when base, amino acid and the like are shown using abbreviations, they are based on abbreviations according to IUPAC-IUB Commission on Biochemical Nomenclature and conventional abbreviations employed in this field. Examples thereof are given in the following. When optical isomer is present due to amino acid, it is an L form unless particularly indicated.

DNA: deoxyribonucleic acid
cDNA: complementary deoxyribonucleic acid
A: adenine
T: thymine
G: guanine
C: cytosine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediamine tetraacetic acid
SDS: sodium dodecylsulfate
EIA: enzyme immunoassay
Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysin
Arg: arginine
His: histidine
Phe: phenylalanine
Tyr: thyrosin
Trp: tryptophan
Pro: proline
Asn: asparagine
Gln: glutamine
pGl: pyroglutamic acid
Me: methyl group
Et: ethyl group
Bu: butyl group
Ph: phenyl group
TC: thiazolidine-4(R)-carboxamide group Substituent, protecting group and reagent frequently appear in the present specification are shown using the following symbols.

Tos: p-toluenesulfonyl
CHO: formyl
Bzl: benzyl
$Cl_2$Bzl: 2,6-dichlorobenzyl
Bom: benzyloxymethyl
Z: benzyloxycarbonyl
Cl-Z: 2-chlorobenzyloxycarbonyl
Br-Z: 2-bromobenzyloxycarbonyl
Boc: t-butoxycarbonyl
DNP: dinitrophenol
Trt: trityl
Bum: t-butoxymethyl
Fmoc: N-9-fluorenylmethoxycarbonyl
HOBt: 1-hydroxybenztriazole
HOOBt: 3,4-dihydro-3-hydroxy-4-oxo-1,2,3-benzotriazine
HONB: 1-hydroxy-5-norbornene-2,3-dicarboxyimide
DCC: N,N'-dicyclohexylcarbodiimide The sequence numbers in the Sequence Listing in the present specification show the following sequences.

[SEQ ID NO:1]
Synthetic DNA used for screening cDNA encoding rat SLC-1.

[SEQ ID NO:2]
Synthetic DNA used for screening cDNA encoding rat SLC-1.

[SEQ ID NO:3]
Full length amino acid sequence of rat SLC-1.

[SEQ ID NO:4]
Full length base sequence of rat SLC-1 cDNA comprising Sal I recognition sequence added on the 5' side and Spe I recognition sequence added on the 3' side.

[SEQ ID NO:5]
Riboprobe used for the determination of expression amount of SLC-1 mRNA in each clone of rat SLC-1 expression CHO cells.

[SEQ ID NO:6]
Synthetic DNA used for obtaining cDNA encoding human SLC-1.

[SEQ ID NO:7]
Primer used to make cDNA encoding human SLC-1 double-stranded.

[SEQ ID NO:8]
Full length base sequence of cDNA encoding human SLC-1.

[SEQ ID NO:9]
Full length amino acid sequence of human SLC-1.

[SEQ ID NO:10]
Synthetic DNA used for screening cDNA encoding human SLC-1 (S).

[SEQ ID NO:11]
Synthetic DNA used for screening cDNA encoding human SLC-1 (S).

[SEQ ID NO:12]
Synthetic DNA used for screening cDNA encoding human SLC-1 (L).

[SEQ ID NO:13]
Synthetic DNA used for screening cDNA encoding human SLC-1 (L).

[SEQ ID NO:14]
Full length base sequence of human SLC-1(S) cDNA comprising Sal I recognition sequence added on the 5' side and Spe I recognition sequence added on the 3' side.

[SEQ ID NO:15]
Full length base sequence of human SLC-1 (L) cDNA comprising Sal I recognition sequence added on the 5' side and Spe I recognition sequence added on the 3' side.

[SEQ ID NO:16]
Riboprobe used for the determination of expression amount of SLC-1 mRNA in each clone of human SLC-1 (S) expression CHO cells and human SLC-1 (L) expression CHO cells.

The transformant *Escherichia coli* DH10B/phSLC1L8 with a plasmid containing DNA encoding the base sequence obtained in Reference Examples 1–6, which is depicted in SEQ:No. 9 has been deposited at International Patent Organism Depositary, National Institute of Advanced Industrial Science and Techonology located at Center No. 6, 1-1, Higashi 1-chome, Tsukuba-shi, Ibaraki 305-5466, Japan, under deposit No. FERM BP-6632 since Feb. 1, 1999; and at the Institute for Fermentation, Osaka (IFO) located at 2-17-85, Jusohonmachi, Yodogawa-ku, Osaka-shi, Osaka 532-8686, Japan, under deposit No. IFO 16254 since Jan. 21, 1999.

EXAMPLES

Reference Example 1

N-[3-(hydroxymethyl)-7-quinolinyl]acetamide

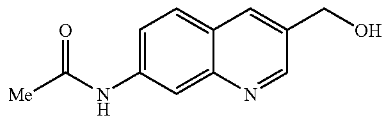

To a suspension of N-(3-(formyl-7-quinolinyl)acetamide (5.68 g, 26.5 mmol) in ethanol (60 ml) was added sodium borohydride (2.01 g, 53.0 mmol) at 0° C., and the mixture was stirred at room temperature for 3 hrs. Ethyl acetate was added to the reaction solution, and the mixture was washed with saturated brine and dried over anhydrous sodium sulfate.

The solvent was concentrated under reduced pressure and the obtained residue was treated with ethyl acetate to give the title compound (4.47 g) as a powder.

$^1$H NMR(DMSO-$d_6$) δ 2.12(3H,s), 4.67(2H,d,J=5.4 Hz), 5.40(1H,t,J=5.4 Hz), 7.67(1H,dd,J=1.8,9.0 Hz), 7.88(1H,d, J=9.0 Hz), 8.12(1H,s), 8.39(1H,s), 8.78(1H,d,J=1.8 Hz), 10.27(1H,s).

Reference Example 2

N-[3-(chloromethyl)-7-quinolinyl]acetamide hydrochloride

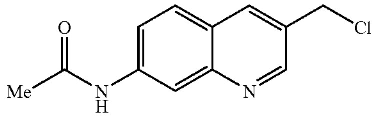

•HCl

N-[3-(Hydroxymethyl)-7-quinolinyl]acetamide (4.47 g, 20.7 mmol) obtained in Reference Example 1 was added to thionyl chloride (60 ml) at 0° C., and the mixture was stirred at room temperature for 2 hrs.

The reaction solution was concentrated under reduced pressure and the obtained residue was treated with isopropyl ether to give the title compound (5.55 g) as a powder.

$^1$H NMR ($CD_3OD$) δ 2.27 (3H, s), 5.02 (2H, s), 7.82 (1H, dd, J=1.8, 9.0 Hz), 8.27 (1H, d, J=9.0 Hz), 9.03 (1H, d, J=1.8 Hz), 9.14 (1H, s), 9.20 (1H, d, J=1.8 Hz).

Reference Example 3

N-{3-[(dimethylamino)methyl]-7-quinolinyl}acetamide

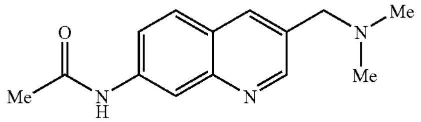

A solution of N-[3-(chloromethyl)-7-quinolinyl]acetamide hydrochloride (200 mg, 0.738 mmol) obtained in Reference Example 2, dimethylamine hydrochloride (601 mg, 7.38 mmol) and potassium carbonate (1.02 g, 7.38 mmol) in dimethylformamide (3.5 ml) was stirred at 80° C. for 3 hrs.

Ethyl acetate was added to the reaction solution and the mixture was washed with saturated brine and dried over anhydrous sodium sulfate. The solvent was concentrated under reduced pressure and the obtained residue was purified by alumina column chromatography (developing solvent; ethyl acetate) to give the title compound (179 mg) as an oil.

$^1$H NMR($CDCl_3$) δ 2.24(3H,s), 2.29(6H,s), 3.59(2H,s) 7.73(1H,d,J=8.8 Hz), 7.93–8.09(4H,m), 8.82(1H,d,J=1.8 Hz).

Reference Example 4

N-[(7-amino-3-quinolinyl)methyl]-N,N-dimethylamine

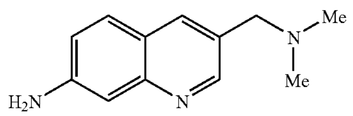

A solution of N-{3-[(dimethylamino)methyl]-7-quinolinyl}acetamide (179 mg, 0.738 mmol) obtained in Reference Example 3 in concentrated hydrochloric acid (3 ml) was stirred at 100° C. for 2 hrs.

The reaction solution was basified by adding potassium carbonate and the mixture was extracted with ethyl acetate. The extract was washed with saturated brine and dried over anhydrous sodium sulfate. The solvent was concentrated under reduced pressure and the obtained residue was purified by alumina column chromatography (developing solvent; ethyl acetate) to give the title compound (87.8 mg) as an oil.

$^1$H NMR ($CDCl_3$) δ 2.28(6H,s), 3.54(2H,s) 4.06(2H,br) 6.97(1H,dd,J=8.7, 1.6 Hz), 7.21(1H,d,J=1.6 Hz), 7.59(1H, d,J=8.7 Hz), 7.89(1H,d,J=1.4 Hz), 8.69(1H,d,J=1.4 Hz).

Reference Example 5

3-(1-pyrrolidinylmethyl)-7-quinolinylamine hydrochloride

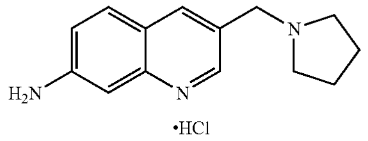

By successively operating in the same manner as in Reference Example 3 and Reference Example 4 and using N-[3-(chloromethyl)-7-quinolinyl]acetamide obtained in Reference Example 2, the title compound was obtained.

$^1$H NMR ($CD_3OD$) δ 2.11(4H,m), 3.40(4H,m), 4.54(2H, m), 7.02(1H,d,J=2.4 Hz), 7.19(1H,dd,J=9.0, 2.1 Hz), 7.78 (1H,d,J=9.0 Hz), 8.46(1H,d,J=2.4 Hz), 8.74(1H,d,J=2.1 Hz).

Reference Example 6

N-[3-(hydroxymethyl)-8-methyl-7-quinolinyl]acetamide

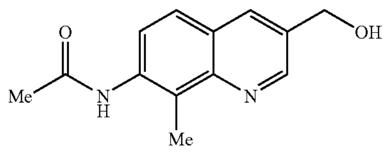

A solution of N-(3-amino-2-methylphenyl)acetamide (1.00 g, 6.09 mmol) and 2-dimethylaminomethylene-1,3-bis (dimethylimmonio)propane bis-tetrafluoroborate (6.52 g, 18.3 mmol) in ethanol (60 ml) was stirred at an oil bath temperature of 100° C. for one day. After allowing to cool to room temperature, the solvent was evaporated under reduced pressure. The residue was dissolved in tetrahydrofuran (30 ml) and 1N hydrochloric acid (30 ml) and the solution was stirred at room temperature for 3 hrs. The solvent was evaporated, the mixture was basified by adding an aqueous potassium carbonate solution, and the resulting precipitate was collected and washed with water. To a suspension of the obtained precipitate in ethanol (30 ml) was added sodium borohydride (461 mg, 12.2 mmol) at 0° C., and the mixture was stirred at room temperature for 3 hrs. Ethyl acetate was added to the reaction solution and the mixture was washed with saturated brine and dried over anhydrous sodium sulfate. The solvent was concentrated under reduced pressure and the obtained residue was treated with ethyl acetate to give the title compound (575 mg) as a powder.

$^1$H NMR (DMSO-$d_6$) δ 2.13 (3H, s), 2.62 (3H, s), 4.71 (2H, d, J=5.4 Hz), 5.42 (1H, t, J=5.4 Hz), 7.70 (2H, m), 8.16 (1H, s), 8.85 (1H, s), 9.65 (1H, s).

Reference Example 7

N-[8-methyl-3-(1-pyrrolidinylmethyl)-7-quinolinyl]acetamide

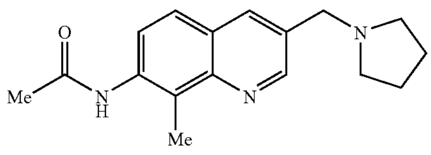

By successively operating in the same manner as in Reference Example 2 and Reference Example 3 and using N-[3-(hydroxymethyl)-8-methyl-7-quinolinyl]acetamide obtained in Reference Example 6, the title compound was obtained.

$^1$H NMR ($CDCl_3$) δ 1.81 (4H, m), 2.29 (3H, s), 2.58 (4H, m), 2.74 (3H, s), 3.80 (2H, s), 7.30 (1H, br), 7.65 (1H, d, J=8.7 Hz), 8.05 (2H, m), 8.88 (1H, d, J=1.8 Hz).

Reference Example 8

N-[3-(hydroxymethyl)-6-methoxy-7-quinolinyl]acetamide

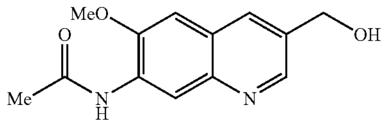

1) 2-Dimethylaminomethylene-1,3-bis(dimethylimmonio)propane bis-tetrafluoroborate (39.6 g, 111 mmol) was suspended in ethanol (550 ml). To the obtained suspension was added N-(5-amino-2-methoxyphenyl)acetamide (10.0 g, 55.5 mmol) and the mixture was stirred at an oil bath temperature of 90° C. for 24 hrs. Tetrahydrofuran (275 ml) and 1N hydrochloric acid (275 ml) were added to the reaction solution and the mixture was stirred at room temperature for 5 hrs. Tetrahydrofuran was evaporated under reduced pressure and the residue was ice-cooled. Chloroform (40 ml) was added and the mixture was neutralized by adding potassium carbonate. The precipitated crystals were collected by filtration, washed with water and dried to give yellow crystals (38.44 g).

2) Sodium borohydride (4.20 g, 111 mmol) was suspended in ethanol (400 ml) and the suspension was ice-cooled. The yellow crystals (38.44 g) obtained in the above 1) were added to the reaction solution and the mixture was stirred at room temperature for 5 hrs. Ethanol was evaporated under reduced pressure, ethyl acetate (500 ml) and saturated brine (400 ml) were added to the residue and the mixture was stirred vigorously. After removing insoluble materials, the aqueous phase and an organic phase were separated, and the aqueous phase was extracted twice with ethyl acetate (250 ml). The extract and the aforementioned organic phase were combined and dried over magnesium sulfate. The obtained residue was concentrated under reduced pressure to give the title compound (7.08 g) as yellow crystals.

$^1$H NMR (DMSO-$d_6$) δ 2.19 (3H, s), 3.98 (3H, s), 4.66 (2H, s), 5.43 (1H, br s), 7.40 (1H, s), 8.06 (1H, d, J=1.0 Hz), 8.65 (1H, d, J=2.0 Hz), 8.70 (1H, s), 9.38 (1H, s).

Reference Example 9

N-[3-(chloromethyl)-6-methoxy-7-quinolinyl]acetamide hydrochloride

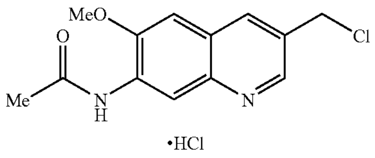

N-[3-(Hydroxymethyl)-6-methoxy-7-quinolinyl]acetamide (7.08 g, 28.8 mmol) obtained in Reference Example 8 was dissolved in thionyl chloride (20 ml) and the mixture was stirred at room temperature for 6.5 hrs. Excess thionyl chloride was evaporated under reduced pressure and toluene was added to the residue. The mixture was concentrated to dryness to give the title compound (6.95 g) as yellow crystals.

$^1$H NMR (DMSO-$d_6$) δ 2.28 (3H, s), 4.09 (3H, s), 5.12 (2H, s), 7.85 (1H, s), 9.01 (1H, s), 9.15 (1H, d, J=2.0 Hz), 9.23 (1H, s), 9.96 (1H, s).

Reference Example 10

N-[3-[(diethylamino)methyl]-6-methoxy-7-quinolinyl]acetamide

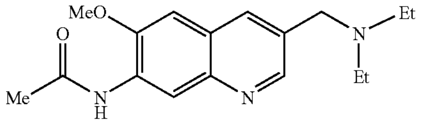

N-[3-(Chloromethyl)-6-methoxy-7-quinolinyl]acetamide hydrochloride (2.00 g, 6.64 mmol) obtained in Reference Example 9 was dissolved in DMF (20 ml) and the mixture was ice-cooled. Diethylamine (3.43 ml, 33.20 mmol) was added to the reaction solution, and the mixture was stirred for 14 hrs. at room temperature. Ethyl acetate was added to the reaction solution, and the mixture was washed twice with a mixed solution of saturated brine (50 ml) and water (50 ml). The organic phase was concentrated under reduced pressure, and the residue was purified by NH-silica gel column to give the title compound (1.16 g) as a brown liquid.

$^1$H NMR ($CDCl_3$) δ 1.07 (6H, t, J=7.1 Hz), 2.27 (3H, s), 2.56 (4H, q, J=7.1 Hz), 3.70 (2H, s), 4.01 (3H, s), 7.04 (1H, s), 7.92 (1H, d, J=1.2 Hz), 8.01 (2H, m), 8.72 (1H, d, J=2.0 Hz).

Reference Example 11

N-[6-methoxy-3-(1-pyrrolidinylmethyl)-7-quinolinyl]acetamide

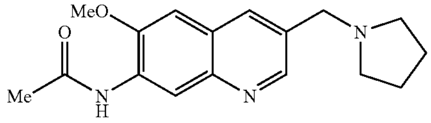

By successively operating in the same manner as in Reference Example 10 and using N-[3-(chloromethyl)-6-methoxy-7-quinolinyl]acetamide hydrochloride obtained in Reference Example 9, the title compound was obtained as a pale-yellow oil.

$^1$H NMR ($CDCl_3$) δ 1.69 (4H, m), 2.27 (3H, s), 2.42 (4H, m) 3.61 (2H, s), 4.01 (3H, s), 7.04 (1H, s), 7.90 (1H, d, J=1.2 Hz), 8.00 (1H, br s), 8.01 (1H, s), 8.71 (1H, d, J=2.0 Hz).

Reference Example 12

N-[6-methoxy-3-(1-piperidinylmethyl)-7-quinolinyl]acetamide

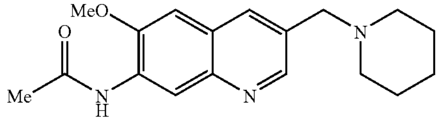

By successively operating in the same manner as in Reference Example 10 and using N-[3-(chloromethyl)-6-methoxy-7-quinolinyl]acetamide hydrochloride obtained in Reference Example 9, the title compound was obtained as a pale-yellow oil.

$^1$H NMR ($CDCl_3$) δ 1.44 (2H, m), 1.58 (4H, m), 2.27 (3H, s), 2.55 (4H, m), 3.76 (2H, s), 4.01 (3H, s), 7.03 (1H, s), 7.93 (1H, d, J=1.5 Hz), 8.00 (1H, br s), 8.01 (1H, s), 8.73 (1H, d, J=2.2 Hz).

Reference Example 13

3-[(diethylamino)methyl]-6-methoxy-7-quinolinylamine

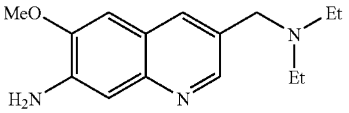

N-[3-[(Diethylamino)methyl]-6-methoxy-7-quinolinyl]acetamide (1.16 g, 3.85 mmol) obtained in Reference Example 10 was dissolved in 6N hydrochloric acid (20 ml) and the mixture was stirred at 100° C. for 3 hrs. The reaction solution was ice-cooled, 4N aqueous sodium hydroxide solution was added, and the mixture was adjusted to pH 10. The reaction solution was extracted with ethyl acetate (100 ml) and the organic layer was concentrated under reduced pressure. The residue was purified by NH-silica gel column to give the title compound (810 mg) as yellow crystals.

$^1$H NMR ($CDCl_3$) δ 1.06 (6H, t, J=7.1 Hz), 2.55 (4H, q, J=7.1 Hz), 3.67 (2H, s), 3.97 (3H, s), 4.27 (2H, br s), 6.94 (1H, s), 7.22 (1H, s), 7.86 (1H, d, J=1.7 Hz), 8.58 (1H, d, J=2.0 Hz).

Reference Example 14

6-methoxy-3-(1-pyrrolidinylmethyl)-7-quinolinylamine

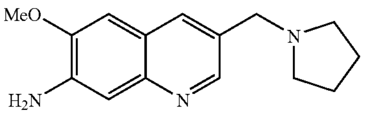

N-[6-Methoxy-3-(1-pyrrolidinylmethyl)-7-quinolinyl]acetamide (1.28 g, 4.28 mmol) obtained in Reference Example 11 was dissolved in 6N hydrochloric acid (20 ml) and the mixture was stirred at 100° C. for 3 hrs. The reaction solution was ice-cooled, 4N aqueous sodium hydroxide solution was added, and the mixture was adjusted to pH 10. The reaction solution was extracted with ethyl acetate (100 ml) and the organic layer was concentrated under reduced pressure. The residue was purified by NH-silica gel column to give the title compound (816 mg) as yellow crystals.

$^1$H NMR ($CDCl_3$) δ 1.79 (4H, m), 2.54 (4H, m), 3.72 (2H, s), 3.97 (3H, s), 4.28 (2H, br s), 6.94 (1H, s), 7.21 (1H, s), 7.87 (1H, d, J=2.0 Hz), 8.60 (1H, d, J=2.0 Hz).

Reference Example 15

6-methoxy-3-(1-piperidinylmethyl)-7-quinolinylamine

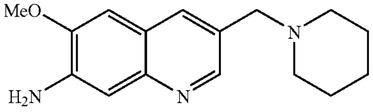

N-[6-Methoxy-3-(1-pyrrolidinylmethyl)-7-quinolinyl]acetamide (1.48 g, 4.94 mmol) obtained in Reference Example 12 was dissolved in 6N hydrochloric acid (20 ml) and the mixture was stirred at 100° C. for 3 hrs. The reaction solution was ice-cooled, 4N aqueous sodium hydroxide solution was added, and the mixture was adjusted to pH 10.

The reaction solution was extracted with ethyl acetate (100 ml) and the organic layer was concentrated under reduced pressure. The residue was purified by NH-silica gel column to give the title compound (800 mg) as yellow crystals.

$^1$H NMR ($CDCl_3$) δ 1.44 (2H, m), 1.57 (4H, m), 2.41 (4H, m), 3.57 (2H, s), 3.98 (3H, s), 4.27 (2H, br s), 6.90 (1H, s), 7.21 (1H, s), 7.84 (1H, d, J=1.7 Hz), 8.57 (1H, d, J=2.2 Hz).

Reference Example 16

N-[6-chloro-3-(hydroxymethyl)-7-quinolinyl]acetamide

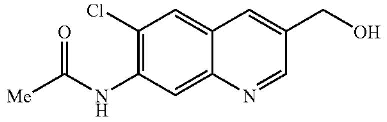

By successively operating in the same manner as in Reference Example 8 and using N-(5-amino-2-chlorophenyl)acetamide, the title compound was obtained as yellow crystals.

$^1$H NMR (DMSO-$d_6$) δ 2.12 (3H, s), 7.42 (1H, d, J=8.8 Hz), 4.66 (2H, s), 7.56 (1H, d, J=8.8 Hz), 7.94 (1H, s), 9.48 (1H, s), 9.63 (1H, s), 9.81 (1H, s).

Reference Example 17

N-[6-chloro-3-(1-pyrrolidinylmethyl)-7-quinolinyl]acetamide

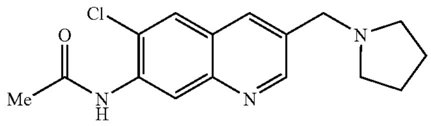

By successively operating in the same manner as in Reference Example 8 and Reference Example 9 and using N-[6-chloro-3-(hydroxymethyl)-7-quinolinyl]acetamide obtained in Reference Example 16, the title compound was obtained as brown crystals.

$^1$H NMR ($CDCl_3$) δ 1.81 (4H, m), 2.30 (3H, s), 2.55 (4H, m), 3.77 (2H, s), 7.08 (1H, d, J=8.5 Hz), 7.80 (1H, br s), 7.82 (1H, s), 7.93 (1H, d, J=1.2 Hz), 8.86 (1H, d, J=2.2 Hz).

Reference Example 18

6-chloro-3-(1-pyrrolidinylmethyl)-7-quinolinylamine

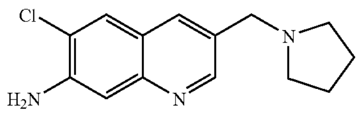

By successively operating in the same manner as in Reference Example 13 and using N-[6-chloro-3-(1-pyrrolidinylmethyl)-7-quinolinyl]acetamide obtained in Reference Example 17, the title compound was obtained as pale-yellow crystals.

$^1$H NMR ($CDCl_3$) δ 1.80 (4H, m), 2.54 (4H, m), 3.72 (2H, s), 4.42 (2H, br s), 7.32 (1H, s), 7.74 (1H, s), 7.85 (1H, m), 8.72 (1H, d, J=2.2 Hz).

Reference Example 19

N-[3-(1-azepanylmethyl)-7-quinolinyl]acetamide

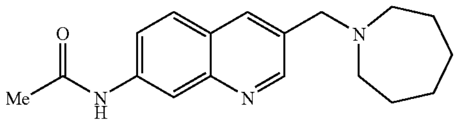

By successively operating in the same manner as in Reference Example 3 and using N-[3-(chloromethyl)-7-quinolinyl]acetamide obtained in Reference Example 2, the title compound was obtained.

$^1$H NMR ($CDCl_3$) δ 1.63 (8H, m), 2.24 (3H, s), 2.66 (4H, m), 3.79 (2H, s), 7.28 (1H, s), 7.73 (1H, d, J=8.8 Hz), 7.97 (1H, m), 8.08 (1H, s), 8.49 (1H, br s), 8.86 (1H, m).

Reference Example 20

3-(1-azepanylmethyl)-7-quinolinylamine

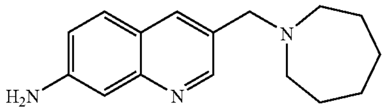

By successively operating in the same manner as in Reference Example 4 and using N-[3-(1-azepanylmethyl)-7-quinolinyl]acetamide obtained in Reference Example 19, the title compound was obtained.

$^1$H NMR ($CDCl_3$) δ 1.62 (8H, m), 2.65 (4H, m), 3.74 (2H, s), 4.02 (2H, br s), 6.96 (1H, dd, J=2.2, 8.5 Hz), 7.20 (1H, d, J=2.2 Hz), 7.58 (1H, d, J=8.5 Hz), 7.89 (1H, d, J=1.2 Hz), 8.74 (1H, d, J=2.2 Hz).

Reference Example 21

6-methyl-3-(1-pyrrolidinylmethyl)-7-quinolinylamine

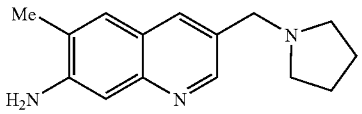

By successively operating in the same manner as in Reference Example 6, Reference Example 2, Reference Example 3 and Reference Example 4 and using N-(5-amino-2-methylphenyl) acetamide, the title compound was obtained.

$^1$H-NMR($CDCl_3$) δ 1.72–1.82 (4H, m), 2.34 (3H, s), 2.48–2.62 (4H, m), 3.71 (2H, s), 4.02 (2H, br), 7.22 (1H, s), 7.44 (1H, s), 7.86 (1H, s), 8.66 (1H, d, J=2.1 Hz).

Reference Example 22

N-[3-(chloromethyl)-7-quinolinyl]-4'-fluoro[1,1'-biphenyl]-4-carboxamide

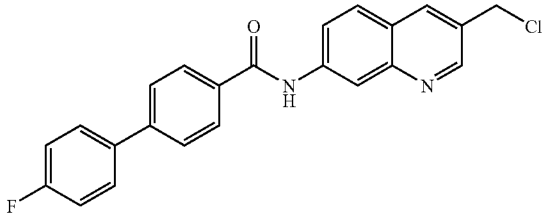

To a suspension of 4'-fluoro-N-[3-(1-pyrrolidinylmethyl)-7-quinolinyl][1,1'-biphenyl-4-carboxamide (550 mg, 1.29 mmol) in THF (6.5 mL) was added ethyl chlorocarbonate (0.245 mL, 2.59 mmol) and the mixture was stirred at room temperature for 4 hrs. Saturated aqueous sodium hydrogen carbonate solution was added and the mixture was extracted with ethyl acetate. The extract was washed with saturated brine and dried over anhydrous magnesium sulfate. The solvent was evaporated under reduced pressure and the obtained residue was treated with isopropyl ether to give the title compound (447 mg) as a powder.

$^1$H-NMR (DMSO-$d_6$) δ 5.02 (2H, s), 7.34 (1H, d, J=8.8 Hz), 7.39 (1H, d, J=8.8 Hz), 7.79–7.92 (4H, m), 7.99–8.05 (2H, m), 8.14 (2H, d, J=8.4 Hz), 8.39 (1H, m), 8.65 (1H, s), 8.93 (1H, d, J=2.2 Hz), 10.70 (1H, s).

Reference Example 23

N-[6-fluoro-3-(hydroxymethyl)-7-quinolinyl]acetamide

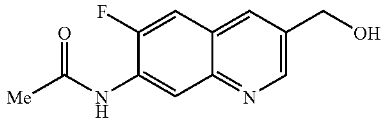

By successively operating in the same manner as in Reference Example 6 and using N-(5-amino-2-fluorophenyl) acetamide, the title compound was obtained.

$^1$H-NMR (DMSO-$d_6$) δ 2.18 (3H, s), 4.69 (2H, d, J=5.6 Hz), 5.44 (1H, t, J=5.6 Hz), 7.83 (1H, d, J=11.8 Hz), 8.15 (1H, s), 8.67 (1H, d, J=7.6 Hz), 8.78 (1H, s), 9.98 (1H, s).

Reference Example 24

N-[3-(chloromethyl)-6-fluoro-7-quinolinyl]acetamide hydrochloride

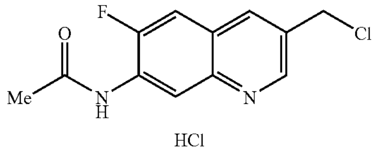

By successively operating in the same manner as in Reference Example 2 and using N-[6-fluoro-3-(hydroxymethyl)-7-quinolinyl]acetamide obtained in Reference Example 23, the title compound was obtained.

$^1$H-NMR ($CD_3OD$) δ 2.33 (3H, s), 5.02 (2H, s), 8.13 (1H, d, J=11.0 Hz), 9.11 (1H, s), 9.22 (1H, d, J=2.0 Hz), 9.35 (1H, d, J=6.8 Hz).

Reference Example 25

6-fluoro-3-(1-pyrrolidinylmethyl)-7-quinolinylamine

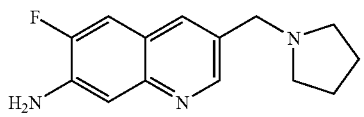

By successively operating in the same manner as in Reference Example 3 and Reference Example 4 and using N-[3-(chloromethyl)-6-fluoro-7-quinolinyl]acetamide hydrochloride obtained in Reference Example 24, the title compound was obtained.

$^1$H-NMR ($CDCl_3$) δ 1.80 (4H, m), 2.52 (4H, m), 3.73 (2H, s), 4.24 (2H, br), 7.32 (2H, m), 7.89 (1H, s), 8.69 (1H, d, J=1.5 Hz).

Reference Example 26

N-[5-amino-2-(1-pyrrolidinyl)phenyl]-4-bromobenzamide

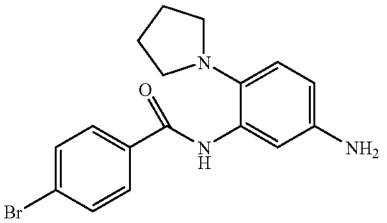

To a solution of 4-bromo-N-(2-fluoro-5-nitrophenyl)benzamide (5.00 g, 14.7 mmol) in dimethyl sulfoxide (25 ml) was added pyrrolidine (6.15 ml, 73.7 mmol) and the mixture was stirred at 60° C. for 30 min. Water was added to the reaction solution, and the resulting precipitate was collected and washed with water. An aqueous solution (180 ml) of the obtained precipitate, reduced iron (4.12 g, 73.7 mmol) and calcium chloride (818 mg, 7.37 mmol) in 85% ethanol was refluxed under heating for 3 hrs. and allowed to cool. After celite filtration, the filtrate was concentrated and water was added to give N-[5-amino-2-(1-pyrrolidinyl)phenyl-4-bromobenzamide (5.00 g).

$^1$H-NMR (DMSO-$d_6$) δ 1.85 (4H, m), 2.91 (4H, m), 4.91 (2H, br), 6.35 (1H, d, J=8.7 Hz), 6.91 (1H, d, J=8.7 Hz), 7.27 (1H, s), 7.75 (2H, d, J=8.4 Hz), 7.82 (2H, d, J=8.4 Hz), 9.66 (1H, s).

Reference Example 27

4-bromo-N-[3-formyl-6-(1-pyrrolidinyl)-7-quinolinyl]benzamide

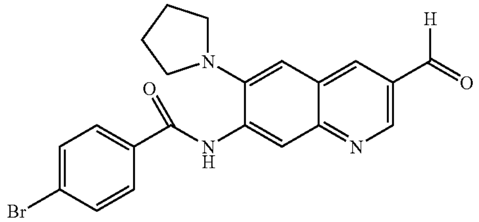

By successively operating in the same manner as in Reference Example 8-1) and using N-[5-amino-2-(1-pyrrolidinyl)phenyl]-4-bromobenzamide obtained in Reference Example 26, the title compound was obtained.

$^1$H-NMR (DMSO-$d_6$) δ 1.91 (4H, m), 3.34 (4H, m), 7.41 (1H, s), 7.78 (2H, d, J=8.4 Hz), 7.99 (2H, d, J=8.4 Hz), 8.07 (1H, s), 8.72 (1H, s), 9.00 (1H, d, J=2.2 Hz), 10.18 (1H, s), 10.34 (1H, s).

Reference Example 28

N-(2-fluoro-3-nitrophenyl)acetamide

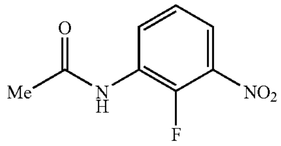

To a solution (233 mL) of 2-fluoro-3-nitroaniline (18.2 g, 116 mol) in pyridine was added acetic anhydride (27.4 mL, 291 mmol) and the mixture was stirrred at room temperature for 16 hrs. The reaction solution was concentrated under reduced pressure and the obtained residue was treated with isopropyl ether to give the title compound (19.2 g) as a powder.

$^1$H-NMR($CDCl_3$) δ 2.30 (3H, s), 7.24–7.34 (1H, m), 7.56–7.70 (1H, br), 7.72–7.81 (1H, m), 8.64–8.72 (1H, m).

Reference Example 29

N-(3-amino-2-fluorophenyl)acetamide

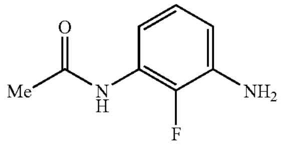

To a solution (183 mL) of N-(2-fluoro-3-nitrophenyl) acetamide (18.2 g, 91.7 mmol) obtained in Reference Example 28 in ethanol were added 10% palladium carbon (1.82 g) and cyclohexene (27.9 mL, 275 mmol) and the mixture was stirred under a nitrogen stream at 60° C. for 21 hrs. Reaction liquid mixture was filtered after cooling in room temperature. The reaction solution was concentrated under reduced pressure and the obtained residue was treated with isopropyl ether to give the title compound (14.2 g) as a powder.

$^1$H-NMR($CDCl_3$) δ 2.20 (3H, s), 3.62–3.82 (2H, br), 6.48–6.58 (1H, m), 6.85–6.94 (1H, m), 7.28–7.46 (1H, br), 7.56–7.76 (1H, m).

Reference Example 30

8-fluoro-3-(1-pyrrolidinylmethyl)-7-quinolinamine

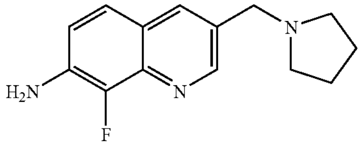

By successively operating in the same manner as in Reference Example 6, Reference Example 2, Reference Example 3 and Reference Example 4 and using N-(3-amino-2-fluorophenyl) acetamide obtained in Reference Example 29, the title compound was obtained.

$^1$H-NMR($CDCl_3$) δ 1.80 (4H, m), 2.55 (4H, m), 3.75 (2H, s), 4.11 (2H, br), 7.06 (1H, m), 7.40 (1H, d, J=8.7 Hz), 7.96 (1H, m), 8.80 (1H, d, J=2.1 Hz).

Reference Example 31

2-methoxy-3-nitrobenzoic acid

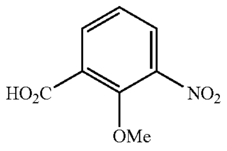

1N Sodium hydroxide was added to a solution (50 ml) of methyl 2-methoxy-3-nitrobenzoate (4.96 g, 23.5 mmol) in methanol and the mixture was stirred at 50° C. for 2 hrs. Methanol was evaporated under reduced pressure and water was added. The aqueous layer was acidified with 1N hydrochloric acid, and the mixture was extracted with ethyl acetate. The organic layer was washed with saturated brine, and dried over anhydrous magnesium sulfate, filtered and concentrated under reduced pressure. The obtained residue was recrystallized from hexane-ethyl acetate to give the title compound (4.37 g) as pale-yellow crystals. melting point: 224–226° C.

$^1$H-NMR ($CDCl_3$) δ 4.02 (3H, s), 7.25–7.34 (1H, m), 7.91 (1H, ddd, J=0.6, 1.8, 8.0 Hz), 8.10 (1H, ddd, J=0.8, 1.8, 8.4 Hz).

Reference Example 32

4-bromo-N-(2-methoxy-3-nitrophenyl)benzamide

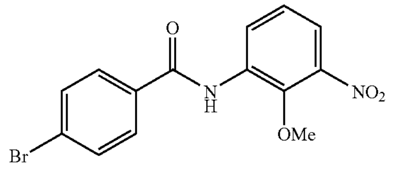

To a solution (350 ml) of 2-methoxy-3-nitrobenzoic acid (9.25 g, 46.9 mmol) obtained in Reference Example 31 in tert-butanol was added triethylamine (9.9 ml, 70.35 mmol) and diphenylphosphoryl azide (11.2 ml, 51.6 mmol), and the mixture was heated under reflux for 5 hrs. The solvent was evaporated under reduced pressure and purified by silica gel column chromatography (hexane:ethyl acetate) to give the object compound as a mixture (13.0 g) with diphenylphosphoryl azide. To a solution (50 ml) of this mixture in ethyl acetate was added 4N hydrogen chloride-ethyl acetate (100 ml), and the mixture was stirred at 50° C. for 2 hrs. The mixture was concentrated under reduced pressure and the resulting crystals were washed with diisopropyl ether. To a suspension (150 ml) of the crystals in tetrahydrofuran was added 4-bromobenzoyl chloride (10.0 g, 45.8 mmol) and triethylamine (17.5 ml, 125 mmol) was added dropwise under ice-cooling. The mixture was stirred at room temperature for 4 hrs. The mixture was diluted with ethyl acetate, washed with 1N sodium hydroxide, water and saturated brine, dried over anhydrous magnesium sulfate, filtered and concentrated under reduced pressure. The obtained residue was recrystallized from hexane-ethyl acetate to give the title compound (14.2 g) as pale-yellow crystals.

$^1$H-NMR ($CDCl_3$) δ 3.99 (3H, s), 7.24–7.33 (1H, m), 7.64–7.79 (5H, m), 8.53 (1H, br) 8.78 (1H, dd, J=1.8, 8.4 Hz). melting point: 162–163° C.

Reference Example 33

N-(3-amino-2-methoxyphenyl)-4-bromobenzamide

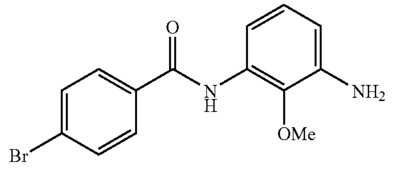

To an aqueous solution (440 ml) of 4-bromo-N-(2-methoxy-3-nitrophenyl)benzamide (14.21 g, 40.5 mmol) obtained in Reference Example 32 in 90% ethanol were added reduced iron (11.3 g, 20.3 mmol) and calcium chloride. (2.25 g, 20.3 mmol), and the mixture was stirred at 100° C. for 4 hrs. Iron was Celite filtered, and the filtrate was washed with ethanol. Ethanol was evaporated under reduced pressure. The residue was diluted with ethyl acetate and washed with water and saturated brine, dried over anhydrous magnesium sulfate, filtered and concentrated under reduced pressure. The residue was recrystallized from hexane-ethyl acetate to give the title compound (11.18 g) as colorless crystals.

$^1$H-NMR ($CDCl_3$) δ 3.76–3.82 (5H, m), 6.54 (1H, dd, J=1.2, 7.8 Hz), 6.94–6.99 (1H, m), 7.62–7.65 (2H, m), 7.73–7.77 (2H, m), 7.82 (1H, dd, J=1.5, 8.4 Hz), 8.37 (1H, br). melting point: 111–112° C.

Reference Example 34

4-bromo-N-[3-(hydroxymethyl)-8-methoxy-7-quinolinyl]benzamide

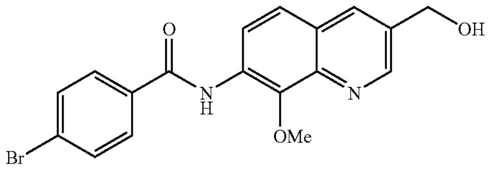

By successively operating in the same manner as in Reference Example 6 and using N-(3-amino-2-methoxyphenyl)-4-bromobenzamide obtained in Reference Example 33, the title compound was obtained.

$^1$H-NMR (DMSO-$d_6$) δ 4.11 (3H, s), 4.73 (2H, d, J=5.7 Hz), 5.48 (1H, t, J=5.4 Hz), 7.71–7.78 (3H, m), 7.96–8.03 (3H, m), 8.22 (1H, s), 8.87 (1H, d, J=1.8 Hz), 10.02 (1H, s). melting point: 185–187° C.

Reference Example 35

4-bromo-N-[3-(chloromethyl)-8-methoxy-7-quinolinyl]benzamide hydrochloride

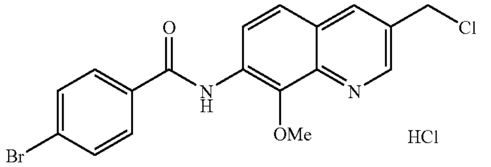

By successively operating in the same manner as in reference example 2 and using 4-bromo-N-[3-(hydroxymethyl)-8-methoxy-7-quinolinyl]benzamide obtained in Reference example 34, the title compound was obtained.

$^1$H-NMR ($CD_3OD$) δ 4.09 (3H, s), 5.07 (2H, s), 7.76 (2H, d, J=8.4 Hz), 7.96 (2H, d, J=8.8 Hz), 8.11 (1H, d, J=9.2 Hz), 8.52 (1H, d, J=9.0 Hz), 9.24 (2H, s). melting point: 167–169° C.

Reference Example 36 methyl 3-nitro-2-{[(trifluoromethyl)sulfonyl]oxy}benzoate

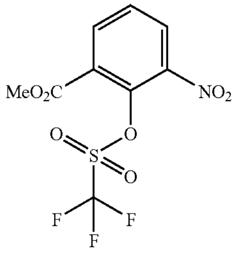

Methyl 2-hydroxy-3-nitrobenzoate (10.03 g, 50.9 mmol) was dissolved in tetrahydrofuran (200 ml) and N,N-diisopropylethylamine (13.3 ml, 76.4 mmol) and N-(methylsulfonyl)-N-phenylmethanesulfonamide (21.82 g, 61 mmol) were added under ice-cooling. The mixture was stirred at room temperature for 2 days. Tetrahydrofuran was evaporated under reduced pressure and the residue was dissolved in ethyl acetate. The solution was washed with saturated aqueous sodium hydrogen carbonate, 1N hydrochloric acid, water and saturated brine, dried over anhydrous magnesium sulfate, filtered and concentrated under reduced pressure. The obtained residue was purified by silica gel column chromatography (hexane:ethyl acetate) to give the title compound (16.7 g) as a pale-yellow oil.

$^1$H-NMR ($CDCl_3$) δ 4.00 (3H, s), 7.60–7.68 (1H, m), 8.19–8.33 (2H, m).

Reference Example 37 methyl 3-nitro-2-vinylbenzoate

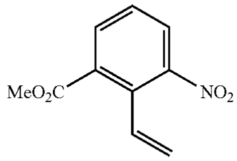

To a solution (150 ml) of methyl 3-nitro-2-{[(trifluoromethyl)sulfonyl]oxy}benzoate (10 g, 30.4 mmol) obtained in Reference Example 36 in DMF were added vinyl tri-n-butyl tin (10.7 ml, 36.48 mmol) and tetrakistriphenylphosphine palladium (1.76 g, 1.52 mmol) under a nitrogen flow, and the mixture was stirred at 80° C. for 4 hrs. The mixture was diluted with ethyl acetate, washed with water, saturated aqueous sodium hydrogen carbonate and saturated brine, dried over anhydrous magnesium sulfate, filtered and concentrated under reduced pressure. The obtained residue was purified by silica gel column chromatography (hexane:ethyl acetate) to give the title compound (4.91 g) as pale-yellow crystals.

$^1$H-NMR ($CDCl_3$) δ 3.89 (3H, s), 5.24 (1H, dd, J=1.0, 17.6 Hz), 5.42 (1H, dd, J=1.2, 11.8 Hz), 7.17 (1H, dd, J=11.4, 17.6 Hz), 7.44–7.52 (1H, m), 7.89 (1H, dd, J=1.4, 8.4 Hz), 7.98 (1H, dd, J=1.6, 7.8 Hz). melting point: 44–45° C.

Reference Example 38

3-nitro-2-vinylbenzoic acid

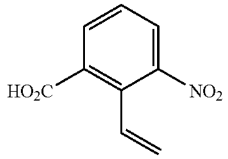

To a solution (50 ml) of methyl 3-nitro-2-vinylbenzoate (4.91 g, 23.7 mmol) obtained in Reference Example 37 in methanol was added 1N sodium hydroxide (50 ml, 50 mmol), and the mixture was stirred at 50° C. for 1 hr. Methanol was evaporated under reduced pressure and water was added. The aqueous layer was washed with diisopropyl ether. The aqueous layer was acidified with 1N hydrochloric acid, and the mixture was extracted with ethyl acetate. The organic layer was washed with saturated brine, dried over anhydrous magnesium sulfate, filtered and concentrated under reduced pressure. The obtained residue was recrystallized from hexane-ethyl acetate to give the title compound (4.23 g) as pale-yellow crystals.

$^1$H-NMR ($CDCl_3$) δ 5.26 (1H, d, J=18.0 Hz), 5.40 (1H, dd, J=0.6, 13.2 Hz), 7.21 (1H, dd, J=11.4, 17.6 Hz), 7.42–7.49 (1H, m), 7.83 (1H, dd, J=1.2, 8.2 Hz), 8.05 (1H, dd, J=1.2, 7.8 Hz), 10–12 (1H, br). melting point: 166–167° C. (crystallization solvent: hexane-ethyl acetate)

Reference Example 39 tert-butyl 3-nitro-2-vinylphenylcarbamate

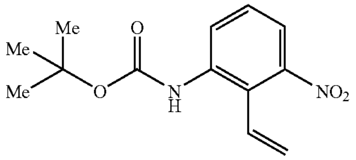

To a solution (400 ml) of 3-nitro-2-vinylbenzoic acid (7.86 g, 40.7 mmol) obtained in Reference Example 38 in tert-butanol were added triethylamine (8.6 ml, 61.1 mmol) and diphenylphosphoryl azide (9.65 ml, 44.8 mmol), and the mixture was heated under reflux for 24 hrs. The solvent was evaporated under reduced pressure, and the residue was purified by silica gel column chromatography (hexane:ethyl acetate) to give the title compound (9.99 g) as pale-yellow crystals.

$^1$H-NMR ($CDCl_3$) δ 1.52 (9H, s), 5.43 (1H, dd, J=1.0, 18.0 Hz), 5.72–5.78 (1H, m), 6.82 (1H, dd, J=11.4, 18.4 Hz), 7.02 (1H, br), 7.33–7.38 (1H, m), 7.42–7.59 (1H, m), 8.42 (1H, d, J=8.4 Hz). melting point: 120–121° C.

Reference Example 40 tert-butyl 3-amino-2-ethylphenylcarbamate

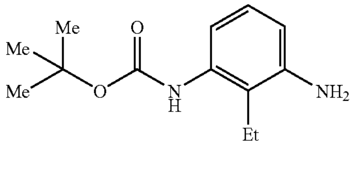

To a solution (100 ml) of tert-butyl 3-nitro-2-vinylphenylcarbamate (5.0 g, 18.9 mmol) obtained in Reference Example 39 in ethanol was added 5% palladium carbon (1 g), and the mixture was stirred under a hydrogen atmosphere at room temperature for 5 hrs. Palladium carbon was removed by Celite filtration, and the solvent was evaporated under reduced pressure. The obtained residue was purified by silica gel column chromatography (hexane:ethyl acetate) to give the title compound (3.88 g) as pale-yellow crystals.

$^1$H-NMR ($CDCl_3$) δ 1.15 (3H, t, J=7.8 Hz), 1.51 (9H, s), 2.52 (2H, q, J=7.5 Hz), 3.62 (2H, br), 6.21 (1H, br), 6.48 (1H, dd, J=1.2, 8.1 Hz), 6.96–7.02 (1H, m), 7.16 (1H, d, J=8.4 Hz). melting point: 109–110° C.

Reference Example 41 tert-butyl 3-[(4-bromobenzoyl)amino]-2-ethylphenylcarbamate

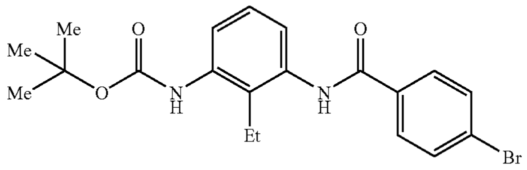

To a solution (50 ml) of tert-butyl 3-amino-2-ethylphenylcarbamate (3.78 g, 16.0 mmol) obtained in Reference Example 40 in tetrahydrofuran were added triethylamine (6.70 ml, 48 mmol) and 4-bromobenzoylchloride (3.87 g, 17.6 mmol) under ice-cooling, and the mixture was stirred for 1 hr. The mixture was diluted with ethyl acetate, washed with 1N sodium hydroxide, water and saturated brine, and dried over anhydrous magnesium sulfate. The solvent was evaporated under reduced pressure and the obtained residue was recrystallized from hexane-ethyl acetate to give the title compound (6.58 g) as pale-yellow crystals.

$^1$H-NMR ($CDCl_3$) δ 1.17 (3H, t, J=7.6 Hz), 1.52 (9H, s) 2.62 (2H, q, J=6.6 Hz), 6.27 (1H, s), 7.19–7.27 (1H, m), 7.48 (1H, d, J=7.8 Hz), 7.59–7.68 (6H, m). melting point: 181–183° C.

Reference Example 42

N-(3-amino-2-ethylphenyl)-4-bromobenzamide

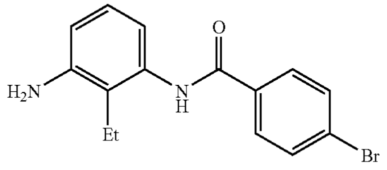

To a solution of tert-butyl 3-[(4-bromobenzoyl)amino]-2-ethylphenylcarbamate(6.48 g, 15.45 mmol) obtained in Reference Example 41 in ethyl acetate-tetrahydrofuran (50 ml–30 ml) was added 4N hydrogen chloride-ethyl acetate (60 ml), and the mixture was stirred at 60° C. for 3 hrs. Water and potassium carbonate were successively added, and the mixture was extracted with ethyl acetate. The organic layer was washed with saturated brine, filtered and concentrated under reduced pressure to give the title compound (4.53 g) as colorless crystals.

$^1$H-NMR ($CDCl_3$) δ 1.20 (3H, d, J=7.6 Hz), 2.57 (2H, q, J=7.6 Hz), 3.70 (2H, br), 6.61 (1H, dd, J=1.2, 7.8 Hz), 7.02–7.09 (1H, m), 7.16–7.20 (1H, br), 7.60–7.64 (3H, m), 7.73 (2H, d, J=8.4 Hz). melting point: 169–170° C.

Reference Example 43

4-bromo-N-[8-ethyl-3-(hydroxymethyl)-7-quinolinyl]benzamide

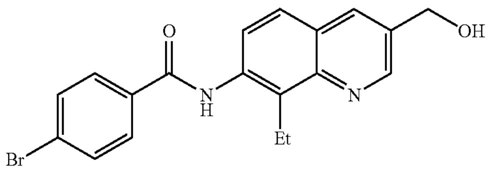

By successively operating in the same manner as in Reference Example 6 and using N-(3-amino-2-ethylphenyl)-4-bromobenzamide obtained in Reference Example 42, the title compound was obtained.

$^1$H-NMR (DMSO-$d_3$) δ 1.15 (3H, t, J=7.4 Hz), 3.28 (2H, q, J=7.0 Hz), 4.74 (2H, s), 5.46 (1H, t, J=3.6 Hz), 7.54 (2H, d, J=8.8 Hz), 7.72–7.80 (3H, m), 7.84–8.00 (2H, m), 8.22 (1H, s), 8.89 (1H, d, J=1.8 Hz), 10.25 (1H, s). melting point: 202–204° C.

Reference Example 44

4-bromo-N-[3-(chloromethyl)-8-ethyl-7-quinolinyl]benzamide hydrochloride

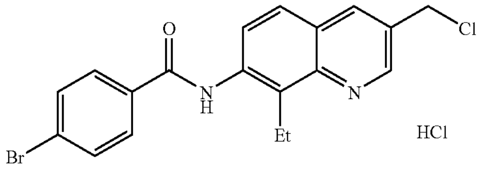

By operating in the same manner as in Reference Example 2 and using 4-bromo-N-[8-ethyl-3-(hydroxymethyl)-7-quinolinyl]benzamide obtained in Reference Example 43, the title compound was obtained.

$^1$H-NMR ($CD_3OD$) δ 1.30 (3H, t, J=7.6 Hz), 3.33 (2H, q, J=7.4 Hz), 5.10 (2H, s), 7.75 (2H, d, J=8.8 Hz), 7.96 (2H, d, J=8.8 Hz), 8.14 (1H, d, J=8.8 Hz), 8.26 (1H, d, J=8.8 Hz), 9.28–9.30 (2H, m). melting point: 170–172° C.

Reference Example 45

4'-chloro-N-[3-(chloromethyl)-7-quinolinyl][1,1'-biphenyl]-4-carboxamide

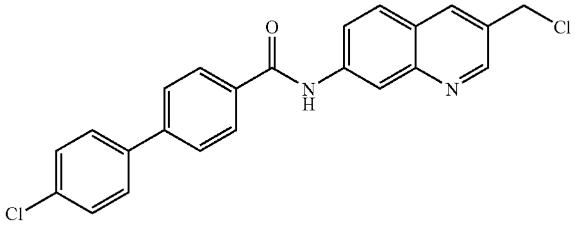

By operating in the same manner as in Reference Example 22 and using 4'-chloro-N-[3-(1-pyrrolidinylmethyl)-7-quinolinyl][1,1'-biphenyl]-4-carboxamide obtained in Reference Example 6, the title compound was obtained.

$^1$H-NMR (DMSO-$d_6$) δ 5.01 (2H, s), 7.58 (2H, d, J=8.6 Hz), 7.82 (2H, d, J=8.6 Hz), 7.89 (2H, d, J=8.6 Hz), 8.02 (2H, m), 8.13 (2H, d, J=8.6 Hz), 8.37 (1H, d, J=2.0 Hz), 8.63 (1H, d, J=1.7 Hz), 8.82 (1H, d, J=2.2 Hz), 10.67 (1H, s).

Reference Example 46

N-(3-amino-2-methylphenyl)-4-bromobenzamide

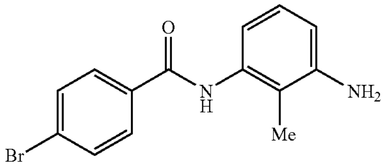

By operating in the same manner as in Reference Example 33 and using 4-bromo-N-(2-methyl-3-nitrophenyl)benzamide, the title compound was obtained.

$^1$H NMR (DMSO-$d_6$) δ 1.90 (3H, s), 4.91 (2H, s), 6.48 (1H, d, J=7.6 Hz), 6.55 (1H, d, J=8.0 Hz), 6.88 (1H, m), 7.72 (2H, d, J=8.6 Hz), 7.90 (2H, d, J=8.6 Hz), 9.81 (1H, s).

Reference Example 47

4-bromo-N-(3-formyl-8-methyl-7-quinolinyl)benzamide

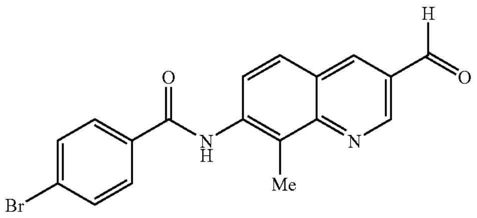

By operating in the same manner as in Reference Example 8-1) and using N-(3-amino-2-methylphenyl)-4-bromobenzamide obtained in Reference Example 46, the title compound was obtained.

$^1$H NMR (DMSO-$d_6$) δ 2.69 (3H, s), 7.78 (2H, d, J=8.8 Hz), 7.80 (1H, d, J=8.8 Hz), 8.01 (2H, d, J=8.8 Hz), 8.07 (1H, d, J=8.8 Hz), 8.94 (1H, d, J=2.2 Hz), 9.32 (1H, d, J=2.2 Hz), 10.26 (1H, s), 10.46 (1H, s).

Reference Example 48

4-bromo-N-[3-(hydroxymethyl)-8-methyl-7-quinolinyl]benzamide

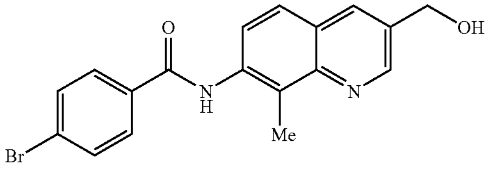

By operating in the same manner as in Reference Example 1 and using 4-bromo-N-(3-formyl-8-methyl-7-quinolinyl]benzamide obtained in Reference Example 47, the title compound was obtained.

$^1$H NMR (DMSO-$d_6$) δ 2.65 (3H, s), 4.74 (2H, d, J=5.4 Hz), 5.48 (1H, t, J=5.4 Hz), 7.60 (1H, d, J=8.7 Hz), 7.78 (2H, d, J=8.1 Hz), 7.82 (1H, d, J=8.7 Hz), 7.99 (2H, d, J=8.1 Hz), 8.22 (1H, d, J=1.5 Hz), 8.89 (1H, d, J=1.5 Hz), 10.31 (1H, s).

Reference Example 49

4-bromo-N-[3-(chloromethyl)-8-methyl-7-quinolinyl]benzamide hydrochloride

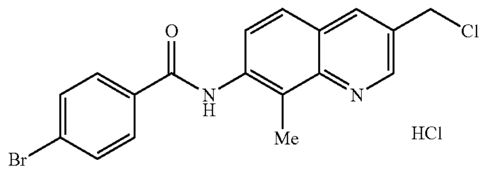

By operating in the same manner as in Reference Example 2 and using 4-bromo-N-[3-(hydroxymethyl)-8-methyl-7-quinolinyl]benzamide obtained in Reference Example 48, the title compound was obtained.

$^1$H NMR ($CD_3OD$) δ 2.74 (3H, s), 5.09 (2H, s), 7.76 (2H, d, J=6.6 Hz), 7.97 (2H, d, J=6.6 Hz), 8.09 (1H, d, J=9.0 Hz), 8.24 (1H, d, J=9.0 Hz), 9.25 (1H, d, J=2.1 Hz), 9.26 (1H, d, J=2.1 Hz).

Reference Example 50

8-methyl-3-(1-piperidinylmethyl)-7-quinolinylamine

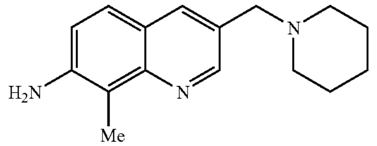

By operating in the same manner as in Reference Example 3 and Reference Example 4 and using 4-bromo-N-[3-(chloromethyl)-8-methyl-7-quinolinyl]benzamide hydrochloride obtained in Reference Example 49, the title compound was obtained.

$^1$H-NMR ($CDCl_3$) δ 1.43 (2H, m), 1.56 (4H, m), 2.40 (4H, m), 2.59 (3H, s), 3.59 (2H, s), 4.02 (2H, s), 6.97 (1H, d, J=8.8 Hz), 7.47 (1H, d, J=8.6 Hz), 7.88 (1H, d, J=1.8 Hz), 8.77 (1H, d, J=2.0 Hz).

Reference Example 51

3-(1-azepanylmethyl)-8-methyl-7-quinolinylamine

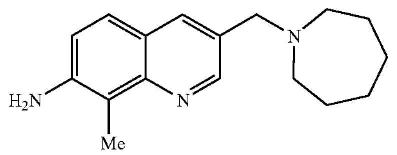

By operating in the same manner as in Reference Example 3 and Reference Example and using 4-bromo-N-[3-(chloromethyl)-8-methyl-7-quinolinyl]benzamide hydrochloride obtained in Reference Example 49, the title compound was obtained.

$^1$H-NMR ($CDCl_3$) δ 1.62 (8H, m), 2.60 (3H, s), 2.65 (4H, m), 3.76 (2H, s), 3.99 (2H, s), 7.00 (1H, d, J=8.8 Hz), 7.49 (1H, d, J=8.8 Hz), 7.89 (1H, d, J=2.2 Hz), 8.81 (1H, d, J=2.2 Hz).

Reference Example 52

N-[3-(chloromethyl)-8-methyl-7-quinolinyl]-4'-fluoro[1,1'-biphenyl]-4-carboxamide

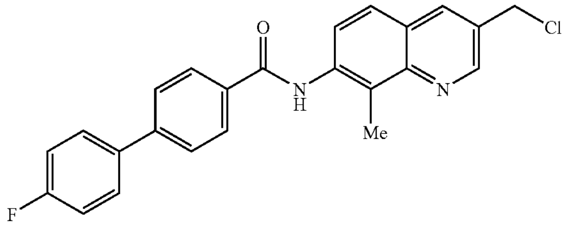

By operating in the same manner as in Reference Example 22 and using 4'-fluoro-N-[8-methyl-3-(1-pyrrolidinylmethyl)-7-quinolinyl][1,1'-biphenyl]-4-carboxamide obtained in Reference Example 19, the title compound was obtained.

$^1$H-NMR (DMSO-$d_6$) δ 2.68 (3H, s), 5.04 (2H, s), 7.25–7.42 (2H, m), 7.70 (1H, d, J=8.8 Hz), 7.74–7.93 (5H, m), 8.15 (2H, d, J=8.4 Hz), 8.42 (1H, d, J=2.4 Hz), 9.00 (1H, d, J=2.2 Hz), 10.32 (1H, s).

Reference Example 53

N-(5-amino-2-methylphenyl)-4-bromobenzamide

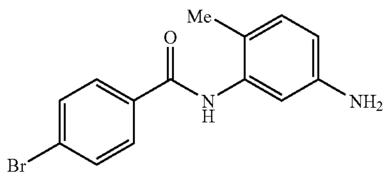

By operating in the same manner as in Reference Example 33 and using 4-bromo-N-(2-methyl-5-nitrophenyl)benzamide, the title compound was obtained.

$^1$H-NMR($CDCl_3$) δ 2.22 (3H, s), 3.66 (2H, br), 6.42–6.52 (1H, m), 6.99 (1H, d, J=8.0 Hz), 7.44–7.50 (1H, m), 7.54–7.68 (3H, m), 7.73 (2H, d, J=8.4 Hz).

Reference Example 54

4-bromo-N-(3-formyl-6-methyl-7-quinolinyl)benzamide

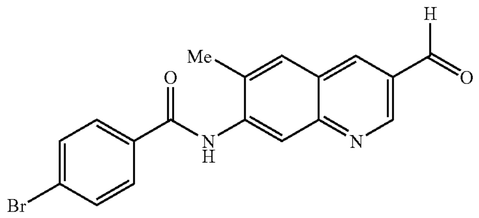

By operating in the same manner as in Reference Example 8-1) and using N-(5-amino-2-methylphenyl)-4-bromobenzamide obtained in Reference Example 53, the title compound was obtained.

$^1$H-NMR(DMSO-$d_6$) δ 2.52 (3H, s), 7.79 (2H, d, J=8.4 Hz), 7.98 (2H, d, J=8.4 Hz), 8.09 (1H, s), 8.31 (1H, s), 8.85 (1H, m), 9.22 (1H, m), 10.22(2H, s).

Reference Example 55

4-bromo-N-[3-(hydroxymethyl)-6-methyl-7-quinolinyl]benzamide

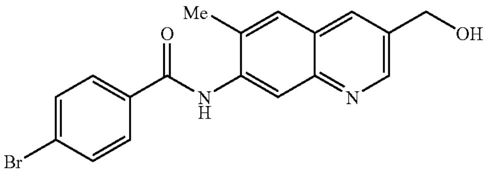

By operating in the same manner as in Reference Example 1 and using 4-bromo-N-(3-formyl-6-methyl-7-quinolinyl)benzamide obtained in Reference Example 54, the title compound was obtained.

$^1$H-NMR(DMSO-$d_6$) δ 2.44 (3H, s), 4.71 (2H, d, J=4.8 Hz), 5.46 (1H, m), 7.78 (2H, d, J=8.4 Hz), 7.84 (1H, s), 7.98 (2H, d, J=8.4 Hz), 8.07 (1H, s), 8.15 (1H, m), 8.80 (1H, m), 10.18 (1H, s).

Reference Example 56

4-bromo-N-[3-(chloromethyl)-6-methyl-7-quinolinyl]benzamide hydrochloride

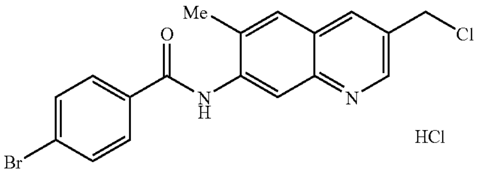

By operating in the same manner as in Reference Example 2 and using 4-bromo-N-[3-(hydroxymethyl)-6-methyl-7-quinolinyl]benzamide obtained in Reference Example 55, the title compound was obtained.

$^1$H-NMR(DMSO-$d_6$) δ 2.55 (3H, s), 5.08 (2H, s), 7.79 (2H, d, J=8.4 Hz), 8.00 (2H, d, J=8.4 Hz), 8.10 (1H, s), 8.50 (1H, s), 8.80 (1H, s), 9.16 (1H, s), 10.34 (1H, s).

Reference Example 57

4'-fluoro-N-(3-formyl-8-methyl-7-quinolinyl)[1,1'-biphenyl]-4-carboxamide

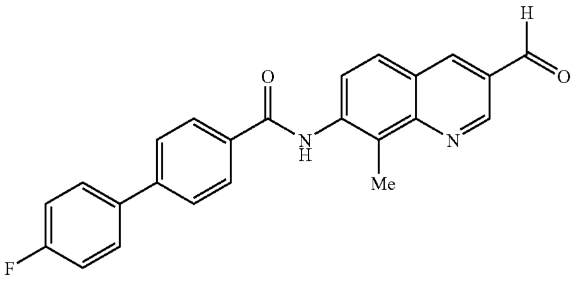

By operating in the same manner as in Reference Example 50 and using 4-bromo-N-(3-formyl-8-methyl-7-quinolinyl)benzamide obtained in Reference Example 47, the title compound was obtained.

$^1$H-NMR (DMSO-$d_6$) δ: 2.72 (3H, s), 7.30–7.44 (2H, m), 7.79–7.93 (5H, m), 8.06–8.20 (3H, m), 8.96 (1H, d, J=2.2 Hz), 9.33 (1H, d, J=2.2 Hz), 10.27 (1H, s), 10.43 (1H, s). melting point: 236–239° C. (dec.) (crystallization solvent: ethyl acetate-tetrahydrofuran)

Reference Example 58

4'-fluoro-N-[3-(1-hydroxyethyl)-8-methyl-7-quinolinyl][1,1'-biphenyl]-4-carboxamide

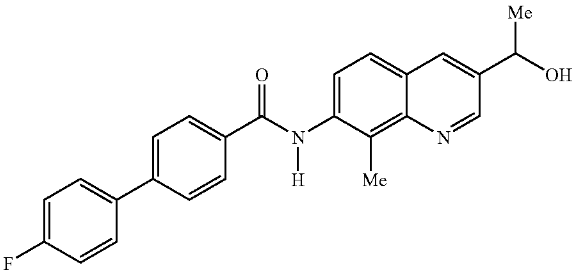

To a solution (30 ml) of 4'-fluoro-N-(3-formyl-8-methyl-7-quinolinyl)[1,1'-biphenyl]-4-carboxamide (1 g) obtained in Reference Example 57 in dry tetrahydrofuran was added 3M methylmagnesium bromide (8.7 ml) under a nitrogen flow at room temperature, and the mixture was stirred at room temperature for 16 hrs. Water was carefully added to the reaction solution, and the mixture was extracted with ethyl acetate-tetrahydrofuran. The extract was washed with saturated brine and dried over anhydrous magnesium sulfate. The solvent was evaporated under reduced pressure and the obtained residue was crystallized from ethyl acetate-diethylether to give the title compound (0.85 g) as pale-yellow crystals.

$^1$H-NMR (DMSO-$d_6$) δ: 1.48 (3H, d, J=6.2 Hz), 2.68 (3H, s), 4.90–5.10 (1H, m), 5.49 (1H, d, J=4.4 Hz), 7.27–7.41 (2H, m), 7.62 (1H, d, J=8.8 Hz), 7.75–7.90 (5H, m), 8.15 (2H, d, J=8.4 Hz), 8.23 (1H, d, J=2.2 Hz), 8.94 (1H, d, J=2.2 Hz), 10.27 (1H, s). melting point: 189–192° C. (crystallization solvent: ethyl acetate-diethylether)

Reference Example 59

N-[3-(1-chloroethyl)-8-methyl-7-quinolinyl]-4'-fluoro[1,1'-biphenyl]-4-carboxamide

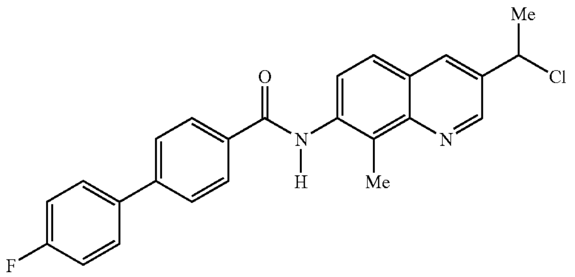

By operating in the same manner as in Reference Example 2 and using 4'-fluoro-N-[3-(1-hydroxyethyl)-8-methyl-7-quinolinyl][1,1'-biphenyl]-4-carboxamide obtained in Reference Example 58, the title compound was obtained.

$^1$H-NMR (DMSO-$d_6$) δ: 1.97 (3H, d, J=6.9 Hz), 5.66 (1H, q, J=6.9 Hz), 7.27–7.41 (2H, m), 7.71 (1H, d, J=8.8 Hz), 7.76–7.96 (5H, m), 8.15 (2H, d, J=8.1 Hz), 8.49 (1H, d, J=2.2 Hz), 9.07 (1H, d, J=2.2 Hz), 10.35 (1H, s).

Reference Example 60

4'-fluoro-N-[3-(1-hydroxypropyl)-8-methyl-7-quinolinyl][1,1'-biphenyl]-4-carboxamide

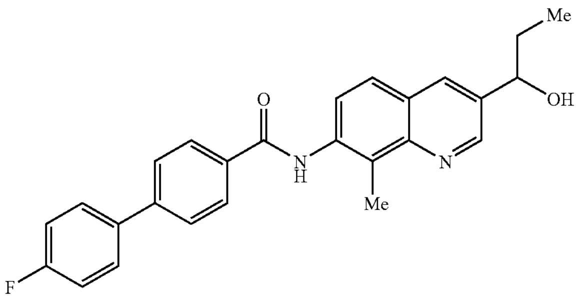

By operating in the same manner as in Reference Example 58 and using 4'-fluoro-N-(3-formyl-8-methyl-7-quinolinyl)[1,1'-biphenyl]-4-carboxamide obtained in Reference Example 57, the title compound was obtained.

$^1$H-NMR (DMSO-$d_6$) δ: 0.89 (3H, t, J=7.3 Hz), 1.68–1.88 (2H, m), 2.68 (3H, s), 4.67–4.80 (1H, m), 5.47 (1H, d, J=4.4 Hz), 7.26–7.41 (2H, m), 7.61 (1H, d, J=8.8 Hz), 7.73–7.90 (5H, m), 8.09–8.25 (3H, m), 8.91 (1H, d, J=2.2 Hz), 10.28 (1H, s). melting point: 204–208° C. (crystallization solvent: diethylether)

Reference Example 61

N-[3-(1-chloropropyl)-8-methyl-7-quinolinyl]-4'-fluoro[1,1'-biphenyl]-4-carboxamide

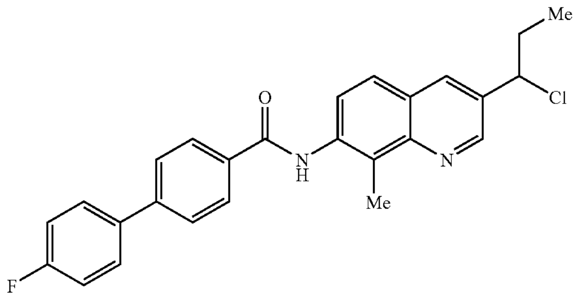

By operating in the same manner as in Reference Example 2 and using 4'-fluoro-N-[3-(1-hydroxypropyl)-8-methyl-7-quinolinyl][1,1'-biphenyl]-4-carboxamide obtained in Reference Example 60, the title compound was obtained.

$^1$H-NMR (DMSO-$d_6$) δ: 1.01 (3H, t, J=7.5 Hz), 2.12–2.37 (2H, m), 2.68 (3H, s), 5.37 (1H, t, J=7.1 Hz), 7.26–7.44 (2H, m), 7.69 (1H, d, J=8.8 Hz), 7.75–7.95 (5H, m), 8.05–8.22 (2H, m), 8.42 (1H, d, J=2.2 Hz), 9.02 (1H, d, J=2.2 Hz), 10.33 (1H, s).

Reference Example 62

4'-fluoro-N-{3-[hydroxy(phenyl)methyl]-8-methyl-7-quinolinyl}[1,1'-biphenyl]-4-carboxamide

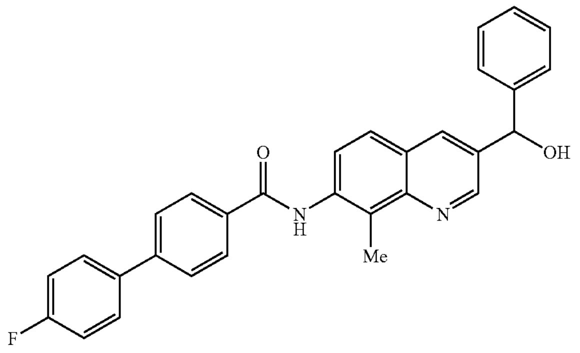

By successively operating in the same manner as in Reference Example 58 and using 4'-fluoro-N-(3-formyl-8-methyl-7-quinolinyl)[1,1'-biphenyl]-4-carboxamide obtained in Reference Example 57, the title compound was obtained.

$^1$H-NMR (DMSO-$d_6$+$H_2O$) δ: 2.64 (3H, s), 6.01 (1H, s), 7.20–7.53 (7H, m), 7.64 (1H, d, J=8.8 Hz), 7.77–7.91 (5H, m), 8.14 (2H, d, J=8.4 Hz), 8.34 (1H, br), 8.92 (1H, d, J=2.2 Hz), 10.30 (1H, s). melting point: 182–186° C. (crystallization solvent: ethyl acetate-diisopropyl ether)

Reference Example 63

N-{3-[chloro(phenyl)methyl]-8-methyl-7-quinolinyl}-4'-fluoro[1,1'-biphenyl]-4-carboxamide

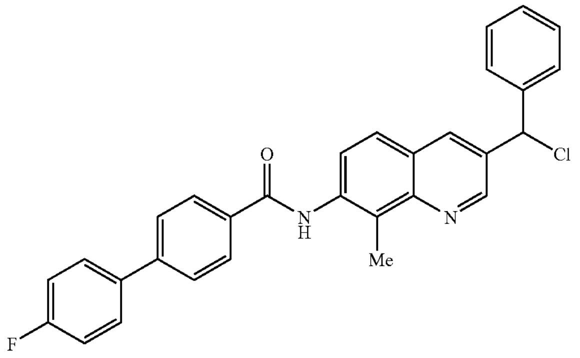

By successively operating in the same manner as in Reference Example 2 and using 4'-fluoro-N-{3-[hydroxy(phenyl)methyl]-8-methyl-7-quinolinyl}[1,1'-biphenyl]-4-carboxamide obtained in Reference Example 62, the title compound was obtained.

$^1$H-NMR (DMSO-$d_6$) δ: 2.67 (3H, s), 6.84 (1H, s), 7.25–7.50 (5H, m), 7.53–7.63 (2H, m), 7.70 (1H, d, J=8.8 Hz), 7.75–7.96 (5H, m), 8.10–8.21 (2H, m), 8.45 (1H, d, J=2.2 Hz), 9.02 (1H, d, J=2.5 Hz), 10.34 (1H, s).

Reference Example 64

N-[3-(chloromethyl)-6-methyl-7-quinolinyl]-4'-fluoro[1,1'-biphenyl]-4-carboxamide

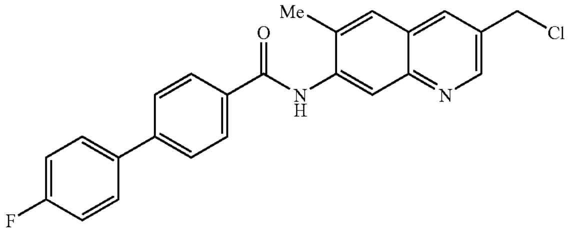

By operating in the same manner as in Reference Example 22 and using 4'-fluoro-N-[6-methyl-3-(1-pyrrolidinylmethyl)-7-quinolinyl][1,1'-biphenyl]-4-carboxamide obtained in Reference Example 37, the title compound was obtained.

$^1$H-NMR (DMSO-$d_6$) δ 2.50 (3H, s), 5.02 (2H, s), 7.36 (2H, m), 7.80–7.90 (5H, m), 8.12–8.18 (3H, m), 8.34 (1H, d, J=1.8 Hz), 8.90 (1H, d, J=2.2 Hz), 10.17 (1H, s).

Reference Example 65

2-methyl-1,2,3,4-tetrahydrobenzo[b][1,6]naphthyridin-7-amine

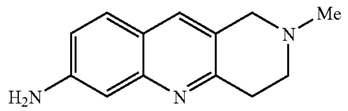

A solution of 2,4-diaminobenzaldehyde (1.00 g, 7.34 mmol), 1-methyl-4-piperidinone (1.08 ml, 8.81 mmol) and 4N aqueous sodium hydroxide solution (11 ml) in ethanol (70 ml) was stirred at 60° C. for 16 hrs, and the solvent was evaporated under reduced pressure. The residue was dissolved in ethyl acetate, washed with aqueous potassium carbonate solution and saturated brine, and dried over anhydrous sodium sulfate. The obtained crude product was purified by NH-silica gel chromatography (elute solvent; ethyl acetate) and treated with ethyl acetate-isopropyl ether (1:5) to give the title compound (666 mg) as a powder.

$^1$H-NMR (DMSO-$d_6$) δ: 2.37 (3H, s), 2.71 (2H, t, J=6.0 Hz), 2.96 (2H, t, J=6.0 Hz), 3.56 (2H, s), 5.58 (2H, br), 6.80 (1H, d, J=2.1 Hz), 6.87 (1H, dd, J=2.1, 8.4 Hz), 7.48 (1H, d, J=8.4 Hz), 7.64 (1H, s).

Reference Example 66

7-amino-8-methyl-3-quinolinecarboaldehyde

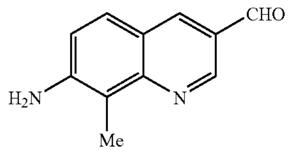

A suspension of 2-methyl-1,3-benzenediamine (30.0 g, 246 mmol) and 2-dimethylaminomethylene-1,3-bis(dimethylimmonio)propane bis-tetrafluoroborate (263 g, 737 mmol) in isopropanol (500 ml) was heated under reflux with stirring for 16 hrs. and allowed to cool to room temperature. To the reaction solution was added 1N hydrochloric acid (500 ml). The mixture was stirred at 70° C. for 5 hrs. with heating and allowed to cool to room temperature. The resulting precipitate was collected and washed with water, acetonitrile and isopropyl ether. A suspension of the obtained precipitate (61.6 g) and potassium carbonate (170 g, 1.23 mol) in ethyl acetate (500 ml)-water (500 ml) was vigorously stirred with heating at 90° C. and allowed to cool to room temperature. The organic layer was separated, washed with saturated brine, dried over sodium sulfate and passed through silica gel (100 g) packed in a glass filter. The solvent was evaporated under reduced pressure and the obtained crude product was treated with isopropyl ether to give the title compound (35.4 g) as a powder.

$^1$H-NMR (DMSO-$d_6$) δ: 2.43 (3H, s), 6.17 (2H, br), 7.15 (1H, t, J=8.7 Hz), 7.71 (1H, d, J=8.7 Hz), 8.51 (1H, d, J=2.4 Hz), 9.04 (1H, d, J=2.4 Hz), 10.03 (1H, s).

Reference Example 67

8-methyl-3-(1-pyrrolidinylmethyl)-7-quinolinamine

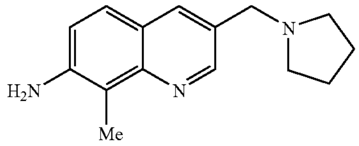

To a suspension of 7-amino-8-methyl-3-quinolinecarboaldehyde (21.00 g, 112.8 mmol) obtained in Reference Example 66 in dichloroethane (210 ml) were added pyrrolidine (28.28 ml, 145.0 mmol) and triacetoxy sodium borohydride (35.84 g, 169.2 mmol), and the mixture was stirred at room temperature for 4.5 hrs. To the reaction solution was added saturated aqueous sodium hydrogen carbonate and the mixture was vigorously stirred. The organic layer was separated and concentrated under reduced pressure. The residue was purified by NH-silica gel column (Fuji Silysia Chemical Lyd., Pro. No. DM1020, eluting solvent: ethyl acetate) to give the title compound (25.7 g) as a viscous oil.

$^1$H-NMR ($CDCl_3$) δ: 1.79 (4H, m), 2.54 (4H, m), 2.59 (3H, s), 3.74 (2H, s), 3.98 (2H, s), 6.98 (1H, d, J=8.6 Hz), 7.47 (1H, d, J=8.8 Hz), 7.91 (1H, d, J=2.2 Hz), 8.76 (1H, d, J=2.2 Hz).

Reference Example 68

2-fluoro-4-(4-fluorobutoxy)benzoic acid

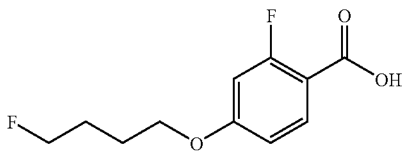

1-Bromo-4-fluorobutane (3.57 g, 23.1 mmol) was added dropwise to a mixture of 2-fluoro-4-hydroxybenzoic acid (3.00 g, 19.2 mmol), ethanol (11.5 ml) and water (2.3 ml), potassium hydroxide (2.37 g, 42.3 mmol) at 80° C., and the mixture was stirred at 80° C. for 17 hrs. The solvent was evaporated under reduced pressure. The residue was dissolved in water and the solution was acidified by adding 1N hydrochloric acid. The insoluble materials were filtered off and dried to give the title compound (1.73 g) as a pale-brown powder.

$^{1}$H-NMR (DMSO-$d_6$) δ: 1.82 (2H, m), 4.09 (2H, t, J=6.0 Hz), 4.42 (2H, t, J=5.8 Hz), 4.58 (2H, m), 6.86 (1H, m), 6.87 (1H, m), 7.80 (1H, t, J=8.6 Hz), 12.84 (1H, s).

Reference Example 69

Fluoro-4-(4,4,4-trifluorobutoxy)benzoic acid

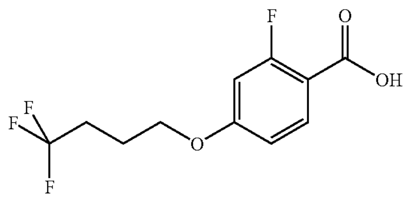

By operating in the same manner as in Reference Example 68 and using 1,1,1-trifluoro-4-iodobutane, the title compound was obtained as colorless powder.

$^{1}$H-NMR (DMSO-$d_6$) δ: 1.97 (2H, m), 2.44 (2H, m), 4.13 (2H, t, J=6.3 Hz), 6.89 (1H, t, J=2.0 Hz), 6.90 (1H, m) 7.84 (1H, t, J=9.0 Hz), 14.44 (1H, s).

Reference Example 70

4-(2-ethoxyethoxy)-2-fluorobenzoic acid

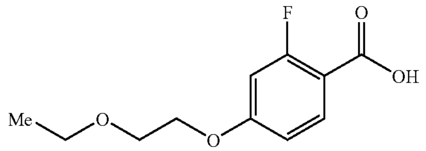

By operating in the same manner as in Reference Example 68 and using 1-bromo-2-ethoxyethane, the title compound was obtained as colorless powder.

$^{1}$H-NMR (DMSO-$d_6$) δ: 1.11 (3H, t, J=7.0 Hz), 3.48 (2H, q, J=7.0 Hz), 3.68 (2H, m), 4.16 (2H, m), 6.87 (1H, d, J=1.7 Hz), 6.89 (1H, m), 7.79 (1H, m), 12.84 (1H, s).

Reference Example 71

2-fluoro-4-(3-methylbutoxy)benzoic acid

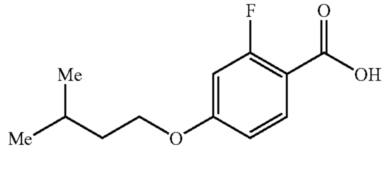

By operating in the same manner as in Reference Example 68 and using 1-iodo-3-methylbutane, the title compound was obtained as colorless powder.

$^{1}$H-NMR (DMSO-$d_6$) δ: 0.93 (6H, d, J=6.6 Hz), 1.62 (2H, q, J=6.8 Hz), 1.77 (1H, s), 4.07 (2H, t, J=6.7 Hz), 6.87 (2H, m), 7.81 (1H, t, J=8.7 Hz), 12.85 (1H, s).

Reference Example 72

Methyl 4-[(1Z)-2-nitropenta-1-enyl]benzoate

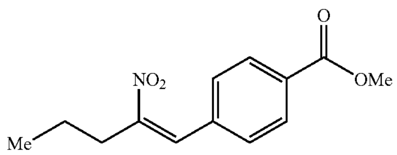

n-Butylamine (8.31 ml, 84.1 mmol) and methyl 4-formylbenzoate (10.6 g, 64.7 mmol) was heated with reflux benzene (50 ml) in a Dean-Stark trap until a theoretical amount of water was recovered. The solvent was evaporated under reduced pressure. To the residue were added glacial acetic acid (30 ml) and nitrobutane (10.0 g, 97.0 mmol), and the mixture was stirred at 110° C. for 4 hrs. and allowed to cool to room temperature. The insoluble materials were filtered off and dried to give the title compound (7.53 g) as a pale-yellow powder.

$^{1}$H-NMR ($CDCl_3$) δ: 1.00 (3H, t, J=7.5 Hz), 1.67 (2H, m), 2.78 (2H, m), 3.95 (3H, s), 7.45 (2H, d, J=8.1 Hz), 8.01 (1H, s), 8.10 (2H, ddd, J=8.2, 2.0, 1.8 Hz).

Reference Example 73

Methyl 4-(2-oxopentyl)benzoate

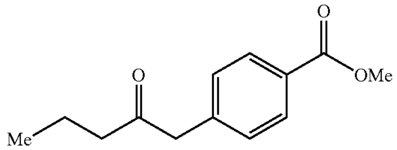

To a solution (82 ml) of methyl 4-[(1Z)-2-nitropenta-1-enyl]benzoate (5.50 g, 22.0 mmol) obtained in Reference Example 72 and iron powder (7.40 g, 132 mmol) in methanol was added dropwise conc. hydrochloric acid (37.0 ml) at 65° C., and the mixture was stirred at 65° C. for 4 hrs. The solvent was evaporated under reduced pressure. Water was added to the residue, and the mixture was extracted with diethyl ether and washed with saturated aqueous sodium hydrogen carbonate. The solvent was evaporated under reduced pressure and the residue was purified by silica gel column chromatography (eluting solvent; hexane:ethyl acetate=4:1) to give the title compound (2.53 g) as a pale-yellow liquid.

$^{1}$H-NMR ($CDCl_3$) δ: 0.88 (3H, t, J=7.3 Hz), 1.59 (2H, m), 2.44 (2H, t, J=7.3 Hz), 3.74 (2H, s), 3.91 (3H, s), 7.27 (2H, m), 7.99 (2H, dt, J=8.5, 1.9 Hz).

Reference Example 74

4-(2-oxopentyl)benzoic acid

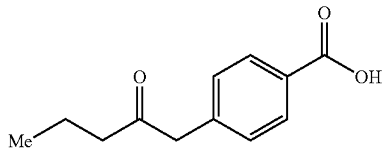

A mixture of methyl 4-(2-oxopentyl)benzoate (2.84 g, 12.9 mmol) obtained in Reference Example 73, 1N aqueous sodium hydroxide solution (20 ml) and methanol (30 ml) was stirred at 65° C. for 1 hr. and the solvent was evaporated under reduced pressure. The residue was dissolved in water and acidified by adding 1N hydrochloric acid. The insoluble materials were filtered off and dried to give the title compound (2.00 g) as a pale-yellow powder.

$^1$H-NMR (DMSO-$d_6$) δ: 0.82 (3H, t, J=7.4 Hz), 1.49 (2H, m), 2.50 (2H, m), 3.85 (2H, s), 7.30 (2H, d, J=8.5 Hz), 7.88 (2H, dt, J=8.3, 1.9 Hz), 12.82 (1H, s).

Reference Example 75

4-(2-oxobutyl)benzoic acid

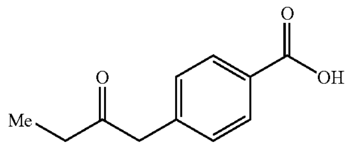

By operating in the same manner as in Reference Example 74 and using methyl 4-(2-oxobutyl)benzoate, the title compound was obtained as colorless powder.

$^1$H-NMR (DMSO-$d_6$) δ: 0.93 (3H, t, J=7.2 Hz), 2.53 (2H, q, J=7.3 Hz), 3.86 (2H, s), 7.29 (2H, dt, J=8.4, 1.9 Hz), 7.87 (2H, dt, J=8.4, 1.9 Hz), 12.88 (1H, s).

Reference Example 76

4-(2-oxohexyl)benzoic acid

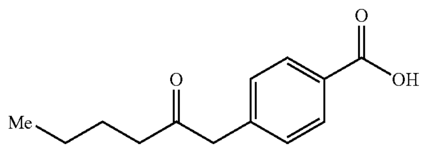

By operating in the same manner as in Reference Example 74 and using methyl 4-(2-oxohexyl)benzoate, the title compound was obtained as colorless powder.

$^1$H-NMR (DMSO-$d_6$) δ: 0.83 (3H, t, J=7.3 Hz), 1.22 (2H, m), 1.44 (2H, m), 2.50 (2H, m), 3.85 (2H, s), 7.28 (2H, d, J=8.4 Hz), 7.86 (2H, dt, J=8.3, 1.8 Hz), 12.83 (1H, s).

Reference Example 77

Methyl 4-(3-methyl-2-oxobutyl)benzoate

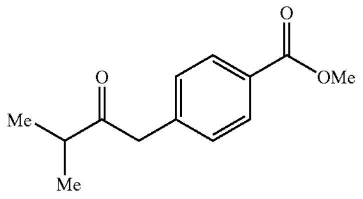

A mixture of zinc powder (1.70 g, 26.0 mmol), 1,2-dibromoethane (0.087 ml, 1.0 mmol) and THF (2 ml) was stirred at 65° C. for 15 min. and the mixture was allowed to cool to room temperature. To the reaction solution was added trimethylsilyl chloride (0.1 ml, 0.8 mmol) and the mixture was stirred at room temperature for 1 hr. and cooled to 0° C. To the reaction solution was added dropwise a solution (11 ml) of methyl 4-(bromomethyl)benzoate (4.93 g, 21.5 mmol) in THF at 0° C. and the mixture was stirred at 5° C. for 3 hrs. to give an organic zinc mixture. A mixture of copper cyanide (1.75 g, 20.0 mmol), lithium chloride (1.70 g, 40.0 mmol) and THF (20 ml) was cooled to −70° C. and the organic zinc mixture was added. The mixture was heated to −20° C. and cooled to −70° C. To the reaction solution was added 2-methylpropanoyl chloride (1.68 ml, 16.0 mmol) and the mixture was gradually heated to 0° C. 6N Hydrochloric acid (10 ml) was added, and the mixture was extracted with ethyl acetate and washed with saturated brine. The solvent was evaporated under reduced pressure and the residue was purified by silica gel column chromatography (eluting solvent; hexane:ethyl acetate=4:1) to give the title compound (3.05 g) as a colorless powder.

$^1$H-NMR ($CDCl_3$) δ: 1.12 (6H, d, J=7.0 Hz), 2.72 (1H, m), 3.81 (2H, s), 3.91 (3H, s), 7.28 (2H, m), 8.00 (2H, dt, J=8.4, 1.8 Hz).

Reference Example 78

4-(3-methyl-2-oxobutyl)benzoic acid

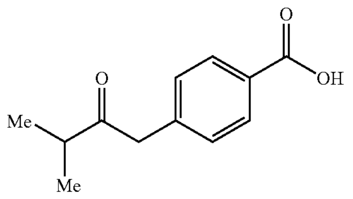

By operating in the same manner as in Reference Example 74 and using methyl 4-(3-methyl-2-oxobutyl)benzoate obtained in Reference Example 77, the title compound was obtained as a colorless powder.

$^1$H-NMR ($CDCl_3$) δ: 1.13 (6H, d, J=7.1 Hz), 2.73 (1H, m), 3.83 (2H, s), 7.30 (2H, d, J=8.3 Hz), 8.06 (2H, d, J=8.3 Hz).

Reference Example 79

Methyl 4-(2-cyclopropyl-2-oxoethyl)benzoate

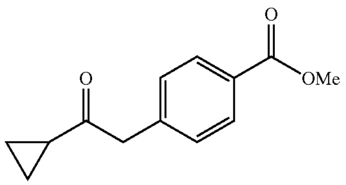

By operating in the same manner as in Reference Example 77 and using cyclopropanecarbonyl chloride, the title compound was obtained as a liquid powder.

$^1$H-NMR ($CDCl_3$) δ: 0.13 (2H, m), 0.88 (2H, m), 1.05 (1H, m), 2.90 (2H, m), 3.92 (3H, s), 7.32 (2H, dt, J=8.3, 1.7 Hz), 7.97 (2H, dt, J=8.4, 1.8 Hz).

Reference Example 80

4-(2-cyclopropyl-2-oxoethyl)benzoic acid

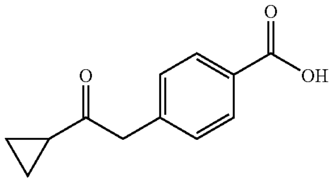

By operating in the same manner as in Reference Example 74 and using methyl 4-(2-cyclopropyl-2-oxoethyl) benzoate obtained in Reference Example 79, the title compound was obtained as a colorless powder.

$^1$H-NMR (DMSO-$d_6$) δ: 0.88 (4H, m), 1.21 (1H, m), 2.80 (2H, s), 7.37 (2H, d, J=8.2 Hz), 7.82 (2H, d, J=8.2 Hz), 12.74 (1H, s).

Reference Example 81

Methyl 4-(4-methyl-2-oxopentyl)benzoate

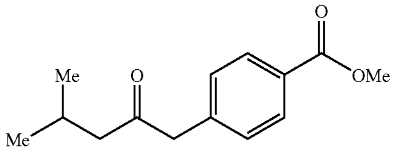

By operating in the same manner as in Reference Example 77 and using 3-methylbutanoyl chloride, the title compound was obtained as a colorless liquid.

$^1$H-NMR ($CDCl_3$) δ: 0.88 (6H, d, J=6.6 Hz), 2.15 (1H, m), 2.34 (2H, m), 3.72 (2H, s), 3.91 (3H, s), 7.27 (2H, d, J=8.4 Hz), 8.00 (2H, dt, J=8.4, 1.8 Hz).

Reference Example 82

4-(4-methyl-2-oxopentyl)benzoic acid

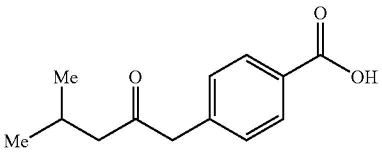

By operating in the same manner as in Reference Example 74 and using methyl 4-(4-methyl-2-oxopentyl) benzoate obtained in Reference Example 81, the title compound was obtained as a colorless powder.

$^1$H-NMR (DMSO-$d_6$) δ: 0.84 (6H, d, J=6.6 Hz), 2.03 (1H, m), 2.39 (2H, d, J=7.0 Hz), 3.83 (2H, s), 7.29 (2H, dt, J=8.3, 1.7 Hz), 7.87 (2H, dt, J=8.4, 1.9 Hz), 12.85 (1H, s).

Reference Example 83

Methyl 4-(2-oxo-2-tetrahydrofuran-2-ylethyl)benzoate

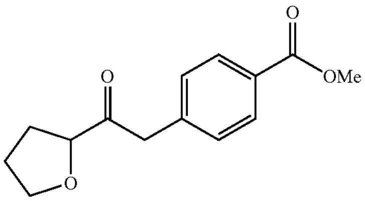

By operating in the same manner as in Reference Example 77 and using tetrahydrofuran-2-carbonyl chloride, the title compound was obtained as a colorless liquid.

$^1$H-NMR ($CDCl_3$) δ: 1.89 (3H, m), 2.18 (1H, m), 3.91 (3H, s), 3.91 (2H, m), 3.94 (2H, s), 4.39 (1H, m), 7.29 (2H, dt, J=8.5, 1.8 Hz), 7.99 (2H, dt, J=8.3, 1.9 Hz).

Reference Example 84

4-(2-oxo-2-tetrahydrofuran-2-ylethyl)benzoic acid

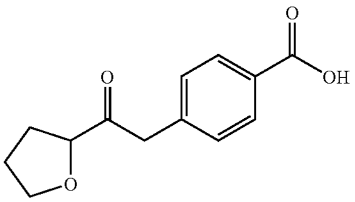

By operating in the same manner as in Reference Example 74 and using methyl 4-(2-oxo-2-tetrahydrofuran-2-ylethyl)benzoate obtained in Reference Example 83, the title compound was obtained as a pale-yellow powder.

$^1$H-NMR (DMSO-$d_6$) δ: 1.96 (4H, m), 3.84 (2H, m), 3.97 (2H, s), 4.41 (1H, m), 7.30 (2H, d, J=8.2 Hz), 7.87 (2H, d, J=8.2 Hz), 12.85 (1H, s).

Reference Example 85

Methyl 4-(2-oxo-2-tetrahydrofuran-3-ylethyl)benzoate

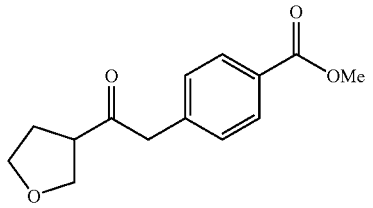

By operating in the same manner as in Reference Example 77 and using tetrahydrofuran-3-carbonyl chloride, the title compound was obtained as a colorless liquid.

$^1$H-NMR ($CDCl_3$) δ: 2.13 (3H, m), 3.30 (1H, m), 3.83 (2H, s), 3.87 (3H, m), 3.92 (3H, s), 7.28 (2H, dt, J=8.5, 1.7 Hz), 8.02 (2H, dt, J=8.3, 1.9 Hz).

Reference Example 86

4-(2-oxo-2-tetrahydrofuran-3-ylethyl)benzoic acid

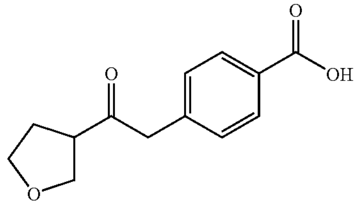

By operating in the same manner as in Reference Example 74 and using methyl 4-(2-oxo-2-tetrahydrofuran-3-ylethyl)benzoate obtained in Reference Example 85, the title compound was obtained as a colorless powder.

$^1$H-NMR (DMSO-$d_6$) δ: 2.02 (2H, m), 3.38 (1H, m), 3.66 (2H, m), 3.79 (2H, d, J=6.9 Hz), 3.98 (2H, s), 7.31 (2H, d, J=8.6 Hz), 7.88 (2H, ddd, J=8.4, 3.9, 2.1 Hz), 12.88 (1H, s).

Reference Example 87

8-methyl-3-[(4-methylpiperazin-1-yl)methyl]-7-quinolinamine

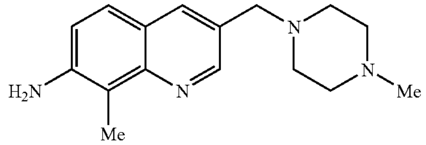

By operating in the same manner as in Reference Example 67 and using 7-amino-8-methyl-3-quinolinecarboaldehyde obtained in Reference Example 66, the title compound was obtained as a powder.

$^1$H-NMR ($CDCl_3$) δ: 2.28 (3H, s), 2.42 (8H, m), 2.59 (3H, s), 3.63 (2H, s), 4.00 (2H, s), 7.00 (1H, d, J=8.5 Hz), 7.49 (1H, d, J=8.5 Hz), 7.88 (1H, d, J=2.2 Hz), 8.78 (1H, d, J=2.2 Hz).

Example 1

4'-chloro-N-[3-[(dimethylamino)methyl]-7-quinolinyl][1,1'-biphenyl]-4-carboxamide

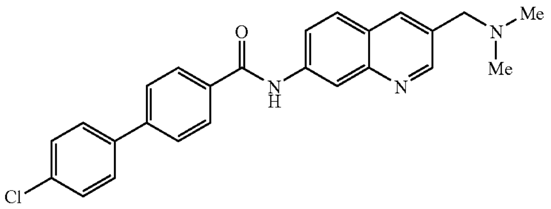

To a solution of N-[(7-amino-3-quinolinyl)methyl]-N,N-dimethylamine (87 mg, 0.432 mmol) obtained in Reference Example 4,4'-chloro[1,1'-biphenyl]-4-carboxylic acid (101 mg, 0.432 mmol) and dimethylaminopyridine (52.8 mg, 0.432 mmol) in dimethylformamide (2 ml) was added ethyldimethylaminopropylcarbodiimide hydrochloride (101 mg, 0.432 mmol) at 0° C., and the mixture was stirred at room temperature for 16 hrs. Ethyl acetate was added to the reaction solution, and the mixture was washed with aqueous potassium carbonate solution and saturated brine, and dried over anhydrous sodium sulfate. The solvent was concentrated under reduced pressure and the obtained residue was purified by alumina column chromatography (eluting solvent; ethyl acetate) and treated with ethyl acetate-isopropyl ether (1:5) to give the title compound (120 mg) as a powder.

$^1$H NMR (DMSO-$d_6$) δ 2.21 (6H, s), 3.59 (2H, s), 7.58 (2H, d, J=8.7 Hz), 7.82 (2H, d, J=8.7 Hz), 7.89 (2H, d, J=8.7 Hz), 7.97 (2H, m), 8.13 (3H, m), 8.60 (1H, m), 8.79 (1H, d, J=2.1 Hz), 10.63 (1H, s). FABMS(pos): 416 $[M+H]^+$ melting point: 236–238° C. (crystallization solvent: ethyl acetate-isopropyl ether)

Example 2

N-[3-(1-pyrrolidinylmethyl)-7-quinolinyl][1,1'-biphenyl]-4-carboxamide

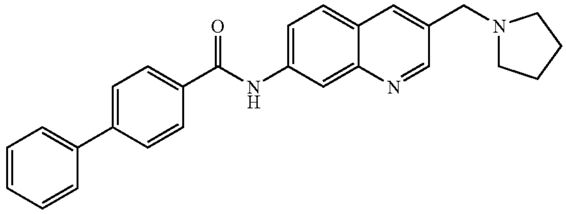

By operating in the same manner as in Example 1 and using 3-(1-pyrrolidinylmethyl)-7-quinolinylamine hydrochloride obtained in Reference Example 5 and [1,1'-biphenyl]-4-carboxylic acid, the title compound was obtained.

$^1$H NMR (DMSO-$d_6$) δ 1.73 (4H, m), 2.50 (4H, m), 3.77 (2H, s), 7.44 (1H, m), 7.53 (2H, m), 7.78 (2H, d, J=6.9 Hz), 7.88 (2H, d, J=8.7 Hz), 7.96 (2H, m), 8.14 (3H, m), 8.59 (1H, s), 8.81 (1H, d, J=2.1 Hz), 10.61 (1H, s). FABMS(pos): 408 $[M+H]^+$ melting point: 192–194° C. (crystallization solvent: ethyl acetate-isopropyl ether)

Example 3

4'-methoxy-N-[3-(1-pyrrolidinylmethyl)-7-quinolinyl][1,1'-biphenyl]-4-carboxamide

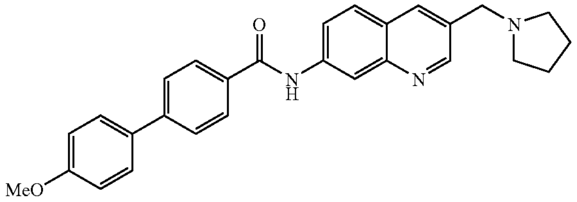

By operating in the same manner as in Example 1 and using 3-(1-pyrrolidinylmethyl)-7-quinolinylamine hydrochloride obtained in Reference Example 5 and 4'-methoxy [1,1'-biphenyl]-4-carboxylic acid, the title compound was obtained.

$^1$H NMR (DMSO-$d_6$) δ 1.72 (4H, m), 2.50 (4H, m), 3.76 (2H, s), 3.82 (3H, s), 7.08 (2H, d, J=8.7 Hz), 7.74 (2H, d, J=8.7 Hz), 7.83 (2H, d, J=8.4 Hz), 7.97 (2H, m), 8.10 (2H, d, J=8.7 Hz), 8.15 (1H, d, J=1.2 Hz), 8.59 (1H, d, J=1.8 Hz), 8.81 (1H, d, J=2.1 Hz), 10.57 (1H, s). FABMS(pos): 438 $[M+H]^+$ melting point: 202–204° C. (crystallization solvent: ethyl acetate-isopropyl ether)

Example 4

4'-fluoro-N-[3-(1-pyrrolidinylmethyl)-7-quinolinyl][1,1'-biphenyl]-4-carboxamide

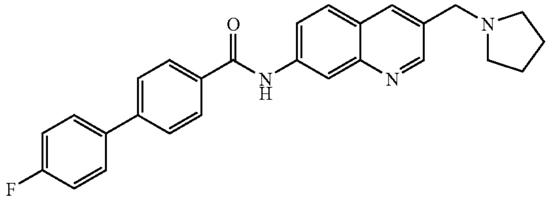

By operating in the same manner as in Example 1 and using 3-(1-pyrrolidinylmethyl)-7-quinolinylamine hydrochloride obtained in Reference Example 5 and 4'-fluoro[1,1'-biphenyl]-4-carboxylic acid, the title compound was obtained.

$^1$H NMR (DMSO-$d_6$) δ 1.72 (4H, m), 2.50 (4H, m), 3.77 (2H, s), 7.35 (2H, m), 7.85 (4H, m), 7.97 (2H, m), 8.14 (3H, m), 8.59 (1H, d, J=1.8 Hz), 8.81 (1H, d, J=2.1 Hz), 10.61 (1H, s). FABMS(pos): 426 $[M+H]^+$ melting point: 210–212° C. (crystallization solvent: ethyl acetate-isopropyl ether)

Example 5

4'-methyl-N-[3-(1-pyrrolidinylmethyl)-7-quinolinyl][1,1'-biphenyl]-4-carboxamide

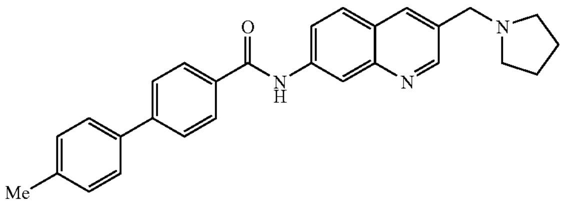

By operating in the same manner as in Example 1 and using 3-(1-pyrrolidinylmethyl)-7-quinolinylamine hydrochloride obtained in Reference Example 5 and 4'-methyl[1,1'-biphenyl]-4-carboxylic acid, the title compound was obtained.

$^1$H NMR (DMSO-$d_6$) δ 1.72 (4H, m), 2.37 (3H, s), 2.50 (4H, m), 3.77 (2H, s), 7.33 (2H, d, J=7.8 Hz), 7.68 (2H, d, J=8.4 Hz), 7.85 (2H, d, J=8.4 Hz), 7.97 (2H, m), 8.11 (2H, d, J=8.7 Hz), 8.16 (1H, d, J=1.5 Hz), 8.59 (1H, d, J=1.8 Hz), 8.81 (1H, d, J=2.1 Hz), 10.59 (1H, s). FABMS(pos): 422 $[M+H]^+$ melting point: 206–208° C. (crystallization solvent: ethyl acetate-isopropyl ether)

Example 6

4'-chloro-N-[3-(1-pyrrolidinylmethyl)-7-quinolinyl][1,1'-biphenyl]-4-carboxamide

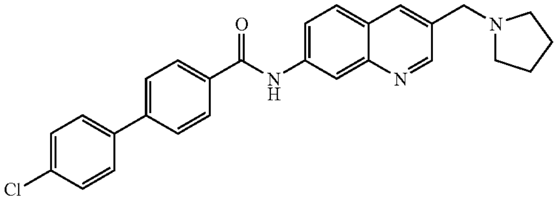

By operating in the same manner as in Example 1 and using 3-(1-pyrrolidinylmethyl)-7-quinolinylamine hydrochloride obtained in Reference Example 5 and 4'-chloro[1,1'-biphenyl]-4-carboxylic acid, the title compound was obtained.

$^1$H NMR (DMSO-$d_6$) δ 1.72 (4H, m), 2.50 (4H, m), 3.77 (2H, s), 7.58 (2H, d, J=8.7 Hz), 7.82 (2H, d, J=8.4 Hz), 7.88 (2H, d, J=8.4 Hz), 7.97 (2H, m), 8.13 (2H, d, J=8.7 Hz), 8.16 (1H, d, J=1.2 Hz), 8.59 (1H, s), 8.81 (1H, d, J=2.1 Hz), 10.62 (1H, s). FABMS(pos): 442 $[M+H]^+$ melting point: 217–220° C. (crystallization solvent: ethyl acetate-isopropyl ether)

Example 7

6-phenyl-N-[3-(1-pyrrolidinylmethyl)-7-quinolinyl]nicotinamide

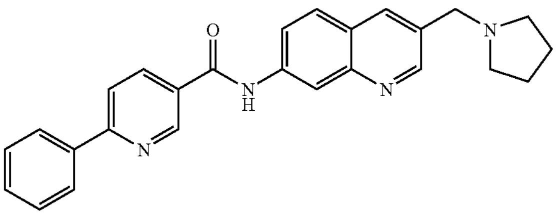

By operating in the same manner as in Example 1 and using 3-(1-pyrrolidinylmethyl)-7-quinolinylamine hydrochloride obtained in Reference Example 5 and 6-phenylnicotinic acid, the title compound was obtained.

$^1$H NMR (DMSO-$d_6$) δ 1.72 (4H, m), 2.50 (4H, m), 3.76 (2H, s), 7.55 (3H, m), 7.96 (2H, m), 8.20 (4H, m), 8.45 (1H, dd, J=8.4, 2.4 Hz), 8.59 (1H, s), 8.82 (1H, d, J=2.1 Hz), 9.26 (1H, d, J=1.8 Hz), 10.76 (1H, s). FABMS(pos): 409 $[M+H]^+$ melting point: 208–210° C. (crystallization solvent: ethyl acetate-isopropyl ether)

Example 8

6-(4-methoxyphenyl)-N-[3-(1-pyrrolidinylmethyl)-7-quinolinyl]nicotinamide

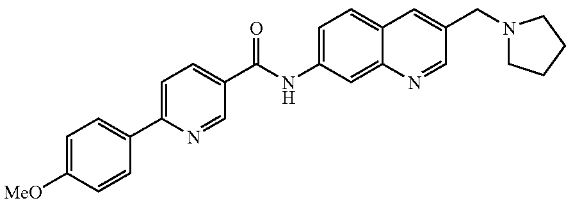

By operating in the same manner as in Example 1 and using 3-(1-pyrrolidinylmethyl)-7-quinolinylamine hydrochloride obtained in Reference Example 5 and 6-(4-methoxyphenyl)nicotinic acid, the title compound was obtained.

$^1$H NMR (DMSO-$d_6$) δ 1.72 (4H, m), 2.50 (4H, m), 3.77 (2H, s), 3.85 (3H, s), 7.10 (2H, d, J=9.3 Hz), 7.96 (2H, m), 8.11 (1H, d, J=8.1 Hz), 8.19 (3H, m), 8.40 (1H, dd, J=8.4, 2.1 Hz), 8.58 (1H, s), 8.82 (1H, d, J=2.1 Hz), 9.21 (1H, d, J=1.5 Hz), 10.72 (1H, s). FABMS(pos): 439 $[M+H]^+$ melting point: 246–248° C. (crystallization solvent: ethyl acetate-isopropyl ether)

Example 9

6-(4-fluorophenyl)-N-[3-(1-pyrrolidinylmethyl)-7-quinolinyl]nicotinamide

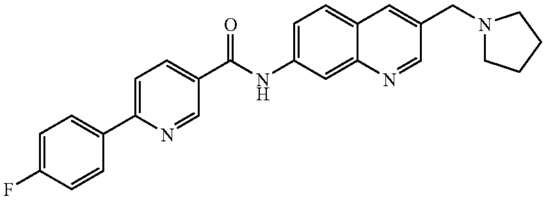

By operating in the same manner as in Example 1 and using 3-(1-pyrrolidinylmethyl)-7-quinolinylamine hydrochloride obtained in Reference Example 5 and 6-(4-fluorophenyl)nicotinic acid, the title compound was obtained.

$^1$H NMR (DMSO-$d_6$) δ 1.72 (4H, m), 2.50 (4H, m), 3.76 (2H, s), 7.38 (2H, m), 7.96 (2H, m), 8.18 (2H, m), 8.28 (2H, m), 8.45 (1H, dd, J=8.4, 2.4 Hz), 8.59 (1H, s), 8.82 (1H, d, J=2.1 Hz), 9.25 (1H, d, J=1.5 Hz), 10.76 (1H, s). FABMS (pos): 427 $[M+H]^+$ melting point: 218–220° C. (crystallization solvent: ethyl acetate-isopropyl ether)

Example 10

6-(4-methylphenyl)-N-[3-(1-pyrrolidinylmethyl)-7-quinolinyl]nicotinamide

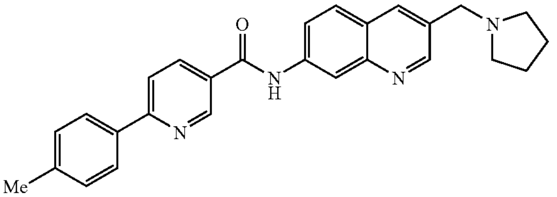

By operating in the same manner as in Example 1 and using 3-(1-pyrrolidinylmethyl)-7-quinolinylamine hydrochloride obtained in Reference Example 5 and 6-(4-methylphenyl)nicotinic acid, the title compound was obtained.

$^1$H NMR (DMSO-$d_6$) δ 1.72 (4H, m), 2.39 (3H, s), 2.50 (4H, m), 3.77 (2H, s), 7.36 (2H, d, J=8.1 Hz), 7.96 (2H, m), 8.11 (2H, d, J=8.1 Hz), 8.17 (2H, m), 8.42 (1H, dd, J=8.4, 2.4 Hz), 8.59 (1H, s), 8.82 (1H, d, J=2.1 Hz), 9.23 (1H, m), 10.74 (1H, s). FABMS(pos): 423 $[M+H]^+$ melting point: 226–228° C. (crystallization solvent: ethyl acetate-isopropyl ether)

Example 11

6-(4-chlorophenyl)-N-[3-(1-pyrrolidinylmethyl)-7-quinolinyl]nicotinamide

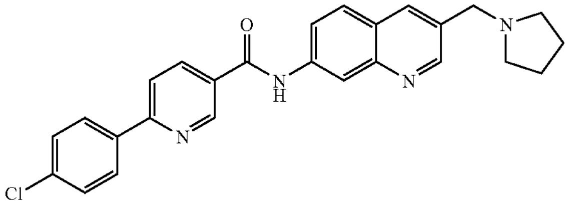

By operating in the same manner as in Example 1 and using 3-(1-pyrrolidinylmethyl)-7-quinolinylamine hydrochloride obtained in Reference Example 5 and 6-(4-chlorophenyl)nicotinic acid, the title compound was obtained.

$^1$H NMR (DMSO-$d_6$) δ 1.72 (4H, m), 2.50 (4H, m), 3.77 (2H, s), 7.62 (2H, d, J=9.0 Hz), 7.96 (2H, m), 8.17–8.26 (4H, m), 8.47 (1H, dd, J=8.4, 2.4 Hz), 8.59 (1H, s), 8.82 (1H, d, J=2.1 Hz), 9.26 (1H, d, J=1.5 Hz), 10.77 (1H, s). FABMS (pos): 443 $[M+H]^+$ melting point: 223–225° C. (crystallization solvent: ethyl acetate-isopropyl ether)

Example 12

4-phenyl-N-[3-(1-pyrrolidinylmethyl)-7-quinolinyl]-1-piperidine carboxamide

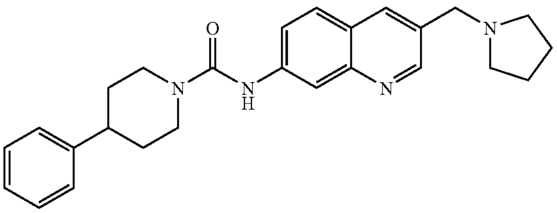

To a solution of 3-(1-pyrrolidinylmethyl)-7-quinolinylamine hydrochloride (150 mg, 0.569 mmol) obtained in Reference Example 5 and triethylamine (0.0791 ml, 0.569 mmol) in dimethylacetamide (3 ml) was added carbonyldiimidazole (111 mg, 0.682 mmol) at 0° C. and the mixture was stirred for 1 hr. To the obtained solution was added 4-phenylpiperidine hydrochloride at room temperature, and the mixture was stirred for 2 hrs. Ethyl acetate was added to the reaction solution, and the mixture was washed with aqueous potassium carbonate solution and saturated brine, and dried over anhydrous sodium sulfate. The solvent was concentrated under reduced pressure and the obtained residue was purified by alumina column chromatography (eluting solvent; ethyl acetate), and treated with ethyl acetate-isopropyl ether (1:5) to give the title compound (18.8 mg) as a powder.

$^1$H NMR (DMSO-$d_6$) δ 1.59–1.67 (2H, m), 1.71 (4H, m), 1.81–1.85 (2H, m), 2.50 (4H, m), 2.77 (1H, m), 2.94 (2H, m), 3.73 (2H, s), 4.32–4.36 (2H, m), 7.18–7.34 (5H, m), 7.73–7.82 (2H, m), 8.07 (1H, s), 8.16 (1H, d, J=2.1 Hz), 8.73 (1H, d, J=2.4 Hz), 8.87 (1H, s). FABMS(pos): 415 $[M+H]^+$ melting point: 222–224° C. (crystallization solvent: ethyl acetate-isopropyl ether)

Example 13

4-(4-methoxyphenyl)-N-[3-(1-pyrrolidinylmethyl)-7-quinolinyl]-1-piperidine carboxamide

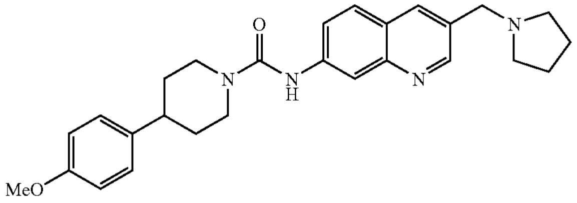

By operating in the same manner as in Example 12 and using 3-(1-pyrrolidinylmethyl)-7-quinolinylamine hydrochloride obtained in Reference Example 5 and 4-(4-methoxyphenyl)piperidine, the title compound was obtained.

$^1$H NMR (DMSO-$d_6$) δ 1.55–1.62 (2H, m), 1.71 (4H, m), 1.78–1.82 (2H, m), 2.49 (4H, m), 2.71 (1H, m), 2.91 (2H, m), 3.72 (5H, m), 4.31–4.35 (2H, m), 6.87 (2H, d, J=8.7 Hz), 7.19 (2H, d, J=8.7 Hz), 7.77 (2H, m), 8.07 (1H, s), 8.16 (1H, s), 8.72 (1H, d, J=2.1 Hz), 8.88 (1H, s). FABMS(pos): 445 $[M+H]^+$ melting point: 241–243° C. (crystallization solvent: ethyl acetate-isopropyl ether)

Example 14

4-(4-fluorophenyl)-N-[3-(1-pyrrolidinylmethyl)-7-quinolinyl]-1-piperidine carboxamide

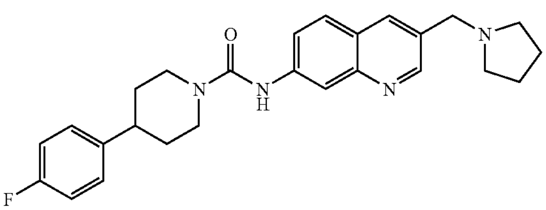

By operating in the same manner as in Example 12 and using 3-(1-pyrrolidinylmethyl)-7-quinolinylamine hydrochloride obtained in Reference Example 5 and 4-(4-fluorophenyl)piperidine, the title compound was obtained.

$^1$H NMR (DMSO-$d_6$) δ 1.56–1.64 (2H, m), 1.71 (4H, m), 1.80–1.84 (2H, m), 2.47 (4H, m), 2.78 (1H, m), 2.92 (2H, m), 3.73 (2H, s), 4.31–4.36 (2H, m), 7.12 (2H, m), 7.32 (2H, m), 7.73–7.82 (2H, m), 8.06 (1H, d, J=1.5 Hz), 8.16 (1H, d, J=2.1 Hz), 8.72 (1H, d, J=1.8 Hz), 8.87 (1H, s). FABMS (pos): 433 $[M+H]^+$ melting point: 239–241° C. (crystallization solvent: ethyl acetate-isopropyl ether)

Example 15

4-(4-methylphenyl)-N-[3-(1-pyrrolidinylmethyl)-7-quinolinyl]-1-piperidine carboxamide

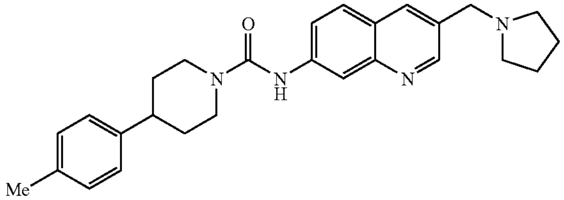

By operating in the same manner as in Example 12 and using 3-(1-pyrrolidinylmethyl)-7-quinolinylamine hydrochloride obtained in Reference Example 5 and 4-(4-methylphenyl)piperidine, the title compound was obtained.

$^1$H NMR (DMSO-$d_6$) δ 1.55–1.65 (2H, m), 1.71 (4H, m), 1.78–1.82 (2H, m), 2.26 (3H, s), 2.47 (4H, m), 2.72 (1H, m), 2.92 (2H, m), 3.72 (2H, s), 4.31–4.35 (2H, m), 7.09–7.17 (4H, m), 7.73–7.82 (2H, m), 8.07 (1H, s), 8.15 (1H, d, J=1.8 Hz), 8.72 (1H, d, J=1.8 Hz), 8.88 (1H, s). FABMS(pos): 429 $[M+H]^+$ melting point: 244–246° C. (crystallization solvent: ethyl acetate-isopropyl ether)

Example 16

4-(4-chlorophenyl)-N-[3-(1-pyrrolidinylmethyl)-7-quinolinyl]-1-piperidine carboxamide

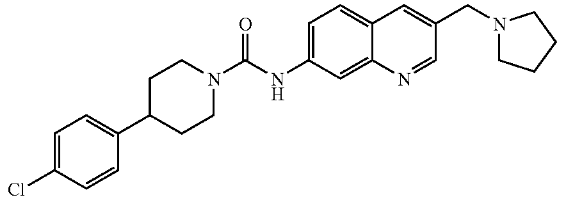

By operating in the same manner as in Example 12 and using 3-(1-pyrrolidinylmethyl)-7-quinolinylamine hydrochloride obtained in Reference Example 5 and 4-(4-chlorophenyl)piperidine, the title compound was obtained.

$^1$H NMR (DMSO-$d_6$) δ 1.56–1.64 (2H, m), 1.71 (4H, m), 1.80–1.84 (2H, m), 2.47 (4H, m), 2.79 (1H, m), 2.92 (2H, m), 3.72 (2H, s), 4.31–4.36 (2H, m), 7.30–7.38 (4H, m), 7.72–7.82 (2H, m), 8.06 (1H, s), 8.16 (1H, s), 8.72 (1H, d, J=1.8 Hz), 8.87 (1H, s). FABMS(pos): 449 $[M+H]^+$ melting point: 249–251° C. (crystallization solvent: ethyl acetate-isopropyl ether)

Example 17

N-[8-methyl-3-(1-pyrrolidinylmethyl)-7-quinolinyl][1,1'-biphenyl]-4-carboxamide

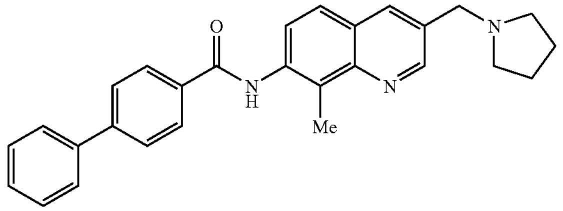

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained as a powder.

$^1$H NMR (DMSO-$d_6$) δ 1.73 (4H, m), 2.50 (4H, m), 2.67 (3H, s), 3.81 (2H, s), 7.46 (1H, m), 7.53 (2H, m), 7.63 (1H, d, J=9.0 Hz), 7.77–7.88 (5H, m), 8.15 (2H, d, J=8.7 Hz), 8.22 (1H, d, J=1.8 Hz), 8.88 (1H, d, J=2.1 Hz), 10.28 (1H, s). FABMS(pos): 422 $[M+H]^+$ melting point: 184–186° C. (crystallization solvent: ethyl acetate-isopropyl ether)

Example 18

4'-methoxy-N-[8-methyl-3-(1-pyrrolidinylmethyl)-7-quinolinyl][1,1'-biphenyl]-4-carboxamide

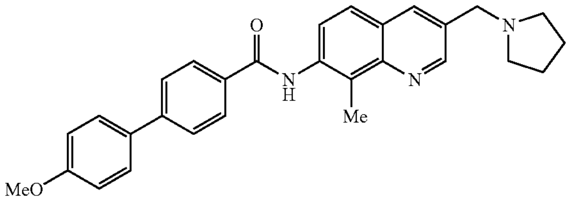

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H NMR (DMSO-$d_6$) δ 1.73 (4H, m), 2.50 (4H, m), 2.67 (3H, s), 3.80 (2H, s), 3.82 (3H, s), 7.08 (2H, d, J=8.7 Hz), 7.62 (1H, d, J=8.7 Hz), 7.74 (2H, d, J=8.7 Hz), 7.83 (3H, m), 8.12 (2H, d, J=8.4 Hz), 8.21 (1H, d, J=2.1 Hz), 8.88 (1H, d, J=1.8 Hz), 10.23 (1H, s). FABMS(pos): 452 $[M+H]^+$ melting point: 210–213° C. (crystallization solvent: ethyl acetate-isopropyl ether)

Example 19

4'-fluoro-N-[8-methyl-3-(1-pyrrolidinylmethyl)-7-quinolinyl][1,1'-biphenyl]-4-carboxamide

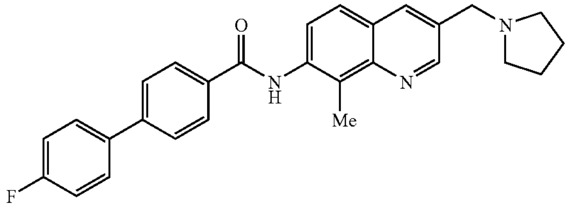

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H NMR (DMSO-$d_6$) δ 1.73 (4H, m), 2.50 (4H, m), 2.67 (3H, s), 3.80 (2H, s), 7.35 (2H, m), 7.62 (1H, d, J=8.7 Hz), 7.81–7.87 (5H, m), 8.14 (2H, d, J=8.1 Hz), 8.22 (1H, d, J=1.8 Hz), 8.88 (1H, d, J=1.8 Hz), 10.28 (1H, s). FABMS (pos): 440 $[M+H]^+$ melting point: 220–222° C. (crystallization solvent: ethyl acetate-isopropyl ether)

Example 20

4'-methyl-N-[8-methyl-3-(1-pyrrolidinylmethyl)-7-quinolinyl][1,1'-biphenyl]-4-carboxamide

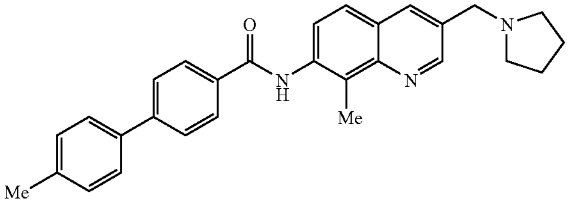

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H NMR (DMSO-$d_6$) δ 1.72 (4H, m), 2.37 (3H, s), 2.50 (4H, m), 2.67 (3H, s), 3.80 (2H, s), 7.34 (2H, m), 7.61–7.72 (3H, m), 7.81–7.85 (2H, m), 7.93 (1H, d, J=8.1 Hz), 8.13 (2H, d, J=8.1 Hz), 8.20 (1H, m), 8.88 (1H, d, J=1.8 Hz), 10.27 (1H, s). FABMS(pos): 436 $[M+H]^+$ melting point: 177–179° C. (crystallization solvent: ethyl acetate-isopropyl ether)

Example 21

4'-chloro-N-[8-methyl-3-(1-pyrrolidinylmethyl)-7-quinolinyl][1,1'-biphenyl]-4-carboxamide

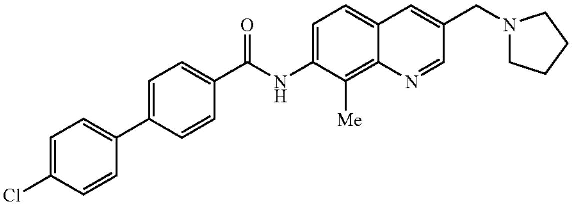

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H NMR (DMSO-$d_6$) δ 1.73 (4H, m), 2.50 (4H, m), 2.67 (3H, s), 3.81 (2H, s), 7.57 (2H, d, J=8.7 Hz), 7.62 (1H, d, J=9.0 Hz), 7.81–7.89 (5H, m), 8.15 (2H, d, J=8.1 Hz), 8.23 (1H, s), 8.88 (1H, d, J=2.1 Hz), 10.29 (1H, s). FABMS(pos): 456 $[M+H]^+$ melting point: 227–229° C. (crystallization solvent: ethyl acetate-isopropyl ether)

Example 22

4'-chloro-N-{3-[(diethylamino)methyl]-6-methoxy-7-quinolinyl}[1,1'-biphenyl]-4-carboxamide

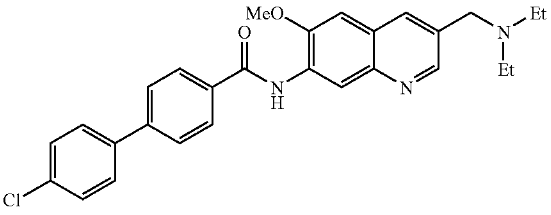

4'-Chloro[1,1'-biphenyl]-4-carboxylic acid (100 mg, 0.430 mmol) was dissolved in tetrahydrofuran (5 ml). To the reaction solution were added oxalyl chloride (0.0375 ml, 0.430 mmol) and one drop of DMF, and the mixture was stirred at room temperature for 1.5 hrs. The reaction solution was concentrated under reduced pressure and the obtained pale-brown crystals were dissolved in DMF (1 ml). Thereto were added a solution of 3-[(diethylamino)methyl]-6-methoxy-7-quinolinylamine (111 mg, 0.430 mmol) obtained in Reference Example 13 in DMF (1 ml) and triethylamine (0.0719 ml, 0.516 mmol), and the mixture was stirred at room temperature for 4 hrs. Ethyl acetate (20 ml) was added to the reaction solution, and the mixture was washed with a mixed solution of aqueous potassium carbonate solution (10 ml) and saturated brine (5 ml), and then with a mixed solution of saturated brine (10 ml) and water (10 ml). The organic layer was purified by NH-silica gel column, and the precipitated crystals were washed with ethyl acetate:isopropyl ether=2:1. The crystals were collected by filtration and dried to give the title compound (27.5 mg) as pale-yellow crystals.

$^1$H NMR (DMSO-$d_6$) δ 1.02 (6H, m), 2.50 (4H, m), 3.71 (2H, s), 4.02 (3H, s), 7.50 (1H, s), 7.58 (2H, d, J=8.3 Hz), 7.81 (2H, d, J=8.5), 7.87 (2H, d, J=8.3 Hz), 8.10 (3H, m), 8.63 (1H, s), 8.69 (1H, s), 9.65 (1H, s). FABMS(pos): 474 $[M+H]^+$ melting point: 271° C. (dec.) (washing solvent: ethyl acetate-isopropyl ether)

Example 23

4'-chloro-N-[6-methoxy-3-(1-pyrrolidinylmethyl)-7-quinolinyl][1,1'-biphenyl]-4-carboxamide

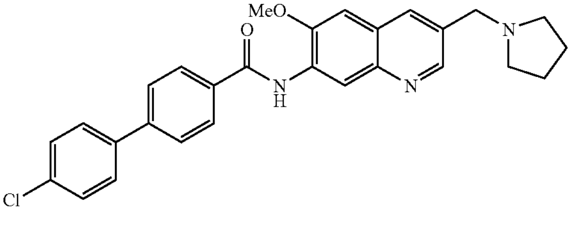

By operating in the same manner as in Example 22 and using 6-methoxy-3-(1-pyrrolidinylmethyl)-7-quinolinylamine obtained in Reference Example 14, the title compound was obtained as pale-yellow crystals.

$^1$H NMR (DMSO-$d_6$) δ 1.72 (4H, m), 2.50 (4H, m), 3.76 (2H, br s), 4.02 (3H, s), 7.50 (1H, s), 7.58 (2H, d, J=8.5 Hz), 7.81 (2H, d, J=8.5), 7.87 (2H, d, J=8.5 Hz), 8.10 (3H, m), 8.64 (1H, s), 8.69 (1H, d, J=2.0 Hz), 9.65 (1H, s). FABMS (pos): 472 $[M+H]^+$ melting point: 271° C. (dec.) (washing solvent: ethyl acetate-isopropyl ether)

Example 24

4'-chloro-N-[6-methoxy-3-(1-piperidinylmethyl)-7-quinolinyl][1,1'-biphenyl]-4-carboxamide

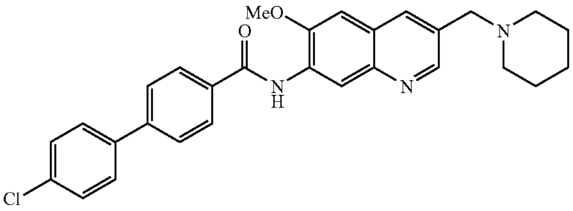

By operating in the same manner as in Example 22 and using 6-methoxy-3-(1-piperidinylmethyl)-7-quinolinylamine obtained in Reference Example 15, the title compound was obtained as colorless crystals.

$^1$H NMR (DMSO-$d_6$) δ 1.40 (2H, m), 1.52 (4H, m), 3.62 (4H, m), 3.62 (2H, br s), 4.02 (3H, s), 7.50 (1H, s), 7.58 (2H, d, J=8.5 Hz), 7.81 (2H, d, J=8.5), 7.87 (2H, d, J=8.3 Hz), 8.11 (3H, m), 8.64 (1H, s), 8.67 (1H, m), 9.65 (1H, s). FABMS(pos): 486 $[M+H]^+$ melting point: 236° C. (dec.) (washing solvent: ethyl acetate-isopropyl ether)

Example 25

4'-chloro-N-[6-chloro-3-(1-pyrrolidinylmethyl)-7-quinolinyl][1,1'-biphenyl]-4-carboxamide

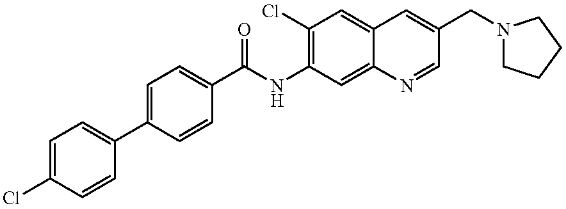

By operating in the same manner as in Example 22 and using 6-chloro-3-(1-pyrrolidinylmethyl)-7-quinolinylamine obtained in Reference Example 18, the title compound was obtained as pale-yellow crystals.

$^1$H NMR (DMSO-$d_6$) δ 1.73 (4H, m), 2.50 (4H, m), 3.80 (2H, br s), 7.58 (2H, d, J=8.5 Hz), 7.82 (2H, d, J=8.5), 7.89 (2H, d, J=8.3 Hz), 8.14 (2H, d, J=8.3 Hz), 8.28 (3H, m), 8.88 (1H, d, J=2.0 Hz), 10.33 (1H, s). FABMS(pos): 476 $[M+H]^+$ melting point: 188° C. (dec.) (washing solvent: ethyl acetate-isopropyl ether)

Example 26

1-[(8-methyl-7-{[(4'-methyl-1,1'-biphenyl-4-yl)carbonyl]amino}-3-quinolinyl)methyl]-4-piperidine carboxamide

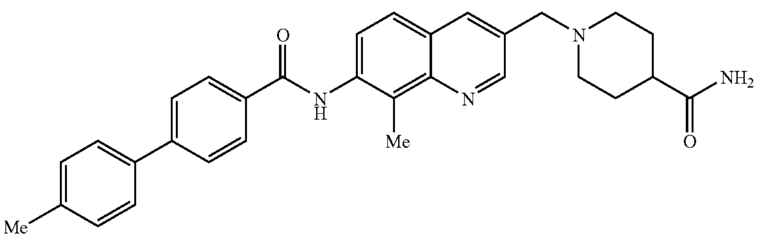

1) 4'-Methyl-N-[8-methyl-3-(1-pyrrolidinylmethyl)-7-quinolinyl][1,1'-biphenyl]-4-carboxamide (50 mg, 0.115 mmol) obtained in Example 20 was dissolved in tetrahydrofuran (1 ml) and the mixture was ice-cooled. To the reaction solution were added potassium carbonate (23.8 mg, 0.172 mmol) and ethyl chlorocarbonate (0.0165 ml, 0.172 mmol), and the mixture was stirred at room temperature for 3 hrs. To the reaction solution was added ethyl acetate (20 ml) and the mixture was washed with aqueous potassium carbonate solution (10 ml). The precipitated crystals were dissolved in tetrahydrofuran and purified by NH-silica gel column to give N-[3-(chloromethyl)-8-methyl-7-quinolinyl]-4'-methyl[1,1'-biphenyl]-4-carboxamide (75 mg) as pale-yellow crystals.

$^1$H NMR (DMSO-$d_6$) δ 2.37 (3H, s), 2.67 (3H, s), 5.04 (2H, s), 7.34 (2H, m), 7.69 (3H, m), 7.84 (2H, d, J=8.5 Hz), 7.88 (1H, m), 8.13 (2H, d, J=8.3 Hz), 8.42 (1H, d, J=2.4 Hz), 8.99 (1H, d, J=2.2 Hz), 10.28 (1H, s).

2) N-[3-(Chloromethyl)-8-methyl-7-quinolinyl]-4'-methyl [1,1'-biphenyl]-4-carboxamide (75 mg) obtained in the above-mentioned 1) was suspended in DMF (1 ml). Potassium carbonate (47.6 mg, 0.344 mmol) and 4-piperidine carboxamide (17.7 mg, 0.126 mmol) were added to the reaction solution and the mixture was stirred at room temperature for 15 hrs. To the reaction solution was added ethyl acetate (20 ml) and the mixture was washed with a mixed solvent of aqueous potassium carbonate solution (10 ml) and saturated brine (5 ml) and then with a mixed solvent of saturated brine (10 ml) and water (10 ml). The organic layer was concentrated under reduced pressure and the precipitated crystals were collected by filtration, washed with ethyl acetate and dried to give the title compound (23.0 mg) as pale-yellow crystals.

$^1$H NMR (DMSO-$d_6$) δ 1.59 (2H, m), 1.67 (2H, m), 1.99 (2H, m), 2.07 (1H, m), 2.37 (3H, s), 2.67 (3H, s), 2.86 (2H, m), 3.67 (2H, s), 6.70 (1H, br s), 7.20 (1H, br s), 7.31 (2H, d, J=7.8 Hz), 7.62 (1H, d, J=8.8 Hz), 7.68 (2H, d, J=8.1 Hz), 7.82 (1H, d, J=8.8 Hz), 7.83 (2H, d, J=8.5 Hz), 8.13 (2H, d, J=8.5 Hz), 8.19 (1H, d, J=2.0 Hz), 8.86 (1H, d, J=2.2 Hz), 10.26 (1H, s). FABMS(pos): 493 [M+H]$^+$ melting point: 287° C. (dec.) (washing solvent: ethyl acetate)

Example 27

N-[3-(1-azepanylmethyl)-7-quinolinyl]-4'-chloro[1,1'-biphenyl]-4-carboxamide

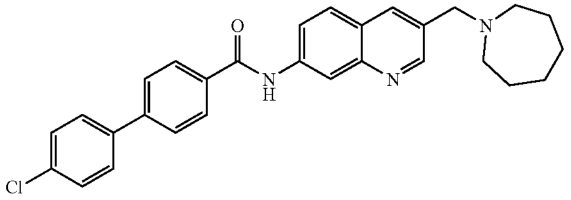

By operating in the same manner as in Example 1 and using 3-(1-azepanylmethyl)-7-quinolinylamine obtained in Reference Example 20, the title compound was obtained.

$^1$H NMR (DMSO-$d_6$) δ 1.59 (8H, m), 2.64 (4H, m), 3.80 (2H, br s), 7.58 (2H, m), 7.82 (2H, m), 7.89 (2H, m), 7.98 (2H, m), 8.13 (3H, m), 8.58 (1H, s), 8.83 (1H, m), 10.61 (1H, s). FABMS(pos): 470 [M+H]$^+$ melting point: 204° C. (washing solvent: ethyl acetate-isopropyl ether)

Example 28

N-[3-(1-azepanylmethyl)-7-quinolinyl]-4'-methyl[1,1'-biphenyl]-4-carboxamide

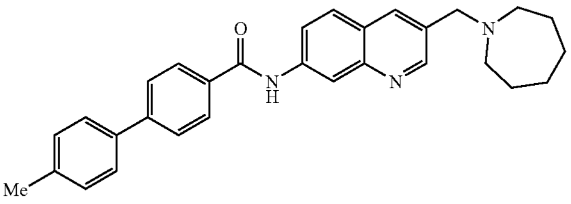

By operating in the same manner as in Example 1 and using 3-(1-azepanylmethyl)-7-quinolinylamine obtained in Reference Example 20, the title compound was obtained.

$^1$H NMR (DMSO-$d_6$) δ 1.59 (8H, m), 2.37 (3H, s), 2.65 (4H, m), 3.81 (2H, br s), 7.33 (2H, d, J=8.1 Hz), 7.68 (2H, d, J=8.1 Hz), 7.85 (2H, d, J=8.5 Hz), 7.96 (2H, m), 8.11 (2H, d, J=8.5 Hz), 8.15 (1H, s), 8.58 (1H, m), 8.83 (1H, m), 10.58

(1H, s). FABMS(pos): 450 $[M+H]^+$ melting point: 209° C. (washing solvent: ethyl acetate-isopropyl ether)

Example 29

N-[3-(1-azepanylmethyl)-7-quinolinyl]-4'-fluoro[1,1'-biphenyl]-4-carboxamide

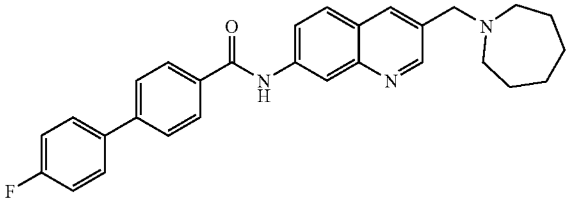

By operating in the same manner as in Example 1 and using 3-(1-azepanylmethyl)-7-quinolinylamine obtained in Reference Example 20, the title compound was obtained.

$^1H$ NMR (DMSO-$d_6$) δ 1.59 (8H, m), 2.64 (4H, m), 3.80 (2H, br s), 7.36 (2H, m), 7.82 (2H, m), 7.86 (2H, d, J=8.1 Hz), 7.97 (2H, m), 8.12 (2H, d, J=8.5 Hz), 8.15 (1H, s), 8.58 (1H, s), 8.83 (1H, m), 10.60 (1H, s). FABMS(pos): 454 $[M+H]^+$ melting point: 202° C. (washing solvent: ethyl acetate-isopropyl ether)

Example 30

N-[3-(1-azepanylmethyl)-7-quinolinyl]-4'-methoxy[1,1'-biphenyl]-4-carboxamide

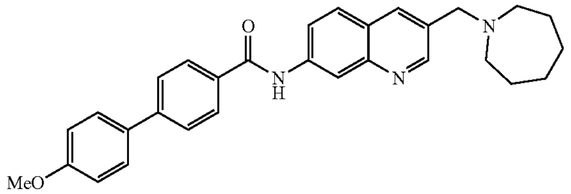

By operating in the same manner as in Example 1 and using 3-(1-azepanylmethyl)-7-quinolinylamine obtained in Reference Example 20, the title compound was obtained.

$^1H$ NMR (DMSO-$d_6$) δ 1.59 (8H, m), 2.64 (4H, m), 3.80 (2H, br s), 3.82 (3H, s), 7.08 (2H, d, J=8.8 Hz), 7.74 (2H, d, J=8.8 Hz), 7.83 (2H, d, J=8.5 Hz), 7.96 (2H, m), 8.09 (2H, d, J=8.5 Hz), 8.14 (1H, s), 8.58 (1H, m), 8.83 (1H, m), 10.56 (1H, s). FABMS(pos): 466 $[M+H]^+$ melting point: 212° C. (dec.) (washing solvent: ethyl acetate-isopropyl ether)

Example 31

N-[3-(1-azepanylmethyl)-7-quinolinyl][1,1'-biphenyl]-4-carboxamide

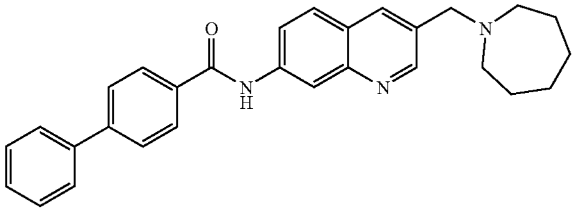

By operating in the same manner as in Example 1 and using 3-(1-azepanylmethyl)-7-quinolinylamine obtained in Reference Example 20, the title compound was obtained.

$^1H$ NMR (DMSO-$d_6$) δ 1.59 (8H, m), 2.64 (4H, m), 3.80 (2H, br s), 7.44 (1H, m), 7.52 (2H, m), 7.78 (2H, d, J=7.1 Hz), 7.88 (2H, d, J=8.3 Hz), 7.96 (2H, m), 8.13 (2H, d, J=8.3 Hz), 8.15 (1H, s), 8.58 (1H, m), 8.83 (1H, m), 10.61 (1H, s). FABMS(pos): 436 $[M+H]^+$ melting point: 205° C. (dec.) (washing solvent: ethyl acetate-isopropyl ether)

Example 32

N-[3-(1-azepanylmethyl)-7-quinolinyl]-6-(4-chlorophenyl)nicotinamide

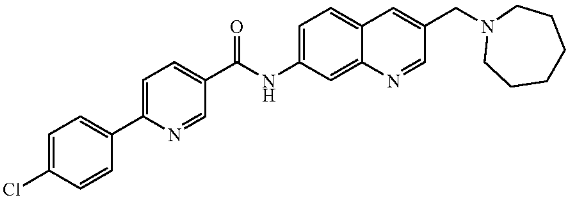

By operating in the same manner as in Example 1 and using 3-(1-azepanylmethyl)-7-quinolinylamine obtained in Reference Example 20, the title compound was obtained.

$^1H$ NMR (DMSO-$d_6$) δ 1.58 (8H, m), 2.64 (4H, m), 3.80 (2H, s), 7.61 (2H, m), 7.96 (2H, s), 8.15 (1H, m), 8.23 (3H, m), 8.47 (1H, dd, J=8.3, 2.4 Hz), 8.58 (1H, s), 8.84 (1H, d, J=2.2 Hz), 9.26 (1H, d, J=2.2 Hz), 10.76 (1H, s). FABMS (pos): 471 $[M+H]^+$ melting point: 233° C. (dec.) (washing solvent: ethyl acetate-isopropyl ether)

Example 33

N-[3-(1-azepanylmethyl)-7-quinolinyl]-6-(4-methylphenyl)nicotinamide

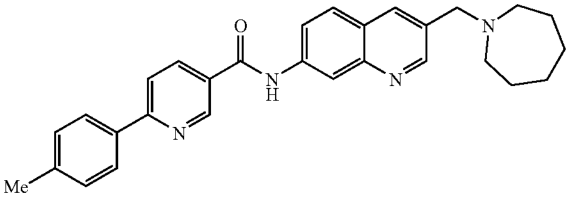

By operating in the same manner as in Example 1 and using 3-(1-azepanylmethyl)-7-quinolinylamine obtained in Reference Example 20, the title compound was obtained.

$^1H$ NMR (DMSO-$d_6$) δ 1.59 (8H, m), 2.39 (3H, s), 2.65 (4H, m), 3.81 (2H, s), 7.36 (2H, d, J=8.5 Hz), 7.96 (2H, s), 8.11 (2H, d, J=8.1 Hz), 8.14 (2H, d, J=8.5 Hz), 8.43 (1H, dd, J=8.5, 2.2 Hz), 8.58 (1H, s), 8.84 (1H, d, J=2.2 Hz), 9.23 (1H, dd, J=3.1, 0.7 Hz), 10.73 (1H, s). FABMS(pos): 451 $[M+H]^+$ melting point: 237° C. (dec.) (washing solvent: ethyl acetate-isopropyl ether)

Example 34

N-[3-(1-azepanylmethyl)-7-quinolinyl]-4-(4-chlorophenyl)-1-piperidine carboxamide

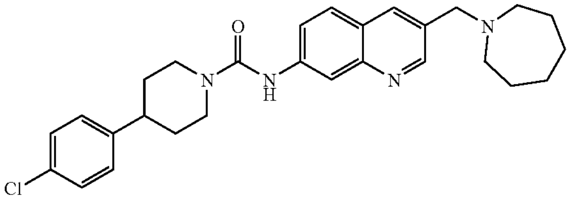

By operating in the same manner as in Example 12 nd using 3-(1-azepanylmethyl)-7-quinolinylamine obtained in Reference Example 20, the title compound was obtained.

$^1$H NMR (DMSO-$d_6$) δ 1.58 (10H, m), 1.81 (2H, m), 2.61 (4H, m), 2.78 (1H, m), 2.92 (2H, m), 3.75 (2H, s), 4.34 (2H, m), 7.31 (2H, d, J=8.5 Hz), 7.36 (2H, d, J=8.3 Hz), 7.74 (1H, dd, J=1.7, 8.7 Hz), 7.80 (1H, d, J=8.7 Hz), 8.05 (1H, s), 8.15 (1H, s), 8.74 (1H, d, J=1.7 Hz), 8.87 (1H, s). FABMS(pos): 477 $[M+H]^+$ melting point: 247° C. (dec.) (washing solvent: ethyl acetate-isopropyl ether)

Example 35

N-[3-(1-azepanylmethyl)-7-quinolinyl]-4-(4-methylphenyl)-1-piperidine carboxamide

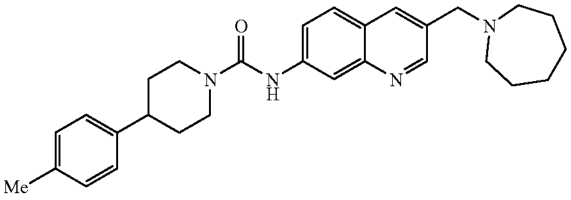

By operating in the same manner as in Example 12 and using 3-(1-azepanylmethyl)-7-quinolinylamine obtained in Reference Example 20, the title compound was obtained.

$^1$H NMR (DMSO-$d_6$) δ 1.58 (10H, m), 1.80 (2H, m), 2.26 (3H, S), 2.61 (4H, m), 2.72 (1H, m), 2.91 (2H, m), 3.75 (2H, s), 4.32 (2H, m), 7.11 (2H, d, J=7.8 Hz), 7.15 (2H, d, J=8.3 Hz), 7.74 (1H, d, J=8.5 Hz), 7.80 (1H, d, J=8.3 Hz), 8.05 (1H, s), 8.15 (1H, s), 8.75 (1H, s), 8.86 (1H, s). FABMS (pos): 457 $[M+H]^+$ melting point: 240° C. (dec.) (washing solvent: ethyl acetate-isopropyl ether)

Example 36

4'-methoxy-N-[6-methyl-3-(1-pyrrolidinylmethyl)-7-quinolinyl][1,1'-biphenyl]-4-carboxamide

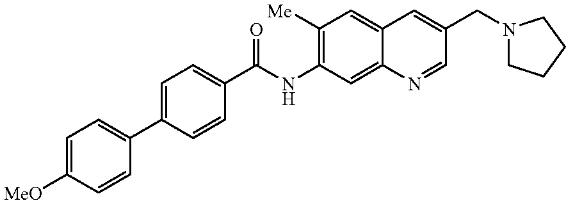

By operating in the same manner as in Example 1 and using 6-methyl-3-(1-pyrrolidinylmethyl)-7-quinolinylamine obtained in Reference Example 21 and 4'-methoxy[1,1'-biphenyl]-4-carboxylic acid, the title compound was obtained.

$^1$H-NMR($CDCl_3$) δ 1.80 (4H, m), 2.52 (3H, s), 2.55 (4H, m), 3.77 (2H, s), 3.86 (3H, s), 7.00 (2H, d, J=8.8 Hz), 7.57 (2H, d, J=8.8 Hz), 7.62 (1H, s), 7.67 (2H, d, J=8.0 Hz), 7.97 (2H, d, J=8.0 Hz), 7.97 (2H, m), 8.74 (1H, s), 8.82 (1H, d, J=1.8 Hz). melting point: 194–198° C. (crystallization solvent: ethyl acetate-isopropyl ether)

Example 37

4'-fluoro-N-[6-methyl-3-(1-pyrrolidinylmethyl)-7-quinolinyl][1,1'-biphenyl]-4-carboxamide

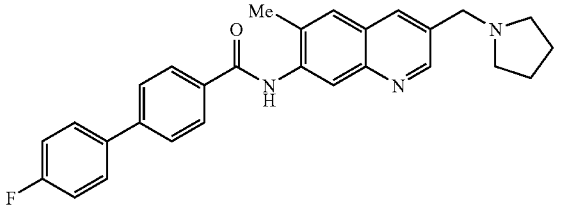

By operating in the same manner as in Example 1 and using 6-methyl-3-(1-pyrrolidinylmethyl)-7-quinolinylamine obtained in Reference Example 21 and 4'-fluoro[1,1'-biphenyl]-4-carboxylic acid, the title compound was obtained.

$^1$H-NMR($CDCl_3$) δ 1.82 (4H, m), 2.53 (3H, s), 2.56 (4H, m), 3.78 (2H, s), 7.12–7.22 (2H, m), 7.54–7.72 (5H, m), 7.94–8.04 (4H, m), 8.75 (1H, s), 8.83 (1H, d, J=1.6 Hz). melting point: 182–187° C. (crystallization solvent: ethyl acetate-isopropyl ether)

Example 38

4'-methyl-N-[6-methyl-3-(1-pyrrolidinylmethyl)-7-quinolinyl][1,1'-biphenyl]-4-carboxamide

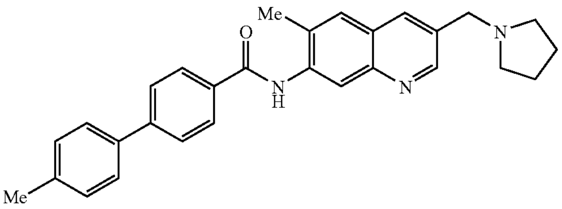

By operating in the same manner as in Example 1 and using 6-methyl-3-(1-pyrrolidinylmethyl)-7-quinolinylamine obtained in Reference Example 21 and 4'-methyl[1,1'-biphenyl]-4-carboxylic acid, the title compound was obtained.

$^1$H-NMR($CDCl_3$) δ 1.81 (4H, m), 2.42 (3H, s), 2.54 (3H, s), 2.56 (4H, m), 3.78 (2H, s), 7.29 (2H, d, J=8.0 Hz), 7.54 (2H, d, J=8.0 Hz), 7.63 (1H, s), 7.72 (2H, d, J=8.4 Hz), 7.97 (2H, m), 7.99 (2H, d, J=8.4 Hz), 8.76 (1H, s), 8.83 (1H, d, J=1.8 Hz). melting point: 191–193° C. (crystallization solvent: ethyl acetate-isopropyl ether)

Example 39

4'-chloro-N-[6-methyl-3-(1-pyrrolidinylmethyl)-7-quinolinyl][1,1'-biphenyl]-4-carboxamide

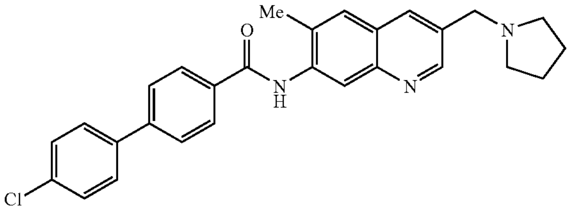

By operating in the same manner as in Example 1 and using 6-methyl-3-(1-pyrrolidinylmethyl)-7-quinolinylamine obtained in Reference Example 21 and 4'chloro[1,1'-biphenyl]-4-carboxylic acid, the title compound was obtained.

$^1$H-NMR($CDCl_3$) δ 1.82 (4H, m), 2.55 (3H, s), 2.57 (4H, m), 3.79 (2H, s), 7.40–7.49 (2H, m), 7.54–7.72 (5H, m), 7.90–8.04 (4H, m), 8.76 (1H, s), 8.84 (1H, d, J=2.2 Hz). elemental analysis for $C_{28}H_{26}N_3ClO$ Calculated: C, 73.75; H, 5.75; N, 9.22; Cl, 7.78. Found: C, 73.47; H, 5.64; N, 9.12, Cl, 7.82. melting point: 214–217° C. (crystallization solvent: ethyl acetate-isopropyl ether)

Example 40

6-(4-methylphenyl)-N-[6-methyl-3-(1-pyrrolidinylmethyl)-7-quinolinyl]nicotinamide

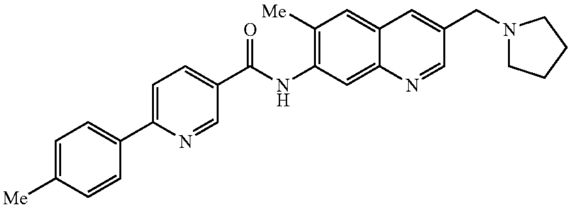

By operating in the same manner as in Example 1 and using 6-methyl-3-(1-pyrrolidinylmethyl)-7-quinolinylamine obtained in Reference Example 21 and 6-(4-methylphenyl) nicotinic acid, the title compound was obtained.

$^1$H-NMR($CDCl_3$) δ 1.82 (4H, m), 2.44 (3H, s), 2.55 (3H, s), 2.57 (4H, m), 3.79 (2H, s), 7.33 (2H, d, J=7.6 Hz), 7.65 (1H, s), 7.87 (1H, d, J=8.6 Hz), 7.95–8.04 (4H, m), 8.33 (1H, dd, J=2.2, 8.6 Hz), 8.75 (1H, s), 8.85 (1H, d, J=2.2 Hz), 9.19 (1H, d, J=1.6 Hz). melting point: 214–218° C. (crystallization solvent: ethyl acetate-isopropyl ether)

Example 41

6-(4-chlorophenyl)-N-[6-methyl-3-(1-pyrrolidinylmethyl)-7-quinolinyl]nicotinamide

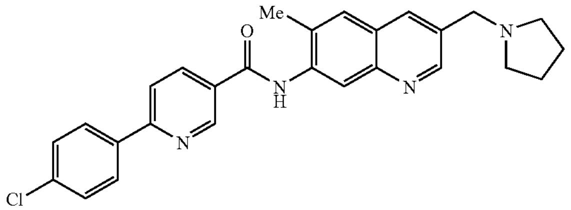

By operating in the same manner as in Example 1 and using 6-methyl-3-(1-pyrrolidinylmethyl)-7-quinolinylamine obtained in Reference Example 21 and 6-(4-chlorophenyl) nicotinic acid, the title compound was obtained.

$^1$H-NMR($CDCl_3$) δ 1.82 (4H, m), 2.55 (3H, s), 2.57 (4H, m), 3.79 (2H, s), 7.49 (2H, d, J=8.8 Hz), 7.66 (1H, s), 7.87 (1H, d, J=8.4 Hz), 7.97–8.07 (4H, m), 8.35 (1H, dd, J=2.6, 8.4 Hz), 8.74 (1H, s), 8.85 (1H, d, J=2.2 Hz), 9.20 (1H, d, J=2.0 Hz). melting point: 232–237° C. (crystallization solvent: ethyl acetate-isopropyl ether)

Example 42

1-[(7-{[(4'-fluoro[1,1'-biphenyl]-4-yl)carbonyl]amino}-3-quinolinyl)methyl]-4-piperidine carboxamide

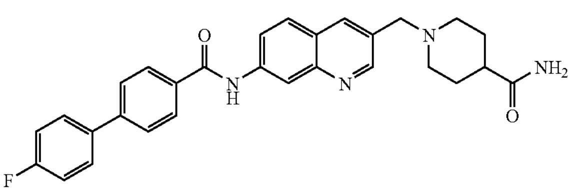

A solution of N-[3-(chloromethyl)-7-quinolinyl]-4'-fluoro[1,1'-biphenyl]-4-carboxamide (150 mg, 0.384 mmol) obtained in Reference Example 22, 4-piperidine carboxamide (68.0 mg, 0.531 mmol) and potassium carbonate (73.0 mg, 0.528 mmol) in dimethylformamide (2.0 ml) was stirred at room temperature for 2 hrs. To the reaction solution was added 1N NaOH, and the mixture was extracted with ethyl acetate. The extract was dried over anhydrous magnesium sulfate and the solvent was evaporated under reduced pressure. The obtained residue was purified by alumina column chromatography (eluting solvent; ethyl acetate) to give the title compound (43.8 mg).

$^1$H-NMR (DMSO-$d_6$) δ 1.50–1.76 (4H, m), 1.91–2.12 (3H, m), 2.87 (2H, m), 3.64 (2H, s), 6.73 (1H, s), 7.22 (1H, s), 7.34 (1H, d, J=8.8 Hz), 7.38 (1H, d, J=8.8 Hz), 7.80–7.90 (4H, m), 7.98 (2H, s), 8.13 (2H, d, J=8.4 Hz), 8.15 (1H, s), 8.60 (1H, s), 8.81 (1H, d, J=1.8 Hz), 10.62 (1H, s). FABMS (pos): 483 $[M+H]^+$ melting point: 261–265° C. (crystallization solvent: ethyl acetate-isopropyl ether)

Example 43

N-(3-{[3-(acetylamino)-1-pyrrolidinyl]methyl}-7-quinolinyl)-4'-fluoro[1,1'-biphenyl]-4-carboxamide

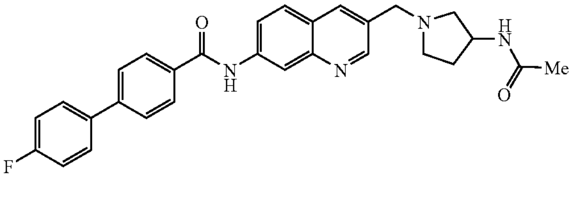

By operating in the same manner as in Example 42 and using N-[3-(chloromethyl)-7-quinolinyl]-4'-fluoro[1,1'-biphenyl]-4-carboxamide obtained in Reference Example 22 and N-(3-pyrrolidinyl)acetamide, the title compound was obtained.

$^1$H-NMR (DMSO-$d_6$) δ 1.57 (1H, m) 1.78 (3H, s), 2.11 (1H, m), 2.31–2.84 (2H, m), 2.65–2.75 (2H, m), 3.78 (2H, s), 4.16 (1H, br), 7.34 (1H, d, J=8.8 Hz), 7.38 (1H, d, J=9.2 Hz), 7.80–8.06 (7H, m), 8.11 (2H, d, J=8.4 Hz), 8.13–8.19

(1H, m), 8.61 (1H, s), 8.83 (1H, d, J=2.0 Hz), 10.63 (1H, s). FABMS(pos): 483 [M+H]$^+$ melting point: 250–253° C. (crystallization solvent: ethyl acetate-isopropyl ether)

Example 44

N-[3-({4-[2-(ethylamino)-2-oxoethyl]-1-piperidinyl}methyl)-7-quinolinyl]-4'-fluoro[1,1'-biphenyl]-4-carboxamide

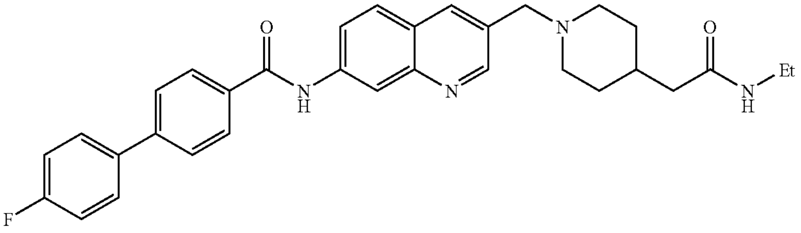

By operating in the same manner as in Example 42 and using N-[3-(chloromethyl)-7-quinolinyl]-4'-fluoro[1,1'-biphenyl]-4-carboxamide obtained in Reference Example 22 and N-ethyl-2-(4-piperidinyl)acetamide, the title compound was obtained.

$^1$H-NMR (DMSO-$d_6$) δ 0.97 (3H, t, J=7.2 Hz), 1.06–1.27 (2H, m), 1.52–1.76 (3H, m), 1.91–2.12 (4H, m), 2.73–2.87 (2H, m), 3.03(2H, q, J=7.2 Hz), 3.61 (2H, s), 7.34 (1H, d, J=8.7 Hz), 7.36 (1H, d, J=9.0 Hz), 7.72–7.89 (5H, m), 7.91–8.03 (2H, m), 8.08–8.15 (3H, m), 8.58 (1H, s), 8.79 (1H, d, J=2.1 Hz), 10.61 (1H, s). FABMS(pos): 525 [M+H]$^+$ melting point: 224–227° C. (crystallization solvent: ethyl acetate-isopropyl ether)

Example 45

4'-fluoro-N-(3-{[4-(hydroxymethyl)-1-piperidinyl]methyl}-7-quinolinyl)[1,1'-biphenyl]-4-carboxamide

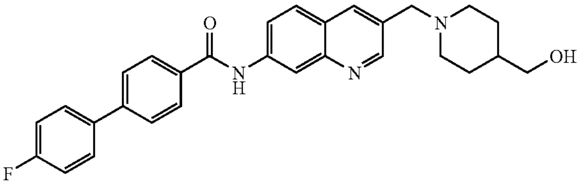

By operating in the same manner as in Example 42 and using N-[3-(chloromethyl)-7-quinolinyl]-4'-fluoro[1,1'-biphenyl]-4-carboxamide obtained in Reference Example 22 and 4-piperidinemethanol, the title compound was obtained.

$^1$H-NMR (DMSO-$d_6$) δ 1.00–1.46 (3H, m), 1.64 (2H, m), 1.96 (2H, m), 2.85 (2H, m), 3.25 (2H, t, J=5.2 Hz), 3.63 (2H, s), 4.43 (1H, t, J=5.2 Hz), 7.33 (1H, d, J=8.8 Hz), 7.38 (1H, d, J=9.0° Hz), 7.78–8.03 (6H, m), 8.08–8.18 (3H, m), 8.60 (1H, s), 8.80 (1H, d, J=2.0 Hz), 10.63 (1H, s). FABMS(pos): 470 [M+H]$^+$ melting point: 191–195° C. (crystallization solvent: ethyl acetate-isopropyl ether)

Example 46

4'-fluoro-N-(3-{[4-(2-hydroxyethyl)-1-piperidinyl]methyl}-7-quinolinyl)[1,1'-biphenyl]-4-carboxamide

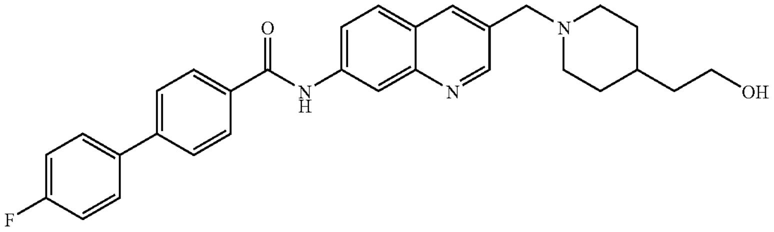

By operating in the same manner as in Example 42 and using N-[3-(chloromethyl)-7-quinolinyl]-4'-fluoro[1,1'-biphenyl]-4-carboxamide obtained in Reference Example 22 and 2-(4-piperidinyl)ethanol, the title compound was obtained

.

$^1$H-NMR (DMSO-$d_6$) δ 1.03–1.52 (5H, m), 1.62 (2H, m), 1.97 (2H, m), 2.83 (2H, m), 3.43 (2H, q, J=5.2 Hz), 3.62 (2H, s), 4.33 (1H, t, J=5.2 Hz), 7.33 (1H, d, J=8.8 Hz), 7.38 (1H, d, J=8.6 Hz), 7.78–8.03 (6H, m), 8.08–8.18 (3H, m), 8.60 (1H, s), 8.80 (1H, d, J.=2.0 Hz), 10.62 (1H, s). FABMS(pos): 484 [M+H]$^+$ melting point: 193–196° C. (crystallization solvent: ethyl acetate-isopropyl ether)

Example 47

N-[3-({4-[4-(ethylamino)-4-oxobutyl]-1-piperidinyl}methyl)-7-quinolinyl]-4'-fluoro[1,1'-biphenyl]-4-carboxamide

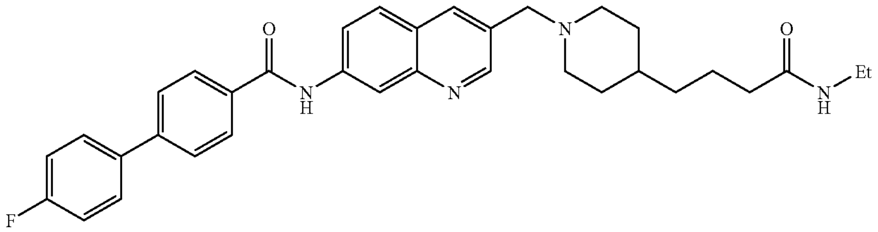

By operating in the same manner as in Example 42 and using N-[3-(chloromethyl)-7-quinolinyl]-4'-fluoro[1,1-biphenyl]-4-carboxamide obtained in Reference Example 22 and N-ethyl-4-(4-piperidinyl)butanamide, the title compound was obtained.

$^1$H-NMR (DMSO-$d_6$) δ 0.98 (3H, t, J=7.2 Hz), 1.06–1.26 (5H, m), 1.42–1.70 (4H, m), 1.88–2.06 (4H, m), 2.83 (2H, m), 3.05 (2H, q, J=7.2 Hz), 3.62 (2H, s), 7.33 (1H, d, J=8.8 Hz), 7.38 (1H, d, J=8.8 Hz), 7.70–7.92 (5H, m), 7.94–7.99 (2H, m), 8.08–8.18 (3H, m), 8.59 (1H, s), 8.79 (1H, d, J=2.2 Hz), 10.61 (1H, s). FABMS(pos): 553 $[M+H]^+$ melting point: 209–213° C. (crystallization solvent: ethyl acetate-isopropyl ether)

Example 48

N-[3-({4-[2-(ethylamino)-2-oxoethoxy]-1-piperidinyl}methyl)-7-quinolinyl]-4'-fluoro[1,1'-biphenyl]-4-carboxamide

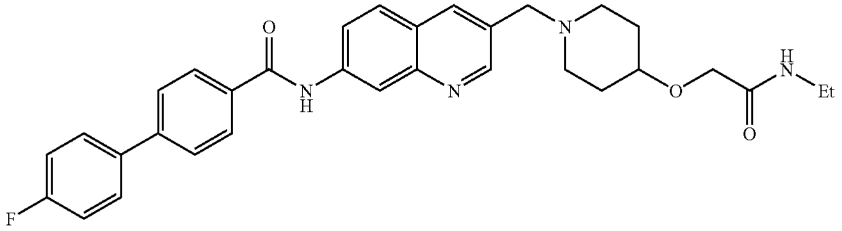

By operating in the same manner as in Example 42 and using N-[3-(chloromethyl)-7-quinolinyl]-4'-fluoro[1,1'-biphenyl]-4-carboxamide obtained in Reference Example 22 and N-ethyl-2-(4-piperidinyloxy)acetamide, the title compound was obtained. FABMS(pos): 541 $[M+H]^+$ melting point: 228–230° C. (crystallization solvent: ethyl acetate-isopropyl ether)

Example 49

4-bromo-N-[6-fluoro-3-(1-pyrrolidinylmethyl)-7-quinolinyl]benzamide

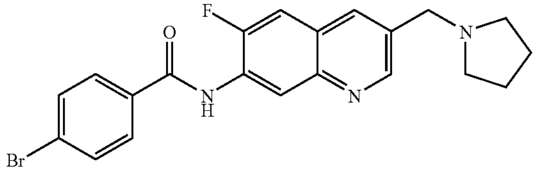

By operating in the same manner as in Example 1 and using 6-fluoro-3-(1-pyrrolidinylmethyl)-7-quinolinylamine obtained in Reference Example 25, the title compound was obtained.

$^1$H-NMR (DMSO-$d_6$) δ 1.73 (4H, m), 2.50 (4H, m), 3.78 (2H, s), 7.78 (2H, d, J=8.4 Hz), 7.89 (1H, d, J=11.1 Hz), 7.95 (2H, d, J=8.4 Hz), 8.22 (1H, s), 8.33 (1H, d, J=7.5 Hz), 8.82

(1H, d, J=1.8 Hz), 10.47 (1H, s). melting point: 119–121° C. (crystallization solvent: ethyl acetate-isopropyl ether)

Example 50

4'-fluoro-N-[6-fluoro-3-(1-pyrrolidinylmethyl)-7-quinolinyl][1,1'-biphenyl]-4-carboxamide

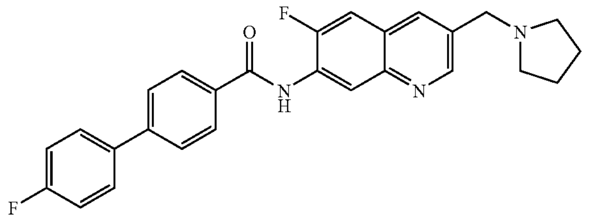

To a solution of 4-bromo-N-[6-fluoro-3-(1-pyrrolidinylmethyl)-7-quinolinyl]benzamide (100 mg, 0.233 mmol) obtained in Example 49, 4-fluorophenylboronic acid (65.3 mg, 0.467 mmol) and 2N sodium carbonate (0.233 ml) in 1,2-dimethoxyethane (3 ml) was added tetrakistriphenylphosphine palladium (8.1 mg, 0.007 mmol) at 90° C., and the mixture was stirred under a nitrogen atmosphere for 16 hrs. The reaction solution was diluted with ethyl acetate and dried over anhydrous sodium sulfate. The obtained crude product was purified by NH-silica gel chromatography (eluting solvent; ethyl acetate) and treated with ethyl acetate-isopropyl ether (1:5) to give the title compound (55.2 mg) as a powder.

$^1$H-NMR (DMSO-$d_6$) δ 1.73 (4H, m), 2.50 (4H, m), 3.80 (2H, s), 7.36 (2H, m), 7.82–7.93 (5H, m), 8.12 (2H, d, J=8.4 Hz), 8.23 (1H, s), 8.37 (1H, d, J=8.1 Hz), 8.83 (1H, s), 10.45 (1H, s). melting point: 198–200° C. (crystallization solvent: ethyl acetate-isopropyl ether) FABMS(pos) 444 [M+H]+

Example 51

4'-chloro-N-[6-fluoro-3-(1-pyrrolidinylmethyl)-7-quinolinyl][1,1'-biphenyl]-4-carboxamide

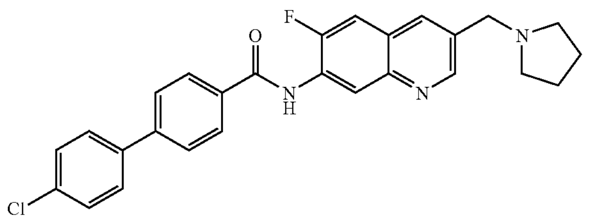

By operating in the same manner as in Example 50 and using 4-bromo-N-[6-fluoro-3-(1-pyrrolidinylmethyl)-7-quinolinyl]benzamide obtained in Example 49, the title compound was obtained.

$^1$H-NMR (DMSO-$d_6$) δ 1.73 (4H, m), 2.50 (4H, m), 3.80 (2H, s), 7.60 (2H, d, J=8.4 Hz), 7.80–7.94 (5H, m), 8.13 (2H, d, J=8.4 Hz), 8.23 (1H, s), 8.37 (1H, d, J=7.6 Hz), 8.83 (1H, s), 10.46 (1H, s). melting point: 218–220° C. (crystallization solvent: ethyl acetate-isopropyl ether) FABMS(pos) 460 [M+H]+

Example 52

N-[6-fluoro-3-(1-pyrrolidinylmethyl)-7-quinolinyl][1,1'-biphenyl]-4-carboxamide

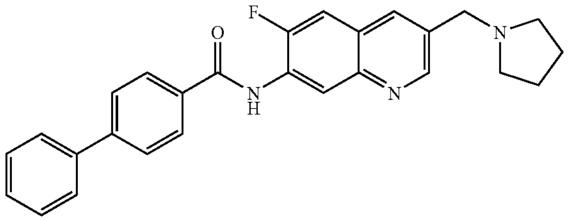

By operating in the same manner as in Example 50 and using 4-bromo-N-[6-fluoro-3-(1-pyrrolidinylmethyl)-7-quinolinyl]benzamide obtained in Example 49, the title compound was obtained.

$^1$H-NMR (DMSO-$d_6$) δ 1.74 (4H, m), 2.50 (4H, m), 3.79 (2H, s), 7.44 (1H, d, J=7.2 Hz), 7.52 (2H, m), 7.77 (2H, d, J=6.9 Hz), 7.89 (3H, m), 8.12 (2H, d, J=8.4 Hz), 8.23 (1H, s), 8.37 (1H, d, J=7.5 Hz), 8.82 (1H, s), 10.42 (1H, s). melting point: 206–208° C. (crystallization solvent: ethyl acetate-isopropyl ether) FABMS(pos) 426 [M+H]+

Example 53

N-[6-fluoro-3-(1-pyrrolidinylmethyl)-7-quinolinyl]-4'-methoxy[1,1'-biphenyl]-4-carboxamide

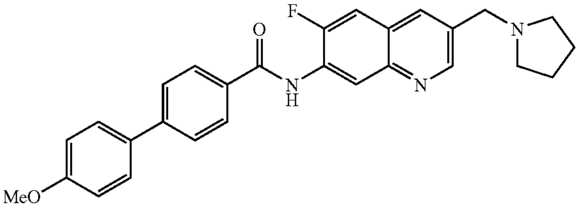

By operating in the same manner as in Example 50 and using 4-bromo-N-[6-fluoro-3-(1-pyrrolidinylmethyl)-7-quinolinyl]benzamide obtained in Example 0.49, the title compound was obtained.

$^1$H-NMR (DMSO-$d_6$) δ 1.73 (4H, m), 2.50 (4H, m), 3.79 (2H, s), 3.82 (3H, s), 7.07 (2H, d, J=8.4 Hz), 7.74 (2H, d, J=8.4 Hz), 7.82 (2H, d, J=8.4 Hz), 7.90 (1H, d, J=11.1 Hz), 8.08 (2H, d, J=8.4 Hz), 8.22 (1H, s), 8.36 (1H, d, J=7.5 Hz), 8.82 (1H, d, J=1.5 Hz), 10.39 (1H, s). melting point: 184–186° C. (crystallization solvent: ethyl acetate-isopropyl ether) FABMS(pos) 456 [M+H]+

Example 54

N-[6-fluoro-3-(1-pyrrolidinylmethyl)-7-quinolinyl]-4'-methyl[1,1'-biphenyl]-4-carboxamide

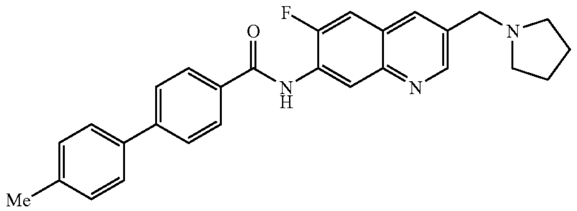

By operating in the same manner as in Example 50 and using obtained 4-bromo-N-[6-fluoro-3-(1-pyrrolidinylmethyl)-7-quinolinyl]benzamide obtained in Example 49, the title compound was obtained.

$^1$H-NMR (DMSO-$d_6$) δ 1.74 (4H, m), 2.37 (3H, s), 2.50 (4H, m), 3.80 (2H, s), 7.32 (2H, d, J=8.4 Hz), 7.68 (2H, d, J=8.1 Hz), 7.84 (2H, d, J=8.4 Hz), 7.90 (1H, d, J=11.1 Hz), 8.10 (2H, d, J=8.7 Hz), 8.22 (1H, s), 8.36 (1H, d, J=7.8 Hz), 8.83 (1H, d, J=1.5 Hz), 10.40 (1H, s). melting point: 202–204° C. (crystallization solvent: ethyl acetate-isopropyl ether) FABMS(pos) 440 [M+H]+

Example 55

N-[6-fluoro-3-(1-pyrrolidinylmethyl)-7-quinolinyl]-4'-(trifluoromethyl)[1,1'-biphenyl]-4-carboxamide

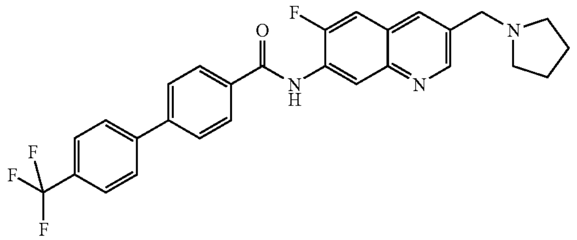

By operating in the same manner as in Example 50 and using 4-bromo-N-[6-fluoro-3-(1-pyrrolidinylmethyl)-7-quinolinyl]benzamide obtained in Example 49, the title compound was obtained.

$^1$H-NMR (DMSO-$d_6$) δ 1.73 (4H, m), 2.50 (4H, m), 3.80 (2H, s), 7.85–8.02 (7H, m), 8.15 (2H, d, J=7.2 Hz), 8.22 (1H, s), 8.37 (1H, d, J=7.2 Hz), 8.82 (1H, s), 10.47 (1H, s). melting point: 209–212° C. (crystallization solvent: ethyl acetate-isopropyl ether) FABMS(pos) 494 [M+H]+

Example 56

N-[6-fluoro-3-(1-pyrrolidinylmethyl)-7-quinolinyl]-4'-(trifluoromethoxy)[1,1'-biphenyl]-4-carboxamide

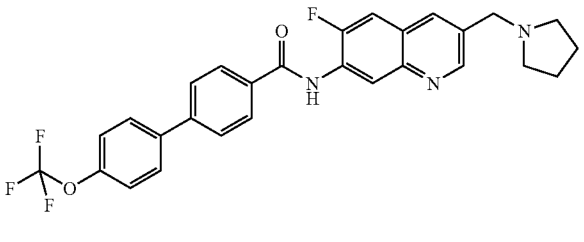

By operating in the same manner as in Example 50 and using 4-bromo-N-[6-fluoro-3-(1-pyrrolidinylmethyl)-7-quinolinyl]benzamide obtained in Example 49, the title compound was obtained.

$^1$H-NMR (DMSO-$d_6$) δ 1.73 (4H, m), 2.50 (4H, m), 3.80 (2H, s), 7.50 (2H, d, J=8.1 Hz), 7.90 (5H, m), 8.13 (2H, d, J=7.8 Hz), 8.22 (1H, s), 8.37 (1H, d, J=7.5 Hz), 8.82 (1H, s), 10.44 (1H, s). melting point: 184–187° C. (crystallization solvent: ethyl acetate-isopropyl ether) FABMS(pos) 510 [M+H]+

Example 57

4-bromo-2-fluoro-N-[6-fluoro-3-(1-pyrrolidinylmethyl)-7-quinolinyl]benzamide

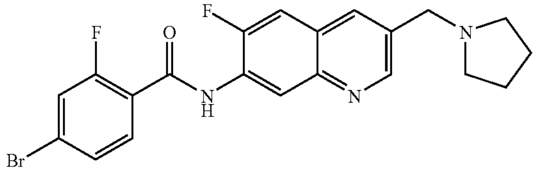

By operating in the same manner as in Example 1 and using 6-fluoro-3-(1-pyrrolidinylmethyl)-7-quinolinylamine obtained in Reference Example 25, the title compound was obtained.

$^1$H-NMR (DMSO-$d_6$) δ 1.72 (4H, m), 2.50 (4H, m), 3.78 (2H, s), 7.59 (1H, dd, J=2.1, 8.4 Hz), 7.73 (1H, d, J=8.1 Hz), 7.78 (1H, d, J=8.1 Hz), 7.90 (1H, d, J=8.4 Hz), 8.21 (1H, s), 8.61 (1H, d, J=7.5 Hz), 8.82 (1H, d, J=2.1 Hz), 10.50 (1H, s). melting point: 149–151° C. (crystallization solvent: ethyl acetate-isopropyl ether)

Example 58

3-fluoro-N-[6-fluoro-3-(1-pyrrolidinylmethyl)-7-quinolinyl][1,1'-biphenyl]-4-carboxamide

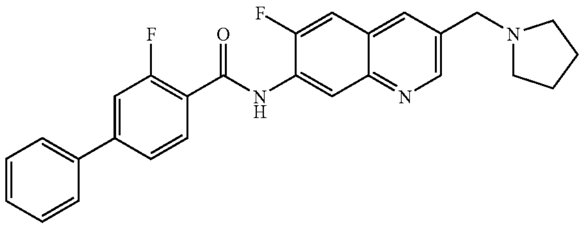

By operating in the same manner as in Example 50 and using 4-bromo-2-fluoro-N-[6-fluoro-3-(1-pyrrolidinylmethyl)-7-quinolinyl]benzamide obtained in Example 57, the title compound was obtained.

$^1$H-NMR (DMSO-$d_6$) δ 1.73 (4H, m), 2.50 (4H, m), 3.79 (2H, s), 7.45–7.57 (3H, s), 7.69–7.94 (6H, m), 8.22 (1H, s), 8.65 (1H, d, J=8.0 Hz), 8.82 (1H, d, J=2.2 Hz), 10.39 (1H, s). melting point: 163–164° C. (crystallization solvent: ethyl acetate-isopropyl ether) FABMS(pos) 444 [M+H]+

Example 59

3-fluoro-N-[6-fluoro-3-(1-pyrrolidinylmethyl)-7-quinolinyl]-4'-methoxy[1,1'-biphenyl]-4-carboxamide

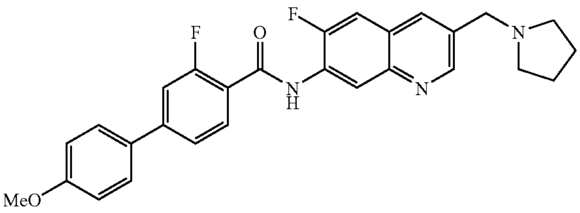

By operating in the same manner as in Example 50 and using 4-bromo-2-fluoro-N-[6-fluoro-3-(1-pyrrolidinylmethyl)-7-quinolinyl]benzamide obtained in Example 57, the title compound was obtained.

$^1$H-NMR (DMSO-$d_6$) δ 1.74 (4H, m), 2.50 (4H, m), 3.83 (5H, m), 7.07 (2H, d, J=9.2 Hz), 7.68–7.94 (6H, m), 8.22 (1H, s), 8.65 (1H, d, J=7.4 Hz), 8.84 (1H, s), 10.32 (1H, s). melting point: 174–176° C. (crystallization solvent: ethyl acetate-isopropyl ether) FABMS(pos) 474 [M+H]+

Example 60

3,4'-difluoro-N-[6-fluoro-3-(1-pyrrolidinylmethyl)-7-quinolinyl][1,1'-biphenyl]-4-carboxamide

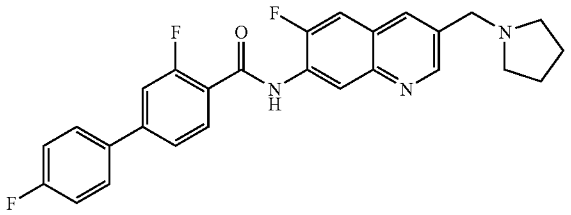

By operating in the same manner as in Example 50 and using 4-bromo-2-fluoro-N-[6-fluoro-3-(1-pyrrolidinylmethyl)-7-quinolinyl]benzamide obtained in Example 57, the title compound was obtained.

$^1$H-NMR (DMSO-$d_6$) δ 1.73 (4H, m), 2.50 (4H, m), 3.79 (2H, s), 7.36 (2H, m), 7.71 (2H, m), 7.88 (4H, m), 8.22 (1H, s), 8.64 (1H, d, J=7.4 Hz), 8.82 (1H, d, J=1.4 Hz), 10.39 (1H, s). melting point: 200–202° C. (crystallization solvent: ethyl acetate-isopropyl ether) FABMS(pos) 462 [M+H]+

Example 61

3-fluoro-N-[6-fluoro-3-(1-pyrrolidinylmethyl)-7-quinolinyl]-4'-methyl[1,1'-biphenyl]-4-carboxamide

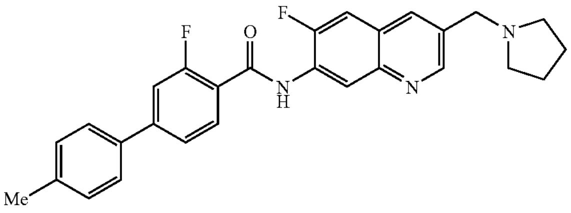

By operating in the same manner as in Example 50 and using 4-bromo-2-fluoro-N-[6-fluoro-3-(1-pyrrolidinylmethyl)-7-quinolinyl]benzamide obtained in Example 57, the title compound was obtained.

$^1$H-NMR (DMSO-$d_6$) δ 1.73 (4H, m), 2.37 (3H, s), 2.50 (4H, m), 3.79 (2H, s), 7.33 (2H, d, J=8.2 Hz), 7.69 (4H, m), 7.88 (2H, m), 8.21 (1H, s), 8.64 (1H, d, J=7.6 Hz), 8.82 (1H, d, J=2.2 Hz), 10.34 (1H, s). melting point: 179–181° C. (crystallization solvent: ethyl acetate-isopropyl ether) FABMS(pos) 458 [M+H]+

Example 62

4'-chloro-3-fluoro-N-[6-fluoro-3-(1-pyrrolidinylmethyl)-7-quinolinyl][1,1'-biphenyl]-4-carboxamide

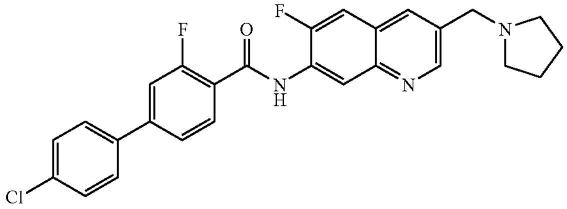

By operating in the same manner as in Example 50 and using 4-bromo-2-fluoro-N-[6-fluoro-3-(1-pyrrolidinylmethyl)-7-quinolinyl]benzamide obtained in Example 57, the title compound was obtained.

$^1$H-NMR (DMSO-$d_6$) δ 1.73 (4H, m), 2.50 (4H, m), 3.78 (2H, s), 7.58 (2H, d, J=8.4 Hz), 7.73–7.93 (6H, m), 8.21 (1H, s), 8.65 (1H, m), 8.82 (1H, s), 10.40 (1H, s). melting point: 217–219° C. (crystallization solvent: ethyl acetate-isopropyl ether) FABMS(pos) 478 [M+H]+

Example 63

4-bromo-N-[6-(1-pyrrolidinyl)-3-(1-pyrrolidinylmethyl)-7-quinolinyl]benzamide

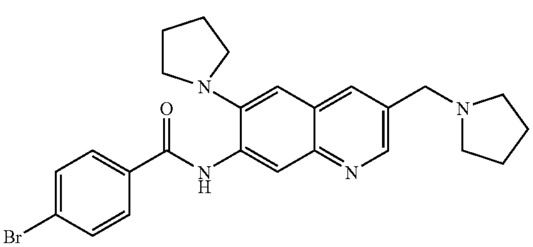

By successively operating in the same manner as in Reference Example 1, Reference Example 2 and Reference Example 3 and using 4-bromo-N-[3-formyl-6-(1-pyrrolidinyl)-7-quinolinyl]benzamide obtained in Reference Example 27, the title compound was obtained.

$^1$H-NMR (DMSO-$d_6$) δ 1.72 (4H, m), 1.89 (4H, m), 2.49 (4H, m), 3.30 (4H, m), 3.71 (2H, s), 7.19 (1H, s), 7.76 (2H, d, J=8.4 Hz), 7.91 (1H, s), 7.96–7.99 (3H, m), 8.55 (1H, d, J=2.1 Hz), 10.17 (1H, s). melting point: 171–173° C. (crystallization solvent: ethyl acetate-isopropyl ether) ESI(pos) 480 [M+H]+

Example 64

4'-fluoro-N-[6-(1-pyrrolidinyl)-3-(1-pyrrolidinylmethyl)-7-quinolinyl][1,1'-biphenyl]-4-carboxamide

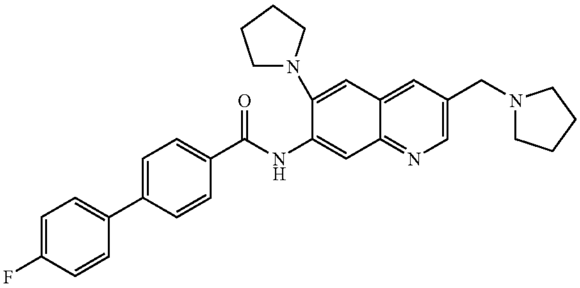

By operating in the same manner as in Example 50 and using 4-bromo-N-[6-(1-pyrrolidinyl)-3-(1-pyrrolidinylmethyl)-7-quinolinyl]benzamide obtained in Example 63, the title compound was obtained.

$^1$H-NMR (DMSO-$d_6$) δ 1.73 (4H, m), 1.90 (4H, m), 2.50 (8H, m), 3.74 (2H, s), 7.22 (1H, s), 7.35 (2H, m), 7.82 (4H, m), 8.00 (2H, m), 8.13 (2H, d, J=8.6 Hz), 8.57 (1H, s) 10.16 (1H, s). melting point: 182–184° C. (crystallization solvent: ethyl acetate-isopropyl ether) FABMS(pos) 495 [M+H]+

Example 65

4-bromo-N-[6-chloro-3-(1-pyrrolidinylmethyl)-7-quinolinyl]benzamide

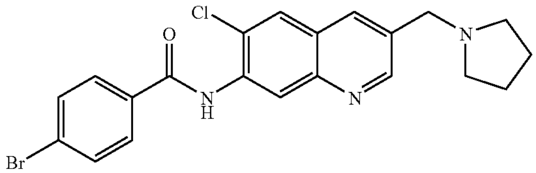

By operating in the same manner as in Example 1 and using 6-chloro-3-(1-pyrrolidinylmethyl)-7-quinolinylamine obtained in Reference Example 18, the title compound was obtained.

$^1$H-NMR (DMSO-$d_6$) δ 1.73 (4H, m), 2.50 (4H, m), 3.80 (2H, s), 1.98 (2H, s), 7.46 (2H, d, J=8.05 Hz), 7.63 (2H, d, J=8.30 Hz), 8.26 (3H, m), 8.88 (1H, d, J=1.47 Hz), 10.37 (1H, s).

Example 66

4'-fluoro-N-[6-chloro-3-(1-pyrrolidinylmethyl)-7-quinolinyl][1,1'-biphenyl]-4-carboxamide

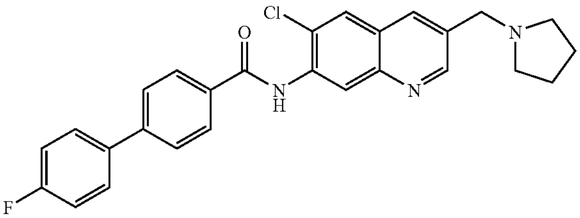

By operating in the same manner as in Example 50 and using 4-bromo-N-[6-chloro-3-(1-pyrrolidinylmethyl)-7-quinolinyl]benzamide obtained in Example 65, the title compound was obtained.

$^1$H-NMR (DMSO-$d_6$) δ 1.73 (4H, m), 2.50 (4H, m), 3.80 (2H, S), 7.36 (2H, m), 7.82 (2H, m), 7.87 (2H, m), 8.14 (2H, d, J=7.8 Hz), 8.26 (1H, s), 8.29 (2H, d, J=6.8 Hz), 8.89 (1H, s), 10.32 (1H, s). melting point: 188° C. (crystallization solvent: ethyl acetate-isopropyl ether)

Example 67

N-[6-chloro-3-(1-pyrrolidinylmethyl)-7-quinolinyl]-4'-methoxy-[1,1'-biphenyl]-4-carboxamide

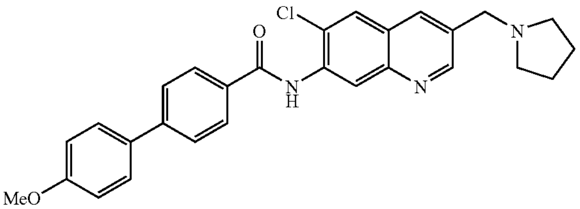

By operating in the same manner as in Example 50 and using 4-bromo-N-[6-chloro-3-(1-pyrrolidinylmethyl)-7-quinolinyl]benzamide obtained in Example 65, the title compound was obtained.

$^1$H-NMR ($CDCl_3$) δ 1.82 (4H, m), 2.56 (4H, m), 3.79 (2H, s) 3.87 (3H, s), 7.02 (2H, m), 7.60 (2H, m), 7.72 (2H, d, J=8.3 Hz), 7.88 (1H, s), 7.97 (1H, d, J=1.7 Hz), 8.02 (2H, d, J=8.3 Hz), 8.69 (1H, s), 8.90 (1H, d, J=2.0 Hz), 9.34 (1H, s). melting point: 184° C. (crystallization solvent: ethyl acetate-isopropyl ether) Elemental analysis for $C_{28}H_{26}ClN_3O_2$ *Calculated:* C, 70.80; H, 5.52; N, 8.85. Found: C, 70.77; H, 5.67; N, 8.60.

Example 68

4-(1-benzofuran-2-yl)-N-[6-chloro-3-(1-pyrrolidinylmethyl)-7-quinolinyl]benzamide

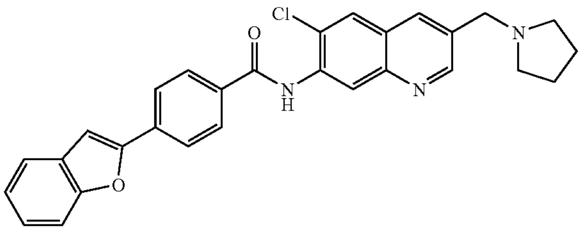

By operating in the same manner as in Example 50 and using 4-bromo-N-[6-chloro-3-(1-pyrrolidinylmethyl)-7-quinolinyl]benzamide obtained in Example 65, the title compound was obtained.

$^1$H-NMR ($CDCl_3$) δ 1.79 (4H, m), 2.54 (4H, m), 3.77 (2H, s), 7.16 (1H, s), 7.24 (1H, m), 7.30 (1H, m), 7.53 (1H, d, J=8.3 Hz), 7.60 (1H, d, J=7.8 Hz), 7.87 (1H, s), 7.94 (1H, m), 8.01 (4H, m), 8.67 (1H, s), 8.88 (1H, d, J=2.0 Hz), 9.31 (1H, s). melting point: 209° C. (crystallization solvent: ethyl acetate-isopropyl ether) elemental analysis for $C_{29}H_{24}N_3ClO_2$ Calculated: C, 72.27; H, 5.02; N, 8.72. Found: C, 72.16; H, 4.79; N, 8.96.

Example 69

N-[6-chloro-3-(1-pyrrolidinylmethyl)-7-quinolinyl]-4-(5-chlorothien-2-yl)benzamide

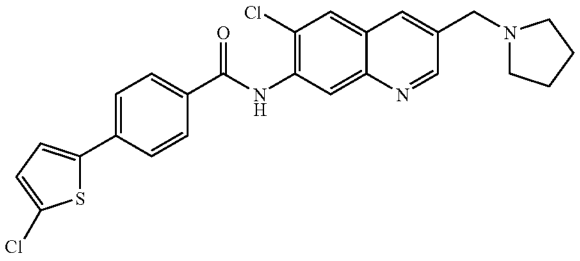

By operating in the same manner as in Example 50 and using 4-bromo-N-[6-chloro-3-(1-pyrrolidinylmethyl)-7-quinolinyl]benzamide obtained in Example 65, the title compound was obtained.

$^1$H-NMR ($CDCl_3$) δ 1.79 (4H, m) 2.54 (4H, m) 3.77 (2H, s) 6.92 (1H, d, J=3.9 Hz) 7.18 (1H, d, J=3.9 Hz) 7.63 (2H, m) 7.86 (1H, s) 7.95 (3H, m) 8.63 (1H, s) 8.88 (1H, d, J=2.0 Hz) 9.29 (1H, s). melting point: 185° C. (crystallization solvent: ethyl acetate-isopropyl ether) Elemental analysis for $C_{25}H_{21}N_3Cl_2OS.0.25H_2O$ Calculated: C, 61.67; H, 4.45; N, 8.62. Found: C, 61.69; H, 4.28; N, 8.44.

Example 70

4-bromo-N-[8-fluoro-3-(1-pyrrolidinylmethyl)-7-quinolinyl]benzamide

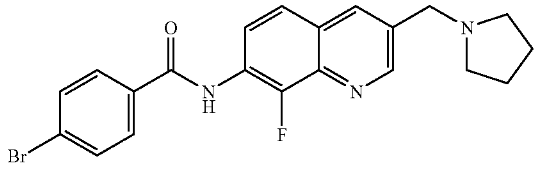

By operating in the same manner as in Example 1 and using 8-fluoro-3-(1-pyrrolidinylmethyl)-7-quinolinamine obtained in Reference Example 30, the title compound was obtained.

$^1$H-NMR(DMSO-$d_6$) δ 1.73 (4H, m), 2.51 (4H, m), 3.81 (2H, s), 7.75–7.83 (4H, m), 7.98 (2H, d, J=8.4 Hz), 8.30 (1H, s), 8.90 (1H, d, J=2.1 Hz), 10.54 (1H, s).

Example 71

N-[8-fluoro-3-(1-pyrrolidinylmethyl)-7-quinolinyl][1,1'-biphenyl]-4-carboxamide

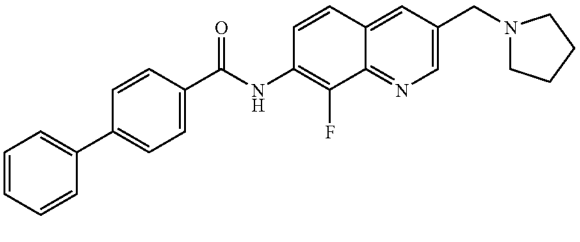

By operating in the same manner as in Example 50 and using 4-bromo-N-[8-fluoro-3-(1-pyrrolidinylmethyl)-7-quinolinyl]benzamide obtained in Example 70, the title compound was obtained.

$^1$H-NMR(DMSO-$d_6$) δ 1.73 (4H, m), 2.51 (4H, m), 3.82 (2H, s), 7.39–7.57 (3H, m), 7.78 (2H, d, J=8.1 Hz), 7.82 (2H, m), 7.87 (2H, d, J=8.1 Hz), 8.14 (2H, d, J=8.1 Hz), 8.30 (1H, s), 8.90 (1H, s), 10.47 (1H, s). melting point: 186–188° C. (crystallization solvent: ethyl acetate-isopropyl ether) FABMS(pos) 426 [M+H]+

Example 72

N-[8-fluoro-3-(1-pyrrolidinylmethyl)-7-quinolinyl]-4'-methoxy[1,1'-biphenyl]-4-carboxamide

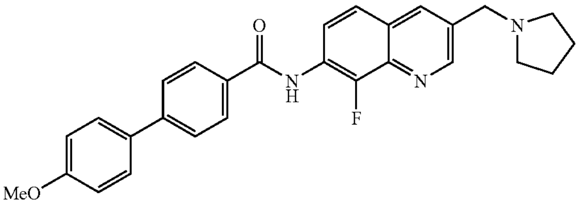

By operating in the same manner as in Example 5.0 and using 4-bromo-N-[8-fluoro-3-(1-pyrrolidinylmethyl)-7-quinolinyl]benzamide obtained in Example 70, the title compound was obtained.

$^1$H-NMR(DMSO-$d_6$) δ 1.73 (4H, m), 2.50 (4H, m) 3.82 (5H, m), 7.07 (2H, d, J=8.4 Hz), 7.73 (2H, d, J=8.4 Hz), 7.77–7.88 (4H, m), 8.10 (2H, d, J=8.1 Hz), 8.29 (1H, s), 8.89 (1H, d, J=1.8 Hz), 10.43 (1H, s). melting point: 217–220° C. (crystallization solvent: ethyl acetate-isopropyl ether) FABMS(pos) 456 [M+H]+

Example 73

4'-fluoro-N-[8-fluoro-3-(1-pyrrolidinylmethyl)-7-quinolinyl][1,1'-biphenyl]-4-carboxamide

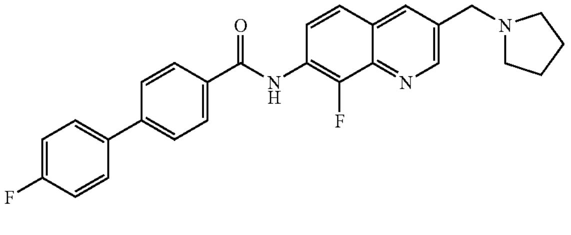

By operating in the same manner as in Example 50 and using 4-bromo-N-[8-fluoro-3-(1-pyrrolidinylmethyl)-7-quinolinyl]benzamide obtained in Example 70, the title compound was obtained.

$^1$H-NMR(DMSO-$d_6$) δ 1.74 (4H, m), 2.51 (4H, m), 3.83 (2H, s), 7.35 (2H, m), 7.80–7.90 (6H, m), 8.14 (2H, d, J=8.4 Hz), 8.31 (1H, s), 8.90 (1H, d, J=1.8 Hz), 10.49 (1H, s). melting point: 178° C. (crystallization solvent: ethyl acetate-isopropyl ether) FABMS(pos) 444 [M+H]+

Example 74

N-[8-fluoro-3-(1-pyrrolidinylmethyl)-7-quinolinyl]-4'-methyl[1,1'-biphenyl]-4-carboxamide

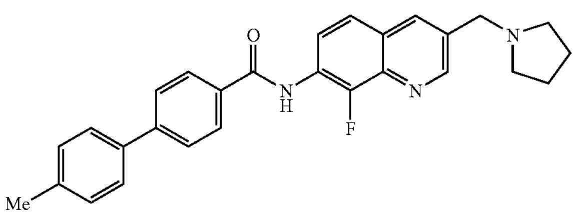

By operating in the same manner as in Example 50 and using 4-bromo-N-[8-fluoro-3-(1-pyrrolidinylmethyl)-7-quinolinyl]benzamide obtained in Example 70, the title compound was obtained.

$^1$H-NMR(DMSO-$d_6$) δ 1.73 (4H, m), 2.37 (3H, s), 2.50 (4H, m), 3.82 (2H, s), 7.32 (2H, d, J=7.8 Hz), 7.68 (2H, d, J=7.8 Hz), 7.80–7.88 (4H, m), 8.12 (2H, d, J=8.1 Hz), 8.30 (1H, s), 8.90 (1H, s), 10.46 (1H, s). melting point: 210–213° C. (crystallization solvent: ethyl acetate-isopropyl ether) FABMS(pos) 440 [M+H]+

Example 75

4'-chloro-N-[8-fluoro-3-(1-pyrrolidinylmethyl)-7-quinolinyl][1,1'-biphenyl]-4-carboxamide

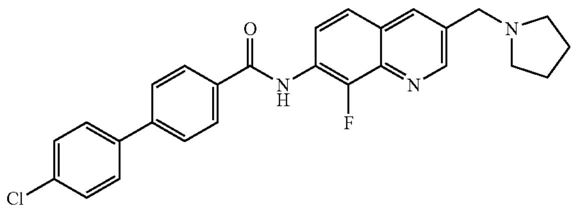

By operating in the same manner as in Example 50 and using 4-bromo-N-[8-fluoro-3-(1-pyrrolidinylmethyl)-7-quinolinyl]benzamide obtained in Example 70, the title compound was obtained.

$^1$H-NMR(DMSO-$d_6$) δ 1.73 (4H, m), 2.50 (4H, m), 3.82 (2H, s), 7.57 (2H, d, J=8.7 Hz), 7.78–7.86 (4H, m), 7.88 (2H, d, J=8.4 Hz), 8.14 (2H, d, J=8.4 Hz), 8.30 (1H, s), 8.90 (1H, d, J=1.8 Hz), 10.50 (1H, s). melting point: 206–208° C. (crystallization solvent: ethyl acetate-isopropyl ether) FABMS(pos) 460 [M+H]+

Example 76

4-bromo-2-fluoro-N-[8-fluoro-3-(1-piperidinylmethyl)-7-quinolinyl]benzamide

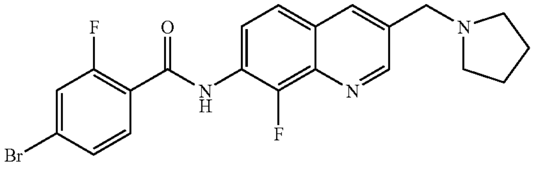

By operating in the same manner as in Example 1 and using 8-fluoro-3-(1-pyrrolidinylmethyl)-7-quinolinamine obtained in Reference Example 30, the title compound was obtained.

$^1$H-NMR (DMSO-$d_6$) δ 1.73 (4H, m), 2.50 (4H, m), 3.81 (2H, s), 7.57–8.10 (5H, m), 8.28 (1H, s), 8.89 (1H, s), 10.53 (1H, s).

Example 77

3-fluoro-N-[8-fluoro-3-(1-pyrrolidinylmethyl)-7-quinolinyl][1,1'-biphenyl]-4-carboxamide

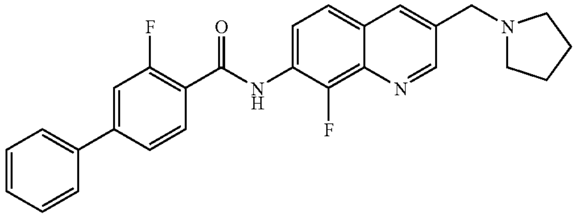

By operating in the same manner as in Example 50 and using 4-bromo-2-fluoro-N-[8-fluoro-3-(1-piperidinylmethyl)-7-quinolinyl]benzamide obtained in Example 76, the title compound was obtained.

$^1$H-NMR (DMSO-$d_6$) δ 1.73 (4H, m), 2.50 (4H, m), 3.81 (2H, s), 7.45–8.00 (10H, m), 8.29 (1H, s), 8.90 (1H, s), 10.48 (1H, s). melting point: 136–137° C. (crystallization solvent: ethyl acetate-isopropyl ether) FABMS(pos) 444 [M+H]+

Example 78

3,4'-difluoro-N-[8-fluoro-3-(1-pyrrolidinylmethyl)-7-quinolinyl][1,1'-biphenyl]-4-carboxamide

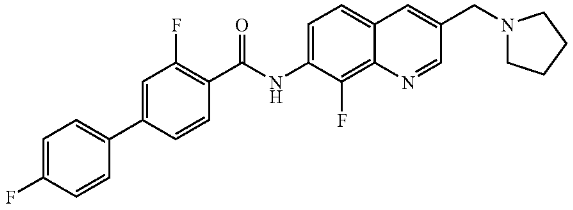

By operating in the same manner as in Example 50 and using 4-bromo-2-fluoro-N-[8-fluoro-3-(1-piperidinylmethyl)-7-quinolinyl]benzamide obtained in Example 76, the title compound was obtained.

$^1$H-NMR (DMSO-$d_6$) δ 1.73 (4H, m), 2.50 (4H, m), 3.81 (2H, s), 7.32–8.30 (11H, m), 8.90 (1H, s), 10.49 (1H, s).

Example 79

3-fluoro-N-[8-fluoro-3-(1-pyrrolidinylmethyl)-7-quinolinyl]-4'-methoxy[1,1'-biphenyl]-4-carboxamide

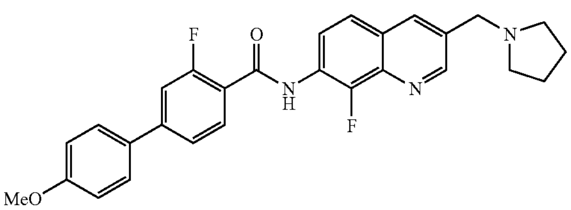

By operating in the same manner as in Example 50 and using 4-bromo-2-fluoro-N-[8-fluoro-3-(1-piperidinylmethyl)-7-quinolinyl]benzamide obtained in Example 76, the title compound was obtained.

$^1$H-NMR (DMSO-$d_6$) δ 1.73 (4H, m), 2.51 (4H, m), 3.82 (5H, m), 7.07 (2H, m), 7.64–8.02 (7H, m), 8.30 (1H, s), 8.90 (1H, s), 10.42 (1H, s). melting point: 182–183° C. (crystallization solvent: ethyl acetate-isopropyl ether) FABMS(pos) 474 [M+H]+

Example 80

4-bromo-N-[8-methoxy-3-(1-pyrrolidinylmethyl)-7-quinolinyl]benzamide

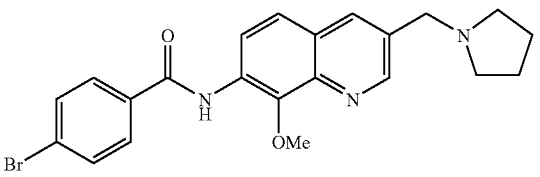

By operating in the same manner as in Reference Example 3 and using 4-bromo-N-[3-(chloromethyl)-8-methoxy-7-quinolinyl]benzamide hydrochloride obtained in Reference Example 35, the title compound was obtained.

$^1$H-NMR (DMSO-$d_6$) δ 1.72 (4H, m), 2.50–2.54 (4H, m), 3.78 (2H, s), 4.11 (3H, s), 7.69–7.79 (3H, m), 7.96–8.00 (3H, m), 8.21 (1H, d, J=1.8 Hz), 8.85 (1H, d, J=1.8 Hz), 10.03 (1H, s). melting point: 121–122° C.

Example 81

4'-fluoro-N-[8-methoxy-3-(1-pyrrolidinylmethyl)-7-quinolinyl][1,1'-biphenyl]-4-carboxamide

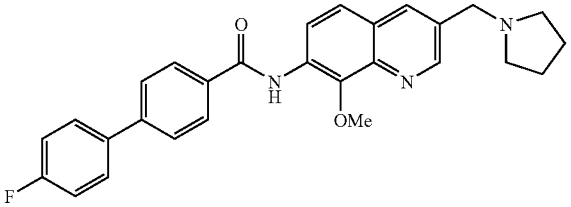

By operating in the same manner as in Example 50 and using 4-bromo-N-[8-methoxy-3-(1-pyrrolidinylmethyl)-7-quinolinyl]benzamide obtained in Example 80, the title compound was obtained.

$^1$H-NMR (DMSO-$d_6$) δ 1.74 (4H, br), 2.48–2.54 (4H, m), 3.81 (2H, s), 4.13 (3H, s) 7.30–7.39 (2H, m), 7.73 (1H, d, J=8.6 Hz), 7.79–7.87 (4H, m), 8.04–8.15 (3H, m), 8.23 (1H, d, J=2.2 Hz), 8.86 (1H, d, J=2.2 Hz), 9.97 (1H, s). melting point: 142–144° C. (crystallization solvent: ethyl acetate-isopropyl ether) Elemental analysis for $C_{28}H_{26}N_3FO_2.0.25H_2O$ Calculated: C, 73.10; H, 5.81; N, 9.13. Found: C, 73.32; H, 5.67; N, 9.34.

Example 82

4-bromo-N-[8-ethyl-3-(1-pyrrolidinylmethyl)-7-quinolinyl]benzamide

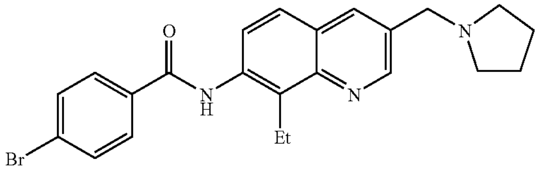

By operating in the same manner as in Reference Example 3 and using 4-bromo-N-[3-(chloromethyl)-8-ethyl-7-quinolinyl]benzamide hydrochloride obtained in Reference Example 44, the title compound was obtained.

$^1$H-NMR (DMSO-$d_6$) δ 1.15 (3H, t, J=7.2 Hz), 1.73–1.79 (4H, m), 2.50–2.51 (4H, m), 3.27 (2H, q, J=7.4 Hz), 3.80 (2H, s), 7.54 (1H, d, J=8.8 Hz), 7.76–7.85 (3H, m), 7.99 (2H, d, J=8.4 Hz), 8.22 (1H, d, J=2.2 Hz), 8.88 (1H, d, J=2.2 Hz), 10.28 (1H, s). melting point: 230–231° C.

Example 83

N-[8-ethyl-3-(1-pyrrolidinylmethyl)-7-quinolinyl]-4'-fluoro[1,1'-biphenyl]-4-carboxamide

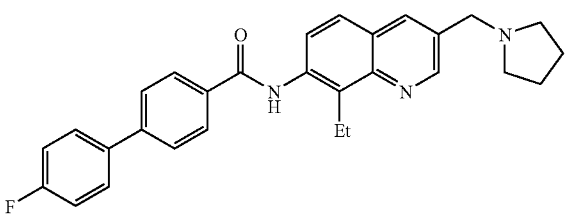

By operating in the same manner as in Example 50 and using 4-bromo-N-[8-ethyl-3-(1-pyrrolidinylmethyl)-7-quinolinyl]benzamide obtained in Example 82, the title compound was obtained.

$^1$H-NMR (DMSO-$d_6$) δ 1.17 (3H, t, J=7.2 Hz), 1.73 (4H, br), 2.50 (4H, br), 2.91–3.35 (2H, m), 3.80 (2H, s), 7.31–7.40 (2H, m), 7.57 (1H, d, J=8.4 Hz), 7.80–7.88 (5H, m), 8.14 (2H, d, J=8.4 Hz), 8.22 (1H, d, J=1.8 Hz), 8.90 (1H, d, J=1.8 Hz), 10.25 (1H, s). melting point: 266–267° C. (crystallization solvent: ethyl acetate-isopropyl ether) FABMS(pos) 454 [M+H]+

Example 84

4-bromo-2-fluoro-N-[3-(1-pyrrolidinylmethyl)-7-quinolinyl]benzamide

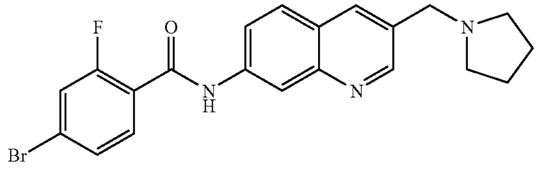

By operating in the same manner as in Example 1 and using 3-(1-pyrrolidinylmethyl)-7-quinolinylamine hydrochloride obtained in Reference Example 5, the title compound was obtained.

$^1$H-NMR (DMSO-$d_6$) δ 1.71 (4H, m), 2.48 (4H, m), 3.74 (2H, s), 7.58 (1H, dd, J=8.30, 1.71 Hz), 7.67 (1H, d, J=7.57 Hz), 7.79 (2H, m), 7.93 (1H, m), 8.14 (1H, d, J=1.46 Hz), 8.49 (1H, s), 8.79 (1H, d, J=1.95 Hz), 10.78 (1H, s).

Example 85

4'-chloro-3-fluoro-N-[3-(1-pyrrolidinylmethyl)-7-quinolinyl][1,1'-biphenyl]-4-carboxamide

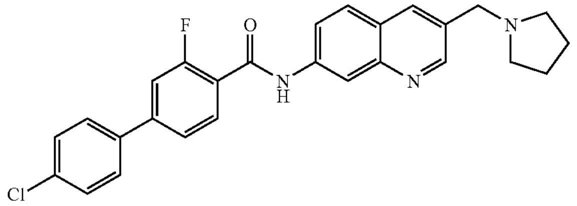

By operating in the same manner as in Example 50 and using 4-bromo-2-fluoro-N-[3-(1-pyrrolidinylmethyl)-7-quinolinyl]benzamide obtained in Example 84, the title compound was obtained.

$^1$H-NMR (DMSO-$d_6$) δ 1.72 (4H, m), 2.50 (4H, m), 3.76 (2H, s), 7.57 (2H, m), 7.69 (1H, m), 7.76 (1H, m), 7.84 (4H, m), 7.95 (1H, m), 8.16 (1H, d, J=1.2 Hz), 8.53 (1H, d, J=1.7 Hz), 8.80 (1H, d, J=2.2 Hz), 10.78 (1H, s). melting point: 232° C. (crystallization solvent: ethyl acetate-isopropyl ether) Elemental analysis for $C_{27}H_{23}N_3ClFO$ Calculated: C, 70.51; H, 5.04; N, 9.14. Found: C, 70.12; H, 5.04; N, 8.74.

Example 86

4'-chloro-3-fluoro-N-[3-(1-pyrrolidinylmethyl)-7-quinolinyl][1,1'-biphenyl]-4-carboxamide

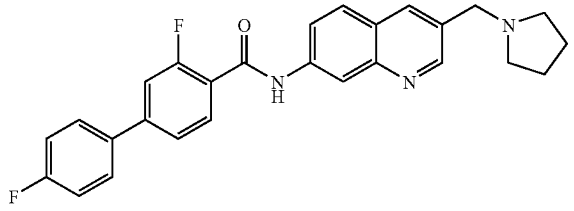

By operating in the same manner as in Example 50 and using 4-bromo-2-fluoro-N-[3-(1-pyrrolidinylmethyl)-7-quinolinyl]benzamide obtained in Example 84, the title compound was obtained.

$^1$H-NMR (DMSO-$d_6$) δ 1.71 (4H, m), 2.49 (4H, m), 3.75 (2H, s), 7.34 (2H, m), 7.66 (1H, dd, J=8.1, 1.7 Hz), 7.73 (1H, m), 7.83 (4H, m), 7.94 (1H, m), 8.14 (1H, d, J=1.2 Hz), 8.52 (1H, d, J=1.5 Hz), 8.79 (1H, d, J=2.2 Hz), 10.76 (1H, s). melting point: 177° C. (crystallization solvent: ethyl acetate-isopropyl ether) Elemental analysis for $C_{27}H_{23}N_3F_2O$ Calculated: C, 73.12; H, 5.23; N, 9.47. Found: C, 73.33; H, 5.26; N, 9.22.

Example 87

3-fluoro-4'-methoxy-N-[3-(1-pyrrolidinylmethyl)-7-quinolinyl][1,1'-biphenyl]-4-carboxamide

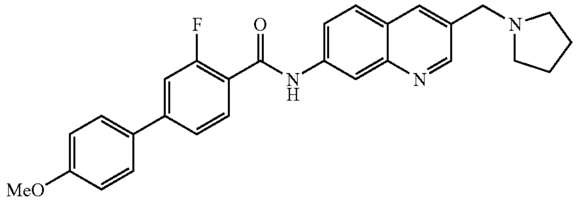

By operating in the same manner as in Example 50 and using 4-bromo-2-fluoro-N-[3-(1-pyrrolidinylmethyl)-7-quinolinyl]benzamide obtained in Example 84, the title compound was obtained.

$^1$H-NMR (DMSO-$d_6$) δ 1.71 (4H, m), 2.49 (4H, m), 3.75 (2H, s), 3.87 (3H, s), 7.57 (2H, m), 7.69 (1H, m), 7.76 (1H, m), 7.84 (4H, m), 7.95 (1H, m), 8.16 (1H, d, J=1.2 Hz), 8.53 (1H, d, J=1.7 Hz), 8.80 (1H, d, J=2.2 Hz), 10.78 (1H, s). melting point: 174° C. (crystallization solvent: ethyl acetate-isopropyl ether) FABMS(pos) 456 [M+H]+

Example 88

3-fluoro-N-[3-(1-pyrrolidinylmethyl)-7-quinolinyl][1,1'-biphenyl]-4-carboxamide

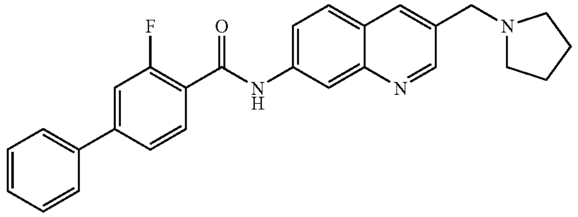

By operating in the same manner as in Example 50 and using 4-bromo-2-fluoro-N-[3-(1-pyrrolidinylmethyl)-7-quinolinyl]benzamide obtained in Example 84, the title compound was obtained.

$^1$H-NMR (DMSO-$d_6$) δ 1.71 (4H, m), 2.49 (4H, m), 3.75 (2H, s), 7.47 (3H, m), 7.68 (1H, m), 7.72 (1H, m), 7.80 (4H, m), 7.94 (1H, m), 8.15 (1H, d, J=1.5 Hz), 8.53 (1H, d, J=1.5 Hz), 8.79 (1H, d, J=2.2 Hz), 10.76 (1H, s). melting point: 166° C. (crystallization solvent: ethyl acetate-isopropyl ether) Elemental analysis for $C_{27}H_{24}N_3FO.0.5H_2O$ Calculated: C, 74.63; H, 5.79; N, 9.67. Found: C, 74.44; H, 5.50; N, 9.42.

Example 89

4'-chloro-N-(3-{[4-(2-hydroxyethyl)-1-piperidinyl] methyl}-7-quinolinyl)-[1,1'-biphenyl]-4-carboxamide

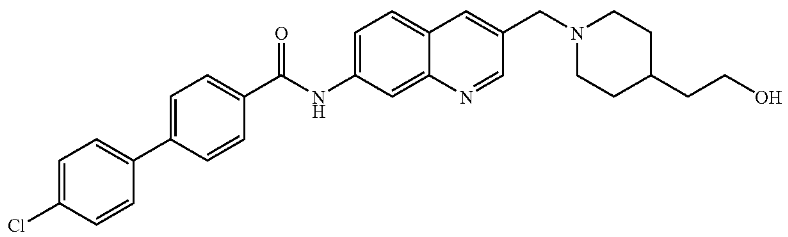

By operating in the same manner as in Example 42 and using 4'-chloro-N-[3-(chloromethyl)-7-quinolinyl][1,1'-biphenyl]-4-carboxamide obtained in Reference Example 45, the title compound was obtained.

$^1$H-NMR (DMSO-$d_6$) δ 1.17 (2H, m), 1.35 (3H, m), 1.61 (2H, m), 1.98 (2H, s), 2.81 (2H, m), 3.42 (2H, m), 3.62 (2H, s), 4.31 (1H, t, J=4.9 Hz), 7.58 (2H, m), 7.82 (2H, m), 7.88 (2H, d, J=8.3 Hz), 7.97 (4H, m), 8.13 (2H, d, J=8.6 Hz), 8.58 (1H, s), 8.79 (1H, d, J=1.5 Hz), 10.62 (1H, s). melting point: 204° C. (crystallization solvent: ethyl acetate-isopropyl ether) Elemental analysis for $C_{30}H_{30}N_3ClO_2.1.25H_2O$ Calculated: C, 68.95; H, 6.26; N, 8.04. Found: C, 69.04; H, 6.56; N, 7.79.

Example 90

1-[(7-{[(4'-chloro-1,1'-biphenyl-4-yl)carbonyl] amino}-3-quinolinyl)methyl]piperidine-4-carboxamide

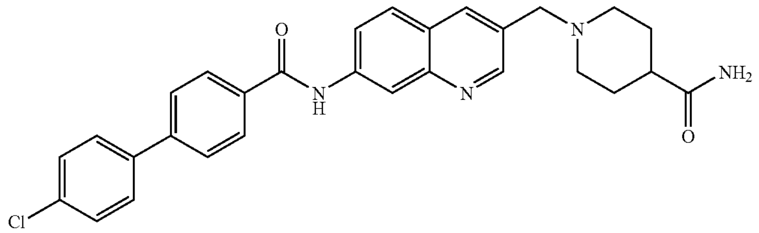

By operating in the same manner as in Example 42 and using 4'-chloro-N-[3-(chloromethyl)-7-quinolinyl][1,1'-biphenyl]-4-carboxamide obtained in Reference Example 45, the title compound was obtained.

$^1$H-NMR (DMSO-$d_6$) δ 1.66 (4H, m), 1.99 (2H, m), 2.06 (1H, m), 2.86 (2H, m), 3.64 (2H, s), 6.70 (1H, s), 7.20 (1H, s), 7.58 (2H, m), 7.83 (2H, m), 7.89 (2H, m), 7.96 (1H, d, J=8.8 Hz), 7.99 (1H, m), 8.14 (3H, m), 8.59 (1H, s), 8.80 (1H, d, J=1.5 Hz), 10.62 (1H, s). melting point: 260° C. (crystallization solvent: ethyl acetate-isopropyl ether) Elemental analysis for $C_{29}H_{27}N_4ClO_2$ Calculated: C, 69.80; H, 5.45; N, 11.23. Found: C, 69.76; H, 5.47; N, 10.83.

Example 91

4'-chloro-N-[3-({4-[2-(ethylamino)-2-oxoethyl]-1-piperidinyl}methyl)-7-quinolinyl][1,1'-biphenyl]-4-carboxamide

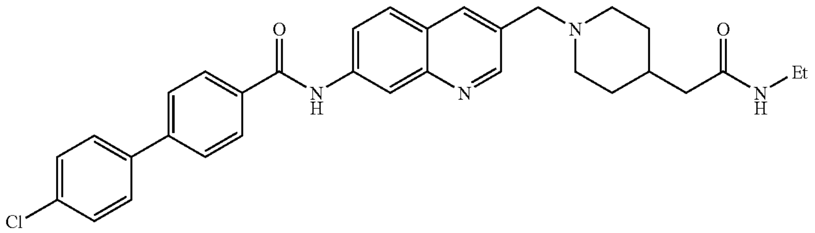

By operating in the same manner as in Example 42 and using 4'-chloro-N-[3-(chloromethyl)-7-quinolinyl][1,1'-biphenyl]-4-carboxamide obtained in Reference Example 45, the title compound was obtained.

$^1$H-NMR (DMSO-$d_6$) δ 0.98 (3H, t, J=7.3 Hz), 1.16 (2H, m) 1.59 (2H, m), 1.66 (1H, s), 1.97 (4H, m), 2.81 (2H, m), 3.03 (2H, m), 3.62 (2H, s), 7.57 (2H, m), 7.75 (1H, m), 7.82 (2H, m), 7.88 (2H, d, J=8.8 Hz), 7.97 (2H, m), 8.13 (3H, m), 8.58 (1H, d, J=1.5 Hz), 8.79 (1H, d, J=1.7 Hz), 10.61 (1H, s). melting point: 250° C. (crystallization solvent: ethyl acetate-isopropyl ether) Elemental analysis $C_{32}H_{33}N_4ClO_2$.0.25$H_2O$ Calculated: C, 70.44; H, 6.18; N, 10.26. Found: C, 70.25; H, 6.24; N, 9.99.

Example 92

N-(3-{[3-(acetylamino)-1-pyrrolidinyl]methyl}-7-quinolinyl)-4'-chloro-[1,1'-biphenyl]-4-carboxamide

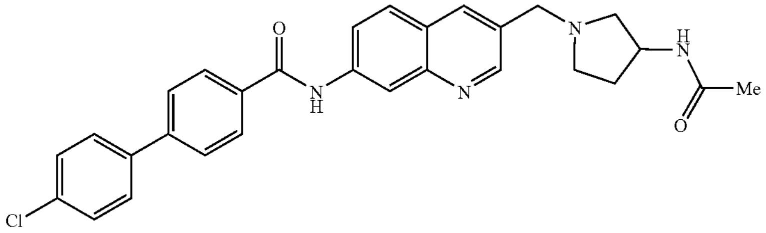

By operating in the same manner as in Example 42 and using 4'-chloro-N-[3-(chloromethyl)-7-quinolinyl][1,1'-biphenyl]-4-carboxamide obtained in Reference Example 45, the title compound was obtained.

$^1$H-NMR (DMSO-$d_6$) δ 1.59 (1H, m), 1.77 (3H, s), 2.12 (1H, m), 2.36 (1H, m), 2.47 (1H, m), 2.69 (2H, m), 3.76 (2H, d, J=6.8 Hz), 4.16 (1H, m), 7.58 (2H, m), 7.83 (2H, m), 7.89 (2H, m), 7.98 (3H, m), 8.14 (2H, d, J=8.6 Hz), 8.16 (1H, s), 8.60 (1H, d, J=1.5 Hz), 8.83 (1H, d, J=2.2 Hz), 10.62 (1H, s). melting point: >285° C. (crystallization solvent: ethyl acetate-isopropyl ether) Elemental analysis for $C_{29}H_{27}ClN_4O_2$.0.5$H_2O$ Calculated: C, 68.56; H, 5.55; N, 11.02. Found: C, 68.95; H, 5.66; N, 10.61.

Example 93

4-bromo-N-[8-methyl-3-(1-pyrrolidinylmethyl)-7-quinolinyl]benzamide

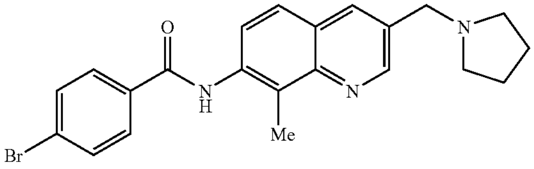

By operating in the same manner as in Reference Example 3 and using 4-bromo-N-[3-(chloromethyl)-8-methyl-7-quinolinyl]benzamide hydrochloride obtained in Reference Example 49, the title compound was obtained.

$^1$H NMR (DMSO-$d_6$) δ 1.72 (4H, m), 2.50 (4H, m), 2.64 (3H, s), 3.80 (2H, s), 7.59 (1H, d, J=8.7 Hz), 7.78 (2H, d, J=9.0 Hz), 7.82 (1H, d, J=8.7 Hz), 7.98 (2H, d, J=9.0 Hz), 8.22 (1H, d, J=2.1 Hz), 8.88 (1H, d, J=2.1 Hz), 10.32 (1H, s).

Example 94

6-(4-methylphenyl)-N-[8-methyl-3-(1-pyrrolidinyl-methyl)-7-quinolinyl]nicotinamide

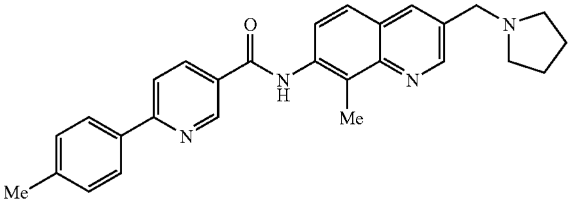

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H-NMR (DMSO-$d_6$) δ 1.73 (4H, m), 2.39 (3H, s), 2.50 (4H, m), 2.68 (3H, s), 3.81 (2H, s), 7.36 (2H, d, J=7.2 Hz), 7.64 (1H, d, J=8.7 Hz), 7.84 (1H, d, J=8.7 Hz), 8.13 (3H, m), 8.23 (1H, s), 8.45 (1H, d, J=8.7 Hz), 8.89 (1H, s), 9.26 (1H, s), 10.43 (1H, s). melting point: 178–180° C. (crystallization solvent: ethyl acetate-isopropyl ether) FABMS(pos) 437 [M+H]+

Example 95

6-(4-chlorophenyl)-N-[8-methyl-3-(1-pyrrolidinylm-ethyl)-7-quinolinyl]nicotinamide

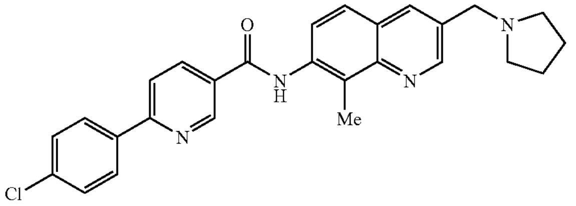

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H-NMR (DMSO-$d_6$) δ 1.73 (4H, m), 2.50 (4H, m), 2.68 (3H, s), 3.81 (2H, s), 7.63 (3H, m), 7.84 (1H, d, J=8.4 Hz), 8.23 (4H, m), 8.49 (1H, d, J=8.4 Hz), 8.89 (1H, d, J=1.8 Hz), 9.28 (1H, s), 10.47 (1H, s). melting point: 234–236° C. (crystallization solvent: ethyl acetate-isopropyl ether) FABMS(pos) 457 [M+H]+

Example 96

6-(4-methoxyphenyl)-N-[8-methyl-3-(1-pyrrolidinyl-methyl)-7-quinolinyl]nicotinamide

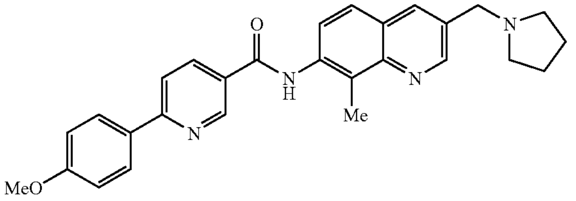

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H-NMR (DMSO-$d_6$) δ 1.73 (4H, m), 2.50 (4H, m), 2.68 (3H, s), 3.85 (5H, m), 7.10 (2H, d, J=8.7 Hz), 7.64 (1H, d, J=8.7 Hz), 7.84 (1H, d, J=8.7 Hz), 8.10–8.24 (4H, m), 8.42 (1H, d, J=9.0 Hz), 8.90 (1H, s), 9.24 (1H, s), 10.41 (1H, s). melting point: 180–182° C. (crystallization solvent: ethyl acetate-isopropyl ether) FABMS(pos) 453 [M+H]+

Example 97

6-(4-fluorophenyl)-N-[8-methyl-3-(1-pyrrolidinylm-ethyl)-7-quinolinyl]nicotinamide

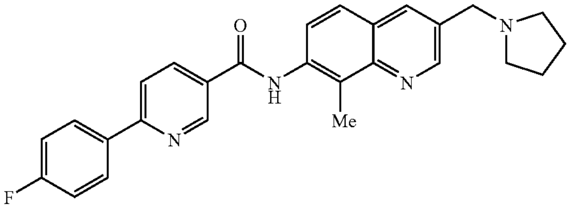

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H-NMR (DMSO-$d_6$) δ 1.73 (4H, m), 2.50 (4H, m), 2.68 (3H, s), 3.82 (2H, s), 7.39 (2H, m), 7.64 (1H, d, J=9.0 Hz), 7.85 (1H, d, J=9.0 Hz), 8.17–8.30 (4H, m), 8.47 (1H, m), 8.89 (1H, d, J=2.1 Hz), 9.27 (1H, s), 10.46 (1H, s). melting point: 207–209° C. (crystallization solvent: ethyl acetate-isopropyl ether) FABMS(pos) 441 [M+H]+

Example 98

4-(4-chlorophenyl)-N-[8-methyl-3-(1-pyrrolidinylm-ethyl)-7-quinolinyl]-1-piperidine carboxamide

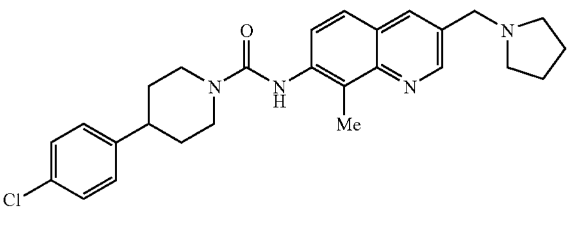

By successively operating in the same manner as in Reference Example 4 and Example 12 and using N-[8-methyl-3-(1-pyrrolidinylmethyl)-7-quinolinyl]acetamide obtained in Reference Example 7, the title compound was obtained.

$^1$H-NMR (DMSO-$d_6$) δ 1.58–1.83 (8H, m), 2.50 (4H, m), 2.58 (3H, s), 2.73–2.79 (1H,m), 2.93 (2H, m), 3.78 (2H, s), 4.27–4.32 (2H, m), 7.30–7.39 (4H, m), 7.50 (1H, d, J=9.0 Hz), 7.71 (1H, d, J=9.0 Hz), 8.14 (1H, s), 8.39 (1H, s), 8.82 (1H, s). melting point: 203–205° C. (crystallization solvent: ethyl acetate-isopropyl ether) FABMS(pos) 463 [M+H]+

Example 99

2'-fluoro-N-[8-methyl-3-(1-pyrrolidinylmethyl)-7-quinolinyl][1,1'-biphenyl]-4-carboxamide

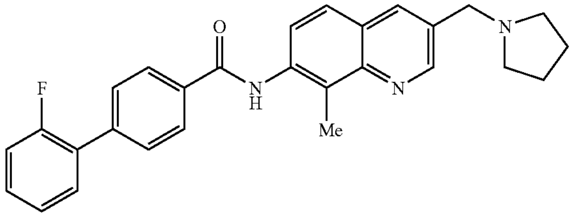

By operating in the same manner as in Example 50 and using 4-bromo-N-[8-methyl-3-(1-pyrrolidinylmethyl)-7-quinolinyl]benzamide obtained in Example 93, the title compound was obtained.

$^1$H-NMR (DMSO-$d_6$) δ 1.73 (4H, m), 2.50 (4H, m), 2.67 (3H, s), 3.81 (2H, s), 7.33–7.86 (8H, m), 8.15 (2H, d, J=8.4 Hz), 8.22 (1H, d, J=2.2 Hz), 8.89 (1H, d, J=2.0 Hz), 10.31 (1H, s). melting point: 133–135° C. (crystallization solvent: ethyl acetate-isopropyl ether) FABMS(pos) 440 [M+H]+

Example 100

2',4'-difluoro-N-[8-methyl-3-(1-pyrrolidinylmethyl)-7-quinolinyl][1,1'-biphenyl]-4-carboxamide

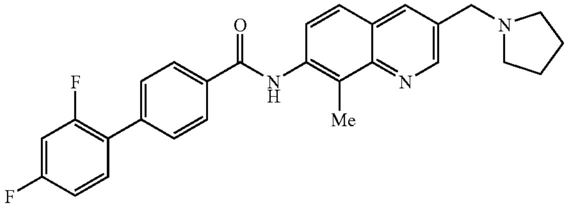

By operating in the same manner as in Example 50 and using 4-bromo-N-[8-methyl-3-(1-pyrrolidinylmethyl)-7-quinolinyl]benzamide obtained in Example 93, the title compound was obtained.

$^1$H-NMR (DMSO-$d_6$) δ 1.73 (4H, m), 2.50 (4H, m), 2.67 (3H, s), 3.81 (2H, s), 7.26 (1H, m), 7.44 (1H, m), 7.60–7.75 (4H, m), 7.83 (1H, d, J=8.8 Hz), 8.15 (2H, d, J=8.4 Hz), 8.22 (1H, d, J=2.2 Hz), 8.88 (1H, d, J=2.2 Hz), 10.31 (1H, s). melting point: 177–179° C. (crystallization solvent: ethyl acetate-isopropyl ether) FABMS(pos) 458 [M+H]+

Example 101

N-[8-methyl-3-(1-pyrrolidinylmethyl)-7-quinolinyl]-4'-(trifluoromethyl)[1,1'-biphenyl]-4-carboxamide

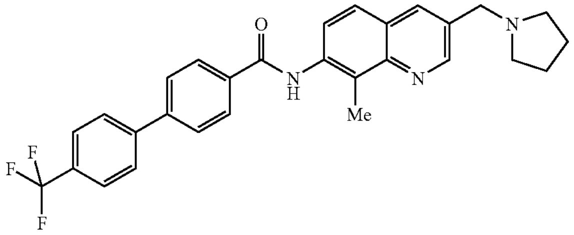

By operating in the same manner as in Example 50 and using 4-bromo-N-[8-methyl-3-(1-pyrrolidinylmethyl)-7-quinolinyl]benzamide obtained in Example 93, the title compound was obtained.

$^1$H-NMR (DMSO-$d_6$) δ 1.73 (4H, m), 2.50 (4H, m), 2.67 (3H, s), 3.81 (2H, s), 7.62 (1H, d, J=8.6 Hz), 7.82–8.03 (7H, m), 8.17–8.22 (3H, m), 8.88 (1H, d, J=2.2 Hz), 10.36 (1H, s). melting point: 220–222° C. (crystallization solvent: ethyl acetate-isopropyl ether) FABMS(pos) 490 [M+H]+

Example 102

3',4'-difluoro-N-[8-methyl-3-(1-pyrrolidinylmethyl)-7-quinolinyl][1,1'-biphenyl]-4-carboxamide

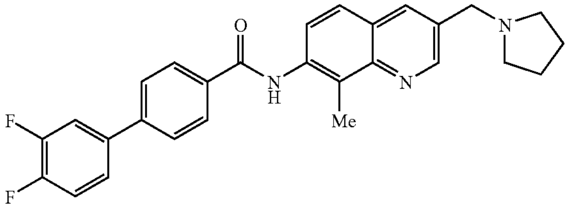

By operating in the same manner as in Example 50 and using 4-bromo-N-[8-methyl-3-(1-pyrrolidinylmethyl)-7-quinolinyl]benzamide obtained in Example 93, the title compound was obtained.

$^1$H-NMR (DMSO-$d_6$) δ 1.73 (4H, m), 2.50 (4H, m), 2.66 (3H, s), 3.81 (2H, s), 7.63 (3H, m), 7.89 (4H, m), 8.15 (2H, d, J=8.1 Hz), 8.22 (1H, s), 8.88 (1H, s), 10.31 (1H, s). melting point: 199–201° C. (crystallization solvent: ethyl acetate-isopropyl ether) FABMS(pos) 458 [M+H]+

Example 103

N-[8-methyl-3-(1-pyrrolidinylmethyl)-7-quinolinyl]-4'-(trifluoromethoxy)[1,1'-biphenyl]-4-carboxamide

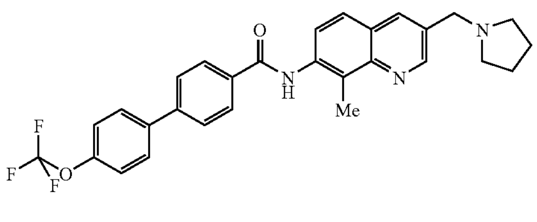

By operating in the same manner as in Example 50 and using 4-bromo-N-[8-methyl-3-(1-pyrrolidinylmethyl)-7-quinolinyl]benzamide obtained in Example 93, the title compound was obtained.

$^1$H-NMR (DMSO-$d_6$) δ 1.74 (4H, m), 2.50 (4H, m), 2.67 (3H, s), 3.80 (2H, s), 7.51 (2H, d, J=7.8 Hz), 7.62 (1H, d, J=9.0 Hz), 7.83 (1H, d, J=9.3 Hz), 7.90 (4H, m), 8.15 (2H, d, J=8.1 Hz), 8.22 (1H, s), 8.88 (1H, s), 10.29 (1H, s). melting point: 200–202° C. (crystallization solvent: ethyl acetate-isopropyl ether) FABMS(pos) 506 [M+H]+

Example 104

4'-ethyl-N-[8-methyl-3-(1-pyrrolidinylmethyl)-7-quinolinyl][1,1'-biphenyl]-4-carboxamide

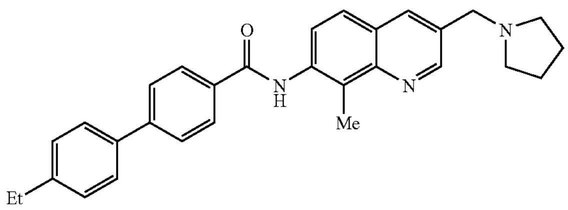

By operating in the same manner as in Example 50 and using 4-bromo-N-[8-methyl-3-(1-pyrrolidinylmethyl)-7-quinolinyl]benzamide obtained in Example 93, the title compound was obtained.

$^{1}$H-NMR (DMSO-$d_6$) δ 1.23 (3H, m), 1.73 (4H, m), 2.50 (4H, m), 2.67 (5H, m), 3.82 (2H, s), 7.35–8.23 (11H, m), 8.79 (1H, m), 10.28 (1H, s). melting point: 189–190° C. (crystallization solvent: ethyl acetate-isopropyl ether)

Example 105

4-(1,3-benzodioxol-5-yl)-N-[8-methyl-3-(1-pyrrolidinylmethyl)-7-quinolinyl]benzamide

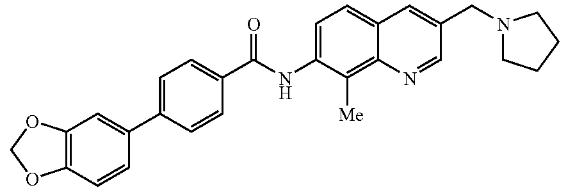

By operating in the same manner as in Example 50 and using 4-bromo-N-[8-methyl-3-(1-pyrrolidinylmethyl)-7-quinolinyl]benzamide obtained in Example 93, the title compound was obtained.

$^{1}$H-NMR (DMSO-$d_6$) δ 1.73 (4H, m), 2.50 (4H, m), 2.66 (3H, s), 3.81 (2H, s), 6.09 (2H, m), 7.06–8.22 (10H, m), 8.89 (1H, m), 10.26 (1H, s). Elemental analysis for $C_{29}H_{27}N_3O_3$.0.5$H_2O$ Calculated: C, 73.40; H, 5.95; N, 8.85. Found: C, 73.09; H, 5.63; N, 8.69. melting point: 171–172° C. (crystallization solvent: ethyl acetate-isopropyl ether)

Example 106

4-(1-benzofuran-2-yl)-N-[8-methyl-3-(1-pyrrolidinylmethyl)-7-quinolinyl]benzamide

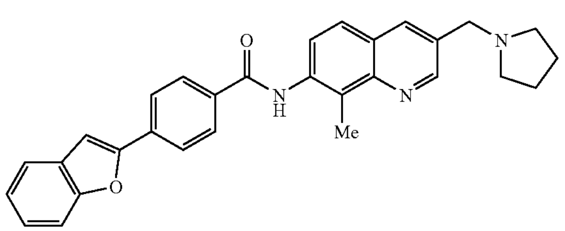

By operating in the same manner as in Example 50 and using 4-bromo-N-[8-methyl-3-(1-pyrrolidinylmethyl)-7-quinolinyl]benzamide obtained in Example 93, the title compound was obtained.

$^{1}$H-NMR (DMSO-$d_6$) δ 1.72 (4H, m), 2.50 (4H, m), 2.68 (3H, s), 3.80 (2H, s), 7.31–8.22 (12H, m), 8.89 (1H, m), 10.36° (1H, s). Elemental analysis for $C_{30}H_{27}N_3O_2$.0.5$H_2O$ Calculated: C, 76.57; H, 6.00; N, 8.93. Found: C, 76.36; H, 5.79; N, 8.74. melting point: 217–218° C. (crystallization solvent: ethyl acetate-isopropyl ether)

Example 107

4-(5-chloro-2-thienyl)-N-[8-methyl-3-(1-pyrrolidinylmethyl)-7-quinolinyl]benzamide

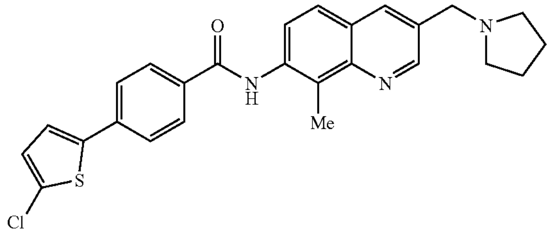

By operating in the same manner as in Example 50 and using 4-bromo-N-[8-methyl-3-(1-pyrrolidinylmethyl)-7-quinolinyl]benzamide obtained in Example 93, the title compound was obtained.

$^{1}$H-NMR (DMSO-$d_6$) δ 1.73 (4H, m), 2.51 (4H, m), 2.66 (3H, s), 3.80 (2H, s), 7.24(1H, m), 7.62 (2H, m), 7.82 (3H, m), 8.10(2H, m), 8.22 (1H, m), 8.88 (1H, m), 10.29 (1H, s). melting point: 210–211° C. (crystallization solvent: ethyl acetate-isopropyl ether) FABMS(pos) 462 [M+H]+

Example 108

2'-chloro-N-[8-methyl-3-(1-pyrrolidinylmethyl)-7-quinolinyl][1,1'-biphenyl]-4-carboxamide

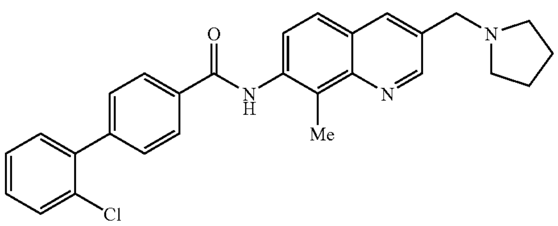

By operating in the same manner as in Example 50 and using 4-bromo-N-[8-methyl-3-(1-pyrrolidinylmethyl)-7-quinolinyl]benzamide obtained in Example 93, the title compound was obtained.

$^{1}$H-NMR (DMSO-$d_6$) δ 1.72 (4H, m), 2.50 (4H, m), 2.68 (3H, s), 3.80 (2H, s), 7.49–8.22 (11H, m), 8.90 (1H, m), 10.35 (1H, s). Elemental analysis for $C_{28}H_{26}ClN_3O$.1.5$H_2O$ Calculated: C, 69.63; H, 6.05; N, 8.70. Found: C, 70.01; H, 5.67; N, 8.30. melting point: 128–129° C. (crystallization solvent: ethyl acetate-isopropyl ether)

Example 109

3'-methyl-N-[8-methyl-3-(1-pyrrolidinylmethyl)-7-quinolinyl][1,1'-biphenyl]-4-carboxamide

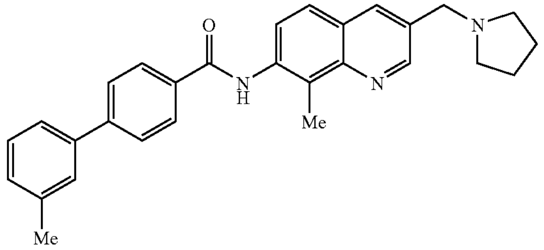

By operating in the same manner as in Example 50 and using 4-bromo-N-[8-methyl-3-(1-pyrrolidinylmethyl)-7-quinolinyl]benzamide obtained in Example 93, the title compound was obtained.

$^1$H-NMR (DMSO-$d_6$) δ 1.73 (4H, m), 2.42 (3H, s), 2.50 (4H, m), 2.68 (3H, s), 3.81 (2H, s), 7.24–8.22 (11H, m), 8.89 (1H, s), 10.29 (1H, s). melting point: 151–152° C. (crystallization solvent: ethyl acetate-isopropyl ether) FABMS(pos) 436 [M+H]+

Example 110

N-[8-methyl-3-(1-pyrrolidinylmethyl)-7-quinolinyl]-4'-(methylsulfanyl)[1,1'-biphenyl]-4-carboxamide

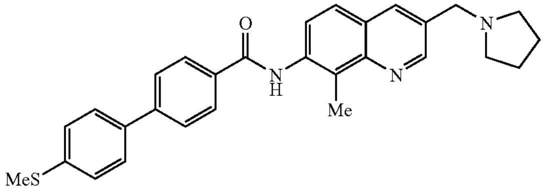

By operating in the same manner as in Example 50 and using 4-bromo-N-[8-methyl-3-(1-pyrrolidinylmethyl)-7-quinolinyl]benzamide obtained in Example 93, the title compound was obtained.

$^1$H-NMR (DMSO-$d_6$) δ 1.73 (4H, m), 2.50 (4H, m), 2.54 (3H, s), 2.67 (3H, s), 3.81 (2H, s), 7.38–7.41 (2H, m), 7.61–8.22 (9H, m), 8.89 (1H, s), 10.28 (1H, s). Elemental analysis for $C_{29}H_{29}N_3OS.H_2O$ Calculated: C, 71.72; H, 6.43; N, 8.65. Found: C, 71.40; H, 6.09; N, 8.86. melting point: 206–208° C. (crystallization solvent: ethyl acetate-isopropyl ether)

Example 111

2'-methyl-N-[8-methyl-3-(1-pyrrolidinylmethyl)-7-quinolinyl][1,1'-biphenyl]-4-carboxamide

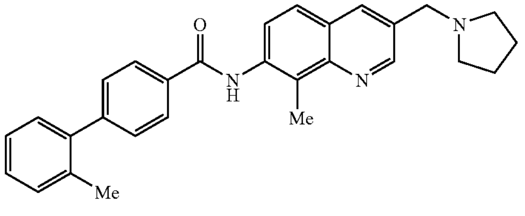

By operating in the same manner as in Example 50 and using 4-bromo-N-[8-methyl-3-(1-pyrrolidinylmethyl)-7-quinolinyl]benzamide obtained in Example 93, the title compound was obtained.

$^1$H-NMR (DMSO-$d_6$) δ 1.73 (4H, m), 2.29 (3H, s), 2.50 (4H, m), 2.68 (3H, s), 3.81 (2H, s), 7.28–8.23 (11H, m), 8.89 (1H, s), 10.30 (1H, s). melting point: 150–151° C. (crystallization solvent: ethyl acetate-isopropyl ether) FABMS(pos) 436 [M+H]+

Example 112

3'-fluoro-N-[8-methyl-3-(1-pyrrolidinylmethyl)-7-quinolinyl][1,1'-biphenyl]-4-carboxamide

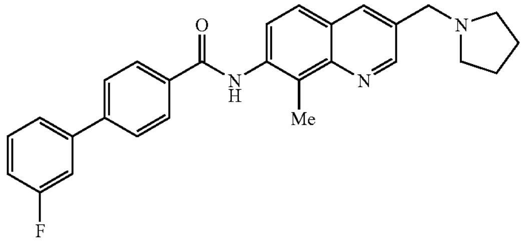

By operating in the same manner as in Example 50 and using 4-bromo-N-[8-methyl-3-(1-pyrrolidinylmethyl)-7-quinolinyl]benzamide obtained in Example 93, the title compound was obtained.

$^1$H-NMR (DMSO-$d_6$) δ 1.73 (4H, m), 2.50 (4H, m), 2.67 (3H, s), 3.81 (2H, s), 7.25–8.22 (11H, m), 8.89 (1H, s), 10.32 (1H, s). melting point: 158–159° C. (crystallization solvent: ethyl acetate-isopropyl ether) FABMS(pos) 440 [M+H]+

Example 113

4-(2,3-dihydro-1-benzofuran-5-yl)-N-[8-methyl-3-(1-pyrrolidinylmethyl)-7-quinolinyl]benzamide

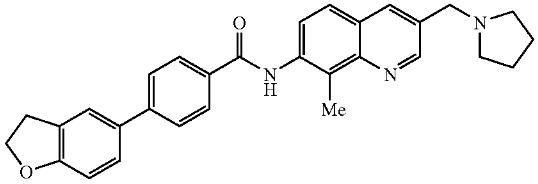

By operating in the same manner as in Example 50 and using 4-bromo-N-[8-methyl-3-(1-pyrrolidinylmethyl)-7-quinolinyl]benzamide obtained in Example 93, the title compound was obtained.

$^1$H-NMR (DMSO-$d_6$) δ 1.73 (4H, m), 2.50 (4H, m), 2.67 (3H, s), 3.27 (2H, t, J=9.0 Hz), 3.83 (2H, s), 4.60 (2H, t, J=9.0 Hz), 6.89 (1H, d, J=8.4 Hz), 7.51–7.84 (6H, m), 8.09–8.23 (3H, m), 8.89 (1H, s), 10.25 (1H, s). Elemental analysis for $C_{30}H_{29}N_3O_2.H_2O$ Calculated: C, 74.82; H, 6.49; N, 8.73. Found: C, 74.75; H, 6.20; N, 8.65. melting point: 176–177° C. (crystallization solvent: ethyl acetate-isopropyl ether)

Example 114

4-(3,4-dihydro-2H-chromen-6-yl)-N-[8-methyl-3-(1-pyrrolidinylmethyl)-7-quinolinyl]benzamide

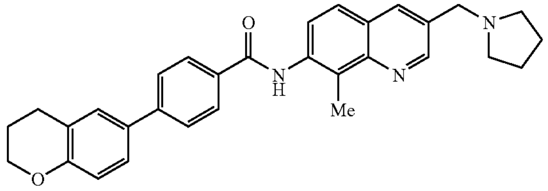

By operating in the same manner as in Example 50 and using 4-bromo-N-[8-methyl-3-(1-pyrrolidinylmethyl)-7-quinolinyl]benzamide obtained in Example 93, the title compound was obtained.

$^1$H-NMR (DMSO-$d_6$) δ 1.73 (4H, m), 1.97 (2H, m), 2.51 (4H, m), 2.67 (3H, s), 2.84 (2H, m), 3.82 (2H, s), 4.19 (2H, m), 6.86 (1H, d, J=8.4 Hz), 7.51–8.23 (9H, m), 8.89 (1H, s), 10.25 (1H, s). melting point: 195–197° C. (crystallization solvent: ethyl acetate-isopropyl ether) FABMS(pos) 478 [M+H]+

Example 115

4-(2,3-dihydro-1,4-benzodioxin-6-yl)-N-[8-methyl-3-(1-pyrrolidinylmethyl)-7-quinolinyl]benzamide

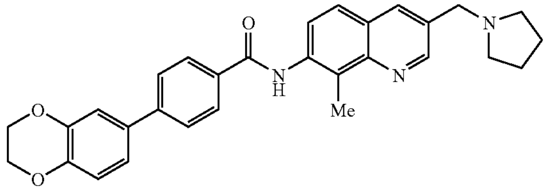

By operating in the same manner as in Example 50 and using 4-bromo-N-[8-methyl-3-(1-pyrrolidinylmethyl)-7-quinolinyl]benzamide obtained in Example 93, the title compound was obtained.

$^1$H-NMR (DMSO-$d_6$) δ 1.73 (4H, m), 2.50 (4H, m), 2.65 (3H, s), 3.81 (2H, s), 4.30 (4H, s), 6.99 (1H, d, J=8.4 Hz), 7.28–7.88 (6H, m), 8.09–8.22 (3H, m), 8.89 (1H, s), 10.25 (1H, s). Elemental analysis for $C_{30}H_{29}N_3O_3$.1.5$H_2O$ Calculated: C, 71.13; H, 6.37; N, 8.29. Found: C, 71.45; H, 6.02; N, 7.98. melting point: 187–188° C. (crystallization solvent: ethyl acetate-isopropyl ether)

Example 116

N-[8-methyl-3-(1-pyrrolidinylmethyl)-7-quinolinyl]-4-(2,3,4,5-tetrahydro-1-benzoxepin-7-yl)benzamide

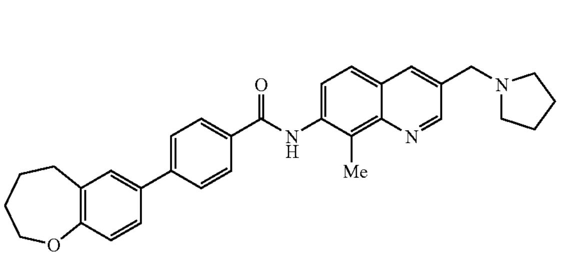

By operating in the same manner as in Example 50 and using 4-bromo-N-[8-methyl-3-(1-pyrrolidinylmethyl)-7-quinolinyl]benzamide obtained in Example 93, the title compound was obtained.

$^1$H-NMR (DMSO-$d_6$) δ 1.73 (6H, m), 1.92 (2H, m), 2.50 (4H, m), 2.67 (3H, s), 2.85 (2H, m), 3.82 (2H, s), 3.99 (2H, m), 7.05 (1H, d, J=8.4 Hz), 7.52–7.84 (6H, m), 8.11–8.22 (3H, m), 8.89 (1H, s), 10.27 (1H, s). Elemental analysis for $C_{32}H_{33}N_3O_2$.1.5$H_2O$ Calculated: C, 74.10; H, 7.00; N, 8.10. Found: C, 74.12; H, 6.61; N, 8.01. melting point: 162–163° C. (crystallization solvent: ethyl acetate-isopropyl ether)

Example 117

N-[8-methyl-3-(1-pyrrolidinylmethyl)-7-quinolinyl]-4-(5-methyl-2-thienyl)benzamide

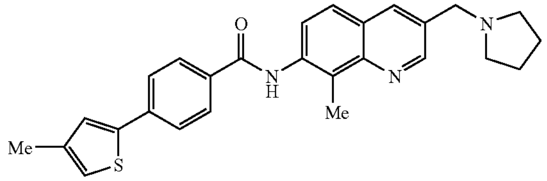

By operating in the same manner as in Example 50 and using 4-bromo-N-[8-methyl-3-(1-pyrrolidinylmethyl)-7-quinolinyl]benzamide obtained in Example 93, the title compound was obtained.

$^1$H-NMR (DMSO-$d_6$) δ 1.73 (4H, m), 2.50 (7H, m), 2.65 (3H, s), 3.81 (2H, s), 7.56–8.22 (9H, m), 8.80 (1H, d, J=2.2 Hz), 10.30 (1H, s). melting point: 220–221° C. (crystallization solvent: ethyl acetate-isopropyl ether)

Example 118

N-[8-methyl-3-(1-pyrrolidinylmethyl)-7-quinolinyl]-4-(4-methyl-2-thienyl)benzamide

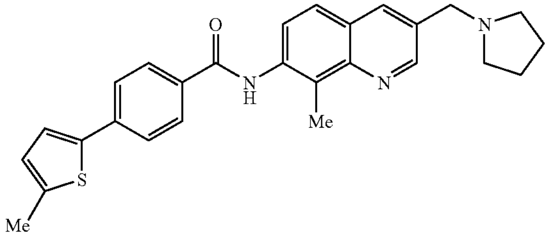

By operating in the same manner as in Example 50 and using 4-bromo-N-[8-methyl-3-(1-pyrrolidinylmethyl)-7-quinolinyl]benzamide obtained in Example 93, the title compound was obtained.

$^1$H-NMR (DMSO-$d_6$) δ 1.73 (4H, m), 2.50 (7H, m), 2.65 (3H, s), 3.81 (2H, s), 7.57–8.22 (9H, m), 8.80 (1H, d, J=2.0 Hz), 10.28 (1H, s). melting point: 224–225° C. (crystallization solvent: ethyl acetate-isopropyl ether)

Example 119

4-(5-acetyl-2-thienyl)-N-[8-methyl-3-(1-pyrrolidinylmethyl)-7-quinolinyl]benzamide

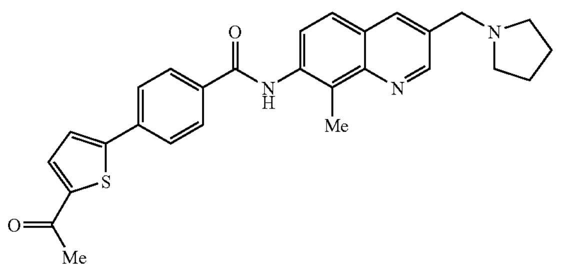

By operating in the same manner as in Example 50 and using 4-bromo-N-[8-methyl-3-(1-pyrrolidinylmethyl)-7-quinolinyl]benzamide obtained in Example 93, the title compound was obtained.

$^1$H-NMR (DMSO-$d_6$) δ 1.73 (4H, m), 2.50 (4H, m), 2.58 (3H, s), 2.66 (3H, s), 2.80 (2H, s), 7.56–8.21 (9H, m), 8.89 (1H, s), 10.31 (1H, s). Elemental analysis for $C_{28}H_{27}N_3O_2S.0.5H_2O$ Calculated: C, 77.03; H, 7.85; N, 9.62. Found: C, 76.95; H, 7.73; N, 9.31. melting point: 194–195° C. (crystallization solvent: ethyl acetate-isopropyl ether)

Example 120

4-(1-benzothien-2-yl)-N-[8-methyl-3-(1-pyrrolidinylmethyl)-7-quinolinyl]benzamide

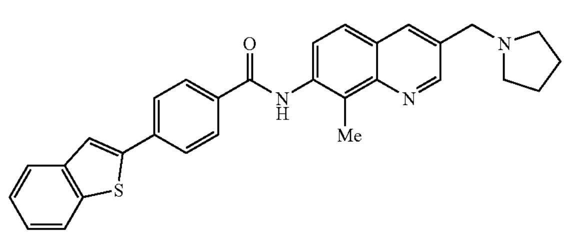

By operating in the same manner as in Example 50 and using 4-bromo-N-[8-methyl-3-(1-pyrrolidinylmethyl)-7-quinolinyl]benzamide obtained in Example 93, the title compound was obtained.

$^1$H-NMR (DMSO-$d_6$) δ 1.73 (4H, m), 2.50 (4H, m), 2.68 (3H, s), 3.80 (2H, s), 7.44–8.21 (12H, m), 8.89 (1H, s), 10.31 (1H, s). Elemental analysis for $C_{30}H_{27}N_3OS.0.5H_2O$ Calculated: C, 74.04; H, 5.80; N, 8.63. Found: C, 74.41; H, 5.61; N, 8.29. melting point: 217–218° C. (crystallization solvent: ethyl acetate-isopropyl ether)

Example 121

4-(benzyloxy)-N-[8-methyl-3-(1-pyrrolidinylmethyl)-7-quinolinyl]benzamide

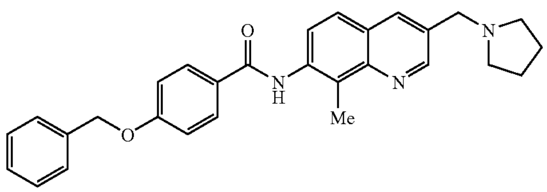

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H-NMR (DMSO-$d_6$) δ 1.72 (4H, m), 2.50 (4H, m), 2.64 (3H, s), 3.80 (2H, s), 5.21 (2H, s), 7.12–8.20 (12H, m), 8.88 (1H, s), 10.06 (1H, s). melting point: 177–178° C. (crystallization solvent: ethyl acetate-isopropyl ether)

Example 122

4-cyclohexyl-N-[8-methyl-3-(1-pyrrolidinylmethyl)-7-quinolinyl]benzamide

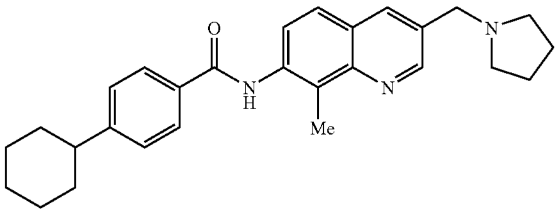

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H-NMR (DMSO-$d_6$) δ 1.44 (6H, m), 1.79 (8H, m), 2.50 (5H, m), 2.64 (3H, s), 3.79 (2H, s), 7.24–8.20 (7H, m), 8.87 (1H, s), 10.13 (1H, s). melting point: 178–179° C. (crystallization solvent: ethyl acetate-isopropyl ether) FABMS(pos) 428 [M+H]+

Example 123

4-[(4-fluorobenzyl)oxy]-N-[8-methyl-3-(1-pyrrolidinylmethyl)-7-quinolinyl]benzamide

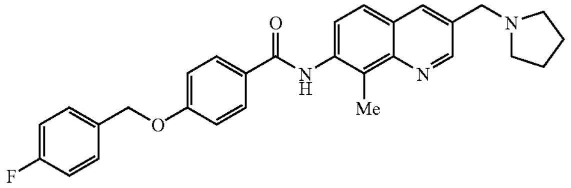

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H-NMR (DMSO-$d_6$) δ 1.53 (4H, m), 2.41 (4H, m), 2.64 (3H, s), 3.68 (2H, s), 5.21 (2H, s), 7.12–8.19 (11H, m), 8.87 (1H, s), 10.08 (1H, s). Elemental analysis for $C_{29}H_{28}FN_3O_2.0.5H_2O$ Calculated: C, 72.78; H, 6.11; N, 8.78. Found: C, 72.90; H, 6.01; N, 9.03. melting point: 177–178° C. (crystallization solvent: ethyl acetate-isopropyl ether)

Example 124

N-[8-methyl-3-(1-pyrrolidinylmethyl)-7-quinolinyl]-4-phenoxybenzamide

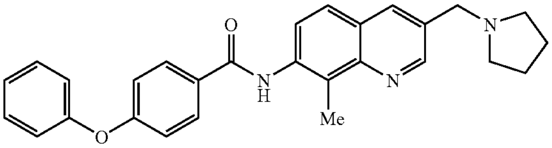

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H-NMR ($CDCl_3$) δ 1.81 (4H, m), 2.57 (4H, m), 2.80 (3H, s), 3.81 (2H, s), 7.08 (4H, m), 7.19 (1H, t, J=7.5 Hz), 7.40 (2H, t, J=7.5 Hz), 7.69 (1H, d, J=9.0 Hz), 7.91 (3H, m), 8.05 (1H, s), 8.21 (1H, d, J=8.4 Hz), 8.88 (1H, s). melting point: 161–162° C. (crystallization solvent: ethyl acetate-isopropyl ether)

Example 125

3-(benzyloxy)-N-[8-methyl-3-(1-pyrrolidinylmethyl)-7-quinolinyl]benzamide

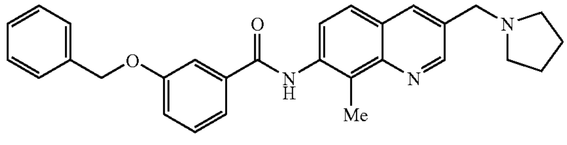

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H-NMR ($CDCl_3$) δ 1.82 (4H, m), 2.58 (4H, m), 2.79 (3H, s), 3.82 (2H, s), 5.16 (2H, s), 7.21–7.59 (9H, m), 7.69 (1H, d, J=13.8 Hz), 7.97 (1H, s), 8.07 (1H, s), 8.23 (1H, d, J=13.2 Hz), 8.90 (1H, s). melting point: 148–149° C. (crystallization solvent: ethyl acetate-isopropyl ether)

Example 126

4-[(4-methoxybenzyl)oxy]-N-[8-methyl-3-(1-pyrrolidinylmethyl)-7-quinolinyl]benzamide

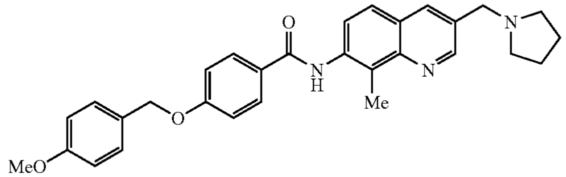

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H-NMR ($CDCl_3$) δ 1.82 (4H, m), 2.58 (4H, m), 2.81 (3H, s), 3.83 (5H, m), 5.08 (2H, s), 6.94 (2H, d, J=8.4 Hz), 7.08 (2H, d, J=8.4 Hz), 7.38 (2H, m), 7.69 (1H, d, J=8.8 Hz), 7.92 (3H, m), 8.07 (1H, s), 8.24 (1H, d, J=8.8 Hz), 8.89 (1H, s). Elemental analysis for $C_{30}H_{31}N_3O_3.H_2O$ Calculated: C, 72.12; H, 6.66; N, 8.41. Found: C, 72.02; H, 6.59; N, 8.16. melting point: 192–193° C. (crystallization solvent: ethyl acetate-isopropyl ether)

Example 127

4-[(2-fluorobenzyl)oxy]-N-[8-methyl-3-(1-pyrrolidinylmethyl)-7-quinolinyl]benzamide

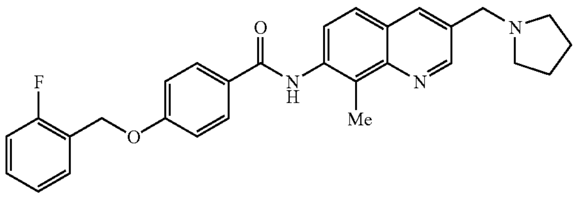

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H-NMR ($CDCl_3$) δ 1.82 (4H, m), 2.59 (4H, m), 2.80 (3H, s) 3.83 (2H, s), 5.22 (2H, s), 7.08–7.35 (6H, m), 7.50 (1H, m), 7.69 (1H, d, J=8.4 Hz), 7.91 (2H, m), 8.07 (1H, s). 8.22 (1H, d, J=9.0 Hz), 8.88 (1H, s). melting point: 104–105° C. (crystallization solvent: ethyl acetate-isopropyl ether)

Example 128

4-[(3-fluorobenzyl)oxy]-N-[8-methyl-3-(1-pyrrolidinylmethyl)-7-quinolinyl]benzamide

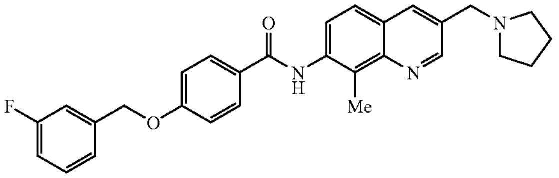

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H-NMR ($CDCl_3$) δ 1.82 (4H, m), 2.58 (4H, m), 2.80 (3H, s), 3.81 (2H, s), 5.14 (2H, s), 7.04–7.37 (6H, m), 7.68 (1H, d, J=8.7 Hz), 7.93 (3H, m), 8.06 (1H, s), 8.21 (1H, d, J=9.0 Hz), 8.88 (1H, s). melting point: 151–152° C. (crystallization solvent: ethyl acetate-isopropyl ether)

Example 129

4-[(4-chlorobenzyl)oxy]-N-[8-methyl-3-(1-pyrrolidinylmethyl)-7-quinolinyl]benzamide

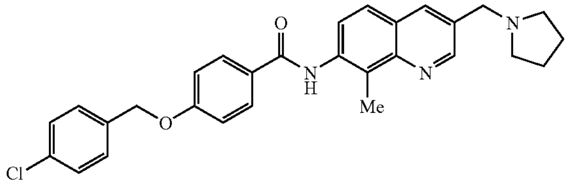

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H-NMR ($CDCl_3$) δ 1.82 (4H, m), 2.58 (4H, m), 2.80 (3H, s), 3.81 (2H, s), 5.11 (2H, s), 7.05 (2H, d, J=8.4 Hz), 7.38 (5H, m), 7.68 (1H, d, J=8.8 Hz), 7.90–8.06 (3H, m), 8.21 (1H, d, J=9.2 Hz), 8.89 (1H, s). melting point: 167–168° C. (crystallization solvent: ethyl acetate-isopropyl ether)

Example 130

N-[8-methyl-3-(1-pyrrolidinylmethyl)-7-quinolinyl]-4-{[4-(trifluoromethyl)benzyl]oxy}benzamide

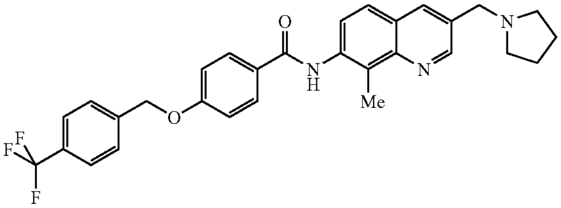

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H-NMR ($CDCl_3$) δ 1.82 (4H, m), 2.58 (4H, m), 2.81 (3H, s), 3.82 (2H, s), 5.22 (2H, s), 7.08 (2H, d, J=8.8 Hz), 7.55–8.06 (9H, m), 8.23 (1H, d, J=8.6 Hz), 8.89 (1H, s). melting point: 196–197° C. (crystallization solvent: ethyl acetate-isopropyl ether)

Example 131

N-[8-methyl-3-(1-pyrrolidinylmethyl)-7-quinolinyl]-3-phenoxybenzamide

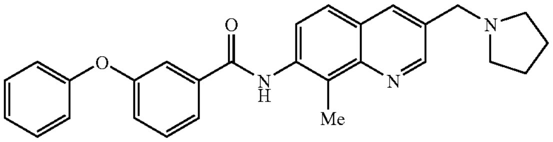

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H-NMR ($CDCl_3$) δ 1.81 (4H, m), 2.57 (4H, m), 2.79 (3H, s), 3.81 (2H, s), 7.05–7.72 (10H, m), 7.92 (1H, s), 8.06 (1H, s), 8.21 (1H, d, J=8.4 Hz), 8.89 (1H, s). melting point: 147–148° C. (crystallization solvent: ethyl acetate-isopropyl ether)

Example 132

4-(benzyloxy)-2-fluoro-N-[8-methyl-3-(1-pyrrolidinylmethyl)-7-quinolinyl]benzamide

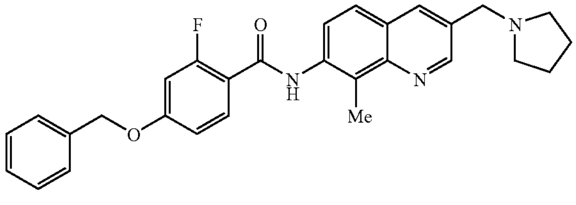

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H-NMR ($CDCl_3$) δ 1.81 (4H, m), 2.57 (4H, m), 2.82 (3H, s), 3.66 (2H, s), 5.15 (2H, s), 6.76–6.96 (2H, m), 7.42 (5H, m), 7.69 (1H, d, J=9.2 Hz), 8.02 (1H, s), 8.20 (1H, t, J=9.4 Hz), 8.36 (1H, d, J=9.2 Hz), 8.59–8.67 (1H, m), 8.88 (1H, s). melting point: 176–177° C. (crystallization solvent: ethyl acetate-isopropyl ether)

Example 133

4-bromo-2-fluoro-N-[8-methyl-3-(1-pyrrolidinylmethyl)-7-quinolinyl]benzamide

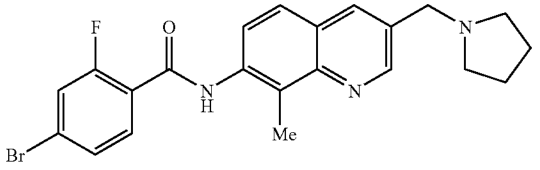

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H NMR (DMSO-$d_6$) δ 1.72 (4H, m), 2.50 (4H, m), 2.67 (3H, s), 3.80 (2H, s), 7.58–7.85 (5H, m), 8.21 (1H, s), 8.88 (1H, d, J=2.2 Hz), 10.26 (1H, s).

Example 134

4-(2,3-dihydro-1-benzofuran-5-yl)-2-fluoro-N-[8-methyl-3-(1-pyrrolidinylmethyl)-7-quinolinyl]benzamide

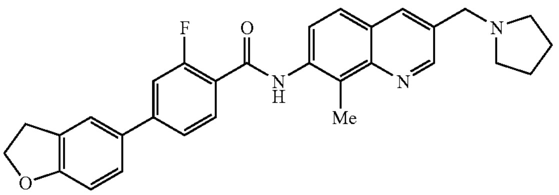

By operating in the same manner as in Example 50 and using 4-bromo-2-fluoro-N-[8-methyl-3-(1-pyrrolidinylmethyl)-7-quinolinyl]benzamide obtained in Example 133, the title compound was obtained.

$^1$H-NMR (DMSO-$d_6$) δ 1.73 (4H, m), 2.50 (4H, m), 2.70 (3H, s), 3.26 (2H, t, J=8.4 Hz), 3.82 (2H, s), 4.60 (2H, t, J=8.7 Hz), 6.88 (1H, d, J=8.4 Hz), 7.52–7.82 (7H, m), 8.20 (1H, s), 8.88 (1H, s), 10.11 (1H, s). melting point: 181–182° C. (crystallization solvent: ethyl acetate-isopropyl ether)

Example 135

3-fluoro-4'-methyl-N-[8-methyl-3-(1-pyrrolidinylmethyl)-7-quinolinyl][1,1'-biphenyl]-4-carboxamide

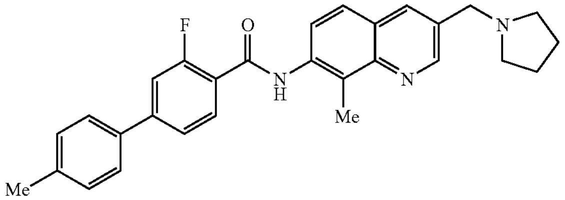

By operating in the same manner as in Example 50 and using 4-bromo-2-fluoro-N-[8-methyl-3-(1-pyrrolidinylmethyl)-7-quinolinyl]benzamide obtained in Example 133, the title compound was obtained.

$^1$H-NMR (DMSO-$d_6$) δ 1.73 (4H, m), 2.37 (3H, s), 2.50 (4H, m), 2.70 (3H, s), 3.80 (2H, s), 7.33 (2H, d, J=8.2 Hz), 7.65–7.86 (7H, m), 8.21 (1H, s), 8.88 (1H, d, J=2.2 Hz), 10.19 (1H, s). melting point: 180–182° C. (crystallization solvent: ethyl acetate-isopropyl ether) FABMS(pos) 454 [M+H]+

Example 136

3-fluoro-N-[8-methyl-3-(1-pyrrolidinylmethyl)-7-quinolinyl]-4'-(trifluoromethoxy)[1,1'-biphenyl]-4-carboxamide

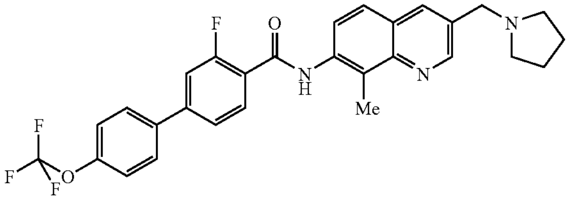

By operating in the same manner as in Example 50 and using 4-bromo-2-fluoro-N-[8-methyl-3-(1-pyrrolidinylmethyl)-7-quinolinyl]benzamide obtained in Example 133, the title compound was obtained.

$^1$H-NMR (DMSO-$d_6$) δ 1.73 (4H, m), 2.50 (4H, m), 2.70 (3H, s), 3.80 (2H, s), 7.52 (2H, d, J=8.4 Hz), 7.70–7.95 (7H, m), 8.21 (1H, s), 8.88 (1H, s), 10.23 (1H, s). melting point: 175–178° C. (crystallization solvent: ethyl acetate-isopropyl ether) FABMS(pos) 524 [M+H]+

Example 137

2',4'-dichloro-3-fluoro-N-[8-methyl-3-(1-pyrrolidinylmethyl)-7-quinolinyl][1,1'-biphenyl]-4-carboxamide

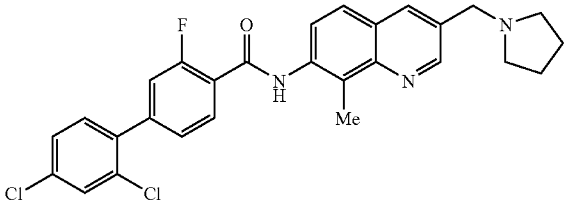

By operating in the same manner as in Example 50 and using 4-bromo-2-fluoro-N-[8-methyl-3-(1-pyrrolidinylmethyl)-7-quinolinyl]benzamide obtained in Example 133, the title compound was obtained.

$^1$H-NMR (DMSO-$d_6$) δ 1.72 (4H, m), 2.50 (4H, m), 2.71 (3H, s), 3.80 (2H, s), 7.43–7.91 (8H, m), 8.22 (1H, s), 8.89 (1H, s), 10.33 (1H, s). Elemental analysis for $C_{28}H_{24}Cl_2FN_3O.0.5H_2O$ Calculated: C, 65.00; H, 4.87; N, 8.12. Found: C, 65.08; H, 4.58; N, 7.78. melting point: 162–163° C. (crystallization solvent: ethyl acetate-isopropyl ether)

Example 138

3-fluoro-N-[8-methyl-3-(1-pyrrolidinylmethyl)-7-quinolinyl]-4'-(trifluoromethyl)[1,1'-biphenyl]-4-carboxamide

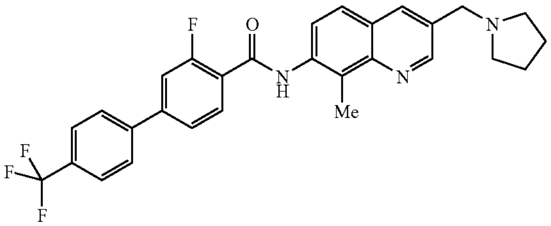

By operating in the same manner as in Example 50 and using 4-bromo-2-fluoro-N-[8-methyl-3-(1-pyrrolidinylmethyl)-7-quinolinyl]benzamide obtained in Example 133, the title compound was obtained.

$^1$H-NMR (DMSO-$d_6$) δ 1.73 (4H, m), 2.51 (4H, m), 2.71 (3H, s), 3.82 (2H, s), 7.77–8.06 (9H, m), 8.23 (1H, s), 8.90 (1H, s), 10.29 (1H, s). Elemental analysis for $C_{29}H_{25}F_4N_3O.H_2O$ Calculated: C, 66.28; H, 5.18; N, 8.00. Found: C, 66.24; H, 4.82; N, 7.98. melting point: 202–203° C. (crystallization solvent: ethyl acetate-isopropyl ether)

Example 139

2',3,4'-trifluoro-N-[8-methyl-3-(1-pyrrolidinylmethyl)-7-quinolinyl][1,1'-biphenyl]-4-carboxamide

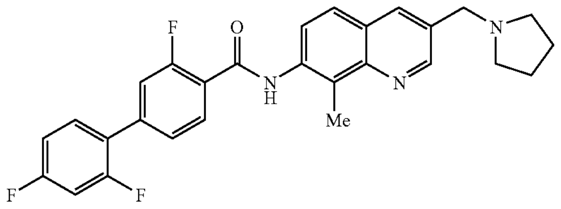

By operating in the same manner as in Example 50 and using 4-bromo-2-fluoro-N-[8-methyl-3-(1-pyrrolidinylmethyl)-7-quinolinyl]benzamide obtained in Example 133, the title compound was obtained.

$^1$H-NMR (DMSO-$d_6$) δ 1.73 (4H, m), 2.50 (4H, m), 2.71 (3H, s), 3.82 (2H, s), 7.23–7.93 (8H, m), 8.21 (1H, d, J=2.2 Hz), 8.88 (1H, d, J=1.8 Hz), 10.25 (1H, s). Elemental analysis for $C_{28}H_{24}F_3N_3O$ Calculated: C, 70.72; H, 5.09; N, 8.84. Found: C, 70.42; H, 4.93; N, 8.45. melting point: 172–173° C. (crystallization solvent: ethyl acetate-isopropyl ether)

Example 140

4'-ethyl-3-fluoro-N-[8-methyl-3-(1-pyrrolidinylmethyl)-7-quinolinyl][1,1'-biphenyl]-4-carboxamide

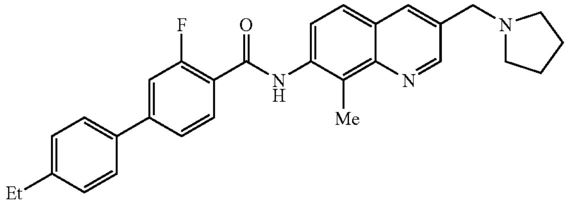

By operating in the same manner as in Example 50 and using 4-bromo-2-fluoro-N-[8-methyl-3-(1-pyrrolidinylmethyl)-7-quinolinyl]benzamide obtained in Example 133, the title compound was obtained.

$^1$H-NMR (DMSO-$d_6$) δ 1.23 (3H, t, J=7.8 Hz), 1.73 (4H, m), 2.50 (4H, m), 2.62 (2H, q, J=7.8 Hz), 2.71 (3H, s), 3.83 (2H, s), 7.35 (2H, d, J=8.0 Hz), 7.65–7.86 (7H, m), 8.21 (1H, s), 8.88 (1H, s), 10.15 (1H, s). Elemental analysis for $C_{30}H_{30}FN_3O$ Calculated: C, 70.06; H, 6.47; N, 8.99. Found: C, 76.78; H, 6.35; N, 8.71. melting point: 178–179° C. (crystallization solvent: ethyl acetate-isopropyl ether)

Example 141

4-(1,3-benzodioxol-5-yl)-2-fluoro-N-[8-methyl-3-(1-pyrrolidinylmethyl)-7-quinolinyl]benzamide

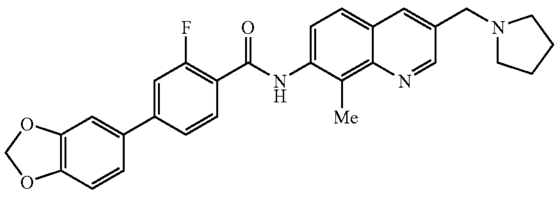

By operating in the same manner as in Example 50 and using 4-bromo-2-fluoro-N-[8-methyl-3-(1-pyrrolidinylmethyl)-7-quinolinyl]benzamide obtained in Example 133, the title compound was obtained.

$^1$H-NMR (DMSO-$d_6$) δ 1.73 (4H, m), 2.50 (4H, m), 2.70 (3H, s), 3.80 (2H, s), 6.11 (2H, s), 7.04–7.85 (8H, m), 8.22 (1H, s), 8.89 (1H, s), 10.18 (1H, s). Elemental analysis for $C_{29}H_{26}FN_3O_3.H_2O$ Calculated: C, 69.45; H, 5.63; N, 8.38. Found: C, 69.45; H, 5.39; N, 8.41. melting point: 181–182° C. (crystallization solvent: ethyl acetate-isopropyl ether)

Example 142

4-(1-benzofuran-2-yl)-2-fluoro-N-[8-methyl-3-(1-pyrrolidinylmethyl)-7-quinolinyl]benzamide

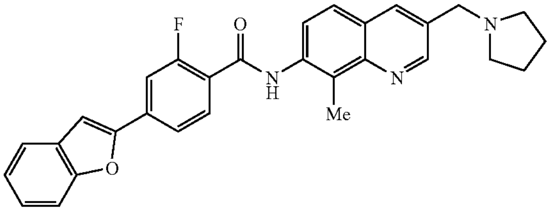

By operating in the same manner as in Example 50 and using 4-bromo-2-fluoro-N-[8-methyl-3-(1-pyrrolidinylmethyl)-7-quinolinyl]benzamide obtained in Example 133, the title compound was obtained.

$^1$H-NMR (DMSO-$d_6$) δ 1.73 (4H, m), 2.50 (4H, m), 2.71 (3H, s), 3.81 (2H, s), 7.31–7.98 (10H, m), 8.21 (1H, s), 8.89 (1H, s), 10.27 (1H, s). Elemental analysis for $C_{30}H_{26}FN_3O_2$ Calculated: C, 75.14; H, 5.46; N, 8.76. Found: C, 74.93; H, 5.28; N, 8.48. melting point: 202–203° C. (crystallization solvent: ethyl acetate-isopropyl ether)

Example 143

4-(5-chloro-2-thienyl)-2-fluoro-N-[8-methyl-3-(1-pyrrolidinylmethyl)-7-quinolinyl]benzamide

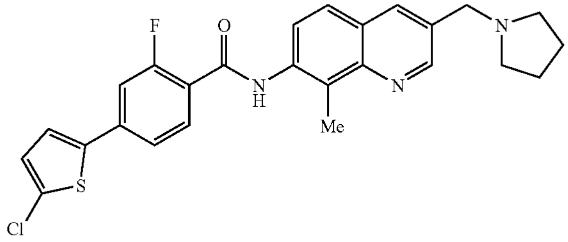

By operating in the same manner as in Example 50 and using 4-bromo-2-fluoro-N-[8-methyl-3-(1-pyrrolidinylmethyl)-7-quinolinyl]benzamide obtained in Example 133, the title compound was obtained.

$^1$H-NMR (DMSO-$d_6$) δ 1.72 (4H, m), 2.50 (4H, m), 2.69 (3H, s), 3.80 (2H, s), 7.26–7.82 (7H, m), 8.21 (1H, s), 8.89 (1H, s), 10.20 (1H, s). Elemental analysis for $C_{26}H_{23}ClFN_3OS.H_2O$ Calculated: C, 62.70; H, 5.06; N, 8.44. Found: C, 62.38; H, 4.71; N, 8.00. melting point: 160–162° C. (crystallization solvent: ethyl acetate-isopropyl ether)

Example 144

3-fluoro-N-[8-methyl-3-(1-pyrrolidinylmethyl)-7-quinolinyl]-4'-(methylsulfanyl)[1,1'-biphenyl]-4-carboxamide

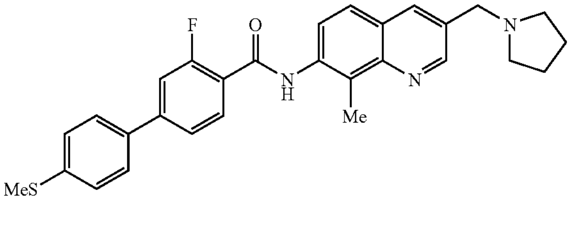

By operating in the same manner as in Example 50 and using 4-bromo-2-fluoro-N-[8-methyl-3-(1-pyrrolidinylmethyl)-7-quinolinyl]benzamide obtained in Example 133, the title compound was obtained.

$^1$H-NMR (DMSO-$d_6$) δ 1.72 (4H, m), 2.50 (4H, m), 2.54 (3H, s), 2.71 (3H, s), 3.79 (2H, s), 7.39 (2H, m), 7.68–7.87 (7H, m), 8.22 (1H, s), 8.89 (1H, s), 10.20 (1H, s). Elemental analysis for $C_{29}H_{28}FN_3OS$ Calculated: C, 71.73; H, 5.81; N, 8.65. Found: C, 71.49; H, 5.71; N, 8.31. melting point: 189–190° C. (crystallization solvent: ethyl acetate-isopropyl ether)

Example 145

3,4'-difluoro-N-[8-methyl-3-(1-pyrrolidinylmethyl)-7-quinolinyl][1,1'-biphenyl]-4-carboxamide

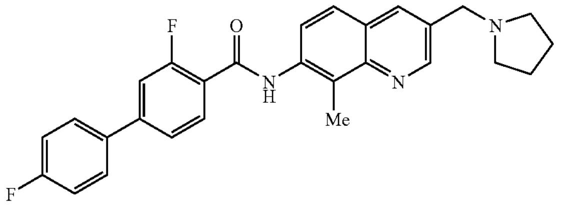

By operating in the same manner as in Example 50 and using 4-bromo-2-fluoro-N-[8-methyl-3-(1-pyrrolidinylmethyl)-7-quinolinyl]benzamide obtained in Example 133, the title compound was obtained.

$^1$H-NMR (DMSO-$d_6$) δ 1.72 (4H, m), 2.50 (4H, m), 2.70 (3H, s), 3.80 (2H, s), 7.36 (2H, m), 7.67–7.76 (3H, m), 7.82–7.89 (4H, m), 8.22 (1H, s), 8.88 (1H, d, J=1.5 Hz), 10.23 (1H, s). melting point: 176–178° C. (crystallization solvent: ethyl acetate-isopropyl ether) FABMS(pos) 458 [M+H]+

Example 146

4'-chloro-3-fluoro-N-[8-methyl-3-(1-pyrrolidinylmethyl)-7-quinolinyl][1,1'-biphenyl]-4-carboxamide

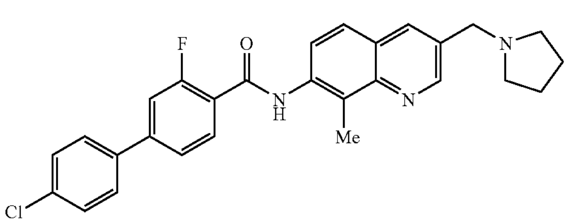

By operating in the same manner as in Example 50 and using 4-bromo-2-fluoro-N-[8-methyl-3-(1-pyrrolidinylmethyl)-7-quinolinyl]benzamide obtained in Example 133, the title compound was obtained.

$^1$H-NMR (DMSO-$d_6$) δ 1.72 (4H, m), 2.50 (4H, m), 2.70 (3H, s), 3.80 (2H, s), 7.58 (2H, d, J=8.4 Hz), 7.69–7.88 (7H, m), 8.21 (1H, s), 8.88 (1H, d, J=1.8 Hz), 10.23 (1H, s). melting point: 181–183° C. (crystallization solvent: ethyl acetate-isopropyl ether) FABMS(pos) 474 [M+H]+

Example 147

3-fluoro-4'-methoxy-N-[8-methyl-3-(1-pyrrolidinyl-methyl)-7-quinolinyl][1,1'-biphenyl]-4-carboxamide

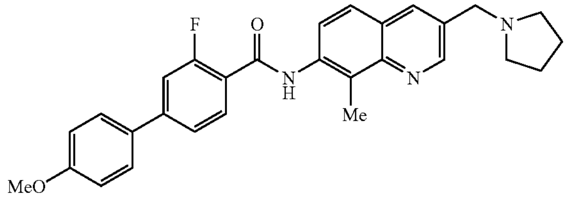

By operating in the same manner as in Example 50 and using 4-bromo-2-fluoro-N-[8-methyl-3-(1-pyrrolidinylm-ethyl)-7-quinolinyl]benzamide obtained in Example 133, the title compound was obtained.

$^1$H-NMR (DMSO-$d_6$) δ 1.73 (4H, m), 2.50 (4H, m), 2.70 (3H, s), 3.80 (2H, s), 3.83 (3H, s), 7.07 (2H, d, J=9.0 Hz), 7.64–7.84 (7H, m), 8.21 (1H, s), 8.88 (1H, d, J=1.8 Hz), 10.17 (1H, s). melting point: 164–166° C. (crystallization solvent: ethyl acetate-isopropyl ether) FABMS(pos) 470 [M+H]+

Example 148

2',3-difluoro-N-[8-methyl-3-(1-pyrrolidinylmethyl)-7-quinolinyl][1,1'-biphenyl]-4-carboxamide

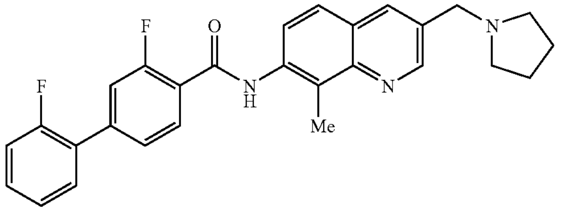

By operating in the same manner as in Example 50 and using 4-bromo-2-fluoro-N-[8-methyl-3-(1-pyrrolidinylm-ethyl)-7-quinolinyl]benzamide obtained in Example 133, the title compound was obtained.

$^1$H-NMR (DMSO-$d_6$) δ 1.72 (4H, m), 2.50 (4H, m), 2.71 (3H, s), 3.80 (2H, s), 7.35–7.42 (2H, m), 7.49–7.68 (4H, m), 7.74 (1H, d, J=9.3 Hz), 7.83–7.92 (2H, m), 8.21 (1H, s), 8.88 (1H, d, J=1.8 Hz), 10.28 (1H, s). melting point: 159–160° C. (crystallization solvent: ethyl acetate-isopropyl ether) FABMS(pos) 458 [M+H]+

Example 149

3-fluoro-N-[8-methyl-3-(1-pyrrolidinylmethyl)-7-quinolinyl][1,1'-biphenyl]-4-carboxamide

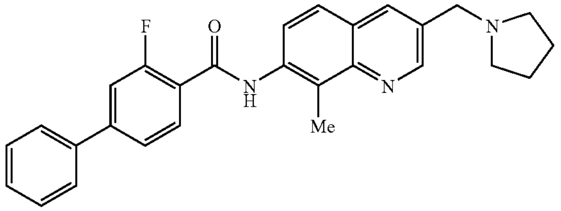

By operating in the same manner as in Example 50 and using 4-bromo-2-fluoro-N-[8-methyl-3-(1-pyrrolidinylm-ethyl)-7-quinolinyl]benzamide obtained in Example 133, the title compound was obtained.

$^1$H-NMR (DMSO-$d_6$) δ 1.72 (4H, m) 2.50 (4H, m), 2.71 (3H, s), 3.80 (2H, s), 7.46–7.55 (3H, m), 7.69–7.88 (7H, m), 8.21 (1H, s), 8.88 (1H, s), 10.23 (1H, s). melting point: 166–168° C. (crystallization solvent: ethyl acetate-isopropyl ether) FABMS(pos) 440 [M+H]+

Example 150

4-bromo-3-fluoro-N-[8-methyl-3-(1-pyrrolidinylm-ethyl)-7-quinolinyl]benzamide

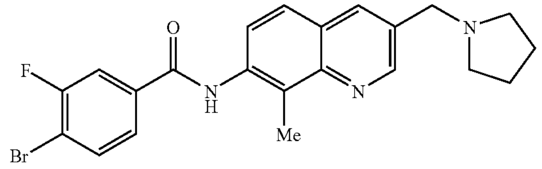

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H NMR (DMSO-$d_6$) δ 1.72 (4H, m), 2.50 (4H, m), 2.64 (3H, s), 3.81 (2H, s), 7.58 (1H, d, J=8.8 Hz), 7.81–8.03 (4H, m), 8.23 (1H, s), 8.89 (1H, d, J=2.2 Hz), 10.38 (1H, s).

Example 151

2-fluoro-N-[8-methyl-3-(1-pyrrolidinylmethyl)-7-quinolinyl][1,1'-biphenyl]-4-carboxamide

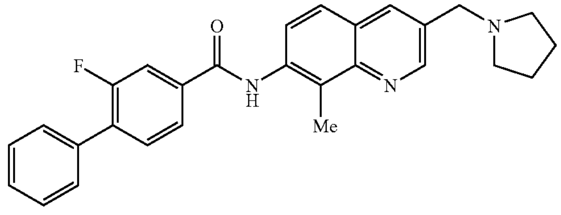

By operating in the same manner as in Example 50 and using 4-bromo-3-fluoro-N-[8-methyl-3-(1-pyrrolidinylm-ethyl)-7-quinolinyl]benzamide obtained in Example 150, the title compound was obtained.

$^1$H-NMR (DMSO-$d_6$) δ 1.73 (4H, m), 2.50 (4H, m), 2.67 (3H, s), 3.81 (2H, s), 7.47–7.66 (6H, m), 7.75 (1H, m), 7.84 (1H, d, J=9.0 Hz), 8.00 (2H, m), 8.23 (1H, s), 8.89 (1H, d, J=2.1 Hz), 10.38 (1H, s). melting point: 156–158° C. (crystallization solvent: ethyl acetate-isopropyl ether) FABMS (pos) 440 [M+H]+

Example 152

2-fluoro-4'-methoxy-N-[8-methyl-3-(1-pyrrolidinyl-methyl)-7-quinolinyl][1,1'-biphenyl]-4-carboxamide

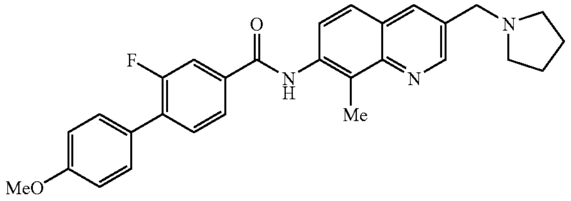

By operating in the same manner as in Example 50 and using 4-bromo-3-fluoro-N-[8-methyl-3-(1-pyrrolidinylm-ethyl)-7-quinolinyl]benzamide obtained in Example 150, the title compound was obtained.

$^1$H-NMR (DMSO-$d_6$) δ 1.76 (4H, m), 2.50 (4H, m), 2.66 (3H, s), 3.83 (5H, m), 7.10 (2H, d, J=8.7 Hz), 7.58–7.64 (3H, m), 7.71 (1H, m), 7.85 (1H, d, J=8.7 Hz), 7.95 (2H, m), 8.28 (1H, s), 8.92 (1H, s), 10.36 (1H, s). melting point: 174–176° C. (crystallization solvent: ethyl acetate-isopropyl ether) FABMS(pos) 470 [M+H]+

Example 153

2,4'-difluoro-N-[8-methyl-3-(1-pyrrolidinylmethyl)-7-quinolinyl][1,1'-biphenyl]-4-carboxamide

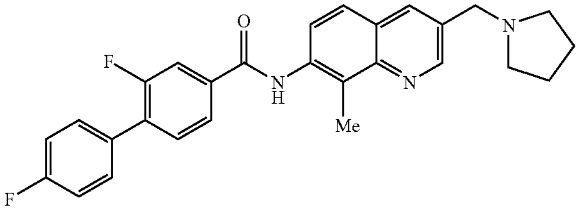

By operating in the same manner as in Example 50 and using 4-bromo-3-fluoro-N-[8-methyl-3-(1-pyrrolidinylm-ethyl)-7-quinolinyl]benzamide obtained in Example 150, the title compound was obtained.

$^1$H-NMR (DMSO-$d_6$) δ 1.73 (4H, m), 2.50 (4H, m), 2.66 (3H, s), 3.82 (2H, s), 7.38 (2H, m), 7.60–7.63 (1H, m), 7.68–7.79 (3H, m), 7.84 (1H, d, J=9.0 Hz), 8.24 (1H, s), 8.89 (1H, s), 10.38 (1H, s). melting point: 176–178° C. (crystallization solvent: ethyl acetate-isopropyl ether) FABMS(pos) 458 [M+H]+

Example 154

4'-chloro-2-fluoro-N-[8-methyl-3-(1-pyrrolidinylm-ethyl)-7-quinolinyl][1,1'-biphenyl]-4-carboxamide

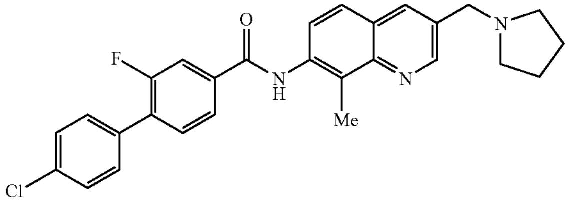

By operating in the same manner as in Example 50 and using 4-bromo-3-fluoro-N-[8-methyl-3-(1-pyrrolidinylm-ethyl)-7-quinolinyl]benzamide obtained in Example 150, the title compound was obtained.

$^1$H-NMR (DMSO-$d_6$) δ 1.73 (4H, m), 2.50 (4H, m), 2.66 (3H, s), 3.81 (2H, s), 7.59–7.83 (6H, m), 7.84 (1H, d, J=9.3 Hz), 8.00 (2H, m), 8.24 (1H, s), 8.90 (1H, s), 10.39 (1H, s). melting point: 190–192° C. (crystallization solvent: ethyl acetate-isopropyl ether) FABMS(pos) 474 [M+H]+

Example 155

2-fluoro-4'-methyl-N-[8-methyl-3-(1-pyrrolidinylm-ethyl)-7-quinolinyl][1,1'-biphenyl]-4-carboxamide

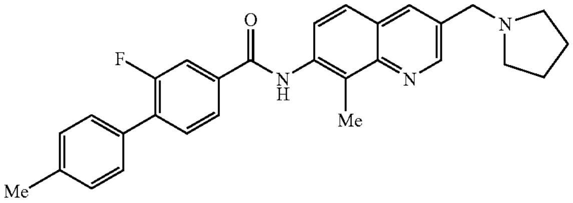

By operating in the same manner as in Example 50 and using 4-bromo-3-fluoro-N-[8-methyl-3-(1-pyrrolidinylm-ethyl)-7-quinolinyl]benzamide obtained in Example 150, the title compound was obtained.

$^1$H-NMR (DMSO-$d_6$) δ 1.73 (4H, m), 2.38 (3H, s), 2.50 (4H, m), 2.66 (3H, s), 3.81 (2H, s), 7.34 (2H, d, J=8.4 Hz), 7.54 (2H, d, J=7.2 Hz), 7.61 (1H, d, J=8.4 Hz), 7.72 (1H, m), 7.84 (1H, d, J=9.0 Hz), 7.97 (2H, m), 8.23 (1H, s), 8.89 (1H, d, J=2.1 Hz), 10.36 (1H, s). melting point: 193–194° C. (crystallization solvent: ethyl acetate-isopropyl ether) FABMS(pos) 454 [M+H]+

Example 156

2,2'-difluoro-N-[8-methyl-3-(1-pyrrolidinylmethyl)-7-quinolinyl][1,1'-biphenyl]-4-carboxamide

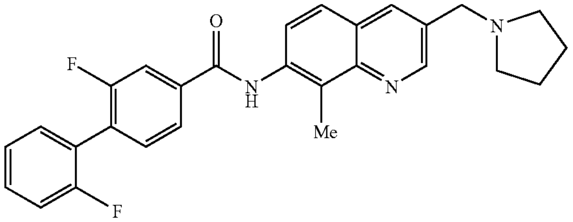

By operating in the same manner as in Example 50 and using 4-bromo-3-fluoro-N-[8-methyl-3-(1-pyrrolidinylm-ethyl)-7-quinolinyl]benzamide obtained in Example 150, the title compound was obtained.

$^1$H-NMR (DMSO-$d_6$) δ 1.73 (4H, m), 2.50 (4H, m), 2.67 (3H, s), 3.80 (2H, s), 7.39 (2H, m), 7.53–7.71 (4H, m), 7.85 (1H, d, J=9.0 Hz), 7.99 (2H, m), 8.23 (1H, s), 8.89 (1H, d, J=2.1 Hz), 10.40 (1H, s). melting point: 139–140° C. (crystallization solvent: ethyl acetate-isopropyl ether) FABMS (pos) 458 [M+H]+

Example 157

4-bromo-2-methyl-N-[8-methyl-3-(1-pyrrolidinylmethyl)-7-quinolinyl]benzamide

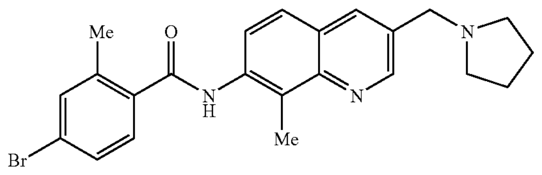

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H-NMR (DMSO-$d_6$) δ 1.73 (4H, m), 2.47 (3H, s), 2.50 (4H, m), 2.68 (3H, s), 3.79 (2H, s), 7.54–7.58 (3H, m), 7.65 (1H, d, J=9.0 Hz), 7.81 (1H, d, J=8.7 Hz), 8.19 (1H, d, J=2.1 Hz), 8.86 (1H, d, J=2.4 Hz), 10.17 (1H, s)

Example 158

4'-fluoro-3-methyl-N-[8-methyl-3-(1-pyrrolidinylmethyl)-7-quinolinyl][1,1'-biphenyl]-4-carboxamide

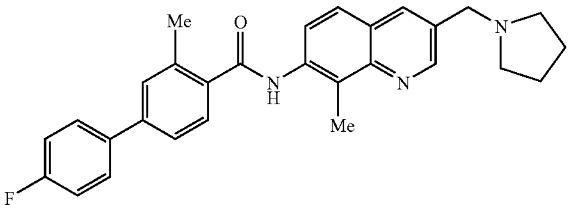

By operating in the same manner as in Example 50 and using 4-bromo-2-methyl-N-[8-methyl-3-(1-pyrrolidinylmethyl)-7-quinolinyl]benzamide obtained in Example 157, the title compound was obtained.

$^1$H-NMR (DMSO-$d_6$) δ 1.73 (4H, m), 2.50 (4H, m), 2.55 (3H, s), 2.70 (3H, s), 3.80 (2H, s), 7.33 (2H, m), 7.64 (4H, m), 7.79 (3H, m), 8.21 (1H, s), 8.88 (1H, d, J=1.8 Hz), 10.18 (1H, s). melting point: 200–203° C. (crystallization solvent: ethyl acetate-isopropyl ether) FABMS(pos) 454 [M+H]+

Example 159

4-bromo-3-methyl-N-[8-methyl-3-(1-pyrrolidinylmethyl)-7-quinolinyl]benzamide

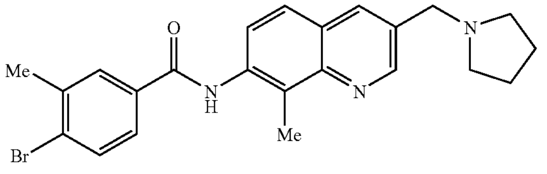

By successively operating in the same manner as in Reference Example 4 and Example 1 and using N-[8-methyl-3-(1-pyrrolidinylmethyl)-7-quinolinyl]acetamide obtained in Reference Example 7, the title compound was obtained.

$^1$H-NMR (DMSO-$d_6$) δ 1.72 (4H, m), 2.46 (3H, s), 2.50 (4H, m), 2.64 (3H, s), 3.79 (2H, s), 7.57 (1H, d, J=8.7 Hz), 7.77–7.82 (3H, m), 8.01 (1H, s), 8.20 (1H, d, J=1.8 Hz), 8.87 (1H, d, J=2.1 Hz), 10.25 (1H, s).

Example 160

4'-fluoro-2-methyl-N-[8-methyl-3-(1-pyrrolidinylmethyl)-7-quinolinyl][1,1'-biphenyl]-4-carboxamide

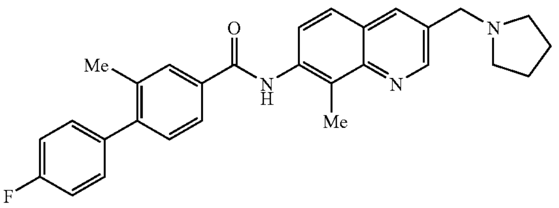

By operating in the same manner as in Example 50 and using 4-bromo-2-methyl-N-[8-methyl-3-(1-pyrrolidinylmethyl)-7-quinolinyl]benzamide obtained in Example 159, the title compound was obtained.

$^1$H-NMR (DMSO-$d_6$) δ 1.73 (4H, m), 2.33 (3H, s), 2.50 (4H, m), 2.66 (3H, s), 3.81 (2H, s), 7.32 (2H, m), 7.38 (1H, d, J=8.4 Hz), 7.46 (2H, m), 7.61 (1H, d, J=9.0 Hz), 7.82 (1H, d, J=8.7 Hz), 7.93 (1H, d, J=7.8 Hz), 7.99 (1H, s), 8.22 (1H, s), 8.88 (1H, d, J=2.1 Hz), 10.25 (1H, s). melting point: 200–202° C. (crystallization solvent: ethyl acetate-isopropyl ether) FABMS(pos) 454 [M+H]+

Example 161

4-(benzyloxy)-N-[8-methyl-3-(1-piperidinylmethyl)-7-quinolinyl]benzamide

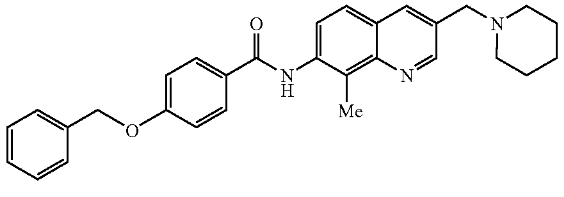

By operating in the same manner as in Example 1 and using 8-methyl-3-(1-piperidinylmethyl)-7-quinolinylamine obtained in Reference Example 50, the title compound was obtained.

$^1$H-NMR (DMSO-$d_6$) δ 1.51 (6H, m), 2.39 (4H, m), 2.64 (3H, s), 3.64 (2H, s), 5.23 (2H, s), 7.16–8.17 (12H, m), 8.86 (1H, s), 10.07 (1H, s). melting point: 186–187° C. (crystallization solvent: ethyl acetate-isopropyl ether) FABMS(pos) 466 [M+H]+

Example 162

4-[(4-fluorobenzyl)oxy]-N-[8-methyl-3-(1-piperidinylmethyl)-7-quinolinyl]benzamide

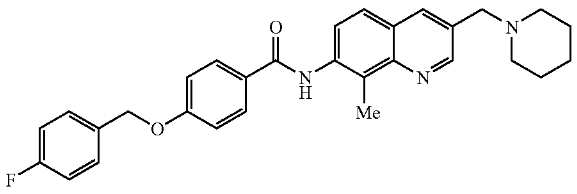

By operating in the same manner as in Example 1 and using 8-methyl-3-(1-piperidinylmethyl)-7-quinolinylamine obtained in Reference Example 50, the title compound was obtained.

$^1$H-NMR (DMSO-$d_6$) δ 1.53 (6H, m), 2.41 (4H, m), 2.64 (3H, s), 3.68 (2H, s), 5.21 (2H, s), 7.12–8.19 (1H, m), 8.87 (1H, s), 10.08 (1H, s). melting point: 159–160° C. (crystallization solvent: ethyl acetate-isopropyl ether) FABMS(pos) 484 [M+H]+

Example 163

4-(benzyloxy)-2-fluoro-N-[8-methyl-3-(1-piperidinylmethyl)-7-quinolinyl]benzamide

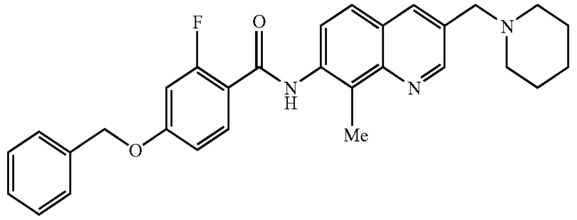

By operating in the same manner as in Example 1 and using 8-methyl-3-(1-piperidinylmethyl)-7-quinolinylamine obtained in Reference Example 50, the title compound was obtained.

$^1$H-NMR ($CDCl_3$) δ 1.46 (2H, m), 1.59 (4H, m), 2.44 (4H, m), 2.82 (3H, s), 3.66 (2H, s), 5.15 (2H, s), 6.76–6.96 (2H, m), 7.42 (5H, m), 7.69 (1H, d, J=9.2 Hz), 8.02 (1H, s), 8.20 (1H, t, J=9.4 Hz), 8.36 (1H, d, J=9.2 Hz), 8.59–8.67 (1H, m), 8.88 (1H, s). melting point: 180–181° C. (crystallization solvent: ethyl acetate-isopropyl ether)

Example 164

4-bromo-N-[8-methyl-3-(1-piperidinylmethyl)-7-quinolinyl]benzamide

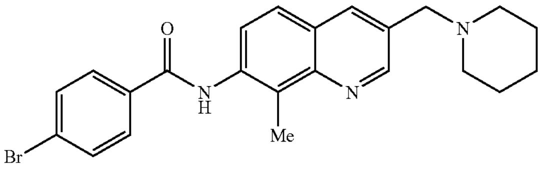

By operating in the same manner as in Reference Example 3 and using 4-bromo-N-[3-(chloromethyl)-8-methyl-7-quinolinyl]benzamide hydrochloride obtained in Reference Example 49, the title compound was obtained.

$^1$H-NMR (DMSO-$d_6$) δ 1.59 (6H, m), 2.65 (7H, m), 3.84 (2H, s), 7.59 (1H, d, J=9.2 Hz), 7.80 (3H, s), 8.00 (2H, d, J=8.4 Hz), 8.21 (1H, m), 8.91 (1H, d, J=1.8 Hz), 10.32 (1H, s).

Example 165

4'-methoxy-N-[8-methyl-3-(1-pyrrolidinylmethyl)-7-quinolinyl][1,1'-biphenyl]-4-carboxamide

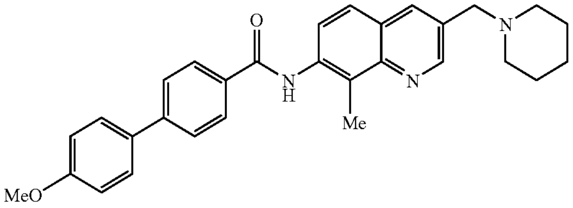

By operating in the same manner as in Example 50 and using 4-bromo-N-[8-methyl-3-(1-piperidinylmethyl)-7-quinolinyl]benzamide obtained in Example 164, the title compound was obtained.

$^1$H-NMR (DMSO-$d_6$) δ 1.42–1.52 (6H, m), 2.40 (4H, s), 2.66 (3H, s), 3.65 (2H, s), 3.82 (3H, s), 7.07 (2H, d, J=8.8 Hz), 7.62 (1H, d, J=8.8 Hz), 7.73 (2H, d, J=8.8 Hz), 7.82 (3H, m), 8.11 (2H, d, J=8.4 Hz), 8.19 (1H, s), 8.87 (1H, d, J=2.2 Hz), 10.25 (1H, s). melting point: 190–192° C. (crystallization solvent: ethyl acetate-isopropyl ether) FABMS (pos) 466 [M+H]+

Example 166

4'-fluoro-N-[8-methyl-3-(1-piperidinylmethyl)-7-quinolinyl][1,1'-biphenyl]-4-carboxamide

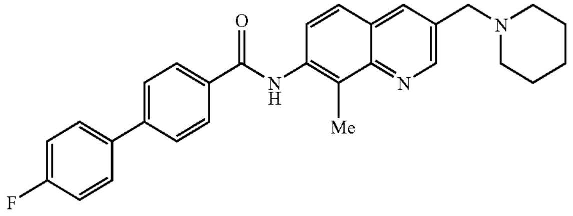

By operating in the same manner as in Example 50 and using 4-bromo-N-[8-methyl-3-(1-piperidinylmethyl)-7-quinolinyl]benzamide obtained in Example 164, the title compound was obtained.

$^1$H-NMR (DMSO-$d_6$) δ 1.41 (2H, m), 1.52 (4H, m), 2.40 (4H, m), 2.67 (3H, s), 3.66 (2H, s), 7.36 (2H, m), 7.62 (1H, d, J=8.4 Hz), 7.84 (5H, m), 8.14 (2H, d, J=8.1 Hz), 8.19 (1H, s), 8.87 (1H, d, J=1.2 Hz), 10.29 (1H, s). melting point: 188–190° C. (crystallization solvent: ethyl acetate-isopropyl ether) FABMS(pos) 454 [M+H]+

Example 167

4-(5-chloro-2-thienyl)-N-[8-methyl-3-(1-piperidinylmethyl)-7-quinolinyl]benzamide

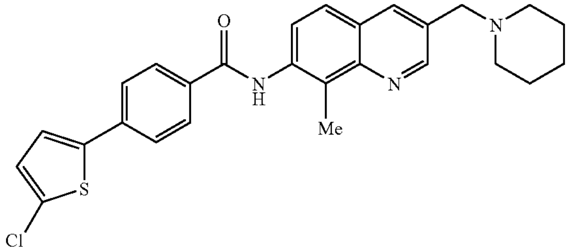

By operating in the same manner as in Example 50 and using 4-bromo-N-[8-methyl-3-(1-piperidinylmethyl)-7-quinolinyl]benzamide obtained in Example 164, the title compound was obtained.

$^1$H-NMR (DMSO-$d_6$) δ 1.41–1.52 (6H, m), 2.40 (4H, m), 2.66 (3H, s), 3.66 (2H, s), 7.25 (1H, m), 7.60–7.84 (5H, m), 8.09–8.20 (3H, m), 8.87 (1H, s), 10.29 (1H, s). Elemental analysis for $C_{27}H_{26}ClN_3OS$ Calculated: C, 68.12; H, 5.51; N, 8.83. Found: C, 67.92; H, 5.42; N, 8.52. melting point: 212–213° C. (crystallization solvent: ethyl acetate-isopropyl ether)

Example 168

4-bromo-2-fluoro-N-[8-methyl-3-(1-piperidinylmethyl)-7-quinolinyl]benzamide

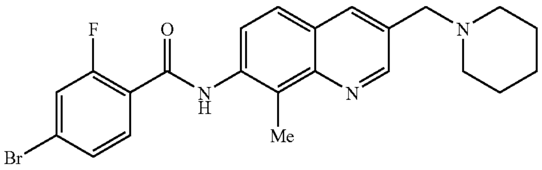

By operating in the same manner as in Example 1 and using 8-methyl-3-(1-piperidinylmethyl)-7-quinolinylamine obtained in Reference Example 50, the title compound was obtained.

$^1$H-NMR (DMSO-$d_6$) δ 1.51 (6H, m), 2.39 (4H, m), 2.67 (3H, s), 3.66 (2H, s), 7.56–7.85 (5H, m), 8.17 (1H, s), 8.86 (1H, d, J=1.8 Hz), 10.26 (1H, s).

Example 169

3-fluoro-N-[8-methyl-3-(1-piperidinylmethyl)-7-quinolinyl][1,1'-biphenyl]-4-carboxamide

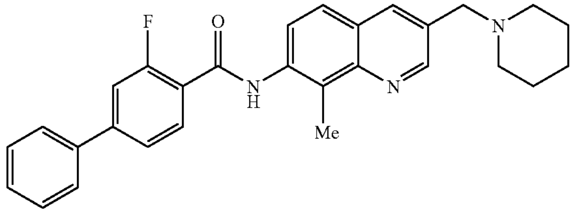

By operating in the same manner as in Example 50 and using 4-bromo-2-fluoro-N-[8-methyl-3-(1-piperidinylmethyl)-7-quinolinyl]benzamide obtained in Example 168, the title compound was obtained.

$^1$H-NMR (DMSO-$d_6$) δ 1.52 (6H, m), 2.39 (4H, m), 2.71 (3H, s), 3.66 (2H, s), 7.45–7.88 (10H, m), 8.17 (1H, s), 8.87 (1H, d, J=2.2 Hz), 10.19 (1H, s). Elemental analysis for $C_{29}H_{28}FN_3O.0.5H_2O$ Calculated: C, 75.30; H, 6.32; N, 9.08. Found: C, 75.60; H, 6.17; N, 9.23. melting point: 187–188° C. (crystallization solvent: ethyl acetate-isopropyl ether)

Example 170

3,4'-difluoro-N-[8-methyl-3-(1-piperidinylmethyl)-7-quinolinyl][1,1'-biphenyl]-4-carboxamide

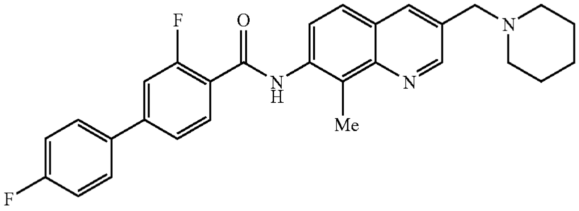

By operating in the same manner as in Example 50 and using 4-bromo-2-fluoro-N-[8-methyl-3-(1-piperidinylmethyl)-7-quinolinyl]benzamide obtained in Example 168, the title compound was obtained.

$^1$H-NMR (DMSO-$d_6$) δ 1.52 (6H, m), 2.39 (4H, m), 2.71 (3H, s), 3.65 (2H, s), 7.31–7.90 (9H, m), 8.18 (1H, s), 8.86(1H, s), 10.20 (1H, s). Elemental analysis for $C_{29}H_{27}F_2N_3O$ Calculated: C, 73.87; H, 5.77; N, 8.91. Found: C, 73.65; H, 5.72; N, 8.88. melting point: 186–187° C. (crystallization solvent: ethyl acetate-isopropyl ether)

Example 171

3-fluoro-4'-methoxy-N-[8-methyl-3-(1-piperidinylmethyl)-7-quinolinyl][1,1'-biphenyl]-4-carboxamide

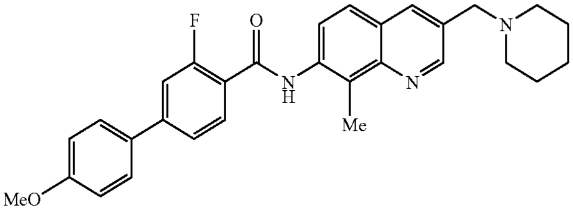

By operating in the same manner as in Example 50 and using 4-bromo-2-fluoro-N-[8-methyl-3-(1-piperidinylmethyl)-7-quinolinyl]benzamide obtained in Example 168, the title compound was obtained.

$^1$H-NMR (DMSO-$d_6$) δ 1.52 (6H, m), 2.39 (4H, m), 2.70 (3H, s), 3.65 (2H, s), 3.83 (3H, s), 7.07 (2H, d, J=8.8 Hz), 7.62–7.84 (7H, m), 8.18 (1H, s), 8.86(1H, s), 10.15 (1H, s). Elemental analysis for $C_{30}H_{30}FN_3O_2$ Calculated: C, 74.51; H, 6.25; N, 8.69. Found: C, 74.31; H, 6.37; N, 8.61. melting point: 191–192° C. (crystallization solvent: ethyl acetate-isopropyl ether)

Example 172

4-(5-chloro-2-thienyl)-2-fluoro-N-[8-methyl-3-(1-piperidinylmethyl)-7-quinolinyl]benzamide

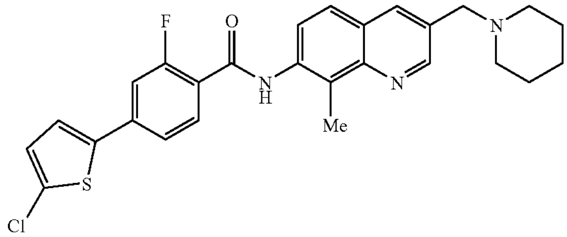

By operating in the same manner as in Example 50 and using 4-bromo-2-fluoro-N-[8-methyl-3-(1-piperidinylmethyl)-7-quinolinyl]benzamide obtained in Example 168, the title compound was obtained.

$^1$H-NMR (DMSO-$d_6$) δ 1.51 (6H, m), 2.39–2.50 (4H, m), 2.69 (3H, s), 3.66 (2H, s), 7.25–7.81 (7H, m), 8.18 (1H, s), 8.87(1H, s), 10.20 (1H, s). Elemental analysis for $C_{27}H_{25}ClFN_3OS.0.5H_2O$ Calculated: C, 64.47; H, 5.21; N, 8.35. Found: C, 64.85; H, 5.04; N, 8.17. melting point: 205–206° C. (crystallization solvent: ethyl acetate-isopropyl ether)

Example 173

4-(2,3-dihydro-1-benzofuran-5-yl)-2-fluoro-N-[8-methyl-3-(1-piperidinylmethyl)-7-quinolinyl]benzamide

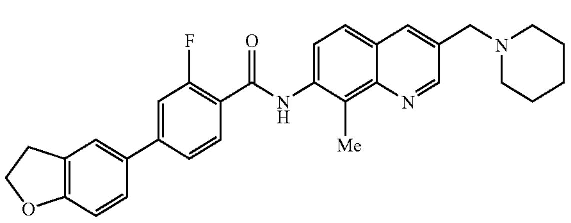

By operating in the same manner as in Example 50 and using 4-bromo-2-fluoro-N-[8-methyl-3-(1-piperidinylmethyl)-7-quinolinyl]benzamide obtained in Example 168, the title compound was obtained.

$^1$H-NMR (DMSO-$d_6$) δ 1.41–1.52 (6H, m), 2.39–2.50 (4H, m), 2.70 (3H, s), 3.29 (2H, t, J=8.4 Hz), 3.65 (2H, s), 4.60 (2H, t, J=8.4 Hz), 6.88 (1H, d, J=8.4 Hz), 7.53–7.83 (7H, m), 8.17 (1H, s), 8.86 (1H, s), 10.12 (1H, s). melting point: 202–203° C. (crystallization solvent: ethyl acetate-isopropyl ether)

Example 174

4-bromo-3-fluoro-N-[8-methyl-3-(1-piperidinylmethyl)-7-quinolinyl]benzamide

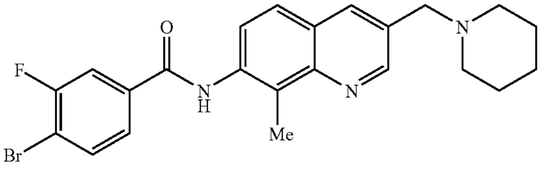

By operating in the same manner as in Example 1 and using 8-methyl-3-(1-piperidinylmethyl)-7-quinolinylamine obtained in Reference Example 50, the title compound was obtained.

$^1$H-NMR (DMSO-$d_6$) δ 1.42 (2H, m), 1.52 (4H, m), 2.39 (4H, m), 2.69 (3H, s), 3.83 (2H, s), 7.56–8.03 (5H, m), 8.20 (1H, m), 8.91 (1H, m), 10.36 (1H, s).

Example 175

2-fluoro-N-[8-methyl-3-(1-piperidinylmethyl)-7-quinolinyl][1,1'-biphenyl]-4-carboxamide

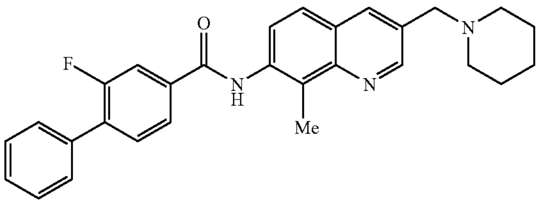

By operating in the same manner as in Example 50 and using 4-bromo-3-fluoro-N-[8-methyl-3-(1-piperidinylmethyl)-7-quinolinyl]benzamide obtained in Example 174, the title compound was obtained.

$^1$H-NMR (DMSO-$d_6$) δ 1.51 (6H, m), 2.40 (4H, m), 2.67 (3H, s), 3.67 (2H, s), 7.30–8.20 (11H, m), 8.87 (1H, s), 10.37 (1H, s). Elemental analysis for $C_{29}H_{28}FN_3O.H_2O$ Calculated: C, 73.86; H, 6.41; N, 8.91. Found: C, 73.95; H, 6.02; N, 8.51. melting point: 138–139° C. (crystallization solvent: ethyl acetate-isopropyl ether)

Example 176

2,4'-difluoro-N-[8-methyl-3-(1-piperidinylmethyl)-7-quinolinyl][1,1'-biphenyl]-4-carboxamide

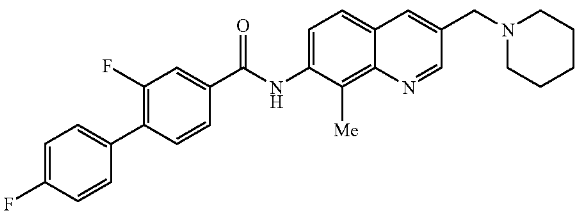

By operating in the same manner as in Example 50 and using 4-bromo-3-fluoro-N-[8-methyl-3-(1-piperidinylmethyl)-7-quinolinyl]benzamide obtained in Example 174, the title compound was obtained.

$^1$H-NMR (DMSO-$d_6$) δ 1.52 (6H, m), 2.39 (4H, m), 2.67 (3H, s), 3.65 (2H, s), 7.30–8.20 (10H, m), 8.88 (1H, s), 10.37 (1H, s). Elemental analysis for $C_{29}H_{27}F_2N_3O.H_2O$ Calculated: C, 71.15; H, 5.97; N, 8.58. Found: C, 70.77; H, 6.02; N, 8.41. melting point: 161–162° C. (crystallization solvent: ethyl acetate-isopropyl ether)

Example 177

2-fluoro-4'-methoxy-N-[8-methyl-3-(1-piperidinylmethyl)-7-quinolinyl][1,1'-biphenyl]-4-carboxamide

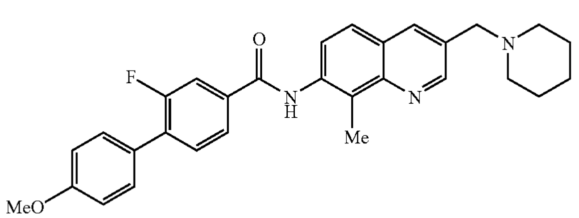

By operating in the same manner as in Example 50 and using 4-bromo-3-fluoro-N-[8-methyl-3-(1-piperidinylmethyl)-7-quinolinyl]benzamide obtained in Example 174, the title compound was obtained.

$^1$H-NMR (DMSO-$d_6$) δ 1.52 (6H, m), 2.40 (4H, m), 2.67 (3H, s), 3.66 (2H, s), 3.83 (3H, s), 7.08–8.20 (10H, m), 8.87 (1H, s), 10.37 (1H, s). melting point: 148–149° C. (crystallization solvent: ethyl acetate-isopropyl ether)

Example 178

N-[3-(1-azepanylmethyl)-8-methyl-7-quinolinyl]-4-bromobenzamide

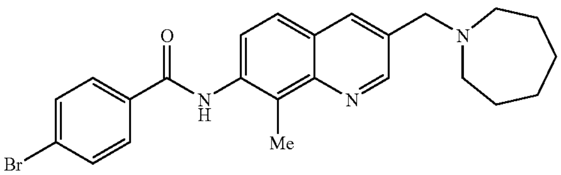

By operating in the same manner as in Example 1 and using 3-(1-azepanylmethyl)-8-methyl-7-quinolinylamine obtained in Reference Example 51, the title compound was obtained.

$^1$H-NMR (DMSO-$d_6$) δ 1.59 (8H, m), 2.66 (11H, m), 3.83 (2H, s), 7.59 (1H, d, J=9.2 Hz), 7.80 (3H, s), 8.00 (2H, d, J=8.4 Hz), 8.21 (1H, m), 8.91 (1H, d, J=1.8 Hz), 10.32 (1H, s).

Example 179

N-[3-(1-azepanylmethyl)-8-methyl-7-quinolinyl]-4'-methoxy[1,1'-biphenyl]-4-carboxamide

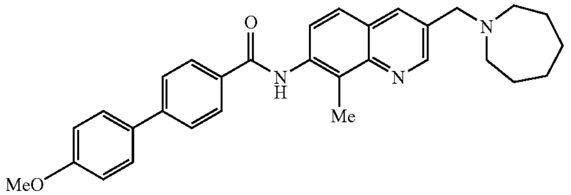

By operating in the same manner as in Example 50 and using N-[3-(1-azepanylmethyl)-8-methyl-7-quinolinyl]-4-bromobenzamide obtained in Example 178, the title compound was obtained.

$^1$H-NMR (DMSO-$d_6$) δ 1.59 (8H, m), 2.67 (7H, m), 3.82 (5H, m), 7.07 (2H, d, J=8.8 Hz), 7.62 (1H, d, J=8.8 Hz), 7.74 (2H, d, J=8.8 Hz), 7.81 (3H, m), 8.12 (2H, d, J=8.8 Hz), 8.19 (1H, d, J=1.8 Hz), 8.91 (1H, d, J=2.2 Hz), 10.25 (1H, s). melting point: 165–167° C. (crystallization solvent: ethyl acetate-isopropyl ether) FABMS(pos) 480 [M+H]+

Example 180

N-[3-(1-azepanylmethyl)-8-methyl-7-quinolinyl]-4'-fluoro[1,1'-biphenyl]-4-carboxamide

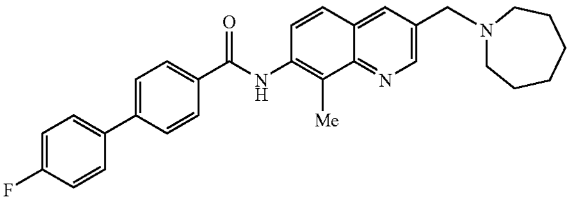

By operating in the same manner as in Example 50 and using N-[3-(1-azepanylmethyl)-8-methyl-7-quinolinyl]-4-bromobenzamide obtained in Example 178, the title compound was obtained.

$^1$H-NMR (DMSO-$d_6$) δ 1.59 (8H, m), 2.64–2.67 (7H, m), 3.83 (2H, s), 7.36 (2H, m), 7.62 (1H, d, J=8.7 Hz), 7.84 (5H, m), 8.14 (2H, d, J=8.4 Hz), 8.21 (1H, s), 8.90 (1H, d, J=1.5 Hz), 10.29 (1H, s). melting point: 166–168° C. (crystallization solvent: ethyl acetate-isopropyl ether) FABMS(pos) 468 [M+H]+

Example 181

N-[3-(1-azepanylmethyl)-8-methyl-7-quinolinyl]-4-(5-chloro-2-thienyl)benzamide

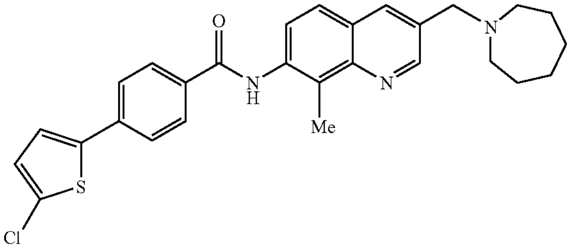

By operating in the same manner as in Example 50 and using N-[3-(1-azepanylmethyl)-8-methyl-7-quinolinyl]-4-bromobenzamide obtained in Example 178, the title compound was obtained.

$^1$H-NMR (DMSO-$d_6$) δ 1.59 (8H, m), 2.66 (7H, m), 3.83 (2H, s), 7.24 (1H, m), 7.61 (2H, m), 7.81 (3H, m), 8.08–8.19 (3H, m), 8.91 (1H, s), 10.29 (1H, s). Elemental analysis for $C_{28}H_{28}ClN_3OS.0.5H_2O$ Calculated: C, 67.39; H, 5.86; N, 8.42. Found: C, 67.71; H, 5.57; N, 8.21. melting point: 186–187° C. (crystallization solvent: ethyl acetate-isopropyl ether)

Example 182

N-[3-(1-azepanylmethyl)-8-methyl-7-quinolinyl]-4-bromo-2-fluorobenzamide

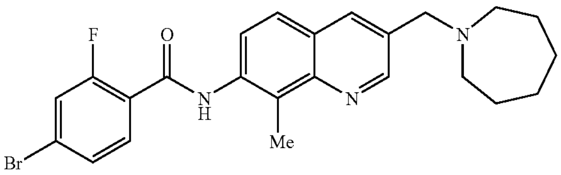

By operating in the same manner as in Example 1 and using 3-(1-azepanylmethyl)-8-ethyl-7-quinolinylamine obtained in Reference Example 51, the title compound was obtained.

$^1$H-NMR (DMSO-$d_6$) δ 1.59 (8H, m), 2.50 (2H, m), 2.64 (2H, m), 2.68 (3H, s), 3.83 (2H, s), 7.61–7.80 (5H, m), 8.19 (1H, s), 8.90 (1H, d, J=1.8 Hz), 10.26 (1H, s).

Example 183

N-[3-(1-azepanylmethyl)-8-methyl-7-quinolinyl]-3-fluoro[1,1'-biphenyl]-4-carboxamide

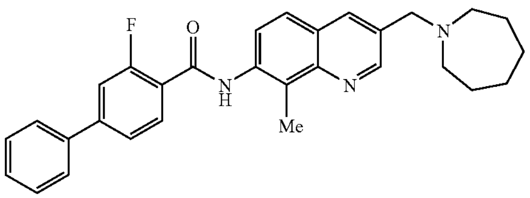

By operating in the same manner as in Example 50 and using N-[3-(1-azepanylmethyl)-8-methyl-7-quinolinyl]-4-bromo-2-fluorobenzamide obtained in Example 182, the title compound was obtained.

$^1$H-NMR (DMSO-$d_6$) δ 1.59 (8H, m), 2.65 (4H, m), 2.71 (3H, s), 3.84 (2H, s), 7.50–7.79 (10H, m), 8.21 (1H, s), 8.92 (1H, s), 10.23 (1H, s). Elemental analysis for $C_{30}H_{30}FN_3O.0.5H_2O$ Calculated: C, 75.60; H, 6.56; N, 8.82. Found: C, 75.92; H, 6.20; N, 8.75. melting point: 151–153° C. (crystallization solvent: ethyl acetate-isopropyl ether)

Example 184

N-[3-(1-azepanylmethyl)-8-methyl-7-quinolinyl]-3,4'-difluoro[1,1'-biphenyl]-4-carboxamide

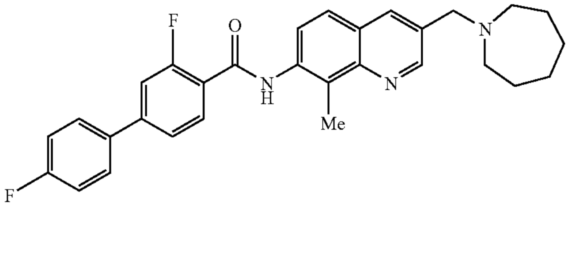

By operating in the same manner as in Example 50 and using N-[3-(1-azepanylmethyl)-8-methyl-7-quinolinyl]-4-bromo-2-fluorobenzamide obtained in Example 182, the title compound was obtained.

$^1$H-NMR (DMSO-$d_6$) δ 1.59 (8H, m), 2.65 (4H, m), 2.70 (3H, s), 3.84 (2H, s), 7.32–7.86 (9H, m), 8.20 (1H, s), 8.91 (1H, s), 10.22 (1H, s). melting point: 159–160° C. (crystallization solvent: ethyl acetate-isopropyl ether)

Example 185

N-[3-(1-azepanylmethyl)-8-methyl-7-quinolinyl]-3-fluoro-4'-methoxy[1,1'-biphenyl]-4-carboxamide

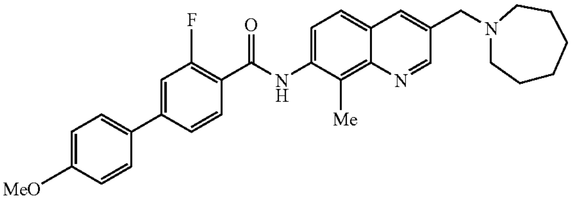

By operating in the same manner as in Example 50 and using N-[3-(1-azepanylmethyl)-8-methyl-7-quinolinyl]-4-bromo-2-fluorobenzamide obtained in Example 182, the title compound was obtained.

$^1$H-NMR (DMSO-$d_6$) δ 1.60 (8H, m), 2.71 (7H, m), 3.83–3.88 (5H, m), 7.08 (2H, d, J=8.8 Hz), 7.67–7.85 (7H, m), 8.22 (1H, s), 8.92 (1H, s), 10.17 (1H, s). Elemental analysis for $C_{31}H_{32}FN_3O_2$ Calculated: C, 74.83; H, 6.48; N, 8.44. Found: C, 74.53; H, 6.30; N, 8.09. melting point: 171–172° C. (crystallization solvent: ethyl acetate-isopropyl ether)

Example 186

N-[3-(1-azepanylmethyl)-8-methyl-7-quinolinyl]-4-(5-chloro-2-thienyl)-2-fluorobenzamide

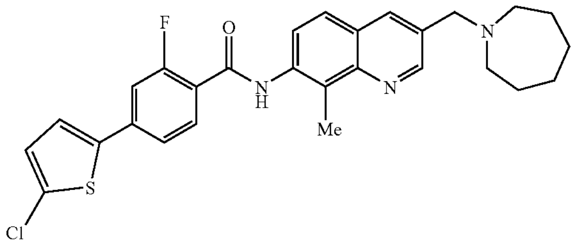

By operating in the same manner as in Example 50 and using N-[3-(1-azepanylmethyl)-8-methyl-7-quinolinyl]-4-bromo-2-fluorobenzamide obtained in Example 182, the title compound was obtained.

$^1$H-NMR (DMSO-$d_6$) δ 1.59 (8H, m), 2.69 (7H, m), 3.86 (2H, s), 7.25–7.85 (7H, m), 8.21 (1H, s), 8.91 (1H, s), 10.21 (1H, s). Elemental analysis for $C_{28}H_{27}ClFN_3OS.0.5H_2O$ Calculated: C, 65.04; H, 5.46; N, 8.13. Found: C, 65.00; H, 5.07; N, 8.00. melting point: 166–167° C. (crystallization solvent: ethyl acetate-isopropyl ether)

Example 187

N-[3-(1-azepanylmethyl)-8-methyl-7-quinolinyl]-4-bromo-3-fluorobenzamide

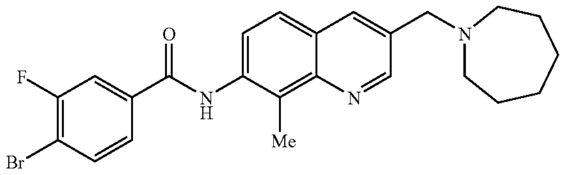

By operating in the same manner as in Example 1 and using 3-(1-azepanylmethyl)-8-methyl-7-quinolinylamine obtained in Reference Example 51, the title compound was obtained.

$^1$H-NMR (DMSO-$d_6$) δ 1.59 (8H, m), 2.65 (4H, m), 2.69 (3H, s), 3.83 (2H, s), 7.56–8.03 (5H, m), 8.20 (1H, m), 8.91 (1H, m), 10.36 (1H, s).

Example 188

N-[3-(1-azepanylmethyl)-8-methyl-7-quinolinyl]-2-fluoro[1,1'-biphenyl]-4-carboxamide

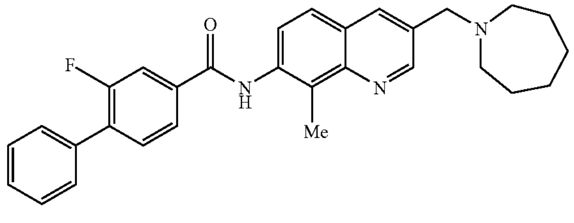

By operating in the same manner as in Example 50 and sing N-[3-(1-azepanylmethyl)-8-methyl-7-quinolinyl]-4-bromo-3-fluorobenzamide obtained in Example 187, the title compound was obtained.

$^1$H-NMR (DMSO-$d_6$) δ 1.59 (8H, m), 2.67 (7H, m), 3.84 (2H, s), 7.33–7.98 (10H, m), 8.21 (1H, s), 8.92 (1H, s), 10.35 (1H, s). Elemental analysis for $C_{30}H_{30}FN_3O.2H_2O$ Calculated: C, 71.55; H, 6.80; N, 8.34. Found: C, 71.94; H, 6.64; N, 8.02. melting point: 129–130° C. (crystallization solvent: ethyl acetate-isopropyl ether)

Example 189

N-[3-(1-azepanylmethyl)-8-methyl-7-quinolinyl]-2,4'-difluoro[1,1'-biphenyl]-4-carboxamide

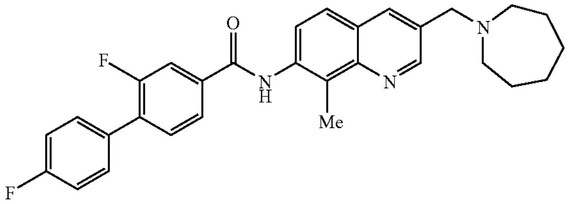

By operating in the same manner as in Example 50 and using N-[3-(1-azepanylmethyl)-8-methyl-7-quinolinyl]-4-bromo-3-fluorobenzamide obtained in Example 187, the title compound was obtained.

$^1$H-NMR (DMSO-$d_6$) δ 1.59 (8H, m), 2.67 (7H, m), 3.83 (2H, m), 7.34–8.01 (9H, m), 8.20 (1H, s), 8.91 (1H, s), 10.37 (1H, s). Elemental analysis for $C_{30}H_{29}F_2N_3O.1.5H_2O$ Calculated: C, 70.29; H, 6.29; N, 8.20. Found: C, 70.63; H, 6.02; N, 8.41. melting point: 162–163° C. (crystallization solvent: ethyl acetate-isopropyl ether)

Example 190

N-[3-(1-azepanylmethyl)-8-methyl-7-quinolinyl]-2-fluoro-4'-methoxy[1,1'-biphenyl]-4-carboxamide

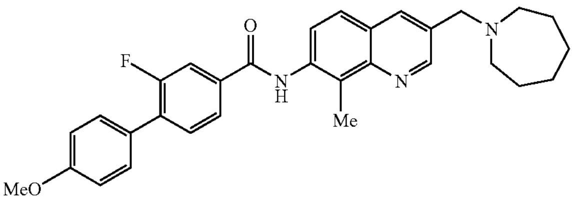

By operating in the same manner as in Example 50 and using N-[3-(1-azepanylmethyl)-8-methyl-7-quinolinyl]-4-bromo-3-fluorobenzamide obtained in Example 187, the title compound was obtained.

$^1$H-NMR (DMSO-$d_6$) δ 1.59 (8H, m), 2.67 (7H, m), 3.83 (5H, m), 7.11–7.98 (9H, m), 8.22 (1H, s), 8.92 (1H, s), 10.33 (1H, s). Elemental analysis for $C_{31}H_{32}FN_3O_2.H_2O$ Calculated: C, 72.21; H, 6.65; N, 8.15. Found: C, 71.90; H, 6.39; N, 8.46. melting point: 160–161° C. (crystallization solvent: ethyl acetate-isopropyl ether)

Example 191

N-[3-(1-azetidinylmethyl)-8-methyl-7-quinolinyl]-4'-fluoro[1,1'-biphenyl]-4-carboxamide

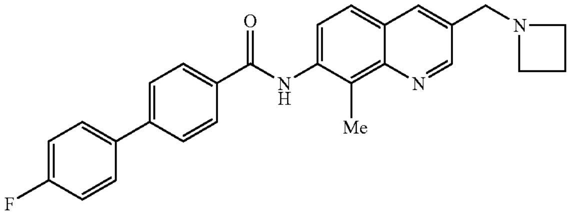

By operating in the same manner as in Example 42 and using N-[3-(chloromethyl)-8-methyl-7-quinolinyl]-4'-fluoro[1,1'-biphenyl]-4-carboxamide obtained in Reference Example 52, the title compound was obtained.

$^1$H-NMR (DMSO-$d_6$) δ 1.99–2.02 (2H, m), 2.50 (4H, m), 2.67 (3H, s), 3.85 (2H, s), 7.36 (2H, m), 7.62 (1H, m), 7.84 (5H, m), 8.16 (3H, m), 8.84–8.95 (1H, m), 10.30 (1H, s). melting point: 153–155° C. (crystallization solvent: ethyl acetate-isopropyl ether) FABMS(pos) 426 [M+H]+

Example 192

N-{3-[(diethylamino)methyl]-8-methyl-7-quinolinyl}-4'-fluoro[1,1'-biphenyl]-4-carboxamide

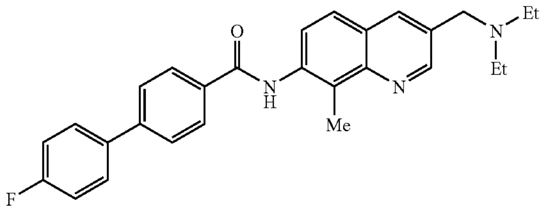

By operating in the same manner as in Example 42 and using N-[3-(chloromethyl)-8-methyl-7-quinolinyl]-4'-fluoro[1,1'-biphenyl]-4-carboxamide obtained in Reference Example 52, the title compound was obtained.

$^1$H-NMR (DMSO-$d_6$) δ 1.03 (6H, m), 2.50 (4H, m), 2.66 (3H, s), 3.77 (2H, s), 7.61–8.22 (11H, m), 8.89 (1H, m), 10.31 (1H, s). melting point: 155–156° C. (crystallization solvent: ethyl acetate-isopropyl ether)

Example 193

N-(3-{[(2R,6S)-2,6-dimethylpiperidinyl]methyl}-8-methyl-7-quinolinyl)-4'-fluoro[1,1'-biphenyl]-4-carboxamide

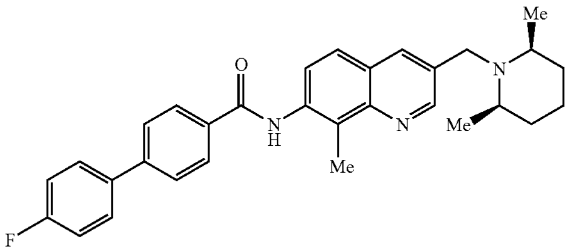

By operating in the same manner as in Example 42 and using N-[3-(chloromethyl)-8-methyl-7-quinolinyl]-4'-fluoro[1,1'-biphenyl]-4-carboxamide obtained in Reference Example 52, the title compound was obtained.

$^1$H-NMR (DMSO-$d_6$) δ 1.02 (6H, m), 1.30 (4H, m), 1.59 (4H, m), 2.50–2.66 (3H, s), 3.94 (2H, s), 7.36–8.26 (11H, m), 8.94 (1H, m), 10.28 (1H, s). melting point: 167–168° C. (crystallization solvent: ethyl acetate-isopropyl ether) FABMS(pos) 482 [M+H]+

Example 194

N-{3-[(diisopropylamino)methyl]-8-methyl-7-quinolinyl}-4'-fluoro[1,1'-biphenyl]-4-carboxamide

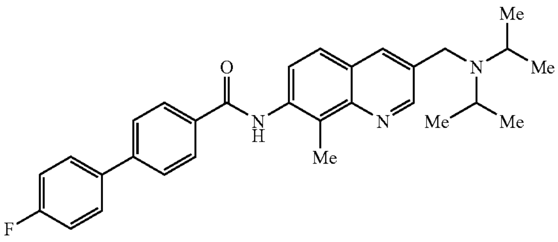

By operating in the same manner as in Example 42 and using N-[3-(chloromethyl)-8-methyl-7-quinolinyl]-4'-fluoro[1,1'-biphenyl]-4-carboxamide obtained in Reference Example 52, the title compound was obtained. melting point: 179–180° C. (crystallization solvent: ethyl acetate-isopropyl ether) FABMS(pos) 470 [M+H]+

Example 195

N-{3-[(dimethylamino)methyl]-8-methyl-7-quinolinyl}-4'-fluoro[1,1'-biphenyl]-4-carboxamide

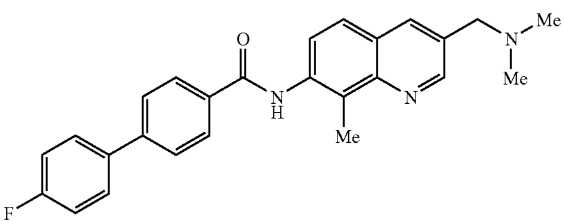

By operating in the same manner as in Example 42 and using N-[3-(chloromethyl)-8-methyl-7-quinolinyl]-4'-fluoro [1,1'-biphenyl]-4-carboxamide obtained in Reference Example 52, the title compound was obtained.

$^1$H-NMR (DMSO-$d_6$) δ 2.25 (6H, s), 2.67 (3H, s), 3.68 (2H, s), 7.36–8.23 (11H, m), 8.88 (1H, m), 10.30 (1H, s). melting point: 161–163° C. (crystallization solvent: ethyl acetate-isopropyl ether)

Example 196

4'-fluoro-N-{8-methyl-3-[(4-phenyl-1-piperidinyl) methyl]-7-quinolinyl}[1,1'-biphenyl]-4-carboxamide

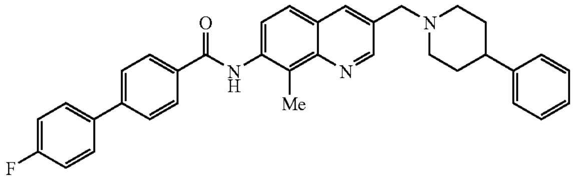

By operating in the same manner as in Example 42 and using N-[3-(chloromethyl)-8-methyl-7-quinolinyl]-4'-fluoro [1,1'-biphenyl]-4-carboxamide obtained in Reference Example 52, the title compound was obtained.

$^1$H-NMR (DMSO-$d_6$) δ 1.74 (4H, m), 2.15 (2H, m), 2.66 (4H, m), 2.98 (2H, m), 3.75 (2H, s), 7.18–7.39 (6H, m), 7.59–8.24 (10H, m), 8.92 (1H, m), 10.30 (1H, s). melting point: 171–172° C. (crystallization solvent: ethyl acetate-isopropyl ether)

Example 197

4'-fluoro-N-{8-methyl-3-[(4-methyl-1-piperazinyl) methyl]-7-quinolinyl}[1,1'-biphenyl]-4-carboxamide

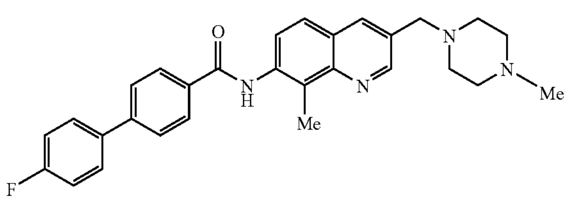

By operating in the same manner as in Example 42 and using N-[3-(chloromethyl)-8-methyl-7-quinolinyl]-4'-fluoro [1,1'-biphenyl]-4-carboxamide obtained in Reference Example 52, the title compound was obtained.

$^1$H-NMR (DMSO-$d_6$) δ 2.19 (3H, s), 2.42 (4H, m), 2.50 (4H, m), 2.66 (3H, s), 3.69 (2H, s), 7.31–8.20 (11H, m), 8.87

(1H, m), 10.30 (1H, s). melting point: 152–153° C. (crystallization solvent: ethyl acetate-isopropyl ether)

Example 198

4'-fluoro-N-[8-methyl-3-(4-morpholinylmethyl)-7-quinolinyl][1,1'-biphenyl]-4-carboxamide

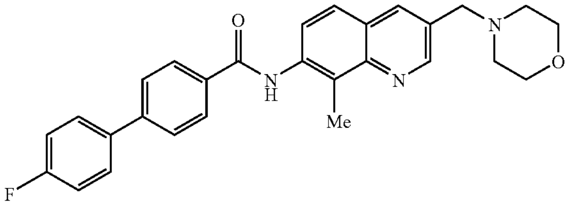

By operating in the same manner as in Example 42 and using N-[3-(chloromethyl)-8-methyl-7-quinolinyl]-4'-fluoro [1,1'-biphenyl]-4-carboxamide obtained in Reference Example 52, the title compound was obtained.

$^1$H-NMR (DMSO-$d_6$) δ 2.43 (4H, m), 2.67 (3H, s), 3.60 (4H, m), 3.70 (2H, s), 7.35 (2H, m), 7.63 (1H, d, J=8.7 Hz), 7.84 (5H, m), 8.14 (2H, d, J=8.1 Hz), 8.23 (1H, s), 8.88 (1H, d, J=1.5 Hz), 10.30 (1H, s). melting point: 176–178° C. (crystallization solvent: ethyl acetate-isopropyl ether) FABMS(pos) 456 [M+H]+

Example 199

4'-fluoro-N-{8-methyl-3-[(2-methyl-4,5-dihydro-1H-imidazol-1-yl)methyl]-7-quinolinyl}[1,1'-biphenyl]-4-carboxamide

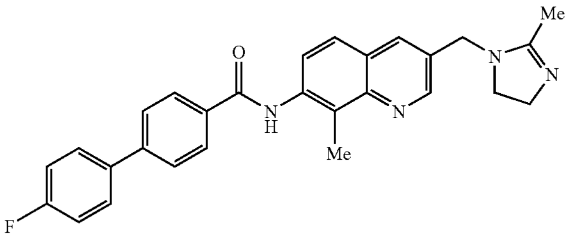

By operating in the same manner as in Example 42 and using N-[3-(chloromethyl)-8-methyl-7-quinolinyl]-4'-fluoro [1,1'-biphenyl]-4-carboxamide obtained in Reference Example 52, the title compound was obtained.

$^1$H-NMR (DMSO-$d_6$) δ 2.00 (3H, s), 2.67 (3H, s), 3.13 (4H, m), 3.50 (4H, m), 4.51 (2H, s), 7.36 (2H, m), 7.65 (1H, d, J=8.7 Hz), 7.84 (5H, m), 8.14 (2H, d, J=7.8 Hz), 8.22 (1H, s), 8.88 (1H, s), 10.31 (1H, s). FABMS(pos) 453 [M+H]+

Example 200

N-(3-{[4-(2-amino-2-oxoethyl)-1-piperidinyl]methyl}-8-methyl-7-quinolinyl)-4'-fluoro[1,1'-biphenyl]-4-carboxamide

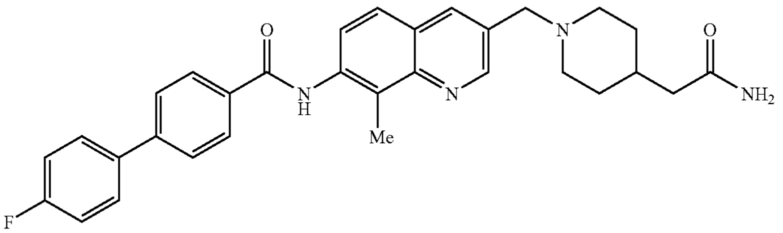

By operating in the same manner as in Example 42 and using N-[3-(chloromethyl)-8-methyl-7-quinolinyl]-4'-fluoro[1,1'-biphenyl]-4-carboxamide obtained in Reference Example 52, the title compound was obtained.

$^1$H-NMR (DMSO-$d_6$) δ 1.18–1.21 (2H, m), 1.65–1.66 (3H, m), 1.96–2.12 (3H, m), 2.68 (3H, s), 2.81–2.87 (2H, m), 3.69 (2H, s), 6.74 (1H, s), 7.26–7.40 (3H, m), 7.64 (1H, d, J=8.8 Hz), 7.81–7.88 (5H, m), 8.13–8.20 (3H, m), 8.87–8.88 (1H, m), 10.30 (1H, s). melting point: 258–260° C. (crystallization solvent: ethyl acetate-isopropyl ether) FABMS(pos) 511 [M+H]+

Example 201

4'-fluoro-N-[8-methyl-3-({4-[2-(methylamino)-2-oxoethyl]-1-piperidinyl}methyl)-7-quinolinyl][1,1'-biphenyl]-4-carboxamide

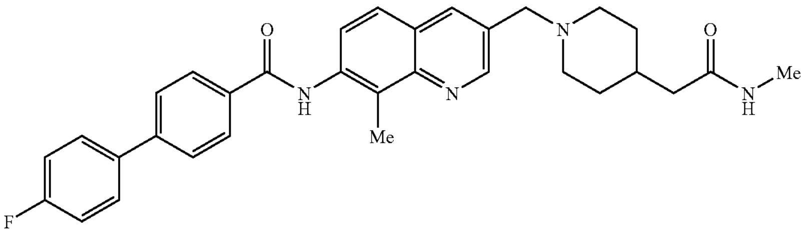

By operating in the same manner as in Example 42 and using N-[3-(chloromethyl)-8-methyl-7-quinolinyl]-4'-fluoro[1,1'-biphenyl]-4-carboxamide obtained in Reference Example 52, the title compound was obtained.

$^1$H-NMR ($CDCl_3$) δ 1.21–1.33 (2H, m), 1.66–1.70 (2H, m), 1.80–1.87 (1H, m), 2.00–2.07 (4H, m), 2.79 (3H, d, J=5.1 Hz), 2.82 (3H, s), 2.88 (2H, d, J=11.4 Hz), 3.65 (2H, s), 5.21 (1H, d, J=4.5 Hz), 7.14–7.20 (2H, m), 7.58–7.63 (2H, m), 7.67–7.70 (3H, m), 8.02 (3H, m), 8.11 (1H, s), 8.21 (1H, d, J=8.7 Hz), 8.88 (1H, d, J=2.1 Hz). melting point: 229–231° C. (crystallization solvent: ethyl acetate-isopropyl ether) Elemental analysis for $C_{32}H_{33}FN_4O_2.0.25H_2O$ Calculated: C, 72.64; H, 6.38; N, 10.59. Found: C, 72.54; H, 6.25; N, 10.54.

Example 202

N-[3-({4-[2-(dimethylamino)-2-oxoethyl]-1-piperidinyl}methyl)-8-methyl-7-quinolinyl]-4'-fluoro[1,1'-biphenyl]-4-carboxamide

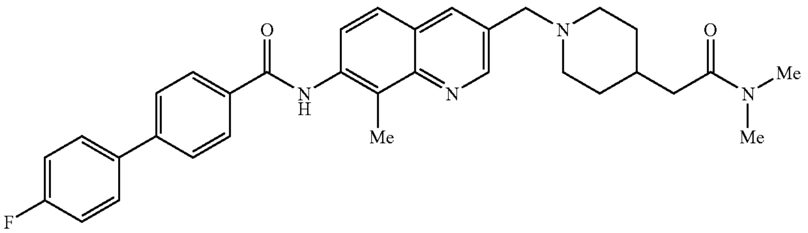

By operating in the same manner as in Example 42 and using N-[3-(chloromethyl)-8-methyl-7-quinolinyl]-4'-fluoro[1,1'-biphenyl]-4-carboxamide obtained in Reference Example 52, the title compound was obtained.

$^1$H-NMR (DMSO-$d_6$) δ 1.18–1.29 (2H, m), 1.62–1.68 (3H, m), 1.95–2.05 (2H, m), 2.20 (2H, d, J=9.3 Hz), 2.67 (3H, s), 2.80 (6H, m), 2.94 (2H, m), 3.66 (2H, s), 7.30–7.39 (2H, m), 7.62 (1H, d, J=8.8 Hz), 7.79–7.87 (5H, m), 8.13–8.18 (3H, m), 8.87 (1H, d, J=2.2 Hz), 10.28 (1H, s). melting point: 200–201° C. (crystallization solvent: ethyl acetate-isopropyl ether) Elemental analysis for $C_{33}H_{35}FN_4O_2$.0.25$H_2O$ Calculated: C, 72.97; H, 6.59; N, 10.31. Found: C, 72.82; H, 6.36; N, 10.30.

Example 203

N-[3-({4-[2-(ethylamino)-2-oxoethyl]-1-piperidinyl}methyl)-8-methyl-7-quinolinyl]-4'-fluoro[1,1'-biphenyl]-4-carboxamide

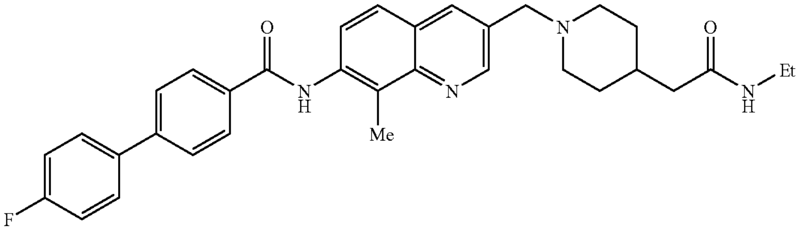

By operating in the same manner as in Example 42 and using N-[3-(chloromethyl)-8-methyl-7-quinolinyl]-4'-fluoro[1,1'-biphenyl]-4-carboxamide obtained in Reference Example 52, the title compound was obtained.

$^1$H-NMR (DMSO-$d_6$) δ 0.99 (3H, t, J=7.4 Hz), 1.63–1.21 (2H, m), 1.57–1.62 (3H, m), 1.96–2.05 (4H, m), 2.67 (3H, m), 2.84 (2H, d, J=9.8 Hz), 2.98–3.11 (2H, m), 3.67 (2H, s), 7.31–7.40 (2H, m), 7.63 (1H, d, J=8.4 Hz), 7.76–7.88 (6H, m), 8.13–8.20 (3H, m), 8.87 (1H, d, J=1.8 Hz), 10.30 (1H, s). melting point: 243–245° C. (crystallization solvent: ethyl acetate-isopropyl ether) Elemental analysis for $C_{33}H_{35}FN_4O_2$.0.25$H_2O$ Calculated: C, 72.97; H, 6.59; N, 10.31. Found: C, 73.15; H, 6.35; N, 10.28.

Example 204

N-[3-({4-[2-(diethylamino)-2-oxoethyl]-1-piperidinyl}methyl)-8-methyl-7-quinolinyl]-4'-fluoro [1,1'-biphenyl]-4-carboxamide

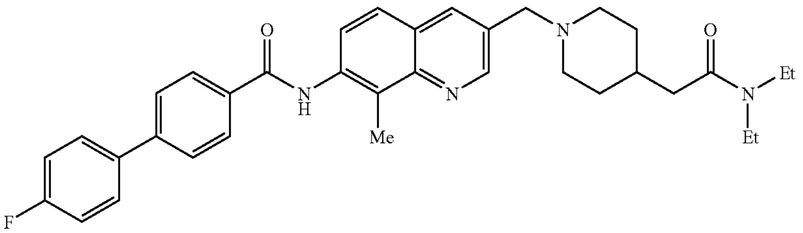

By operating in the same manner as in Example 42 and using N-[3-(chloromethyl)-8-methyl-7-quinolinyl]-4'-fluoro [1,1'-biphenyl]-4-carboxamide obtained in Reference Example 52, the title compound was obtained.

$^1$H-NMR (DMSO-$d_6$) δ 0.99 (3H, t, J=7.0 Hz), 1.08 (3H, t, J=7.0 Hz), 1.19–1.31 (2H, m), 1.61–1.76 (3H, m), 1.95–2.06 (2H, m), 2.19 (2H, d, J=6.2 Hz), 2.68 (3H, s), 2.84 (2H, d, J=10.8 Hz), 3.19–3.30 (4H, m), 3.67 (2H, s), 7.31–7.40 (1H, m), 7.63 (2H, d, J=8.4 Hz), 7.81–7.88 (5H, m), 8.13–8.19 (3H, m), 8.87 (1H, d, J=1.8 Hz), 10.30 (1H, s). melting point: 158–160° C. (crystallization solvent: ethyl acetate-isopropyl ether) Elemental analysis for $C_{35}H_{39}FN_4O_2.0.25H_2O$ Calculated: C, 73.59; H, 6.97; N, 9.81. Found: C, 73.32; H, 6.72; N, 9.73.

Example 205

4'-fluoro-N-[8-methyl-3-({4-[2-oxo-2-(1-piperidinyl) ethyl]-1-piperidinyl}methyl)-7-quinolinyl][1,1'-biphenyl]-4-carboxamide

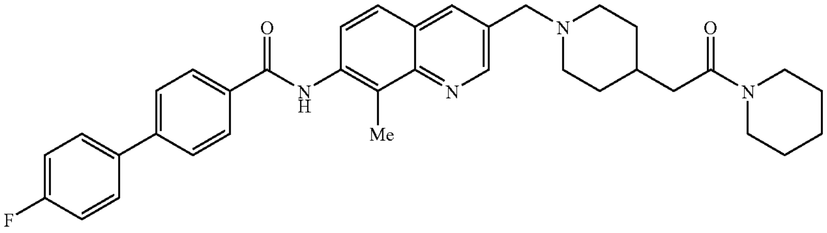

By operating in the same manner as in Example 42 and using N-[3-(chloromethyl)-8-methyl-7-quinolinyl]-4'-fluoro [1,1'-biphenyl]-4-carboxamide obtained in Reference Example 52, the title compound was obtained.

$^1$H-NMR (DMSO-$d_6$) δ 1.18–1.67 (11H, m),1.94–2.06 (2H, m), 2.21 (2H, d, J=8.2 Hz), 2.67 (3H, s), 2.83 (2H, d, J=11.0 Hz), 3.39 (4H, d, J=5.0 Hz), 3.66 (2H, s), 7.30–7.39 (2H, m), 7.62 (1H, d, J=8.4 Hz), 7.79–7.87 (5H, m), 8.13–8.17 (3H, m) 8.87 (1H, d, J=2.2 Hz), 10.28 (1H, s). melting point: 189–190° C. (crystallization solvent: ethyl acetate-isopropyl ether) FABMS(pos) 579 [M+H]+

Example 206

N-(3-{[4-(4-amino-4-oxobutyl)-1-piperidinyl]methyl}-8-methyl-7-quinolinyl)-4'-fluoro[1,1'-biphenyl]-4-carboxamide

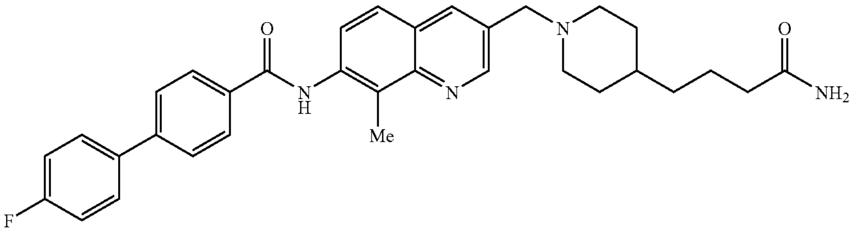

By operating in the same manner as in Example 42 and using N-[3-(chloromethyl)-8-methyl-7-quinolinyl]-4'-fluoro [1,1'-biphenyl]-4-carboxamide obtained in Reference Example 52, the title compound was obtained.

$^1$H-NMR (DMSO-$d_6$) δ 1.17 (5H, br), 1.49 (2H, br), 1.60–1.65 (2H, d, J=9.6 Hz), 1.97–2.04 (4H, m), 2.67 (3H, s), 2.82–2.89 (2H, m), 3.67 (2H, s), 6.68 (1H, br), 7.22 (1H, br), 7.30–7.39 (2H, m), 7.62 (1H, d, J=8.8 Hz), 7.80–7.87 (5H, m), 8.13–8.17 (3H, m), 8.87 (1H, d, J=1.8 Hz), 10.29 (1H, s). melting point: 232–234° C. (crystallization solvent: ethyl acetate-isopropyl ether) Elemental analysis for $C_{33}H_{35}FN_4O_2$.0.25$H_2O$ Calculated: C, 72.97; H, 6.59; N, 10.31. Found: C, 72.86; H, 6.44; N, 10.29.

Example 207

4'-fluoro-N-[8-methyl-3-({4-[4-(methylamino)-4-oxobutyl]-1-piperidinyl}methyl)-7-quinolinyl][1,1'-biphenyl]-4-carboxamide

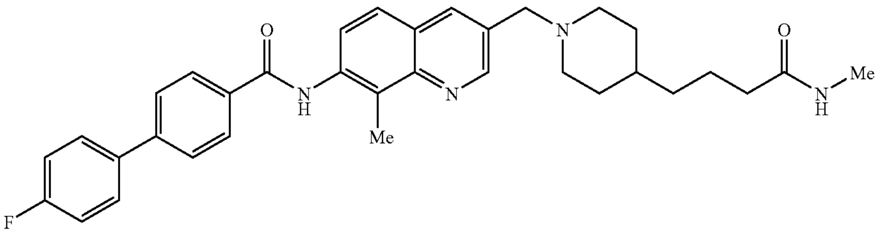

By operating in the same manner as in Example 42 and using N-[3-(chloromethyl)-8-methyl-7-quinolinyl]-4'-fluoro [1,1'-biphenyl]-4-carboxamide obtained in Reference Example 52, the title compound was obtained.

$^1$H-NMR (DMSO-$d_6$) δ 1.17 (5H, br), 1.48 (2H, br), 1.62–1.64 (2H, br), 1.98–2.05 (4H, m), 2.55 (3H, s), 2.67 (3H, s), 2.25 (2H, d, J=10.0 Hz) 3.67 (2H, s), 7.30–7.39 (2H, m), 7.60–7.64 (2H, m), 7.80–7.87 (5H, m), 8.13–8.17 (3H, m), 8.87 (1H, d, J=1.8 Hz), 10.29 (1H, s) melting point: 210–212° C. (crystallization solvent: ethyl acetate-isopropyl ether) Elemental analysis for $C_{34}H_{37}FN_4O_2$.0.5$H_2O$ Calculated: C, 72.70; H, 6.82; N, 9.97. Found: C, 72.38; H, 6.59; N, 9.91.

Example 208

N-[3-({4-[4-(dimethylamino)-4-oxobutyl]-1-piperidinyl}methyl)-8-methyl-7-quinolinyl]-4'-fluoro[1,1'-biphenyl]-4-carboxamide

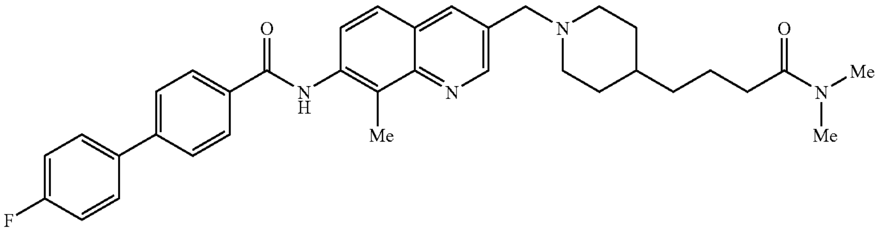

By operating in the same manner as in Example 42 and using N-[3-(chloromethyl)-8-methyl-7-quinolinyl]-4'-fluoro[1,1'-biphenyl]-4-carboxamide obtained in Reference Example 52, the title compound was obtained.

$^1$H-NMR (DMSO-$d_6$) δ 1.19 (5H, br), 1.48 (2H, br), 1.59–1.65 (2H, m), 1.93–1.98 (2H, m), 2.23 (2H, t, J=5.4 Hz), 2.67 (3H, s), 2.79 (3H, s), 2.87 (2H, br), 2.93 (3H, s), 3.66 (2H, s), 7.34 (2H, t, J=8.8 Hz), 7.62 (1H, d, J=8.4 Hz), 7.80–7.87 (5H, m), 8.13–8.17 (3H, m), 8.86 (1H, d, J=1.8 Hz), 10.29 (1H, s). melting point: 202–204° C. (crystallization solvent: ethyl acetate-isopropyl ether) Elemental analysis for $C_{35}H_{39}FN_4O_2.0.25H_2O$ Calculated: C, 73.59; H, 6.97; N, 9.81. Found: C, 73.37; H, 6.69; N, 9.75.

Example 209

N-[3-({4-[4-(ethylamino)-4-oxobutyl]-1-piperidinyl}methyl)-8-methyl-7-quinolinyl]-4'-fluoro[1,1'-biphenyl]-4-carboxamide

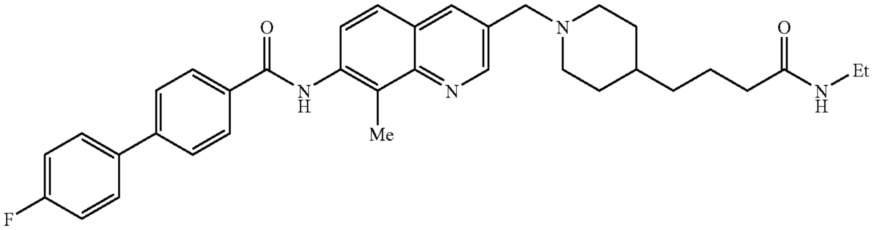

By operating in the same manner as in Example 42 and using N-[3-(chloromethyl)-8-methyl-7-quinolinyl]-4'-fluoro[1,1'-biphenyl]-4-carboxamide obtained in Reference Example 52, the title compound was obtained.

$^1$H-NMR (DMSO-$d_6$) δ 0.99 (3H, t, J=7.2 Hz), 1.17 (5H, br), 1.49–1.63 (4H, m), 1.91–2.04 (4H, m), 2.68 (3H, s), 2.83 (2H, d, J=10.8 Hz), 2.98–3.07 (2H, m), 3.65 (2H, s), 7.34 (2H, t, J=8.8 Hz), 7.63 (1H, d, J=8.8 Hz), 7.74–7.86 (6H, m), 8.13–8.17 (3H, m), 8.86 (1H, d, J=1.6 Hz), 10.29 (1H, s). melting point: 217–220° C. (crystallization solvent: ethyl acetate-isopropyl ether) Elemental analysis for $C_{35}H_{39}FN_4O_2.0.25H_2O$ Calculated: C, 73.59; H, 6.97; N, 9.81. Found: C, 73.54; H, 6.80; N, 9.88.

Example 210

N-[3-({4-[4-(diethylamino)-4-oxobutyl]-1-piperidinyl}methyl)-8-methyl-7-quinolinyl]-4'-fluoro[1,1'-biphenyl]-4-carboxamide

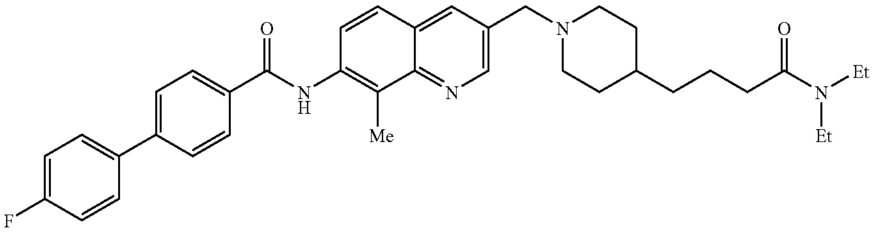

By operating in the same manner as in Example 42 and using N-[3-(chloromethyl)-8-methyl-7-quinolinyl]-4'-fluoro[1,1'-biphenyl]-4-carboxamide obtained in Reference Example 52, the title compound was obtained.

$^1$H-NMR (DMSO-$d_6$) δ 0.98 (3H, t, J=6.8 Hz), 1.07 (3H, t, J=7.2 Hz), 1.19 (5H, br), 1.50–1.64 (4H, m), 1.92–1.97 (2H, m), 2.18–2.25 (2H, m), 2.67 (3H, s), 2.84 (2H, d, J=11.0 Hz), 3.18–3.35 (4H, m), 3.65 (2H, s), 7.34 (2H, t, J=8.8 Hz), 7.62 (1H, d, J=8.4 Hz), 7.80–7.86 (5H, m), 8.13–8.17 (3H, m), 8.85 (1H, d, J=1.8 Hz), 10.29 (1H, s). melting point: 145–146° C. (crystallization solvent: ethyl acetate-isopropyl ether) Elemental analysis for $C_{37}H_{43}FN_4O_2.0.5H_2O$ Calculated: C, 73.60; H, 7.35; N, 9.28. Found: C, 73.79; H, 7.04; N, 9.34.

Example 211

4'-fluoro-N-[8-methyl-3-({4-[4-oxo-4-(1-piperidinyl)butyl]-1-piperidinyl}methyl)-7-quinolinyl][1,1'-biphenyl]-4-carboxamide

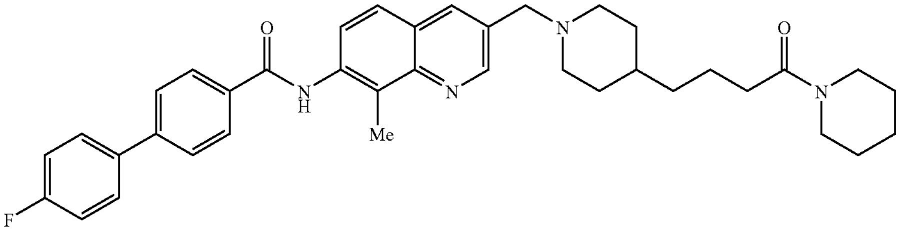

By operating in the same manner as in Example 42 and using N-[3-(chloromethyl)-8-methyl-7-quinolinyl]-4'-fluoro[1,1'-biphenyl]-4-carboxamide obtained in Reference Example 52, the title compound was obtained.

$^1$H-NMR (DMSO-$d_6$) δ 1.19 (6H, m), 1.45 (9H, m), 1.92–1.97 (2H, m), 2.20–2.27 (2H, m), 2.67 (3H, s), 2.83 (2H, d, J=11.0 Hz), 3.34 (4H, m), 3.65 (2H, s), 7.34 (2H, t, J=8.8 Hz), 7.62 (1H, d, J=8.8 Hz), 7.80–7.86 (5H, m), 8.13–8.17 (3H, m), 8.85 (1H, d, J=1.8 Hz), 10.29 (1H, s). melting point: 154–156° C. (crystallization solvent: ethyl acetate-isopropyl ether) Elemental analysis for $C_{38}H_{43}FN_4O_2.0.25H_2O$ Calculated: C, 74.12; H, 7.20; N, 9.10. Found: C, 74.23; H, 7.05; N, 9.25.

Example 212

4-bromo-N-[6-methyl-3-(1-pyrrolidinylmethyl)-7-quinolinyl]benzamide

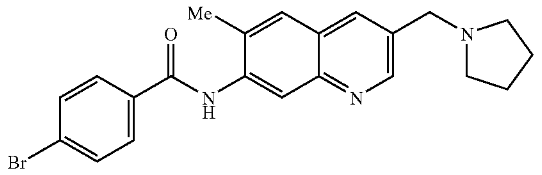

By operating in the same manner as in Reference Example 3 and using 4-bromo-N-[3-(chloromethyl)-6-methyl-7-quinolinyl]benzamide hydrochloride obtained in Reference Example 56, the title compound was obtained.

$^1$H-NMR(DMSO-$d_6$) δ 1.71 (4H, m), 2.44 (3H, s), 2.48 (4H, m), 3.76 (2H, s), 7.77 (2H, d, J=8.8 Hz), 7.83 (1H, s), 7.97 (2H, d, J=8.8 Hz), 8.06 (1H, s), 8.12 (1H, m), 8.78 (1H, d, J=2.2 Hz), 10.16 (1H, s).

Example 213

2'-fluoro-N-[6-methyl-3-(1-pyrrolidinylmethyl)-7-quinolinyl][1,1'-biphenyl]-4-carboxamide

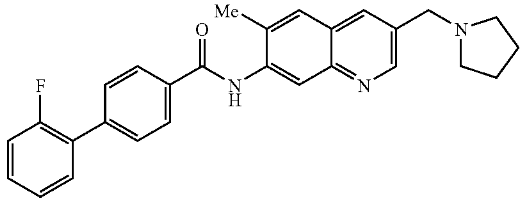

By operating in the same manner as in Example 50 and using 4-bromo-N-[6-methyl-3-(1-pyrrolidinylmethyl)-7-quinolinyl]benzamide obtained in Example 212, the title compound was obtained.

$^1$H-NMR(DMSO-$d_6$) δ 1.72 (4H, m), 2.48 (3H, s), 2.50 (4H, m), 3.78 (2H, s), 7.30–7.68 (4H, m), 7.75 (2H, dd, J=1.4, 8.4 Hz), 7.85 (1H, s), 8.09–8.18 (4H, m), 8.79 (1H, d, J=1.8 Hz), 10.16 (1H, s). melting point: 148–149° C. (crystallization solvent: ethyl acetate-isopropyl ether) FABMS(pos) 440 [M+H]+

Example 214

2',4'-difluoro-N-[6-methyl-3-(1-pyrrolidinylmethyl)-7-quinolinyl][1,1'-biphenyl]-4-carboxamide

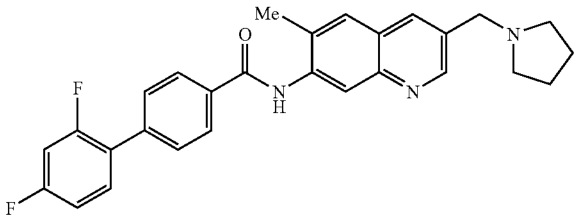

By operating in the same manner as in Example 50 and using 4-bromo-N-[6-methyl-3-(1-pyrrolidinylmethyl)-7-quinolinyl]benzamide obtained in Example 212, the title compound was obtained.

$^1$H-NMR(DMSO-$d_6$) δ 1.72 (4H, m), 2.47 (3H, s), 2.50 (4H, m), 3.78 (2H, s), 7.26 (1H, m), 7.43 (1H, m), 7.61–7.77 (3H, m), 7.85 (1H, s), 8.08–8.18 (4H, m), 8.79 (1H, d, J=2.2 Hz), 10.16 (1H, s). melting point: 158–160° C. (crystallization solvent: ethyl acetate-isopropyl ether) Elemental analysis for $C_{28}H_{25}F_2N_3O$ Calculated: C, 73.51; H, 5.51; N, 9.18. Found: C, 73.31; H, 5.38; N, 9.12.

Example 215

N-[6-methyl-3-(1-pyrrolidinylmethyl)-7-quinolinyl]-4'-(trifluoromethyl)[1,1'-biphenyl]-4-carboxamide

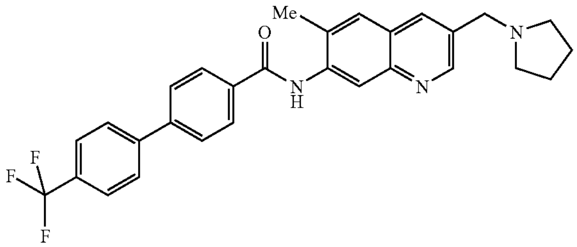

By operating in the same manner as in Example 50 and using 4-bromo-N-[6-methyl-3-(1-pyrrolidinylmethyl)-7-quinolinyl]benzamide obtained in Example 212, the title compound was obtained.

$^1$H-NMR(DMSO-$d_6$) δ 1.72 (4H, m), 2.48 (3H, s), 2.50 (4H, m), 3.78 (2H, s), 7.83–8.05 (7H, m), 8.09–8.21 (4H, m), 8.79 (1H, d, J=2.2 Hz), 10.19 (1H, s). melting point: 216–219° C. (crystallization solvent: ethyl acetate-isopropyl ether) Elemental analysis for $C_{29}H_{26}F_3N_3O$ Calculated: C, 71.15; H, 5.35; N, 8.58. Found: C, 70.92; H, 5.06; N, 8.53.

Example 216

3',4'-difluoro-N-[6-methyl-3-(1-pyrrolidinylmethyl)-7-quinolinyl][1,1'-biphenyl]-4-carboxamide

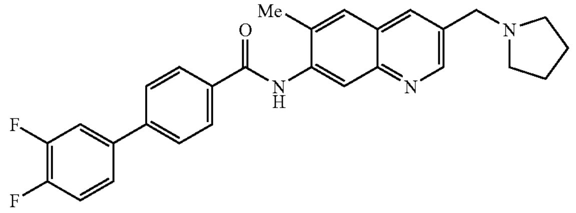

By operating in the same manner as in Example 50 and using 4-bromo-N-[6-methyl-3-(1-pyrrolidinylmethyl)-7-quinolinyl]benzamide obtained in Example 212, the title compound was obtained.

$^1$H-NMR(DMSO-$d_6$) δ 1.72 (4H, m), 2.47 (3H, s), 2.50 (4H, m), 3.78 (2H, s), 7.52–7.71 (2H, m), 7.82–7.98 (4H, m), 8.06–8.18 (4H, m), 8.79 (1H, d, J=1.8 Hz), 10.16 (1H, s). melting point: 220–223° C. (crystallization solvent: ethyl acetate-isopropyl ether) FABMS(pos) 458 [M+H]+

Example 217

4'-ethyl-N-[6-methyl-3-(1-pyrrolidinylmethyl)-7-quinolinyl][1,1'-biphenyl]-4-carboxamide

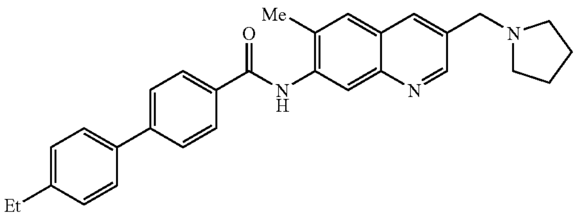

By operating in the same manner as in Example 50 and using 4-bromo-N-[6-methyl-3-(1-pyrrolidinylmethyl)-7-quinolinyl]benzamide obtained in Example 212, the title compound was obtained.

$^1$H-NMR (DMSO-$d_6$) δ 1.22 (3H, t, J=7.6 Hz), 1.71 (4H, m), 2.47 (3H, s), 2.49 (4H, m), 2.66 (2H, q, J=7.6 Hz), 3.77 (2H, s), 7.35 (2H, d, J=8.3 Hz), 7.69 (2H, d, J=8.3 Hz), 7.84 (3H, m), 8.11 (4H, m), 8.78 (1H, d, J=2.0 Hz), 10.10 (1H, s). melting point: 188° C. (crystallization solvent: ethyl acetate-isopropyl ether) Elemental analysis for $C_{30}H_{31}N_3O$ Calculated: C, 80.14; H, 6.95; N, 9.35. Found: C, 97.82; H, 7.10; N, 9.14.

Example 218

2'-chloro-N-[6-methyl-3-(1-pyrrolidinylmethyl)-7-quinolinyl][1,1'-biphenyl]-4-carboxamide hydrochloride

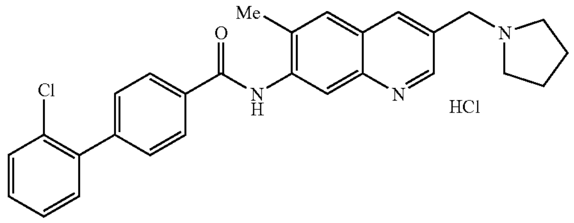

By operating in the same manner as in Example 50 and using 4-bromo-N-[6-methyl-3-(1-pyrrolidinylmethyl)-7-quinolinyl]benzamide obtained in Example 212, the title compound was obtained.

$^1$H-NMR (DMSO-$d_6$) δ 1.91 (2H, m), 2.05 (2H, m), 2.61 (3H, s), 3.15 (2H, dd, J=10.74, 7.32 Hz), 3.44 (2H, m, J=5.13 Hz), 4.66 (2H, d, J=5.62 Hz), 7.47 (2H, m), 7.61 (1H, m), 7.64 (2H, d, J=8.30 Hz), 8.10 (1H, s), 8.15 (2H, d, J=8.30 Hz), 8.61 (1H, s), 9.02 (1H, s), 9.33 (1H, d, J=1.71 Hz), 10.38 (1H, s), 11.71 (1H, s). melting point: 283° C. (crystallization solvent: ethyl acetate-isopropyl ether) Elemental analysis for $C_{28}H_{26}ClN_3O.HCl$ Calculated: C, 68.29; H, 5.52; N, 8.53. Found: C, 69.07; H, 5.85; N, 8.30.

Example 219

N-[6-methyl-3-(1-pyrrolidinylmethyl)-7-quinolinyl]-4'-(methylthio)-[1,1'-biphenyl]-4-carboxamide

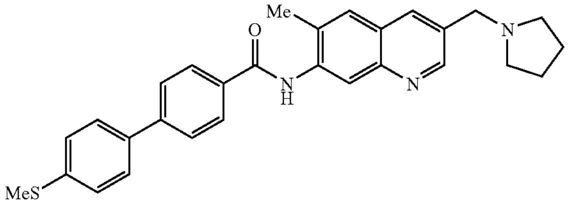

By operating in the same manner as in Example 50 and using 4-bromo-N-[6-methyl-3-(1-pyrrolidinylmethyl)-7-quinolinyl]benzamide obtained in Example 212, the title compound was obtained.

$^1$H-NMR (DMSO-$d_6$) δ 1.74 (4H, m), 2.47 (3H, s), 2.50 (4H, m), 2.53 (3H, s), 3.77 (2H, s), 7.39 (2H, d, J=8.6 Hz), 7.74 (2H, d, J=8.3 Hz), 7.85 (3H, m), 8.11 (4H, m), 8.79 (1H, d, J=2.0 Hz), 10.10 (1H, s). melting point: 198° C. (crystallization solvent: ethyl acetate-isopropyl ether) Elemental analysis for $C_{29}H_{29}N_3OS$ Calculated: C, 74.48; H, 6.25; N, 8.99. Found: C, 74.33; H, 6.36, N, 8.82.

Example 220

4-(5-chlorothien-2-yl)-N-[6-methyl-3-(1-pyrrolidinylmethyl)-7-quinolinyl]benzamide

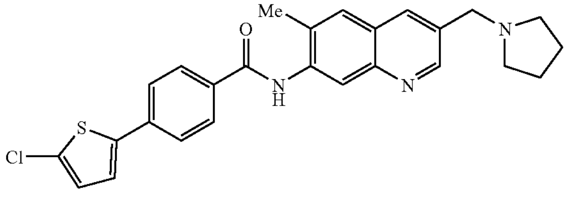

By operating in the same manner as in Example 50 and using 4-bromo-N-[6-methyl-3-(1-pyrrolidinylmethyl)-7-quinolinyl]benzamide obtained in Example 212, the title compound was obtained.

$^1$H-NMR (DMSO-$d_6$) δ 1.72 (4H, m), 2.45 (3H, s), 2.50 (4H, m), 3.77 (2H, s), 7.23 (1H, d, J=3.9 Hz), 7.59 (1H, d, J=3.9 Hz), 7.80 (2H, d, J=8.3 Hz), 7.84 (1H, s), 8.09 (3H, m), 8.13 (1H, s), 8.78 (1H, d, J=2.0 Hz), 10.11 (1H, s). melting point: 216° C. (crystallization solvent: ethyl acetate-isopropyl ether) Elemental analysis for $C_{26}H_{24}ClN_3OS$ Calculated: C, 67.59; H, 5.24; N, 9.10. Found: C, 67.26; H, 5.28; N, 8.84.

Example 221

4-(1-benzofuran-2-yl)-N-[6-methyl-3-(1-pyrrolidinylmethyl)-7-quinolinyl]benzamide

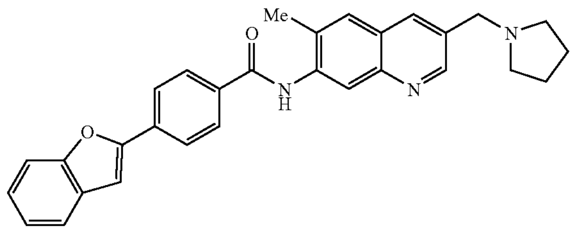

By operating in the same manner as in Example 50 and using 4-bromo-N-[6-methyl-3-(1-pyrrolidinylmethyl)-7-quinolinyl]benzamide obtained in Example 212, the title compound was obtained.

$^1$H-NMR (DMSO-$d_6$) δ 1.75 (4H, m), 2.47 (3H, s), 2.49 (4H, m), 3.78 (2H, s), 7.36 (3H, m), 7.65 (1H, s), 7.70 (2H, m), 7.85 (1H, s), 8.11 (2H, d, J=8.8 Hz), 8.14 (1H, s), 8.17 (2H, m), 8.79 (1H, d, J=1.7 Hz), 10.18 (1H, s). melting point: 219° C. (crystallization solvent: ethyl acetate-isopropyl ether)

Example 222

N-[6-methyl-3-(1-pyrrolidinylmethyl)-7-quinolinyl]-4-(2-naphthyl)benzamide

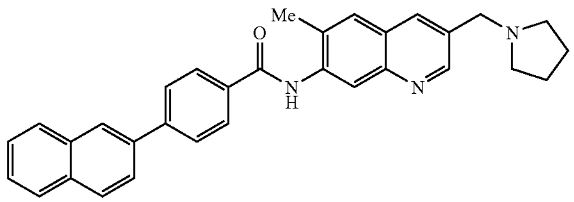

By operating in the same manner as in Example 50 and using 4-bromo-N-[6-methyl-3-(1-pyrrolidinylmethyl)-7-quinolinyl]benzamide obtained in Example 212, the title compound was obtained.

$^1$H-NMR (DMSO-$d_6$) δ 1.74 (4H, m), 2.50 (3H, s), 2.51 (4H, m), 3.78 (2H, s), 7.58 (2H, m), 7.86 (1H, s), 7.97 (2H, m), 8.06 (4H, m), 8.13 (1H, s), 8.14 (1H, s), 8.20 (2H, d, J=8.6 Hz), 8.37 (1H, d, J=1.2 Hz), 8.80 (1H, d, J=2.2 Hz), 10.17 (1H, s). melting point: 194° C. (crystallization solvent: ethyl acetate-isopropyl ether) Elemental analysis for $C_{32}H_{29}N_3O.0.25H_2O$ Calculated: C, 80.72; H, 6.24; N, 8.82. Found: C, 80.96; H, 6.25; N, 8.51.

Example 223

N-[6-methyl-3-(1-pyrrolidinylmethyl)-7-quinolinyl]-4-thien-3-ylbenzamide

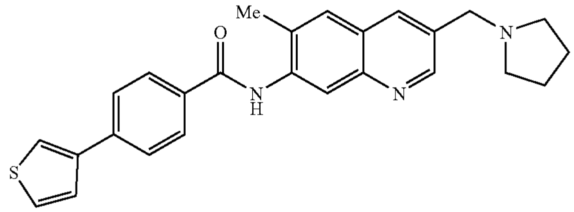

By operating in the same manner as in Example 50 and using 4-bromo-N-[6-methyl-3-(1-pyrrolidinylmethyl)-7-quinolinyl]benzamide obtained in Example 212, the title compound was obtained.

$^1$H-NMR (DMSO-$d_6$) δ 1.73 (4H, m), 2.47 (3H, s), 2.50 (4H, m), 3.78 (2H, s), 7.70 (2H, m), 7.85 (1H, s), 7.93 (2H, d, J=8.6 Hz), 8.09 (4H, m), 8.14 (1H, s), 8.79 (1H, d, J=2.0 Hz), 10.09 (1H, s). melting point: 187° C. (crystallization solvent: ethyl acetate-isopropyl ether) Elemental analysis for $C_{26}H_{25}N_3OS$ Calculated: C, 73.04; H, 5.89; N, 9.83. Found: C, 72.64; H, 5.91; N, 9.46.

Example 224

4-(2-furyl)-N-[6-methyl-3-(1-pyrrolidinylmethyl)-7-quinolinyl]benzamide

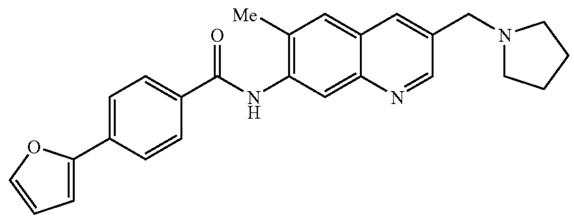

By operating in the same manner as in Example 50 and using 4-bromo-N-[6-methyl-3-(1-pyrrolidinylmethyl)-7-quinolinyl]benzamide obtained in Example 212, the title compound was obtained.

$^1$H-NMR (DMSO-$d_6$) δ 1.69 (4H, m), 2.44 (3H, s), 2.47 (4H, m), 3.75 (2H, s), 6.64 (1H, dd, J=3.4, 2.0 Hz), 7.13 (1H, d, J=3.4 Hz), 7.82 (2H, m), 7.85 (2H, d, J=8.6 Hz), 8.07 (4H, m), 8.76 (1H, d, J=2.0 Hz), 10.08 (1H, s). melting point: 154° C. (crystallization solvent: ethyl acetate-isopropyl ether) Elemental analysis for $C_{26}H_{25}N_3O_2$ Calculated: C, 75.89; H, 6.12; N, 10.21. Found: C, 75.67; H, 6.11; N, 9.87.

Example 225

4-bromo-2-fluoro-N-[6-methyl-3-(1-pyrrolidinylmethyl)-7-quinolinyl]benzamide

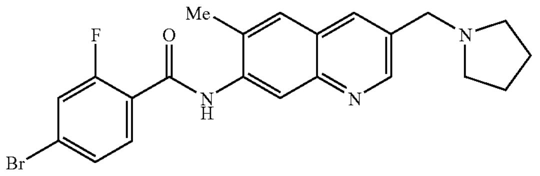

By successively operating in the same manner as in Reference Example 4 and Example 1 and using 4-bromo-N-[6-methyl-3-(1-pyrrolidinylmethyl)-7-quinolinyl]benzamide obtained in Example 212, the title compound was obtained.

$^1$H-NMR(DMSO-$d_6$) δ 1.71 (4H, m), 2.47 (3H, s), 2.50 (4H, m), 3.76 (2H, s), 7.60 (1H, dd, J=1.4, 8.0 Hz), 7.72–7.84 (3H, m), 8.10 (1H, m), 8.26 (1H, m), 8.77 (1H, d, J=1.8 Hz), 10.04 (1H, s).

Example 226

3-fluoro-N-[6-methyl-3-(1-pyrrolidinylmethyl)-7-quinolinyl][1,1'-biphenyl]-4-carboxamide

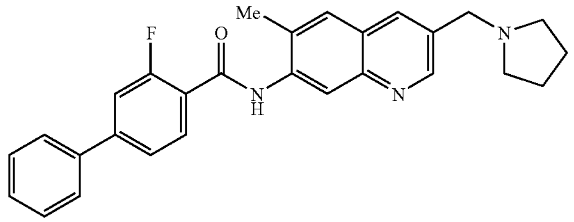

By operating in the same manner as in Example 50 and using 4-bromo-2-fluoro-N-[6-methyl-3-(1-pyrrolidinylmethyl)-7-quinolinyl]benzamide obtained in Example 225, the title compound was obtained.

$^1$H-NMR(DMSO-$d_6$) δ 1.72 (4H, m), 2.49 (4H, m), 2.51 (3H, s), 3.79 (2H, s), 7.42–7.56 (3H, m), 7.67–7.86 (5H, m), 7.92 (1H, m), 8.12 (1H, s), 8.34 (1H, s), 8.79 (1H, d, J=1.8 Hz), 9.99 (1H, s). melting point: 180–183° C. (crystallization solvent: ethyl acetate-isopropyl ether) FABMS(pos) 440 [M+H]+

Example 227

3-fluoro-4'-methoxy-N-[6-methyl-3-(1-pyrrolidinylmethyl)-7-quinolinyl][1,1'-biphenyl]-4-carboxamide

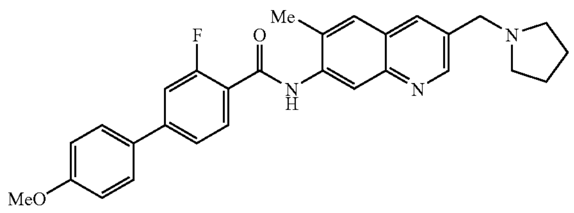

By operating in the same manner as in Example 50 and using 4-bromo-2-fluoro-N-[6-methyl-3-(1-pyrrolidinylmethyl)-7-quinolinyl]benzamide obtained in Example 225, the title compound was obtained.

$^1$H-NMR(DMSO-$d_6$) δ 1.73 (4H, m), 2.50 (7H, m), 3.82 (5H, m), 7.07 (2H, d, J=8.4 Hz), 7.63–7.73 (2H, m), 7.77 (2H, d, J=8.4 Hz), 7.82–7.92 (2H, m), 8.14 (1H, s), 8.35 (1H, s), 8.80 (1H, s), 9.94 (1H, d, J=3.0 Hz). melting point: 187–190° C. (crystallization solvent: ethyl acetate-isopropyl ether) FABMS(pos) 470 [M+H]+

Example 228

3,4'-difluoro-N-[6-methyl-3-(1-pyrrolidinylmethyl)-7-quinolinyl][1,1'-biphenyl]-4-carboxamide

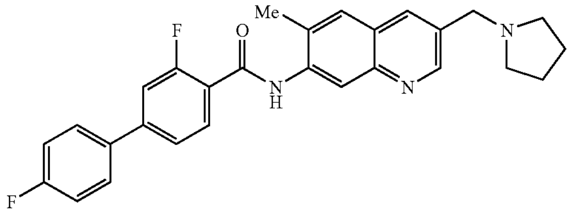

By operating in the same manner as in Example 50 and using 4-bromo-2-fluoro-N-[6-methyl-3-(1-pyrrolidinylmethyl)-7-quinolinyl]benzamide obtained in Example 225, the title compound was obtained.

$^1$H-NMR(DMSO-$d_6$) δ 1.73 (4H, m), 2.51 (7H, m), 3.81 (2H, s), 7.37 (2H, m), 7.67–7.80 (2H, m), 7.82–7.96 (4H, m), 8.14 (1H, s), 8.34 (1H, s), 8.80 (1H, s), 10.04 (1H, m). melting point: 174–177° C. (crystallization solvent: ethyl acetate-isopropyl ether) FABMS(pos) 458 [M+H]+

Example 229

3-fluoro-4'-methyl-N-[6-methyl-3-(1-pyrrolidinylmethyl)-7-quinolinyl][1,1'-biphenyl]-4-carboxamide

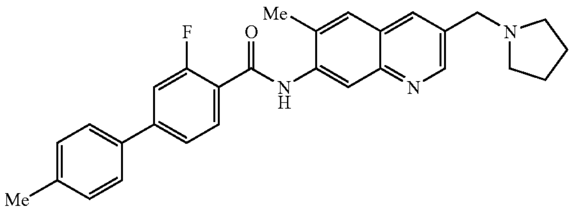

By operating in the same manner as in Example 50 and using 4-bromo-2-fluoro-N-[6-methyl-3-(1-pyrrolidinylmethyl)-7-quinolinyl]benzamide obtained in Example 225, the title compound was obtained.

$^1$H-NMR(DMSO-$d_6$) δ 1.73 (4H, m), 2.37 (3H, s), 2.50 (7H, m), 3.82 (2H, s), 7.33 (2H, d, J=8.0 Hz), 7.64–7.75 (4H, m), 7.82–7.94 (2H, m), 8.13 (1H, s), 8.34 (1H, s), 8.79 (1H, d, J=1.8 Hz), 9.93 (1H, s). melting point: 176–179° C. (crystallization solvent: ethyl acetate-isopropyl ether) FABMS(pos) 454 [M+H]+

Example 230

4'-chloro-3-fluoro-N-[6-methyl-3-(1-pyrrolidinylmethyl)-7-quinolinyl][1,1'-biphenyl]-4-carboxamide

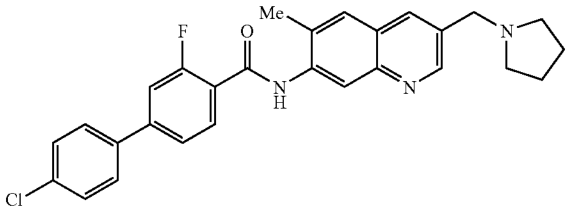

By operating in the same manner as in Example 50 and using 4-bromo-2-fluoro-N-[6-methyl-3-(1-pyrrolidinylmethyl)-7-quinolinyl]benzamide obtained in Example 225, the title compound was obtained.

$^1$H-NMR(DMSO-$d_6$) δ 1.72 (4H, m), 2.50 (7H, m), 3.79 (2H, s), 7.58 (2H, d, J=8.4 Hz), 7.66–7.97 (6H, m), 8.12 (1H, s), 8.33 (1H, s), 8.79 (1H, d, J=1.8 Hz), 10.01 (1H, s). melting point: 195–198° C. (crystallization solvent: ethyl acetate-isopropyl ether) FABMS(pos) 474 [M+H]+

Example 231

4-bromo-3-fluoro-N-[6-methyl-3-(1-pyrrolidinylmethyl)-7-quinolinyl]benzamide

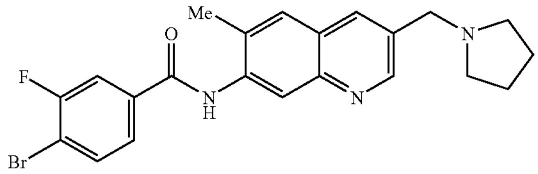

By successively operating in the same manner as in Reference Example 4 and Example 1 and using 4-bromo-N-[6-methyl-3-(1-pyrrolidinylmethyl)-7-quinolinyl]benzamide obtained in Example 212, the title compound was obtained.

$^1$H-NMR(DMSO-$d_6$) δ 1.71 (4H, m), 2.44 (3H, s), 2.50 (4H, m), 3.76 (2H, s), 7.78–8.06 (5H, m), 8.12 (1H, m), 8.78 (1H, d, J=1.8 Hz), 10.24 (1H, s).

Example 232

2-fluoro-N-[6-methyl-3-(1-pyrrolidinylmethyl)-7-quinolinyl][1,1'-biphenyl]-4-carboxamide

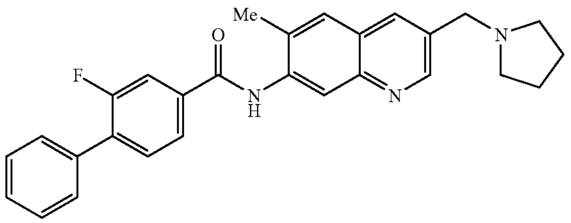

By operating in the same manner as in Example 50 and using 4-bromo-3-fluoro-N-[6-methyl-3-(1-pyrrolidinylmethyl)-7-quinolinyl]benzamide obtained in Example 231, the title compound was obtained.

$^1$H-NMR(DMSO-$d_6$) δ 1.74 (4H, m), 2.50 (7H, m), 3.80 (2H, s), 7.46–7.82 (6H, m), 7.87 (1H, s), 7.92–8.03 (2H, m), 8.09 (1H, s), 8.16 (1H, m), 8.80 (1H, m), 10.23 (1H, s). melting point: 167–170° C. (crystallization solvent: ethyl acetate-isopropyl ether) FABMS(pos) 440 [M+H]+

Example 233

2,4'-difluoro-N-[6-methyl-3-(1-pyrrolidinylmethyl)-7-quinolinyl][1,1'-biphenyl]-4-carboxamide

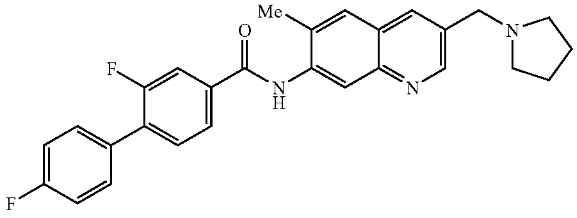

By operating in the same manner as in Example 50 and using 4-bromo-3-fluoro-N-[6-methyl-3-(1-pyrrolidinylmethyl)-7-quinolinyl]benzamide obtained in Example 231, the title compound was obtained.

$^1$H-NMR(DMSO-$d_6$) δ 1.73 (4H, m), 2.47 (3H, s), 2.50 (4H, m), 3.79 (2H, s), 7.39 (2H, m), 7.64–7.80 (3H, m), 7.86 (1H, s), 7.92–8.03 (2H, m), 8.06–8.17 (2H, m), 8.80 (1H, d, J=2.2 Hz), 10.24 (1H, s). melting point: 163–166° C. (crystallization solvent: ethyl acetate-isopropyl ether) FABMS (pos) 458 [M+H]+

Example 234

2-fluoro-4'-methyl-N-[6-methyl-3-(1-pyrrolidinylmethyl)-7-quinolinyl][1,1'-biphenyl]-4-carboxamide

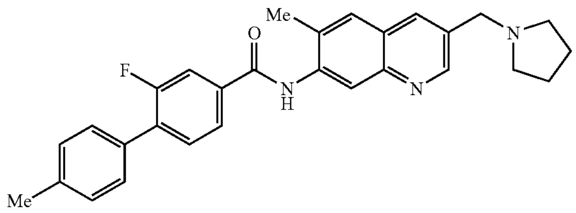

By operating in the same manner as in Example 50 and using 4-bromo-3-fluoro-N-[6-methyl-3-(1-pyrrolidinylmethyl)-7-quinolinyl]benzamide obtained in Example 231, the title compound was obtained.

$^1$H-NMR(DMSO-$d_6$) δ 1.72 (4H, m), 2.38 (3H, s), 2.46 (3H, s), 2.50 (4H, m), 3.78 (2H, s), 7.34 (2H, d, J=8.4 Hz), 7.53 (2H, m), 7.71 (1H, m), 7.85 (1H, s), 7.89–8.00 (2H, m), 8.08 (1H, s), 8.13 (1H, s), 8.79 (1H, m), 10.21 (1H, s). melting point: 175–178° C. (crystallization solvent: ethyl acetate-isopropyl ether) FABMS(pos) 454 [M+H]+

Example 235

4'-chloro-2-fluoro-N-[6-methyl-3-(1-pyrrolidinylmethyl)-7-quinolinyl][1,1'-biphenyl]-4-carboxamide

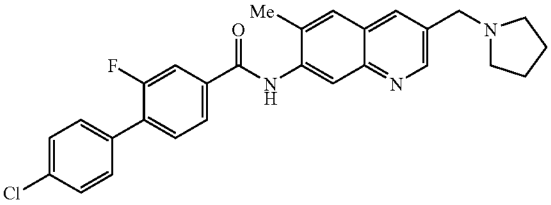

By operating in the same manner as in Example 50 and using 4-bromo-3-fluoro-N-[6-methyl-3-(1-pyrrolidinylmethyl)-7-quinolinyl]benzamide obtained in Example 231, the title compound was obtained.

$^1$H-NMR(DMSO-$d_6$) δ 1.72 (4H, m), 2.46 (3H, s), 2.50 (4H, m), 3.78 (2H, s), 7.56–7.73 (4H, m), 7.75 (1H, m), 7.85 (1H, s), 7.92–8.02 (2H, m), 8.08 (1H, s), 8.14 (1H, m), 8.79 (1H, d, J=1.8 Hz), 10.24 (1H, s). melting point: 181–185° C. (crystallization solvent: ethyl acetate-isopropyl ether) FABMS(pos) 474 [M+H]+

Example 236

2-fluoro-4'-methoxy-N-[6-methyl-3-(1-pyrrolidinylmethyl)-7-quinolinyl][1,1'-biphenyl]-4-carboxamide

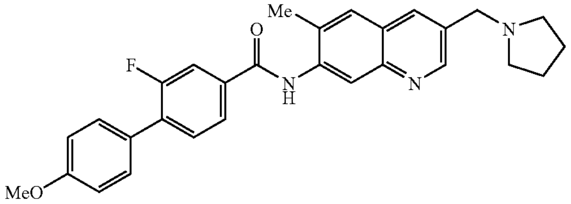

By operating in the same manner as in Example 50 and using 4-bromo-3-fluoro-N-[6-methyl-3-(1-pyrrolidinylmethyl)-7-quinolinyl]benzamide obtained in Example 231, the title compound was obtained.

$^1$H-NMR(DMSO-$d_6$) δ 1.72 (4H, m), 2.46 (3H, s), 2.50 (4H, m), 3.78 (2H, s), 3.83 (3H, s), 7.09 (2H, d, J=8.8 Hz), 7.60 (2H, m), 7.71 (1H, m), 7.85 (1H, s), 7.89–7.99 (2H, m), 8.08 (1H, s), 8.14 (1H, m), 8.79 (1H, d, J=1.8 Hz), 10.19 (1H, s). melting point: 165–167° C. (crystallization solvent: ethyl acetate-isopropyl ether) FABMS(pos) 470 [M+H]+

Example 237

N-[3-(1-azepanylmethyl)-6-methyl-7-quinolinyl]-4-bromobenzamide

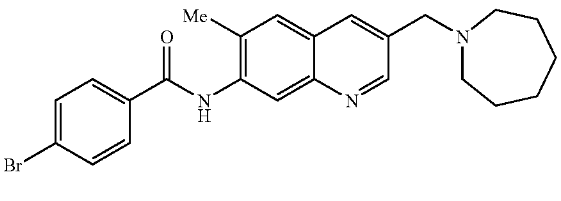

By operating in the same manner as in Reference Example 3 and using 4-bromo-N-[3-(chloromethyl)-6-methyl-7-quinolinyl]benzamide hydrochloride obtained in Reference Example 56, the title compound was obtained.

$^1$H-NMR (DMSO-$d_6$) δ 1.59 (8H, m), 2.44 (3H, s), 2.63 (4H, m), 3.80 (2H, s), 7.78 (2H, d, J=8.8 Hz), 7.84 (1H, s), 7.98 (2H, d, J=8.8 Hz), 8.06 (1H, s), 8.12 (1H, m), 8.81 (1H, d, J=2.2 Hz), 10.19 (1H, s).

Example 238

N-[3-(1-azepanylmethyl)-6-methyl-7-quinolinyl]-4'-chloro[1,1'-biphenyl]-4-carboxamide

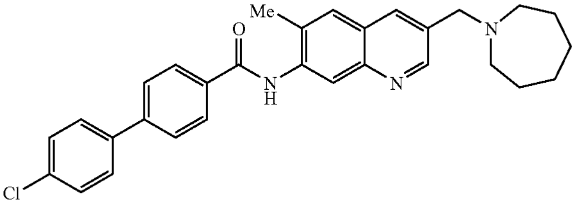

By operating in the same manner as in Example 50 and using N-[3-(1-azepanylmethyl)-6-methyl-7-quinolinyl]-4-bromobenzamide obtained in Example 237, the title compound was obtained.

$^1$H-NMR ($CDCl_3$) δ 1.60 (4H, s), 1.63 (4H, m), 2.54 (3H, s), 2.66 (4H, m), 3.80 (2H, s), 7.45 (2H, m), 7.57 (2H, m), 7.65 (1H, s), 7.70 (2H, d, J=8.1 Hz), 7.94 (2H, m), 8.01 (2H, d, J=8.3 Hz), 8.74 (1H, s), 8.87 (1H, d, J=2.0 Hz). melting point: 204° C. (crystallization solvent: ethyl acetate-isopropyl ether) Elemental analysis for $C_{30}H_{30}ClN_3O$ Calculated: C, 74.44; H, 6.25; N, 8.68. Found: C, 74.30; H, 6.15; N, 8.59.

Example 239

N-[3-(1-azepanylmethyl)-6-methyl-7-quinolinyl]-4'-methoxy[1,1'-biphenyl]-4-carboxamide

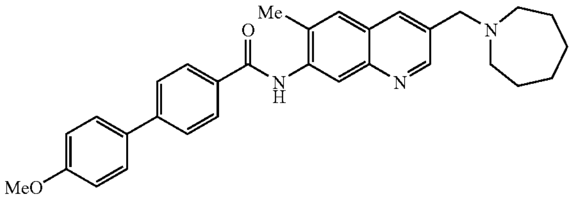

By operating in the same manner as in Example 50 and using N-[3-(1-azepanylmethyl)-6-methyl-7-quinolinyl]-4-bromobenzamide obtained in Example 237, the title compound was obtained.

$^1$H-NMR ($CDCl_3$) δ 1.57 (4H, m), 1.60 (4H, m), 2.51 (3H, s), 2.63 (4H, m), 3.77 (2H, s), 3.84 (3H, s), 6.99 (2H, m), 7.56 (2H, m), 7.61 (1H, s), 7.67 (2H, d, J=8.1 Hz), 7.90 (1H, s), 7.93 (1H, d, J=1.2 Hz), 7.96 (2H, d, J=8.1 Hz), 8.72 (1H, s), 8.83 (1H, d, J=2.2 Hz). melting point: 161° C. (crystallization solvent: ethyl acetate-isopropyl ether)

Example 240

N-[3-(1-azepanylmethyl)-6-methyl-7-quinolinyl]-4-(1-benzofuran-2-yl)benzamide

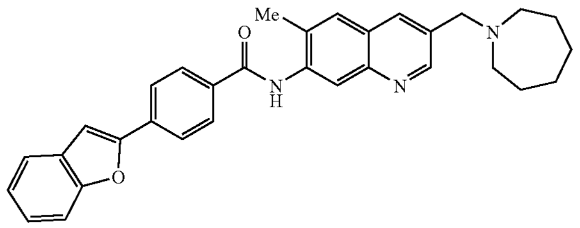

By operating in the same manner as in Example 50 and using N-[3-(1-azepanylmethyl)-6-methyl-7-quinolinyl]-4-bromobenzamide obtained in Example 237, the title compound was obtained.

$^1$H-NMR ($CDCl_3$) δ 1.62 (8H, m), 2.55 (3H, s), 2.67 (4H, m), 3.79 (2H, s), 7.17 (1H, s), 7.26 (2H, m), 7.33 (1H, m), 7.56 (1H, d, J=8.1 Hz), 7.63 (2H, m), 7.95 (2H, m), 8.01 (3H, m), 8.74 (1H, s), 8.86 (1H, d, J=2.0 Hz). melting point: 207° C. (crystallization solvent: ethyl acetate-isopropyl ether) Elemental analysis for $C_{32}H_{31}N_3O_2$ Calculated: C, 78.50; H, 6.38; N, 8.58. Found: C, 78.78; H, 6.38; N, 8.29.

Example 241

N-[3-(1-azepanylmethyl)-6-methyl-7-quinolinyl]-4-(5-chlorothien-2-yl)benzamide

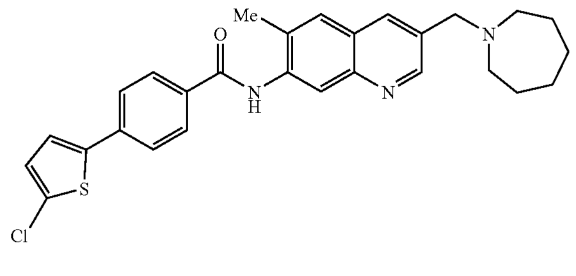

By operating in the same manner as in Example 50 and using N-[3-(1-azepanylmethyl)-6-methyl-7-quinolinyl]-4-bromobenzamide obtained in Example 237, the title compound was obtained.

$^1$H-NMR ($CDCl_3$) δ 1.62 (8H, m), 2.52 (3H, s), 2.66 (4H, m), 3.79 (2H, s), 6.94 (1H, d, J=3.9 Hz), 7.19 (1H, d, J=3.9 Hz), 7.63 (3H, m), 7.90 (1H, s), 7.94 (2H, d, J=8.3 Hz), 7.95 (1H, s), 8.72 (1H, s), 8.86 (1H, d, J=2.2 Hz). melting point: 180° C. (crystallization solvent: ethyl acetate-isopropyl ether) Elemental analysis for $C_{28}H_{28}ClN_3OS$ Calculated: C, 68.62; H, 5.76; N, 8.57. Found: C, 68.42; H, 5.74; N, 8.43.

Example 242

N-[3-(1-azepanylmethyl)-6-methyl-7-quinolinyl]-4-bromo-2-fluorobenzamide

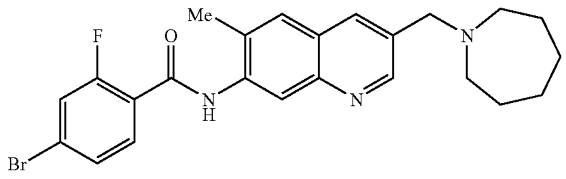

By successively operating in the same manner as in four Reference Example and Example 1 and using N-[3-(1-azepanylmethyl)-6-methyl-7-quinolinyl]-4-bromobenzamide obtained in Example 237, the title compound was obtained.

$^1$H-NMR (DMSO-$d_6$) δ 1.58 (8H, m), 2.47 (3H, s), 2.62 (4H, m), 3.79 (2H, s), 7.61 (1H, dd, J=8.2, 1.7 Hz), 7.81 (3H, m), 8.11 (1H, s), 8.27 (1H, m), 8.81 (1H, d, J=2.2 Hz), 10.06 (1H, s).

Example 243

N-[3-(1-azepanylmethyl)-6-methyl-7-quinolinyl]-4'-chloro-3-fluoro[1,1'-biphenyl]-4-carboxamide

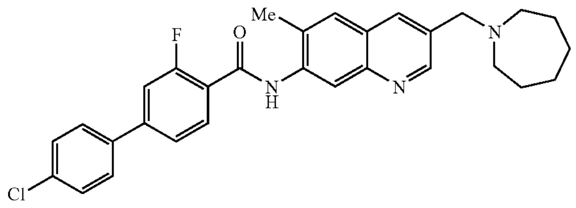

By operating in the same manner as in Example 50 and using N-[3-(1-azepanylmethyl)-6-methyl-7-quinolinyl]-4-bromo-2-fluorobenzamide obtained in Example 242, the title compound was obtained.

$^1$H-NMR ($CDCl_3$) δ 1.61 (8H, m), 2.52 (3H, s), 2.64 (4H, m), 3.77 (2H, s), 7.37 (1H, m), 7.43 (2H, m), 7.52 (3H, m), 7.61 (1H, s), 7.92 (1H, s), 8.31 (1H, t, J=8.4 Hz), 8.66 (1H, d, J=16.9 Hz), 8.84 (1H, d, J=2.0 Hz), 8.94 (1H, s). melting point: 209° C. (crystallization solvent: ethyl acetate-isopropyl ether) Elemental analysis for $C_{30}H_{29}ClFN_3O$ Calculated: C, 71.77; H, 5.82; N, 8.37. Found: C, 72.25; H, 5.63; N, 8.06.

Example 244

N-[3-(1-azepanylmethyl)-6-methyl-7-quinolinyl]-3,4'-difluoro[1,1'-biphenyl]-4-carboxamide

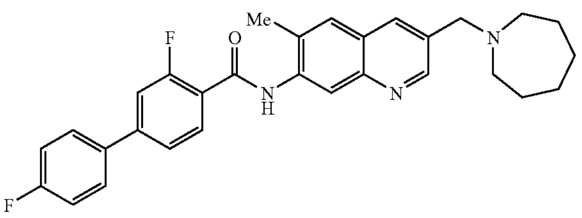

By operating in the same manner as in Example 50 and using N-[3-(1-azepanylmethyl)-6-methyl-7-quinolinyl]-4-bromo-2-fluorobenzamide obtained in Example 242, the title compound was obtained.

$^1$H-NMR ($CDCl_3$) δ 1.62 (8H, m), 2.55 (3H, s), 2.67 (4H, m), 3.80 (2H, s), 7.18 (2H, m), 7.39 (1H, m), 7.53 (1H, dd, J=8.3, 1.7 Hz), 7.61 (2H, m), 7.64 (1H, s), 7.96 (1H, s), 8.34 (1H, m), 8.69 (1H, d, J=16.6 Hz), 8.87 (1H, d, J=2.0 Hz), 8.97 (1H, s). melting point: 170° C. (crystallization solvent: ethyl acetate-isopropyl ether) Elemental analysis for $C_{30}H_{29}F_2N_3O$ Calculated: C, 74.21; H, 6.02; N, 8.65. Found: C, 74.72; H, 5.75; N, 8.41.

Example 245

N-[3-(1-azepanylmethyl)-6-methyl-7-quinolinyl]-3-fluoro-4'-methoxy[1,1'-biphenyl]-4-carboxamide

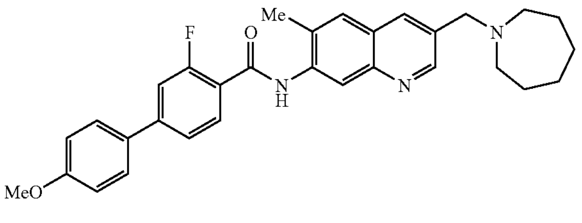

By operating in the same manner as in Example 50 and using N-[3-(1-azepanylmethyl)-6-methyl-7-quinolinyl]-4-bromo-2-fluorobenzamide obtained in Example 242, the title compound was obtained.

$^1$H-NMR ($CDCl_3$) δ 1.63 (8H, m), 2.55 (3H, s), 2.67 (4H, m), 3.80 (2H, s), 3.87 (3H, s), 7.02 (2H, m), 7.39 (1H, m), 7.54 (1H, dd, J=8.2, 1.6 Hz), 7.59 (2H, m), 7.64 (1H, s), 7.95 (1H, s), 8.31 (1H, m), 8.70 (1H, d, J=17.1 Hz), 8.86 (1H, d, J=2.2 Hz), 8.98 (1H, s). melting point: 168° C. (crystallization solvent: ethyl acetate-isopropyl ether) Elemental analysis for $C_{31}H_{32}FN_3O_2$ Calculated: C, 74.83; H, 6.48; N, 8.44. Found: C, 75.02; H, 6.62; N, 8.10.

Example 246

N-[3-(1-azepanylmethyl)-6-methyl-7-quinolinyl]-3-fluoro[1,1'-biphenyl]-4-carboxamide

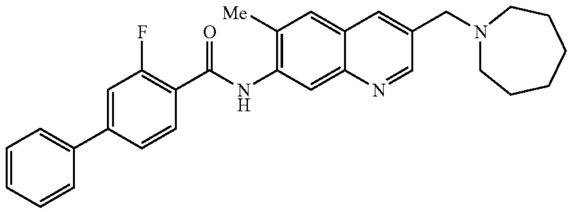

By operating in the same manner as in Example 50 and using N-[3-(1-azepanylmethyl)-6-methyl-7-quinolinyl]-4-bromo-2-fluorobenzamide obtained in Example 242, the title compound was obtained.

$^1$H-NMR ($CDCl_3$) δ 1.62 (8H, m), 2.54 (3H, s), 2.66 (4H, m), 3.79 (2H, s), 7.45 (4H, m), 7.57 (1H, dd, J=8.2, 1.6 Hz), 7.63 (3H, m), 7.94 (1H, s), 8.33 (1H, m), 8.69 (1H, d, J=17.1 Hz), 8.86 (1H, d, J=2.0 Hz), 8.96 (1H, s). melting point: 151° C. (crystallization solvent: ethyl acetate-isopropyl ether) Elemental analysis for $C_{30}H_{30}FN_3O$ Calculated: C, 77.06; H, 6.47; N, 8.99. Found: C, 77.34; H, 6.52; N, 8.65.

Example 247

4-butoxy-N-[8-methyl-3-(1-pyrrolidinylmethyl)-7-quinolinyl]benzamide

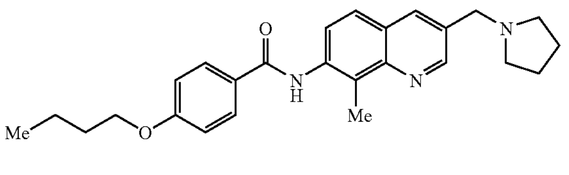

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ 0.99 (3H, t, J=7.3 Hz), 1.51 (2H, m), 1.80 (6H, m), 2.55 (4H, m), 2.80 (3H, s), 3.80 (2H, s), 4.03 (2H, t, J=6.5 Hz), 6.98 (2H, m), 7.68 (1H, d, J=9.0 Hz), 7.89 (3H, m), 8.04 (1H, d, J=2.2 Hz), 8.22 (1H, d, J=8.8 Hz), 8.87 (1H, d, J=2.2 Hz). melting point: 161° C. (crystallization solvent: diisopropyl ether)

Example 248

N-{3-[(dimethylamino)methyl]-6-methyl-7-quinolinyl}-4'-fluoro[1,1'-biphenyl]-4-carboxamide

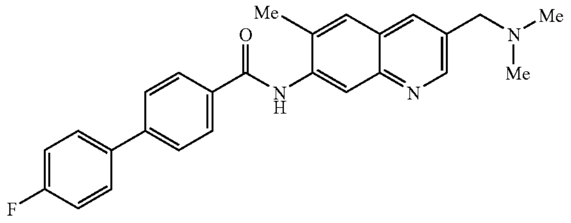

By operating in the same manner as in Example 42 and using N-[3-(chloromethyl)-6-methyl-7-quinolinyl]-4'-fluoro[1,1'-biphenyl]-4-carboxamide obtained in Reference Example 64, the title compound was obtained.

$^1$H-NMR (DMSO-$d_6$) δ 2.20 (6H, s), 2.47 (3H, s), 3.59 (2H, s), 7.35 (2H, m), 7.80–7.90 (5H, m), 8.08–8.16 (4H, m), 8.77 (1H, d, J=1.5 Hz), 10.15 (1H, s). melting point: 183–186° C. (crystallization solvent: ethyl acetate-isopropyl ether) FABMS(pos) 414 [M+H]+

Example 249

N-{3-[(diethylamino)methyl]-6-methyl-7-quinolinyl)-4'-fluoro[1,1'-biphenyl]-4-carboxamide

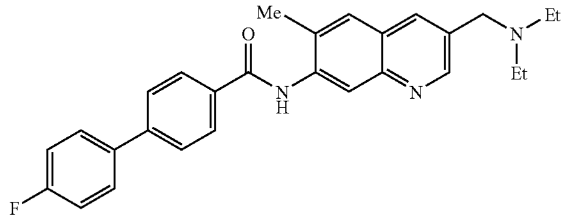

By operating in the same manner as in Example 42 and using N-[3-(chloromethyl)-6-methyl-7-quinolinyl]-4'-fluoro[1,1'-biphenyl]-4-carboxamide obtained in Reference Example 64, the title compound was obtained.

$^1$H-NMR (DMSO-$d_6$) δ 1.02 (6H, t, J=7.2 Hz), 2.20–2.64 (4H, m), 2.48 (3H, s), 3.74 (2H, s), 7.35 (2H, m), 7.77–7.92 (5H, m), 8.06–8.18 (4H, m), 8.79 (1H, d, J=1.8 Hz), 10.14 (1H, s). melting point: 145–148° C. (crystallization solvent: ethyl acetate-isopropyl ether) FABMS(pos) 442 [M+H]+

Example 250

4'-fluoro-N-[6-methyl-3-(1-piperidinylmethyl)-7-quinolinyl][1,1'-biphenyl]-4-carboxamide

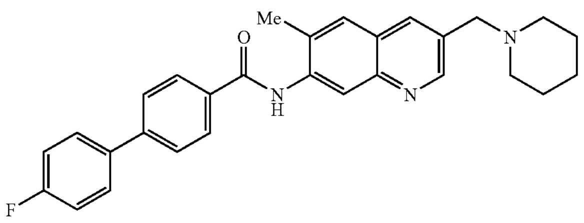

By operating in the same manner as in Example 42 and using N-[3-(chloromethyl)-6-methyl-7-quinolinyl]-4'-fluoro[1,1'-biphenyl]-4-carboxamide obtained in Reference Example 64, the title compound was obtained.

$^1$H-NMR (DMSO-$d_6$) δ 1.32–1.60 (6H, m), 2.39 (4H, m), 2.48 (3H, s), 3.63 (2H, s), 7.36 (2H, m), 7.76–7.92 (5H, m), 8.08–8.14 (4H, m), 8.78 (1H, d, J=1.8 Hz), 10.14 (1H, s). melting point: 185–188° C. (crystallization solvent: ethyl acetate-isopropyl ether) FABMS(pos) 454 [M+H]+

Example 251

N-[3-(1-azepanylmethyl)-6-methyl-7-quinolinyl]-4'-fluoro[1,1'-biphenyl]-4-carboxamide

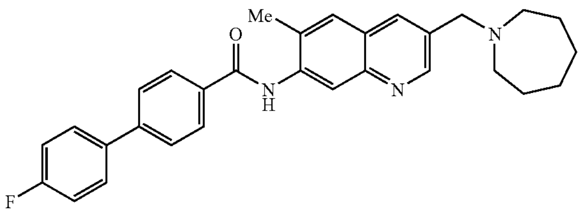

By operating in the same manner as in Example 42 and using N-[3-(chloromethyl)-6-methyl-7-quinolinyl]-4'-fluoro[1,1'-biphenyl]-4-carboxamide obtained in Reference Example 64, the title compound was obtained.

$^1$H-NMR (DMSO-$d_6$) δ 1.59 (8H, m), 2.48 (3H, s), 2.64 (4H, m), 3.81 (2H, s), 7.35 (2H, m), 7.78–7.92 (5H, m), 8.08–8.20 (4H, m), 8.81 (1H, d, J=1.8 Hz), 10.14 (1H, s). melting point: 170–174° C. (crystallization solvent: ethyl acetate-isopropyl ether) FABMS(pos) 468 [M+H]+

Example 252

4'-fluoro-N-[6-methyl-3-(4-morpholinylmethyl)-7-quinolinyl][1,1'-biphenyl]-4-carboxamide

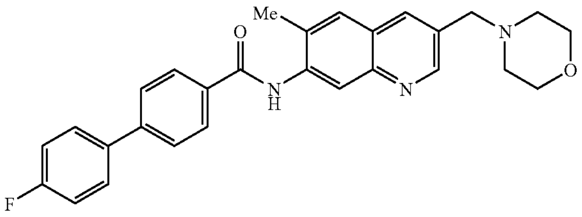

By operating in the same manner as in Example 42 and using N-[3-(chloromethyl)-6-methyl-7-quinolinyl]-4'-fluoro[1,1'-biphenyl]-4-carboxamide obtained in Reference Example 64, the title compound was obtained.

$^1$H-NMR (DMSO-$d_6$) δ 2.42 (4H, m), 2.47 (3H, s), 3.59 (4H, m), 3.67 (2H, s), 7.35 (2H, m), 7.79–7.89 (5H, m), 8.08–8.16 (4H, m), 8.79 (1H, d, J=1.8 Hz), 10.15 (1H, s). melting point: 153–158° C. (crystallization solvent: ethyl acetate-isopropyl ether) FABMS(pos) 456 [M+H]+

Example 253

N-(3-{[4-(3-amino-3-oxopropyl)-1-piperidinyl]methyl}-6-methyl-7-quinolinyl)-4'-fluoro[1,1'-biphenyl]-4-carboxamide

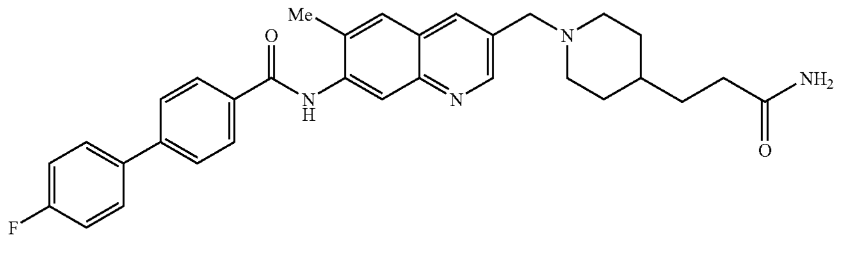

By operating in the same manner as in Example 42 and using N-[3-(chloromethyl)-6-methyl-7-quinolinyl]-4'-fluoro [1,1'-biphenyl]-4-carboxamide obtained in Reference Example 64, the title compound was obtained.

$^1$H-NMR (DMSO-$d_6$) δ 1.03–1.24 (3H, m), 1.42 (2H, m), 1.62 (2H, m), 1.95 (2H, m), 2.04 (2H, m), 2.47 (3H, s), 2.77 (2H, m), 3.63 (2H, s), 6.69 (1H, s), 7.24 (1H, s), 7.35 (2H, m), 7.78–7.90 (5H, m), 8.07–8.16 (4H, m), 8.76 (1H, s), 10.14 (1H, s). melting point: 223–227° C. (crystallization solvent: ethyl acetate-isopropyl ether) FABMS(pos) 525 [M+H]+

Example 254

4'-fluoro-N-[6-methyl-3-({4-[3-(methylamino)-3-oxopropyl]-1-piperidinyl}methyl)-7-quinolinyl][1,1'-biphenyl]-4-carboxamide

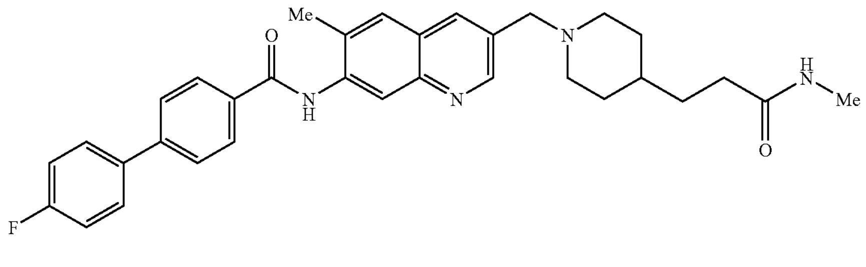

By operating in the same manner as in Example 42 and using N-[3-(chloromethyl)-6-methyl-7-quinolinyl]-4'-fluoro [1,1'-biphenyl]-4-carboxamide obtained in Reference Example 64, the title compound was obtained.

$^1$H-NMR (DMSO-$d_6$) δ 1.15 (3H, m), 1.43 (2H, m), 1.62 (2H, m), 1.95 (2H, m), 2.06 (2H, m), 2.48 (3H, s), 2.54 (3H, d, J=4.5 Hz), 2.83 (2H, m), 3.63 (2H, s), 7.36 (2H, m), 7.71 (1H, d, J=4.5 Hz), 7.80–7.90 (5H, m), 8.08–8.17 (4H, m), 8.77 (1H, d, J=1.2 Hz), 10.16 (1H, s). melting point: 207–211° C. (crystallization solvent: ethyl acetate-isopropyl ether) FABMS(pos) 539 [M+H]+

Example 255

N-[3-({4-[3-(ethylamino)-3-oxopropyl]-1-piperidinyl}methyl)-6-methyl-7-quinolinyl]-4'-fluoro[1,1'-biphenyl]-4-carboxamide

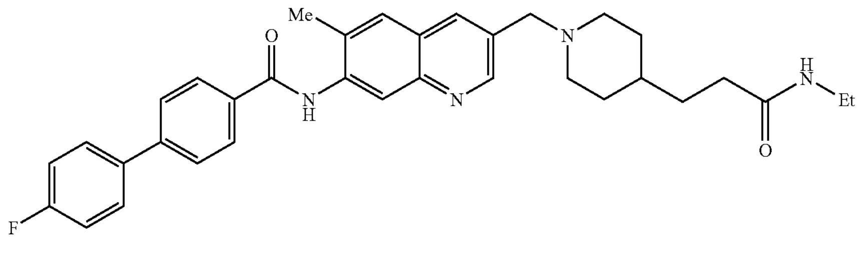

By operating in the same manner as in Example 42 and using N-[3-(chloromethyl)-6-methyl-7-quinolinyl]-4'-fluoro[1,1'-biphenyl]-4-carboxamide obtained in Reference Example 64, the title compound was obtained.

$^1$H-NMR (DMSO-$d_6$) δ 0.98 (3H, t, J=7.2 Hz), 1.14 (3H, m), 1.41 (2H, m), 1.61 (2H, m), 1.94 (2H, m), 2.04 (2H, m), 2.47 (3H, s), 2.82 (2H, m), 3.02 (2H, m), 3.63 (2H, s), 7.35 (2H, m), 7.72–7.92 (6H, m), 8.06–8.17 (4H, m), 8.76 (1H, s), 10.15 (1H, s). melting point: 227–230° C. (crystallization solvent: ethyl acetate-isopropyl ether) FABMS(pos) 553 [M+H]+

Example 256

N-[3-({4-[3-(dimethylamino)-3-oxopropyl]-1-piperidinyl}methyl)-6-methyl-7-quinolinyl]-4'-fluoro[1,1'-biphenyl]-4-carboxamide

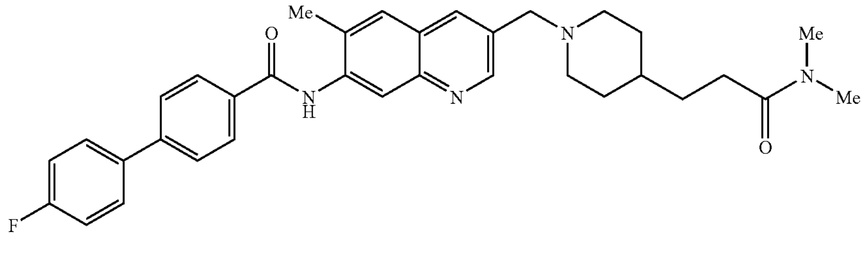

By operating in the same manner as in Example 42 and using N-[3-(chloromethyl)-6-methyl-7-quinolinyl]-4'-fluoro[1,1'-biphenyl]-4-carboxamide obtained in Reference Example 64, the title compound was obtained.

$^1$H-NMR (DMSO-$d_6$) δ 1.06–1.28 (3H, m), 1.42 (2H, m), 1.65 (2H, m), 1.96 (2H, m), 2.28 (2H, m), 2.48 (3H, s), 2.79 (3H, s), 2.84 (2H, m), 2.94 (3H, s), 3.64 (2H, s), 7.36 (2H, m), 7.80–7.90 (5H, m), 8.08–8.16 (4H, m), 8.78 (1H, s), 10.15 (1H, s). melting point: 193–196° C. (crystallization solvent: ethyl acetate-isopropyl ether) FABMS(pos) 553 [M+H]+

Example 257

N-[3-({4-[3-(diethylamino)-3-oxopropyl]-1-piperidinyl}methyl)-6-methyl-7-quinolinyl]-4'-fluoro[1,1'-biphenyl]-4-carboxamide

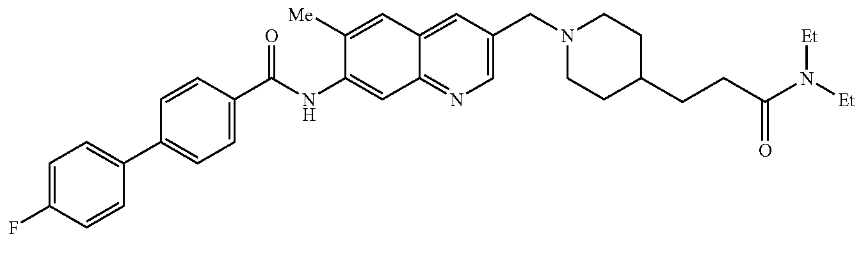

By operating in the same manner as in Example 42 and using N-[3-(chloromethyl)-6-methyl-7-quinolinyl]-4'-fluoro[1,1'-biphenyl]-4-carboxamide obtained in Reference Example 64, the title compound was obtained.

$^1$H-NMR (DMSO-$d_6$) δ 0.98 (3H, t, J=6.9 Hz), 1.07 (3H, t, J=6.9 Hz), 1.10–1.30 (3H, m), 1.43 (2H, m), 1.63 (2H, m), 1.95 (2H, m), 2.25 (2H, m), 2.47 (3H, s), 2.83 (2H, m), 3.18–3.30 (4H, m), 3.63 (2H, s), 7.35 (2H, m), 7.79–7.88 (5H, m), 8.08–8.16 (4H, m), 8.77 (1H, d, J=1.5 Hz), 10.14 (1H, s). melting point: 150–154° C. (crystallization solvent: ethyl acetate-isopropyl ether) FABMS(pos) 581 [M+H]+

Example 258

4'-fluoro-N-[6-methyl-3-({4-[3-oxo-3-(1-piperidinyl)propyl]-1-piperidinyl}methyl)-7-quinolinyl][1,1'-biphenyl]-4-carboxamide

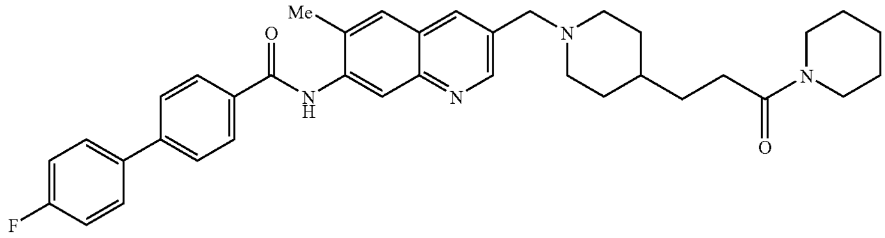

By operating in the same manner as in Example 42 and using N-[3-(chloromethyl)-6-methyl-7-quinolinyl]-4'-fluoro[1,1'-biphenyl]-4-carboxamide obtained in Reference Example 64, the title compound was obtained.

$^1$H-NMR (DMSO-$d_6$) δ 1.04–1.27 (3H, m), 1.32–1.50 (6H, m), 1.54 (2H, m), 1.64 (2H, m), 1.95 (2H, m), 2.27 (2H, m), 2.47 (3H, s), 2.82 (2H, m), 3.27–3.42 (4H, m), 3.63 (2H, s), 7.35 (2H, m), 7.79–7.89 (5H, m), 8.08–8.16 (4H, m), 8.76 (1H, s), 10.14 (1H, s). melting point: 189–191° C. (crystallization solvent: ethyl acetate-isopropyl ether) FABMS(pos) 593 [M+H]+

Example 259

4'-fluoro-N-[6-methyl-3-({4-[4-oxo-4-(1-piperidinyl) butyl]-1-piperidinyl}methyl)-7-quinolinyl][1,1'-bi-phenyl]-4-carboxamide

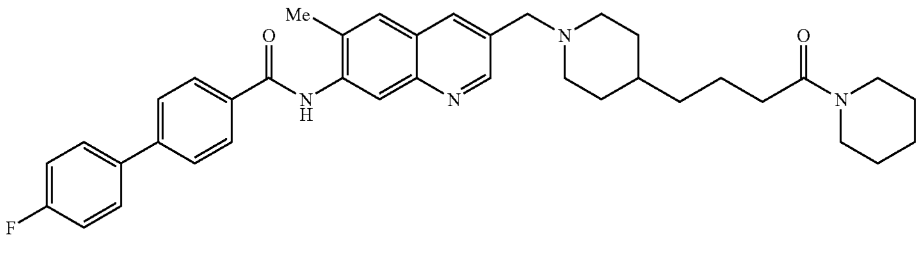

By operating in the same manner as in Example 42 and using N-[3-(chloromethyl)-6-methyl-7-quinolinyl]-4'-fluoro [1,1'-biphenyl]-4-carboxamide obtained in Reference Example 64, the title compound was obtained.

$^1$H-NMR (DMSO-$d_6$) δ 1.18 (5H, m), 1.37 (2H, m), 1.46 (4H, m), 1.54 (2H, m), 1.61 (2H, m), 1.98 (2H, m), 2.23 (2H, t, J=7.5 Hz), 2.46 (3H, s), 2.82 (2H, m), 3.36 (4H, m), 3.63 (2H, s), 7.34 (2H, m), 7.82 (5H, m), 8.10 (2H, m), 8.12 (2H, d, J=8.5 Hz), 8.76 (1H, d, J=1.5 Hz), 10.12 (1H, s). melting point: 179° C. (crystallization solvent: ethyl acetate-isopropyl ether) Elemental analysis for $C_{38}H_{43}FN_4O_2.0.25H_2O$ Calculated: C, 7.4.66; H, 7.17; N, 9.16. Found: C, 74.70; H, 7.09; N, 9.03.

Example 260

N-[3-({4-[4-(diethylamino)-4-oxobutyl]-1-piperidinyl}methyl)-6-methyl-7-quinolinyl]-4'-fluoro [1,1'-biphenyl]-4-carboxamide

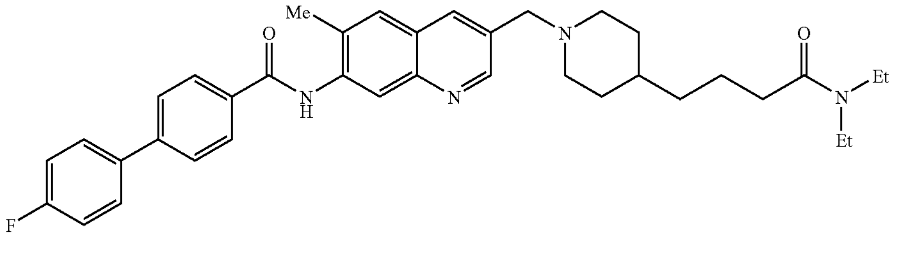

By operating in the same manner as in Example 42 and using N-[3-(chloromethyl)-6-methyl-7-quinolinyl]-4'-fluoro [1,1'-biphenyl]-4-carboxamide obtained in Reference Example 64, the title compound was obtained.

$^1$H-NMR (DMSO-$d_6$) δ 0.97 (3H, t, J=7.0 Hz), 1.07 (3H, t, J=7.0 Hz), 1.13 (1H, m), 1.18 (3H, m), 1.49 (2H, m), 1.61 (2H, m), 1.96 (2H, m), 2.21 (2H, t, J=7.3 Hz), 2.46 (3H, s), 2.82 (2H, m), 3.24 (5H, m), 3.63 (2H, s), 7.34 (2H, m), 7.82 (5H, m), 8.11 (4H, m), 8.76 (1H, d, J=1.7 Hz), 10.12 (1H, s). melting point: 181° C. (crystallization solvent: ethyl acetate-isopropyl ether) Elemental analysis for $C_{37}H_{43}FN_4O_2.0.25H_2O$ Calculated: C, 74.15; H, 7.32; N, 9.34. Found: C, 74.18; H, 7.38; N, 9.28.

Example 261

N-[3-({4-[4-(ethylamino)-4-oxobutyl]-1-piperidinyl}methyl)-6-methyl-7-quinolinyl]-4'-fluoro[1,1'-biphenyl]-4-carboxamide

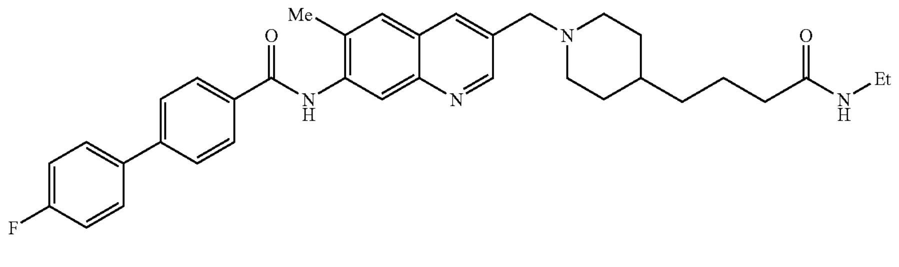

By operating in the same manner as in Example 42 and using N-[3-(chloromethyl)-6-methyl-7-quinolinyl]-4'-fluoro[1,1'-biphenyl]-4-carboxamide obtained in Reference Example 64, the title compound was obtained.

$^1$H-NMR (DMSO-$d_6$) δ 0.97 (3H, t, J=7.2 Hz), 1.14 (5H, m), 1.47 (2H, m), 1.60 (2H, m), 1.97 (4H, m), 2.46 (3H, s), 2.82 (2H, m), 3.02 (2H, m), 3.62 (2H, s), 7.34 (2H, m), 7.72 (1H, m), 7.82 (5H, m), 8.09 (2H, s), 8.13 (2H, d, J=8.3 Hz), 8.76 (1H, d, J=2.0 Hz), 10.15 (1H, s). melting point: 240° C. (crystallization solvent: ethyl acetate-isopropyl ether) Elemental analysis for $C_{35}H_{39}FN_4O_2$ Calculated: C, 74.18; H, 6.94; N, 9.89. Found: C, 74.42; H, 6.92; N, 9.66.

Example 262

N-[3-({4-[4-(dimethylamino)-4-oxobutyl]-1-piperidinyl}methyl)-6-methyl-7-quinolinyl]-4'-fluoro[1,1'-biphenyl]-4-carboxamide

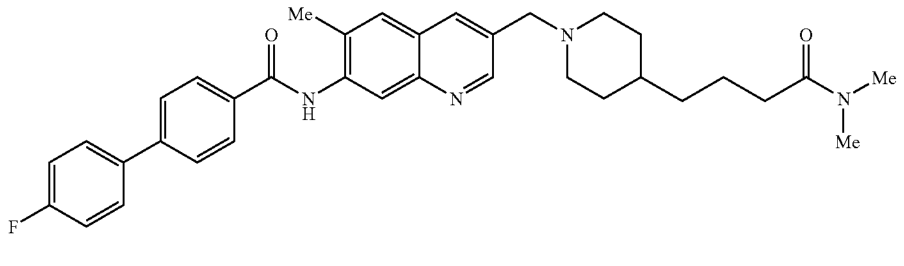

By operating in the same manner as in Example 42 and using N-[3-(chloromethyl)-6-methyl-7-quinolinyl]-4'-fluoro[1,1'-biphenyl]-4-carboxamide obtained in Reference Example 64, the title compound was obtained.

$^1$H-NMR (DMSO-$d_6$) δ 1.17 (5H, m), 1.47 (2H, m), 1.61 (2H, m), 1.96 (2H, m), 2.23 (2H, t, J=7.45 Hz), 2.46 (3H, s), 2.78 (3H, s), 2.82 (2H, m), 2.92 (3H, s), 3.63 (2H, s), 7.34 (2H, m), 7.82 (5H, m), 8.11 (4H, m), 8.76 (1H, d, J=1.5 Hz), 10.12 (1H, s). melting point: 194° C. (crystallization solvent: ethyl acetate-isopropyl ether) Elemental analysis for $C_{35}H_{39}FN_4O_2$ Calculated: C, 74.18; H, 6.94; N, 9.89. Found: C, 73.64; H, 6.97; N, 9.65.

Example 263

4'-fluoro-N-[6-methyl-3-({4-[4-(methylamino)-4-oxobutyl]-1-piperidinyl}methyl)-7-quinolinyl][1,1'-biphenyl]-4-carboxamide

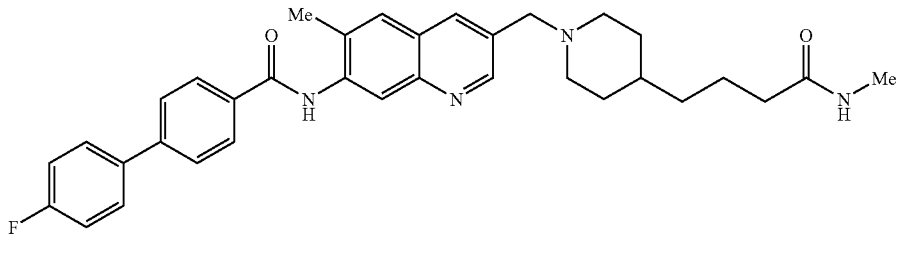

By operating in the same manner as in Example 42 and using N-[3-(chloromethyl)-6-methyl-7-quinolinyl]-4'-fluoro[1,1'-biphenyl]-4-carboxamide obtained in Reference Example 64, the title compound was obtained.

$^1$H-NMR (DMSO-$d_6$) δ 1.15 (5H, m), 1.49 (2H, m), 1.61 (2H, m), 1.99 (4H, m), 2.47 (3H, s), 2.54 (3H, d, J=4.6 Hz), 2.83 (2H, m), 3.63 (2H, s), 7.35 (2H, m), 7.67 (1H, d, J=4.2 Hz), 7.83 (5H, m), 8.10 (1H, d, J=1.2 Hz), 8.13 (3H, m), 8.76 (1H, d, J=2.0 Hz), 10.14 (1H, s). melting point: 223° C. (crystallization solvent: ethyl acetate-isopropyl ether)

Example 264

N-(3-{[4-(4-amino-4-oxobutyl)-1-piperidinyl]methyl}-6-methyl-7-quinolinyl)-4'-fluoro[1,1'-biphenyl]-4-carboxamide

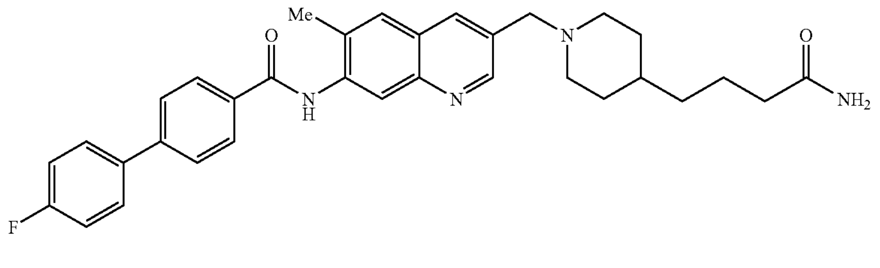

By operating in the same manner as in Example 42 and using N-[3-(chloromethyl)-6-methyl-7-quinoliny]-4'-fluoro[1,1'-biphenyl]-4-carboxamide obtained in Reference Example 64, the title compound was obtained.

$^1$H-NMR (DMSO-$d_6$) δ 1.16 (5H, m), 1.49 (2H, m), 1.62 (2H, m), 1.99 (4H, m), 2.48 (3H, s), 2.83 (2H, m), 3.64 (2H, s), 6.66 (1H, s), 7.21 (1H, s), 7.36 (2H, m), 7.83 (5H, m), 8.13 (4H, m), 8.77 (1H, d, J=2.0 Hz), 10.13 (1H, s). melting point: 228° C. (crystallization solvent: ethyl acetate-isopropyl ether) Elemental analysis for $C_{33}H_{35}FN_4O_2.0.4H_2O$ Calculated: C, 72.61; H, 6.61; N, 10.26. Found: C, 72.70; H, 6.71; N, 10.20.

Example 265

4'-fluoro-N-[6-methyl-3-({4-[2-oxo-2-(1-piperidinyl) ethyl]-1-piperidinyl}methyl)-7-quinolinyl][1,1'-biphenyl]-4-carboxamide

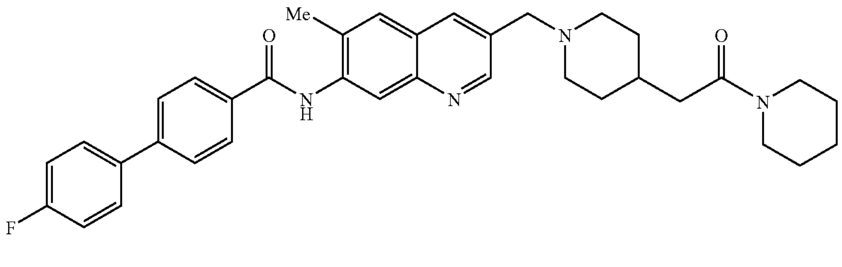

By operating in the same manner as in Example 42 and using N-[3-(chloromethyl)-6-methyl-7-quinolinyl]-4'-fluoro [1,1'-biphenyl]-4-carboxamide obtained in Reference Example 64, the title compound was obtained.

$^1$H-NMR (DMSO-$d_6$) δ 1.22 (2H, m), 1.40 (2H, m), 1.45 (2H, m), 1.56 (2H, m), 1.64 (3H, m), 1.99 (2H, m), 2.22 (2H, d, J=6.6 Hz), 2.48 (3H, s), 2.82 (2H, d, J=9.8 Hz), 3.39 (4H, m), 3.64 (2H, s), 7.36 (2H, m), 7.84 (5H, m), 8.11 (2H, s), 8.13 (2H, d, J=8.5 Hz), 8.78 (1H, d, J=1.2 Hz), 10.13 (1H, s). melting point: 216° C. (crystallization solvent: ethyl acetate-isopropyl ether) Elemental analysis for $C_{36}H_{39}FN_4O_2$ Calculated: C, 74.71; H, 6.79; N, 9.68. Found: C, 74.26; H, 6.73; N, 9.46.

Example 266

N-[3-({4-[2-(diethylamino)-2-oxoethyl]-1-piperidinyl}methyl)-6-methyl-7-quinolinyl]-4'-fluoro [1,1'-biphenyl]-4-carboxamide

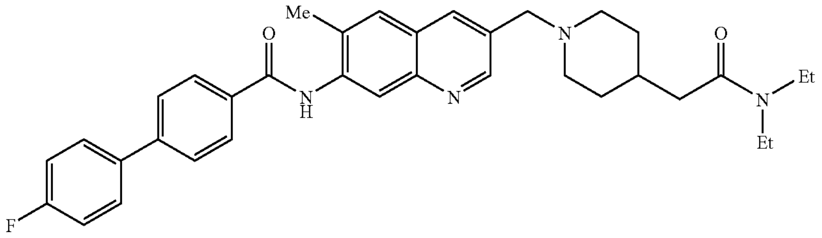

By operating in the same manner as in Example 42 and using N-[3-(chloromethyl)-6-methyl-7-quinolinyl]-4'-fluoro [1,1'-biphenyl]-4-carboxamide obtained in Reference Example 64, the title compound was obtained.

$^1$H-NMR (DMSO-$d_6$) δ 0.98 (3H, t, J=7.1 Hz), 1.07 (3H, t, J=7.1 Hz), 1.21 (2H, m), 1.63 (2H, m), 1.72 (1H, s), 1.98 (2H, m), 2.17 (2H, d, J=6.6 Hz), 2.47 (3H, s), 2.81 (2H, m), 3.25 (4H, m), 3.63 (2H, s), 7.34 (2H, m), 7.83 (5H, m), 8.10 (2H, s), 8.12 (2H, d, J=8.6 Hz), 8.76 (1H, d, J=1.7 Hz), 10.11 (1H, s). melting point: 197° C. (crystallization solvent: ethyl acetate-isopropyl ether) Elemental analysis for $C_{35}H_{39}FN_4O_2$ Calculated: C, 74.18; H, 6.94; N, 9.89. Found: C, 73.50; H, 6.87; N, 9.52.

Example 267

N-[3-({4-[2-(ethylamino)-2-oxoethyl]-1-piperidinyl}methyl)-6-methyl-7-quinolinyl]-4'-fluoro[1,1'-biphenyl]-4-carboxamide

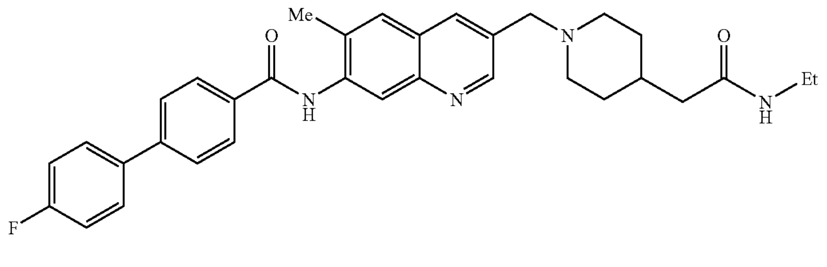

By operating in the same manner as in Example 42 and using N-[3-(chloromethyl)-6-methyl-7-quinolinyl]-4'-fluoro[1,1'-biphenyl]-4-carboxamide obtained in Reference Example 64, the title compound was obtained.

$^1$H-NMR (DMSO-$d_6$) δ 0.97 (3H, t, J=7.3 Hz), 1.17 (2H, m), 1.58 (2H, m), 1.64 (1H, m), 1.97 (4H, m), 2.46 (3H, s), 2.80 (2H, m), 3.03 (2H, m), 3.62 (2H, s), 7.34 (2H, m), 7.75 (1H, m), 7.81 (5H, m), 8.07 (1H, d, J=1.2 Hz), 8.12 (1H, s), 8.13 (2H, m), 8.74 (1H, d, J=2.0 Hz), 10.13 (1H, s). melting point: 251° C. (crystallization solvent: ethyl acetate-isopropyl ether) Elemental analysis for $C_{33}H_{35}FN_4O_2$ Calculated: C, 73.58; H, 6.55; N, 10.40. Found: C, 73.65; H, 6.76; N, 10.11.

Example 268

N-[3-({4-[2-(dimethylamino)-2-oxoethyl]-1-piperidinyl}methyl)-6-methyl-7-quinolinyl]-4'-fluoro[1,1'-biphenyl]-4-carboxamide

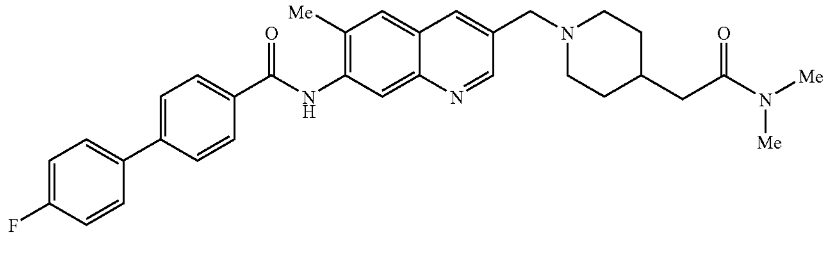

By operating in the same manner as in Example 42 and using N-[3-(chloromethyl)-6-methyl-7-quinolinyl]-4'-fluoro[1,1'-biphenyl]-4-carboxamide obtained in Reference Example 64, the title compound was obtained.

$^1$H-NMR (DMSO-$d_6$) δ 1.19 (2H, m), 1.66 (3H, m), 1.98 (2H, m), 2.20 (2H, d, J=6.6 Hz), 2.47 (3H, s), 2.81 (5H, m) 2.94 (3H, s), 3.63 (2H, s), 7.35 (2H, m), 7.83 (5H, m), 8.10 (2H, s), 8.12 (2H, d, J=8.3 Hz), 8.77 (1H, s), 10.12 (1H, s). melting point: 219° C. (crystallization solvent: ethyl acetate-isopropyl ether) Elemental analysis for $C_{33}H_{35}FN_4O_2.0.5H_2O$ Calculated: C, 72.37; H, 6.62; N, 10.22. Found: C, 72.64; H, 6.51; N, 9.98.

Example 269

4'-fluoro-N-[6-methyl-3-({4-[2-(methylamino)-2-oxoethyl]-1-piperidinyl}methyl)-7-quinolinyl][1,1'-biphenyl]-4-carboxamide

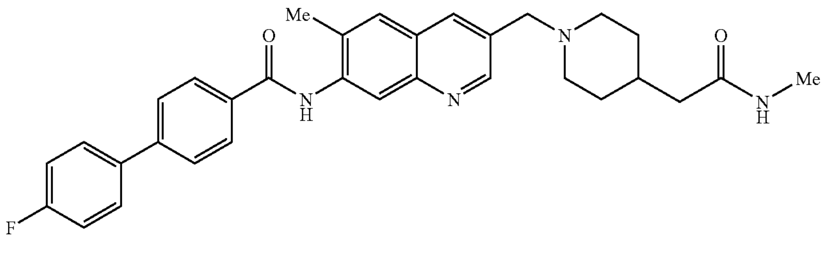

By operating in the same manner as in Example 42 and using N-[3-(chloromethyl)-6-methyl-7-quinolinyl]-4'-fluoro [1,1'-biphenyl]-4-carboxamide obtained in Reference Example 64, the title compound was obtained.

$^1$H-NMR (DMSO-$d_6$) δ 1.16 (2H, m), 1.57 (2H, m), 1.63 (1H, m), 1.97 (4H, m), 2.46 (3H, s), 2.53 (3H, d, J=4.6 Hz), 2.80 (2H, m), 3.62 (2H, s), 7.34 (2H, m), 7.69 (1H, d, J=4.6 Hz), 7.82 (5H, m), 8.07 (1H, s), 8.12 (2H, m), 8.14 (1H, s), 8.74 (1H, d, J=2.0 Hz), 10.13 (1H, s). melting point: 243° C. (crystallization solvent: ethyl acetate-isopropyl ether) Elemental analysis for $C_{32}H_{33}FN_4O_2$ Calculated: C, 73.26; H, 6.34; N, 10.68. Found: C, 73.47; H, 6.40; N, 10.40.

Example 270

N-(3-{[4-(2-amino-2-oxoethyl)-1-piperidinyl]methyl}-6-methyl-7-quinolinyl)-4'-fluoro[1,1'-biphenyl]-4-carboxamide

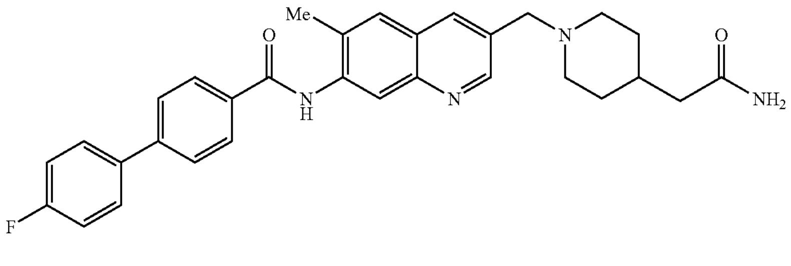

By operating in the same manner as in Example 42 and using N-[3-(chloromethyl)-6-methyl-7-quinolinyl]-4'-fluoro [1,1'-biphenyl]-4-carboxamide obtained in Reference Example 64, the title compound was obtained.

$^1$H-NMR (DMSO-$d_6$) δ 1.16 (2H, m), 1.63 (3H, m), 1.96 (4H, m), 2.46 (3H, s), 2.81 (2H, m), 3.62 (2H, s), 6.69 (1H, s), 7.22 (1H, s), 7.34 (2H, m), 7.82 (5H, m), 8.07 (1H, s), 8.13 (3H, m), 8.75 (1H, d, J=2.0 Hz), 10.13 (1H, s). melting point: 249° C. (crystallization solvent: ethyl acetate-isopropyl ether) Elemental analysis for $C_{31}H_{31}FN_4O_2$ Calculated: C, 72.92; H, 6.12; N, 10.97. Found: C, 72.91; H, 6.43; N, 10.66.

Example 271

4'-fluoro-N-(6-methyl-3-{[4-(1-piperidinylcarbonyl)-1-piperidinyl]methyl}-7-quinolinyl)[1,1'-biphenyl]-4-carboxamide

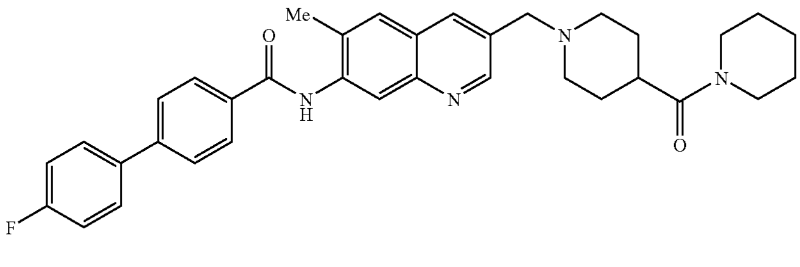

By operating in the same manner as in Example 42 and using N-[3-(chloromethyl)-6-methyl-7-quinolinyl]-4'-fluoro [1,1'-biphenyl]-4-carboxamide obtained in Reference Example 64, the title compound was obtained.

$^1$H-NMR (DMSO-$d_6$) δ 1.39 (2H, m), 1.46 (2H, m), 1.58 (6H, m), 2.07 (2H, m), 2.47 (3H, s), 2.53 (1H, m), 2.86 (2H, m), 3.40 (4H, m), 3.66 (2H, s), 7.34 (2H, m), 7.83 (5H, m), 8.12 (4H, m), 8.77 (1H, s), 10.12 (1H, s). melting point: 250° C. (crystallization solvent: ethyl acetate-isopropyl ether) Elemental analysis for $C_{35}H_{37}FN_4O_2$ Calculated: C, 74.44; H, 6.60; N, 9.92. Found: C, 74.13; H, 6.51; N, 9.79.

Example 272

N,N-diethyl-1-[(7-{[(4'-fluoro-1,1'-biphenyl-4-yl)carbonyl]amino}-6-methyl-3-quinolinyl)methyl]piperidine-4-carboxamide

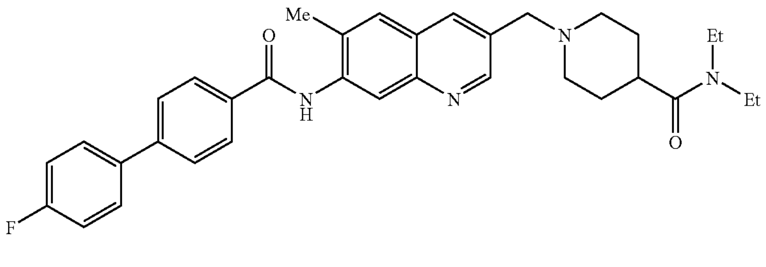

By operating in the same manner as in Example 42 and using N-[3-(chloromethyl)-6-methyl-7-quinolinyl]-4'-fluoro [1,1'-biphenyl]-4-carboxamide obtained in Reference Example 64, the title compound was obtained.

$^1$H-NMR (DMSO-$d_6$) δ 0.97 (3H, t, J=7.0 Hz), 1.09 (3H, t, J=7.0 Hz), 1.61 (2H, m), 2.05 (2H, m), 2.47 (3H, s), 2.51 (1H, m), 2.87 (2H, m), 3.23 (2H, q, J=7.0 Hz), 3.30 (4H, m), 3.66 (2H, s), 7.34 (2H, m), 7.83 (5H, m), 8.12 (4H, m), 8.77 (1H, d, J=1.7 Hz), 10.12 (1H, s). melting point: 203° C. (crystallization solvent: ethyl acetate-isopropyl ether) Elemental analysis for $C_{34}H_{37}FN_4O_2.0.25H_2O$ Calculated: C, 73.29; H, 6.78; N, 10.05. Found: C, 73.26; H, 6.97; N, 9.94.

Example 273

N-ethyl-1-[(7-{[(4'-fluoro-1,1'-biphenyl-4-yl)carbonyl]amino}-6-methyl-3-quinolinyl)methyl]piperidine-4-carboxamide

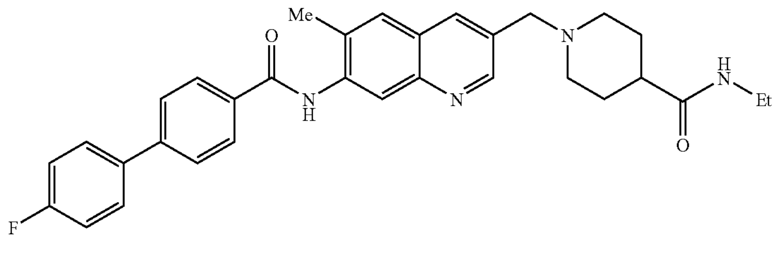

By operating in the same manner as in Example 42 and using N-[3-(chloromethyl)-6-methyl-7-quinolinyl]-4'-fluoro[1,1'-biphenyl]-4-carboxamide obtained in Reference Example 64, the title compound was obtained.

$^1$H-NMR (DMSO-$d_6$) δ 0.97 (3H, t, J=7.2 Hz), 1.61 (4H, m), 1.97 (2H, m), 2.04 (1H, m), 2.46 (3H, s), 2.86 (2H, m), 3.03 (2H, m), 3.63 (2H, s), 7.34 (2H, m), 7.70 (1H, m), 7.81 (5H, m), 8.08 (1H, s), 8.13 (3H, m), 8.74 (1H, d, J=2.0 Hz), 10.13 (1H, s). melting point: 254° C. (crystallization solvent: ethyl acetate-isopropyl ether) Elemental analysis for $C_{32}H_{33}FN_4O_2$ Calculated: C, 73.26; H, 6.34; N, 10.68. Found: C, 73.46; H, 6.64; N, 10.17.

Example 274

1-[(7-{[(4'-fluoro-1,1'-biphenyl-4-yl)carbonyl]amino}-6-methyl-3-quinolinyl)methyl]-N,N-dimethylpiperidine-4-carboxamide

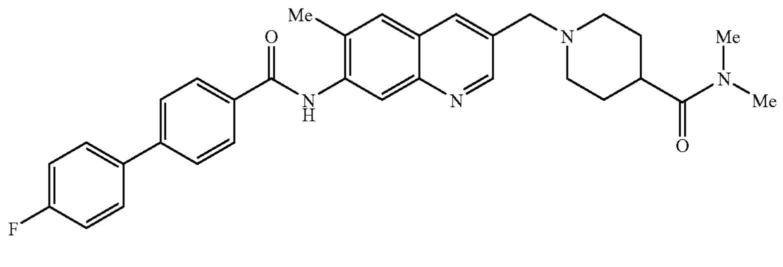

By operating in the same manner as in Example 42 and using N-[3-(chloromethyl)-6-methyl-7-quinolinyl]-4'-fluoro[1,1'-biphenyl]-4-carboxamide obtained in Reference Example 64, the title compound was obtained.

$^1$H-NMR (DMSO-$d_6$) δ 1.59 (4H, m), 2.07 (2H, m), 2.47 (3H, s), 2.54 (1H, m), 2.78 (3H, s), 2.87 (2H, m), 2.98 (3H, s), 3.66 (2H, s), 7.34 (2H, m), 7.83 (5H, m), 8.11 (4H, m), 8.77 (1H, d, J=2.0 Hz), 10.12 (1H, s). melting point: 229° C. (crystallization solvent: ethyl acetate-isopropyl ether) Elemental analysis for $C_{32}H_{33}FN_4O_2$ Calculated: C, 73.26; H, 6.34; N, 10.68. Found: C, 72.89; H, 6.54; N, 10.38.

Example 275

1-[(7-{[(4'-fluoro-1,1'-biphenyl-4-yl)carbonyl]amino}-6-methyl-3-quinolinyl)methyl]-N-methylpiperidine-4-carboxamide

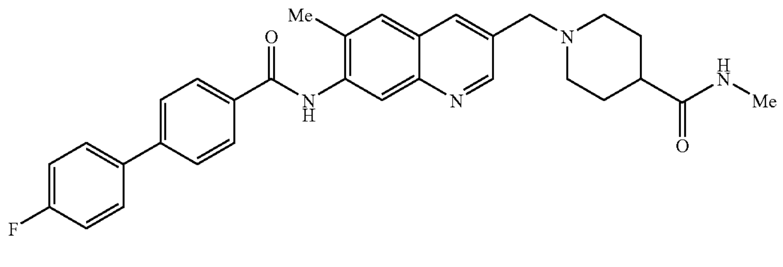

By operating in the same manner as in Example 42 and using N-[3-(chloromethyl)-6-methyl-7-quinolinyl]-4'-fluoro[1,1'-biphenyl]-4-carboxamide obtained in Reference Example 64, the title compound was obtained.

$^1$H-NMR (DMSO-$d_6$) δ 1.60 (4H, m), 1.97 (2H, m), 2.06 (1H, m), 2.46 (3H, s), 2.54 (3H, m), 2.85 (2H, m), 3.63 (2H, s), 7.34 (2H, m), 7.66 (1H, m), 7.83 (5H, m), 8.12 (4H, m), 8.75 (1H, s), 10.13 (1H, s). melting point: 257° C. (crystallization solvent: ethyl acetate-isopropyl ether) Elemental analysis for $C_{31}H_{31}FN_4O_2$ Calculated: C, 72.92; H, 6.12; N, 10.97. Found: C, 73.10; H, 6.08; N, 10.82.

Example 276

1-[(7-{[(4'-fluoro-1,1'-biphenyl-4-yl)carbonyl]amino}-6-methyl-3-quinolinyl) methyl]piperidine-4-carboxamide

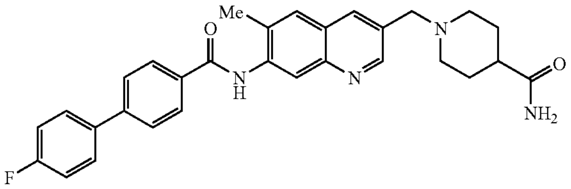

By operating in the same manner as in Example 42 and using N-[3-(chloromethyl)-6-methyl-7-quinolinyl]-4'-fluoro[1,1'-biphenyl]-4-carboxamide obtained in Reference Example 64, the title compound was obtained.

$^1$H-NMR (DMSO-$d_6$) δ 1.58 (2H, m), 1.67 (2H, m), 1.98 (2H, m), 2.06 (1H, m), 2.47 (3H, s), 2.85 (2H, m), 3.64 (2H, s), 6.70 (1H, s), 7.19 (1H, s), 7.34 (2H, m), 7.82 (5H, m), 8.12 (4H, m), 8.76 (1H, d, J=2.0 Hz), 10.12 (1H, s). melting point: 265° C. (crystallization solvent: ethyl acetate-isopropyl ether) Elemental analysis for $C_{30}H_{29}FN_4O_2.H_2O$ Calculated: C, 70.02; H, 6.07; N, 10.88. Found: C, 69.66; H, 6.01; N, 10.59.

Example 277

3-fluoro-4'-methyl-N-[3-(1-pyrrolidinylmethyl)-7-quinolinyl][1,1'-biphenyl]-4-carboxamide

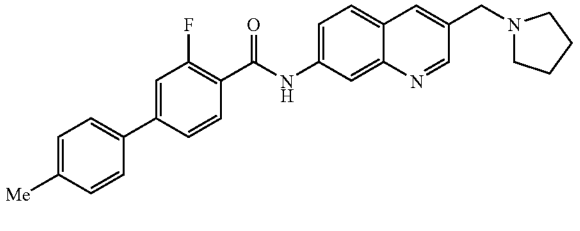

By operating in the same manner as in Example 50 and using 4-bromo-2-fluoro-N-[3-(pyrrolidin-1-ylmethyl)quinoline-7-yl]benzamide obtained in Example 84, the title compound was obtained.

$^1$H-NMR (DMSO-$d_6$) δ 1.72 (4H, m), 2.37 (3H, s), 2.50 (4H, m), 3.75 (2H, s), 7.32 (2H, d, J=8.3 Hz), 7.68 (4H, m), 7.80 (1H, m), 7.86 (1H, d, J=2.0 Hz), 7.95 (1H, m), 8.15 (1H, d, J=2.2 Hz), 8.54 (1H, s), 8.80(1H, d, J=2.0 Hz), 10.76 (1H, s). melting point: 173° C. (crystallization solvent: ethyl acetate-isopropyl ether) FABMS(pos) 440 [M+H]+

Example 278

3-fluoro-N-[8-fluoro-3-(1-pyrrolidinylmethyl)-7-quinolinyl]-4'-methyl[1,1'-biphenyl]-4-carboxamide

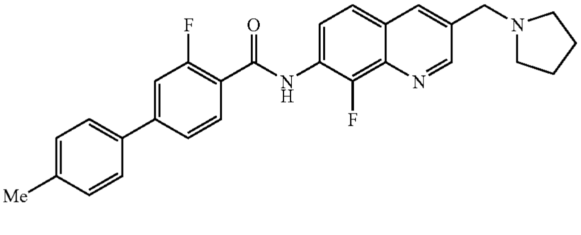

By operating in the same manner as in Example 50 and using 4-bromo-2-fluoro-N-[8-fluoro-3-(1-piperidinylmethyl)-7-quinolinyl]benzamide obtained in Example 76, the title compound was obtained.

$^1$H-NMR (DMSO-$d_6$) δ 1.73 (4H, m), 2.37 (3H, s), 2.50 (4H, m), 3.81 (2H, s), 7.33 (2H, d, J=8.4 Hz), 7.68 (4H, m), 7.85 (2H, m), 8.01 (1H, m), 8.31 (1H, s), 8.91 (1H, d, J=1.8

Hz), 10.47 (1H, s). melting point: 173° C. (crystallization solvent: ethyl acetate-isopropyl ether) FABMS(pos) 458 [M+H]+

Example 279

4'-chloro-3-fluoro-N-[8-fluoro-3-(1-pyrrolidinylm-ethyl)-7-quinolinyl][1,1'-biphenyl]-4-carboxamide

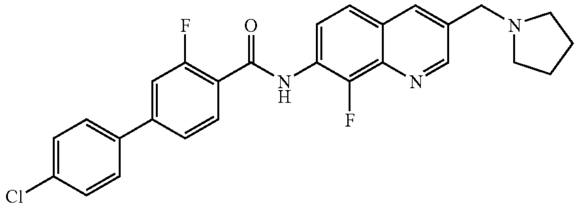

By operating in the same manner as in Example 50 and using 4-bromo-2-fluoro-N-[8-fluoro-3-(1-piperidinylm-ethyl)-7-quinolinyl]benzamide obtained in Example 76, the title compound was obtained.

$^1$H-NMR (DMSO-$d_6$) δ 1.74 (4H, m), 2.50 (4H, m), 3.81 (2H, s), 7.59 (2H, d, J=8.8 Hz), 7.81 (6H, m), 8.01 (1H, m) 8.31 (1H, s), 8.91 (1H, d, J=1.8 Hz), 10.53 (1H, s). melting point: 208° C. (crystallization solvent: ethyl acetate-isopropyl ether) FABMS(pos) 478 [M+H]+

Example 280

4'-fluoro-N-{8-methyl-3-[1-(1-pyrrolidinyl)ethyl]-7-quinolinyl}[1,1'-biphenyl]-4-carboxamide

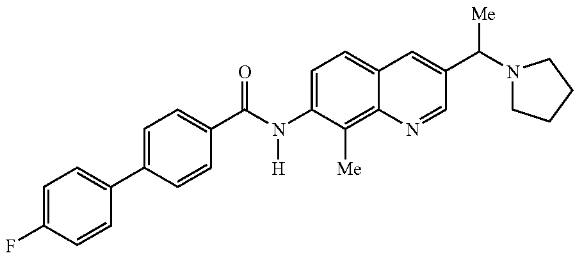

By operating in the same manner as in Example 42 and using N-[3-(1-chloroethyl)-8-methyl-7-quinolinyl]-4'-fluoro [1,1'-biphenyl]-4-carboxamide obtained in Reference Example 59, the title compound was obtained.

$^1$H-NMR (DMSO-$d_6$) δ: 1.45 (3H, d, J=6.6 Hz), 1.62–1.83 (4H, m), 2.26–2.72 (7H, m), 3.49 (1H, q, J=6.6 Hz), 7.28–7.42 (2H, m), 7.61 (1H, d, J=8.8 Hz), 7.74–7.92 (5H, m), 8.15 (2H, d, J=8.1 Hz), 8.20 (1H, d, J=2.2 Hz), 8.92 (1H, d, J=2.2 Hz), 10.29 (1H, s). melting point: 179–182° C. (crystallization solvent: ethyl acetate-diisopropyl ether)

Example 281

4'-fluoro-N-{8-methyl-3-[1-(1-piperidinyl)ethyl]-7-quinolinyl}[1,1'-biphenyl]-4-carboxamide

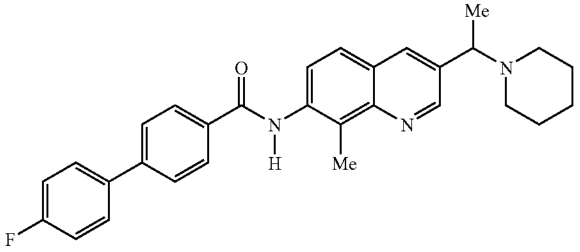

By operating in the same manner as in Example 42 and using N-[3-(1-chloroethyl)-8-methyl-7-quinolinyl]-4'-fluoro [1,1'-biphenyl]-4-carboxamide obtained in Reference Example 59, the title compound was obtained.

$^1$H-NMR (DMSO-$d_6$) δ: 1.27–1.62 (9H, m), 2.26–2.46 (4H, m), 2.67 (3H, s), 3.76 (1H, q, J=6.6 Hz), 7.27–7.42 (2H, m), 7.61 (1H, d, J=8.8 Hz), 7.77–7.90 (5H, m), 8.10–8.21 (3H, m), 8.91 (1H, d, J=1.8 Hz), 10.29 (1H, s). melting point: 168–170° C. (crystallization solvent: ethyl acetate-diisopropyl ether)

Example 282

N-{3-[(2-benzyl-1-pyrrolidinyl)methyl]-8-methyl-7-quinolinyl}-4'-fluoro[1,1'-biphenyl]-4-carboxamide

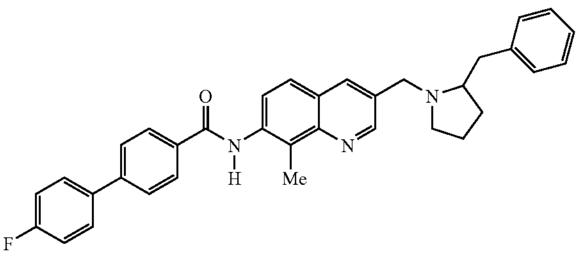

By operating in the same manner as in Example 42 and using N-[3-(chloromethyl)-8-methyl-7-quinolinyl]-4'-fluoro [1,1'-biphenyl]-4-carboxamide obtained in Reference Example 52, the title compound was obtained.

$^1$H-NMR (DMSO-$d_6$) δ: 1.43–1.80 (4H, m), 2.13–2.33 (1H, m), 2.45–2.92 (6H, m), 3.00–3.17 (1H, m), 3.50 (1H, d, J=13.6 Hz), 4.30 (1H, d, J=13.6 Hz), 7.12–7.45 (7H, m), 7.63 (1H, d, J=8.8 Hz), 7.74–7.92 (5H, m), 8.10–8.25 (3H, m), 8.90 (1H, d, J=2.2 Hz), 10.28 (1H, s). melting point: 172–174° C. (crystallization solvent: isopropanol-diisopropyl ether)

Example 283

4'-fluoro-N-{3-[(2-isobutyl-1-pyrrolidinyl)methyl]-8-methyl-7-quinolinyl}[1,1'-biphenyl]-4-carboxamide

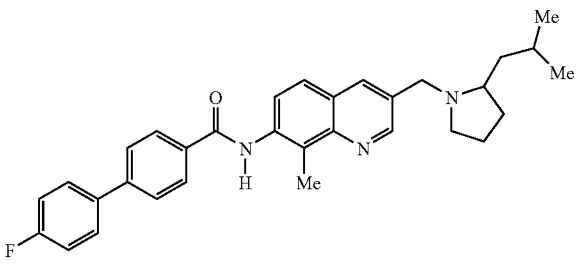

By operating in the same manner as in Example 42 and using N-[3-(chloromethyl)-8-methyl-7-quinolinyl]-4'-fluoro[1,1'-biphenyl]-4-carboxamide obtained in Reference Example 52, the title compound was obtained.

$^1$H-NMR (DMSO-$d_6$) δ: 0.93 (6H, t like, J=ca. 5.7 Hz), 1.18–1.73 (7H, m), 1.86–2.22 (2H, m), 2.62–2.92 (4H, m), ca. 3.36 (1H, d, J=13.9 Hz), 4.20 (1H, d, J=13.9 Hz), 7.25–7.40 (2H, m), 7.61 (1H, d, J=8.4 Hz), 7.73–7.92 (5H, m), 8.08–8.23 (3H, m), 8.86 (1H, d, J=1.8 Hz), 10.27 (1H, s). melting point: 193–196° C. (crystallization solvent: isopropanol-diisopropyl ether)

Example 284

N-{3-[(2-cyclohexyl-1-pyrrolidinyl)methyl]-8-methyl-7-quinolinyl}-4'-fluoro[1,1'-biphenyl]-4-carboxamide

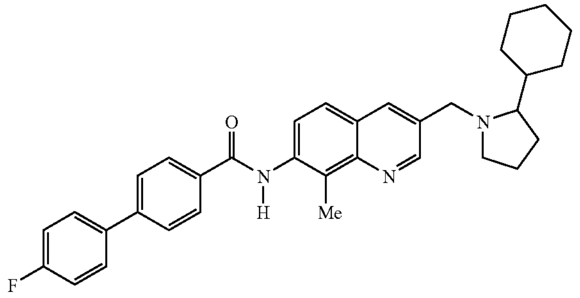

By operating in the same manner as in Example 42 and using N-[3-(chloromethyl)-8-methyl-7-quinolinyl]-4'-fluoro[1,1'-biphenyl]-4-carboxamide obtained in Reference Example 52, the title compound was obtained.

$^1$H-NMR ($CDCl_3$) δ: 0.90–1.35 (6H, m), 1.50–2.50 (11H, m), 2.78–2.97 (4H, m), 3.34 (1H, d, J=13.6 Hz), 4.21 (1H, d, J=13.6 Hz), 7.10–7.24 (2H, m), 7.57–7.78 (5H, m), 7.98–8.10 (4H, m), 8.25 (1H, d, J=9.2 Hz), 8.94 (1H, d, J=1.8 Hz). melting point: 204–205° C. (crystallization solvent: isopropanol-diisopropyl ether)

Example 285

4'-fluoro-N-{8-methyl-3-[1-(1-pyrrolidinyl)propyl]-7-quinolinyl}[1,1'-biphenyl]-4-carboxamide

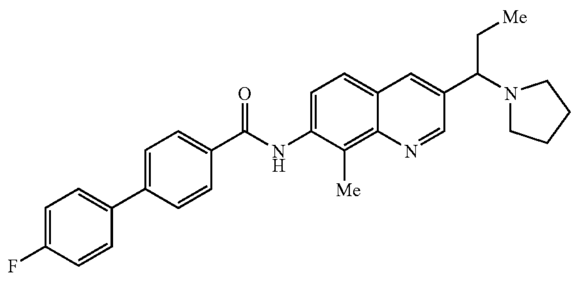

By operating in the same manner as in Example 42 and using N-[3-(1-chloropropyl)-8-methyl-7-quinolinyl]-4'-fluoro[1,1'-biphenyl]-4-carboxamide obtained in Reference Example 61, the title compound was obtained.

$^1$H-NMR (DMSO-$d_6$) δ: 0.67 (3H, t, J=7.3 Hz), 1.60–2.75 (13H, m), ca. 3.35 (1H, br), 7.26–7.43 (2H, m), 7.61 (1H, d, J=8.8 Hz), 7.72–7.91 (5H, m), 8.05–8.26 (3H, m), 8.87 (1H, s), 10.30 (1H, s). melting point: 188–191° C. (crystallization solvent: diisopropyl ether)

Example 286

4'-fluoro-N-{8-methyl-3-[phenyl(1-pyrrolidinyl)methyl]-7-quinolinyl}[1,1'-biphenyl]-4-carboxamide

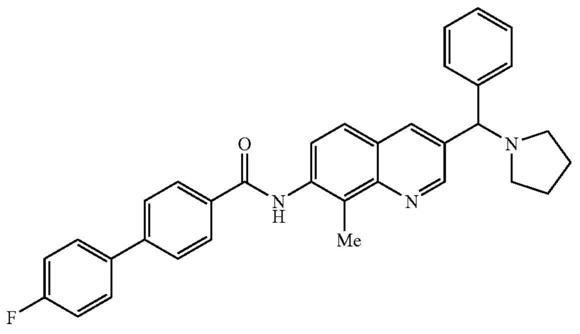

By operating in the same manner as in Example 42 and using N-{3-[chloro(phenyl)methyl]-8-methyl-7-quinolinyl}-4'-fluoro[1,1'-biphenyl]-4-carboxamide obtained in Reference Example 63, the title compound was obtained.

$^1$H-NMR ($CDCl_3$) δ: 1.82 (4H, br), 2.49 (4H, br), 2.79 (3H, s), 4.41 (1H, s), 7.10–7.35 (5H, m), 7.47–7.77 (7H, m), 7.93–8.09 (3H, m), 8.16 (1H, d, J=1.8 Hz), 8.25 (1H, d, J=8.8 Hz), 9.05 (1H, d, J=1.8 Hz). melting point: 192–195° C. (crystallization solvent: isopropanol-diisopropyl ether)

Example 287

N-[8-methyl-3-(1-pyrrolidinylmethyl)-7-quinolinyl]-4-pentylbenzamide

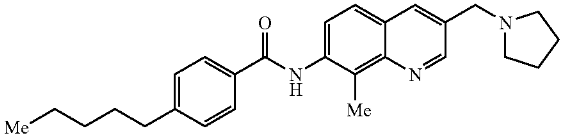

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ 0.91 (3H, m), 1.35 (4H, m), 1.67 (2H, m), 1.81 (4H, dt, J=6.6, 3.3 Hz), 2.57 (4H, m), 2.69 (2H, m), 2.81 (3H, s), 3.81 (2H, s), 7.33 (2H, d, J=8.3 Hz), 7.70 (1H, d, J=9.0 Hz), 7.87 (2H, d, J=8.1 Hz), 7.95 (1H, s), 8.06 (1H, d, J=2.2 Hz), 8.25 (1H, d, J=8.8 Hz), 8.88 (1H, d, J=2.0 Hz). melting point: 121° C. (crystallization solvent: diisopropyl ether)

Example 288

4-butyl-N-[8-methyl-3-(1-pyrrolidinylmethyl)-7-quinolinyl]benzamide

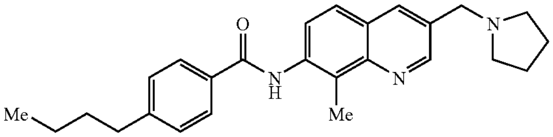

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ 0.95 (3H, t, J=7.3 Hz), 1.38 (2H, m), 1.65 (2H, m), 1.81 (4H, ddd, J=6.8, 3.3, 3.1 Hz), 2.57 (4H, m), 2.70 (2H, m), 2.81 (3H, s), 3.81 (2H, s), 7.33 (2H, d, J=8.1 Hz), 7.70 (1H, d, J=9.0 Hz), 7.86 (2H, d, J=8.1 Hz), 7.95 (1H, s), 8.06 (1H, d, J=2.2 Hz), 8.25 (1H, d, J=8.8 Hz), 8.88 (1H, d, J=2.2 Hz). melting point: 131° C. (crystallization solvent: diisopropyl ether)

Example 289

4-hexyl-N-[8-methyl-3-(1-pyrrolidinylmethyl)-7-quinolinyl]benzamide

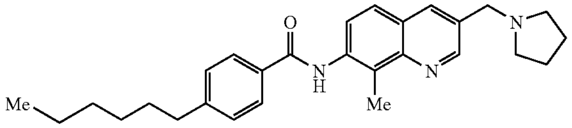

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 0.88 (3H, m), 1.33 (6H, m), 1.63 (2H, m), 1.80 (4H, m), 2.56 (4H, m), 2.69 (2H, m), 2.80 (3H, s), 3.80 (2H, s), 7.32 (2H, d, J=8.0 Hz), 7.70 (1H, d, J=9.1 Hz), 7.86 (2H, d, J=8.0 Hz), 7.95 (1H, s), 8.06 (1H, d, J=2.2 Hz), 8.25 (1H, d, J=9.1 Hz), 8.88 (1H, d, J=2.2 Hz). melting point: 116° C. (crystallization solvent: ethyl acetate-isopropyl ether)

Example 290

N-[8-methyl-3-(1-pyrrolidinylmethyl)-7-quinolinyl]-4-(pentyloxy)benzamide

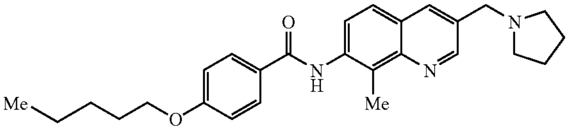

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 0.94 (3H, t, J=7.0 Hz), 1.42 (4H, m), 1.82 (6H, m), 2.56 (4H, m), 2.80 (3H, s), 3.80 (2H, s), 4.03 (2H, t, J=6.6 Hz), 6.99 (2H, d, J=8.8 Hz), 7.69 (1H, d, J=8.8 Hz), 7.91 (3H, m), 8.06 (1H, d, J=2.2 Hz), 8.24 (1H, d, J=8.8 Hz), 8.88 (1H, d, J=2.2 Hz). melting point: 155° C. (crystallization solvent: ethyl acetate-isopropyl ether)

Example 291

4-(benzoylamino)-N-[8-methyl-3-(1-pyrrolidinylmethyl)-7-quinolinyl]benzamide

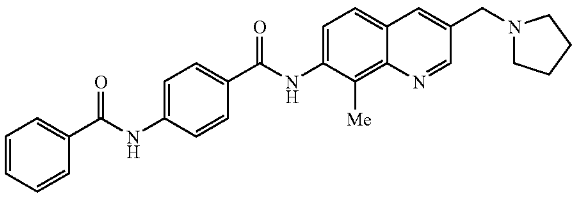

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR (DMSO-$d_6$) δ: 1.74 (4H, m), 2.50 (4H, m), 2.66 (3H, s), 3.80 (2H, s), 7.59 (4H, m), 7.81 (1H, d, J=8.8 Hz), 7.98 (4H, m), 8.06 (2H, m), 8.21 (1H, d, J=1.7 Hz), 8.87 (1H, d, J=2.2 Hz), 10.14 (1H, s), 10.53 (1H, s). melting point: 242° C. (crystallization solvent: ethyl acetate-isopropyl ether)

Example 292

4-butoxy-2-fluoro-N-[8-methyl-3-(1-pyrrolidinylmethyl)-7-quinolinyl]benzamide

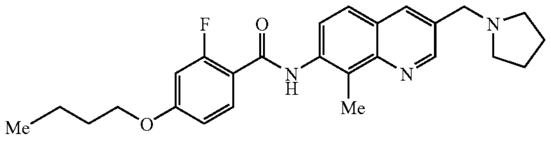

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 0.99 (3H, t, J=7.3 Hz), 1.51 (2H, m), 1.80 (6H, m), 2.55 (4H, m), 2.81 (3H, s), 3.80 (2H, s), 4.03 (2H, t, J=6.6 Hz), 6.70 (1H, dd, J=14.5, 2.3 Hz), 6.84 (1H, dd, J=8.9, 2.3 Hz), 7.68 (1H, d, J=9.0 Hz), 8.04 (1H, d, J=2.0 Hz), 8.17 (1H, t, J=9.2 Hz), 8.35 (1H, d, J=9.0 Hz), 8.63 (1H, d, J=17.3 Hz), 8.87 (1H, d, J=2.2 Hz). melting point: 138° C. (crystallization solvent: ethyl acetate-isopropyl ether)

Example 293

2-fluoro-N-[8-methyl-3-(1-pyrrolidinylmethyl)-7-quinolinyl]-4-(pentyloxy)benzamide

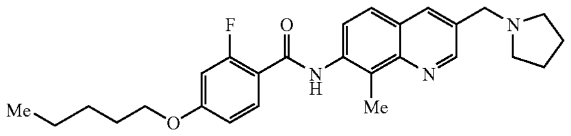

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 0.94 (3H, m), 1.42 (4H, m), 1.81 (6H, m), 2.55 (4H, m), 2.81 (3H, s), 3.80 (2H, s), 4.02 (2H, t, J=6.6 Hz), 6.70 (1H, dd, J=14.7, 2.4 Hz), 6.84 (1H, dd, J=9.0, 2.4 Hz), 7.68 (1H, d, J=9.0 Hz), 8.04 (1H, d, J=2.2 Hz), 8.17 (1H, m), 8.35 (1H, d, J=8.8 Hz), 8.63 (1H, d, J=16.9 Hz,), 8.87 (1H, d, J=2.2 Hz). melting point: 143° C. (crystallization solvent: ethyl acetate-isopropyl ether)

Example 294

4-(butylthio)-N-[8-methyl-3-(1-pyrrolidinylmethyl)-7-quinolinyl]benzamide

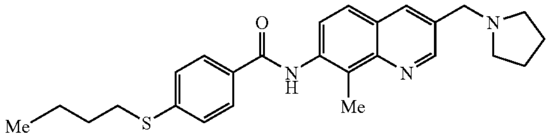

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 0.95 (3H, t, J=7.1 Hz), 1.48 (2H, m), 1.68 (2H, m), 1.81 (4H, m), 2.55 (4H, m), 2.80 (3H, s), 3.00 (2H, m), 3.80 (2H, s), 7.37 (2H, d, J=8.4 Hz), 7.69 (1H, d, J=8.8 Hz), 7.85 (2H, d, J=8.4 Hz), 7.92 (1H, s), 8.05 (1H, d, J=2.2 Hz), 8.22 (1H, d, J=8.8 Hz), 8.88 (1H, d, J=2.2 Hz). melting point: 147° C. (crystallization solvent: ethyl acetate-isopropyl ether)

Example 295

2-fluoro-N-[8-methyl-3-(1-pyrrolidinylmethyl)-7-quinolinyl]-4-(4,4,4-trifluorobutoxy)benzamide

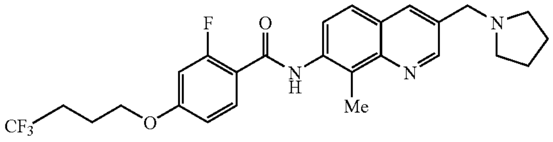

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 1.80 (4H, m), 2.10 (2H, m), 2.35 (2H, m), 2.56 (4H, m), 2.81 (3H, s), 3.80 (2H, s), 4.09 (2H t, J=6.0 Hz,), 6.71 (1H, dd, J=14.5, 2.4 Hz), 6.85 (1H, dd, J=9.0, 2.4 Hz), 7.69 (1H, d, J=9.2 Hz,), 8.05 (1H, d, J=2.2 Hz), 8.20 (1H, t, J=9.2 Hz), 8.35 (1H, d, J=8.8 Hz), 8.63 (1H, d, J=16.9 Hz,), 8.88 (1H, d, J=2.2 Hz). melting point: 148° C. (crystallization solvent: ethyl acetate-isopropyl ether)

Example 296

4-(butylsulfonyl)-N-[8-methyl-3-(1-pyrrolidinylmethyl)-7-quinolinyl]benzamide

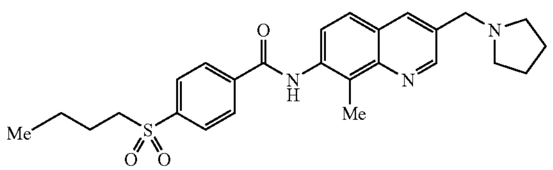

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 0.90 (3H, t, J=7.3 Hz), 1.38 (2H, m), 1.67 (2H, m), 1.81 (4H, m), 2.56 (4H, m), 2.81 (3H, s), 3.12 (2H, m), 3.81 (2H, s), 7.72 (1H, d, J=8.4 Hz), 8.07 (7H, m), 8.90 (1H, d, J=2.2 Hz). melting point: 210° C. (crystallization solvent: ethyl acetate-isopropyl ether)

Example 297

4-(cyclopropylmethoxy)-N-[8-methyl-3-(1-pyrrolidinylmethyl)-7-quinolinyl]benzamide

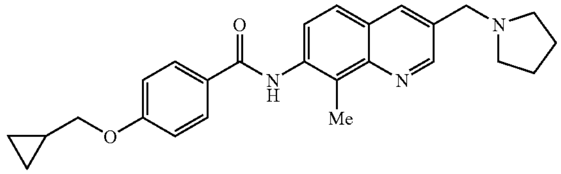

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^{1}$H-NMR ($CDCl_3$) δ: 0.39 (2H, m), 0.69 (2H, m), 1.30 (1H, m), 1.81 (4H, m), 2.56 (4H, m), 2.80 (3H, s), 3.80 (2H, s), 3.88 (2H, d, J=6.8 Hz), 7.00 (2H, m), 7.68 (1H, d, J=8.6 Hz), 7.90 (3H, m), 8.05 (1H, d, J=2.0 Hz), 8.23 (1H, d, J=8.8 Hz), 8.87 (1H, d, J=2.0 Hz). melting point: 168° C. (crystallization solvent: ethyl acetate-isopropyl ether)

Example 298

2-fluoro-N-[8-methyl-3-(1-pyrrolidinylmethyl)-7-quinolinyl]-4-propoxybenzamide

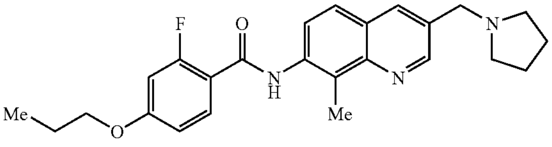

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^{1}$H-NMR ($CDCl_3$) δ: 1.06 (3H, t, J=7.3 Hz), 1.83 (6H, m), 2.55 (4H, m), 2.81 (3H, s), 3.79 (2H, s), 3.98 (2H, t, J=6.6 Hz), 6.70 (1H, dd, J=14.4, 2.4 Hz), 6.84 (1H, dd, J=9.0, 2.2 Hz), 7.68 (1H, d, J=8.8 Hz), 8.04 (1H, d, J=1.7 Hz), 8.17 (1H, t, J=9.3 Hz), 8.35 (1H, d, J=9.0 Hz), 8.63 (1H, d, J=17.3 Hz), 8.87 (1H, d, J=2.2 Hz). melting point: 146° C. (crystallization solvent: ethyl acetate-isopropyl ether)

Example 299

2-fluoro-4-(3-methylbutoxy)-N-[8-methyl-3-(1-pyrrolidinylmethyl)-7-quinolinyl]benzamide

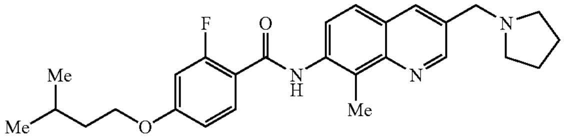

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^{1}$H-NMR ($CDCl_3$) δ: 0.98 (6H, d, J=6.6 Hz), 1.71 (2H, q, J=6.8 Hz), 1.80 (4H, m), 1.84 (1H, m), 2.55 (4H, m), 2.81 (3H, s), 3.80 (2H, s), 4.05 (2H, t, J=6.6 Hz), 6.70 (1H, dd, J=14.7, 2.4 Hz), 6.84 (1H, dd, J=8.8, 2.4 Hz), 7.68 (1H, d, J=8.8 Hz), 8.04 (1H, d, J=2.2 Hz), 8.17 (1H, t, J=9.2 Hz), 8.35 (1H, d, J=9.0 Hz), 8.63 (1H, d, J=16.9 Hz,), 8.87 (1H, d, J=2.0 Hz). melting point: 131° C. (crystallization solvent: ethyl acetate-isopropyl ether)

Example 300

2-fluoro-4-(4-fluorobutoxy)-N-[8-methyl-3-(1-pyrrolidinylmethyl)-7-quinolinyl]benzamide

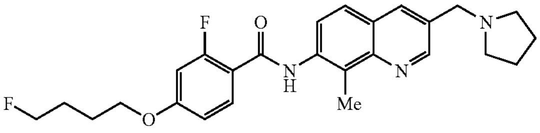

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^{1}$H-NMR ($CDCl_3$) δ: 1.81 (4H, m), 1.98 (4H, m), 2.56 (4H, m), 2.82 (3H, s), 3.80 (2H, s), 4.09 (2H, m), 4.47 (1H, t, J=5.6 Hz), 4.62 (1H, t, J=4.8 Hz), 6.71 (1H, dd, J=14.7, 2.4 Hz), 6.85 (1H, dd, J=8.9, 2.3 Hz), 7.69 (1H, d, J=8.8 Hz), 8.05 (1H, d, J=2.2 Hz), 8.19 (1H, t, J=9.4 Hz), 8.36 (1H, d, J=9.3 Hz), 8.64 (1H, d, J=17.1 Hz), 8.88 (1H, d, J=2.0 Hz). melting point: 140° C. (crystallization solvent: ethyl acetate-isopropyl ether)

Example 301

4-(2-ethoxyethoxy)-2-fluoro-N-[8-methyl-3-(1-pyrrolidinylmethyl)-7-quinolinyl]benzamide

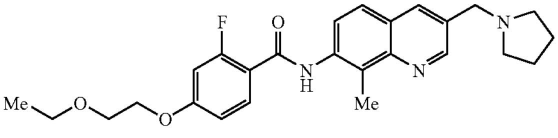

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 1.27 (3H, t, J=7.0 Hz), 1.81 (4H, m), 2.56 (4H, m), 2.82 (3H, s), 3.62 (2H, q, J=7.0 Hz), 3.80 (2H, s), 3.83 (2H, m), 4.20 (2H, m), 6.76 (1H, dd, J=14.2, 2.2 Hz), 6.89 (1H, dd, J=8.9, 2.6 Hz), 7.69 (1H, d, J=8.8 Hz), 8.05 (1H, d, J=2.2 Hz), 8.18 (1H, m), 8.36 (1H, d, J=8.8 Hz), 8.64 (1H, d, J=16.6 Hz), 8.88 (1H, d, J=2.4 Hz). melting point: 132° C. (crystallization solvent: ethyl acetate-isopropyl ether)

Example 302

N-[8-methyl-3-(1-pyrrolidinylmethyl)-7-quinolinyl]-4-(2-oxo-2-phenylethyl)benzamide

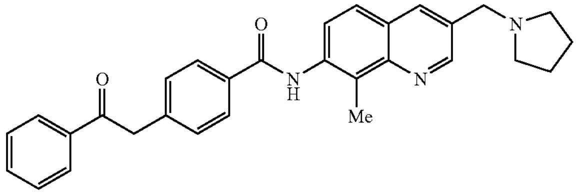

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 1.81 (4H, m), 2.55 (4H, m), 2.79 (3H, s), 3.80 (2H, s), 4.39 (2H, s), 7.42 (2H, d, J=8.6 Hz,), 7.48 (2H, m), 7.58 (1H, m), 7.68 (1H, d, J=9.0 Hz), 7.91 (3H, m), 8.02 (3H, m), 8.22 (1H, d, J=9.0 Hz), 8.87 (1H, d, J=2.2 Hz). melting point: 187° C. (crystallization solvent: ethyl acetate-isopropyl ether)

Example 303

N-[8-methyl-3-(1-pyrrolidinylmethyl)-7-quinolinyl]-4-(2-oxobutyl)benzamide

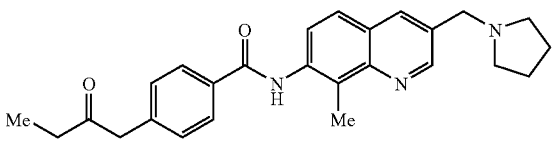

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 1.07 (3H, t, J=7.3 Hz), 1.80 (4H, m), 2.55 (6H, m), 2.80 (3H, s), 3.79 (2H, s), 3.80 (2H, s), 7.35 (2H, d, J=8.1 Hz), 7.69 (1H, d, J=8.8 Hz), 7.91 (3H, d, J=8.1 Hz), 8.05 (1H, d, J=2.2 Hz), 8.22 (1H, d, J=9.0 Hz), 8.88 (1H, d, J=2.2 Hz). melting point: 157° C. (crystallization solvent: ethyl acetate-isopropyl ether)

Example 304

N-[8-methyl-3-(1-pyrrolidinylmethyl)-7-quinolinyl]-4-pentanoylbenzamide

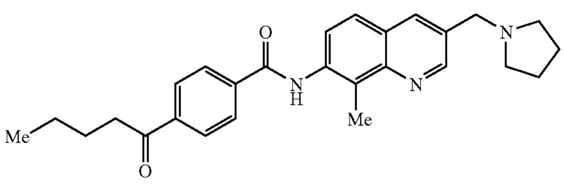

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 0.97 (3H, t, J=7.3 Hz), 1.42 (2H, m), 1.74 (2H, m), 1.81 (4H, m), 2.56 (4H, m), 2.81 (3H, s), 3.01 (2H, m), 3.80 (2H, s), 7.70 (1H, d, J=8.8 Hz), 8.05 (6H, m), 8.18 (1H, d, J=8.8 Hz), 8.88 (1H, d, J=2.2 Hz). melting point: 180° C. (crystallization solvent: ethyl acetate-isopropyl ether)

Example 305

4-hexanoyl-N-[8-methyl-3-(1-pyrrolidinylmethyl)-7-quinolinyl]benzamide

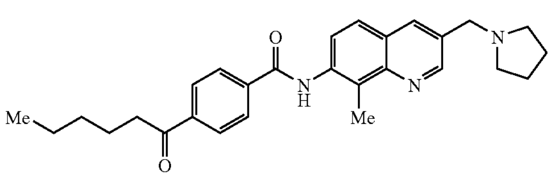

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 0.93 (3H, m), 1.39 (4H, m), 1.82 (6H, m), 2.57 (4H, m), 2.82 (3H, s), 3.02 (2H, t, J=7.5 Hz), 3.82 (2H, s), 7.72 (1H, d, J=9.2 Hz), 8.02 (1H, d, J=2.2 Hz), 8.09 (5H, m), 8.19 (1H, d, J=8.8 Hz), 8.91 (1H, d, J=2.2 Hz). melting point: 175° C. (crystallization solvent: ethyl acetate-isopropyl ether)

Example 306

N-[8-methyl-3-(1-pyrrolidinylmethyl)-7-quinolinyl]-4-(2-oxopentyl)benzamide

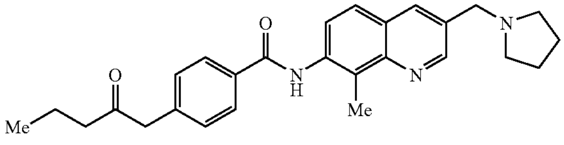

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 0.91 (3H, t, J=7.5 Hz), 1.63 (2H, m), 1.81 (4H, m), 2.48 (2H, t, J=7.2 Hz), 2.57 (4H, m), 2.81 (3H, s), 3.79 (2H, s), 3.82 (2H, s), 7.36 (2H, d, J=8.3 Hz), 7.70 (1H, d, J=9.0 Hz), 7.91 (3H, m), 8.06 (1H, d, J=2.0 Hz), 8.23 (1H, d, J=8.6 Hz), 8.89 (1H, d, J=2.2 Hz). melting point: 139–140° C. (crystallization solvent: ethyl acetate-isopropyl ether)

Example 307

4-(butyrylamino)-N-[8-methyl-3-(1-pyrrolidinylmethyl)-7-quinolinyl]benzamide

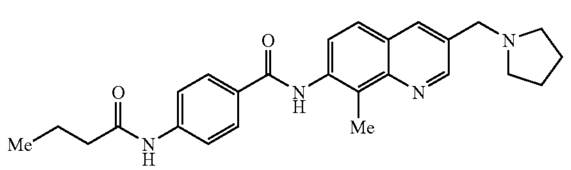

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 1.03 (3H, t, J=7.3 Hz), 1.80 (6H, m), 2.39 (2H, t, J=7.5 Hz), 2.57 (4H, m), 2.81 (3H, s), 3.81 (2H, s), 7.31 (1H, s), 7.72 (3H, m), 7.93 (3H, m), 8.05 (1H, d, J=2.0 Hz), 8.21 (1H, d, J=8.8 Hz), 8.88 (1H, d, J=2.0 Hz). melting point: 192–194° C. (crystallization solvent: ethyl acetate-isopropyl ether)

Example 308

N-[8-methyl-3-(1-pyrrolidinylmethyl)-7-quinolinyl]-4-(pentanoylamino)benzamide

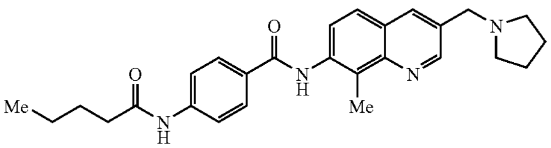

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 0.97 (3H, t, J=7.2 Hz), 1.44 (2H, m) 1.73 (2H, m), 1.81 (4H, m), 2.41 (2H, m), 2.57 (4H, m), 2.81 (3H, s), 3.81 (2H, s), 7.30 (1H, s), 7.69 (3H, m), 7.92 (3H, m), 8.05 (1H, d, J=2.2 Hz), 8.21 (1H, d, J=8.8 Hz), 8.88 (1H, d, J=2.4 Hz). melting point: 206–207° C. (crystallization solvent: ethyl acetate-isopropyl ether)

Example 309

N-[8-methyl-3-(1-pyrrolidinylmethyl)-7-quinolinyl]-4-(2-oxohexyl)benzamide

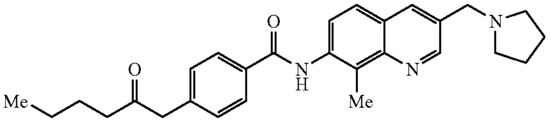

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 0.89 (3H, t, J=7.3 Hz), 1.30 (2H, m), 1.57 (2H, m), 1.81 (4H, m), 2.50 (2H, t, J=7.3 Hz), 2.57 (4H, m), 2.81 (3H, s), 3.79 (2H, s), 3.81 (2H, s), 7.35 (2H, d, J=8.3 Hz), 7.70 (1H, d, J=9.0 Hz), 7.92 (3H, m), 8.05 (1H, d, J=2.2 Hz), 8.22 (1H, d, J=8.8 Hz), 8.88 (1H, d, J=2.2 Hz). melting point: 156° C. (crystallization solvent: ethyl acetate-isopropyl ether)

Example 310

N-[8-methyl-3-(1-pyrrolidinylmethyl)-7-quinolinyl]-4-[(propylsulfonyl)methyl]benzamide

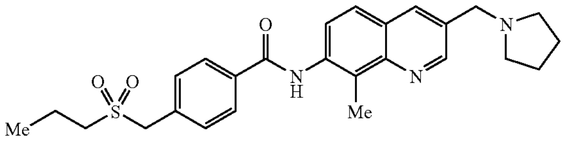

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 1.07 (3H, t, J=7.5 Hz), 1.88 (6H, m), 2.57 (4H, m), 2.82 (3H, s), 2.86 (2H, m), 3.82 (2H, s), 4.30 (2H, s), 7.58 (2H, d, J=8.4 Hz), 7.71 (1H, d, J=8.8 Hz), 8.00 (3H, m), 8.07 (1H, d, J=2.2 Hz), 8.19 (1H, d, J=8.8 Hz), 8.90 (1H, d, J=2.2 Hz). melting point: 191° C. (crystallization solvent: ethyl acetate-isopropyl ether)

Example 311

4-[(butylsulfonyl)methyl]-N-[8-methyl-3-(1-pyrrolidinylmethyl)-7-quinolinyl]benzamide

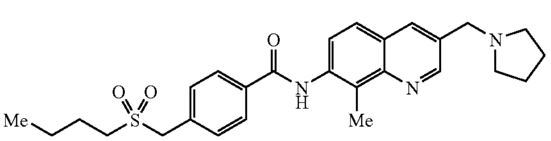

By successively operating in the same manner as in Reference Example 4 and Example 1 and using 4-bromo- N-[8-methyl-3-(1-pyrrolidinylmethyl)-7-quinolinyl]benzamide obtained in Example 93, the title compound was obtained.

$^1$H-NMR ($CDCl_3$) δ: 0.95 (3H, t, J=7.3 Hz), 1.46 (2H, m), 1.83 (6H, m), 2.56 (4H, m), 2.82 (3H, s), 2.89 (2H, m), 3.82 (2H, s), 4.31 (2H, s), 7.59 (2H, d, J=8.4 Hz), 7.72 (1H, d, J=9.2 Hz,), 8.00 (3H, m), 8.07 (1H, d, J=2.2 Hz), 8.20 (1H, d, J=8.8 Hz), 8.91 (1H, d, J=2.2 Hz). melting point: 199° C. (crystallization solvent: ethyl acetate-isopropyl ether)

Example 312

3'-(isobutyrylamino)-N-[8-methyl-3-(1-pyrrolidinylmethyl)-7-quinolinyl]-1,1'-biphenyl-4-carboxamide

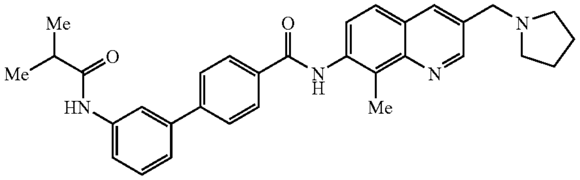

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 1.28 (6H, d, J=6.9 Hz), 1.82 (4H, m), 2.57 (5H, m), 2.84 (3H, s), 3.82 (2H, s), 7.33 (1H, s), 7.39 (1H, m), 7.43 (1H, t, J=7.6 Hz), 7.51 (1H, ddd, J=7.8, 1.9, 1.7 Hz), 7.74 (3H, m), 7.95 (1H, s), 8.01 (3H, m), 8.08 (1H, d, J=2.2 Hz), 8.24 (1H, d, J=8.8 Hz), 8.91 (1H, d, J=2.2 Hz). melting point: 152–155° C. (crystallization solvent: ethyl acetate-isopropyl ether)

Example 313

4-(2-cyclopropyl-2-oxoethyl)-N-[8-methyl-3-(1-pyrrolidinylmethyl)-7-quinolinyl]benzamide

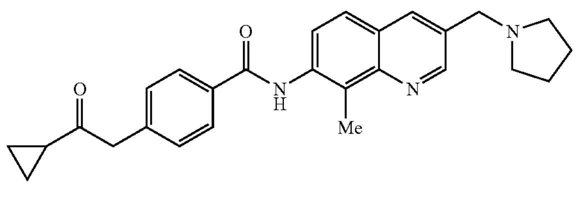

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR (DMSO-$d_6$) δ: 0.89 (4H, m), 1.88 (4H, m), 2.02 (1H, m), 2.66 (4H, m), 2.69 (3H, s), 3.57 (2H, s), 4.02 (2H, s), 7.39 (2H, dd, J=8.3, 1.7 Hz), 7.73 (1H, d, J=9.0 Hz), 7.91 (1H, d, J=8.6 Hz), 7.99 (2H, dd, J=8.6, 2.2 Hz), 8.65 (1H, m), 9.09 (1H, m), 10.29 (1H, s). melting point: 200–201° C. (crystallization solvent: ethyl acetate-isopropyl ether)

Example 314

N-[8-methyl-3-(1-piperidinylmethyl)-7-quinolinyl]-4-(2-oxopentyl)benzamide

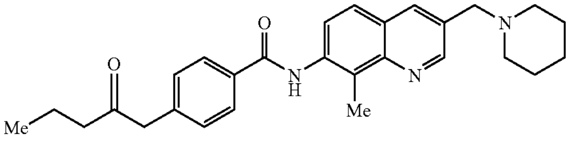

By operating in the same manner as in Example 1 and using 8-methyl-3-(1-piperidinylmethyl)-7-quinolinylamine obtained in Reference Example 50, the title compound was obtained.

$^1$H-NMR ($CDCl_3$) δ: 0.91 (3H, t, J=7.5 Hz), 1.45 (2H, m), 1.61 (6H, m), 2.45 (4H, m), 2.48 (2H, t, J=7.3 Hz), 2.81 (3H, s), 3.66 (2H, s), 3.79 (2H, s), 7.35 (2H, d, J=8.3 Hz), 7.70 (1H, d, J=8.8 Hz), 7.92 (2H, dt, J=8.4, 1.9 Hz), 7.96 (1H, s), 8.02 (1H, d, J=2.2 Hz), 8.22 (1H, d, J=9.0 Hz), 8.88 (1H, d, J=2.0 Hz). melting point: 164–165° C. (crystallization solvent: ethyl acetate-isopropyl ether)

Example 315

N-[3-(1-azepanylmethyl)-8-methyl-7-quinolinyl]-4-(2-oxopentyl)benzamide

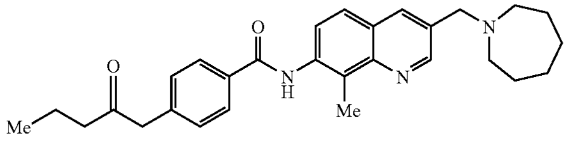

By operating in the same manner as in Example 1 and using 3-(1-azepanylmethyl)-8-methyl-7-quinolinylamine obtained in Reference Example 51, the title compound was obtained.

$^1$H-NMR ($CDCl_3$) δ: 0.91 (3H, t, J=7.5 Hz), 1.63 (10H, m), 2.48 (2H, t, J=7.3 Hz), 2.65 (4H, m), 2.81 (3H, s), 3.79 (2H, s), 3.82 (2H, s), 7.35 (2H, d, J=8.3 Hz), 7.70 (1H, d, J=8.8 Hz), 7.91 (2H, m), 7.96 (1H, s), 8.02 (1H, d, J=2.0 Hz), 8.20 (1H, d, J=8.8 Hz), 8.92 (1H, d, J=2.2 Hz). melting point: 136–137° C. (crystallization solvent: ethyl acetate-isopropyl ether)

Example 316

4-(3-methyl-2-oxobutyl)-N-[8-methyl-3-(1-pyrrolidinylmethyl)-7-quinolinyl]benzamide

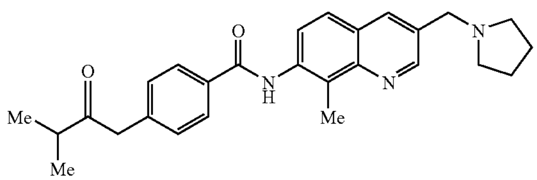

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 1.15 (6H, d, J=6.8 Hz), 1.81 (4H, m), 2.57 (4H, m), 2.77 (1H, m), 2.80 (3H, s), 3.81 (2H, s), 3.85 (2H, s), 7.34 (2H, d, J=8.3 Hz), 7.69 (1H, d, J=8.8 Hz), 7.91 (2H, dt, J=8.4, 1.9 Hz), 7.97 (1H, s), 8.05 (1H, d, J=2.2 Hz), 8.21 (1H, d, J=9.0 Hz), 8.88 (1H, d, J=2.2 Hz). melting point: 146–147° C. (crystallization solvent: ethyl acetate-isopropyl ether)

Example 317

4-(4-methyl-2-oxopentyl)-N-[8-methyl-3-(1-pyrrolidinylmethyl)-7-quinolinyl]benzamide

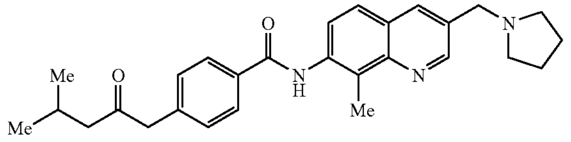

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 0.91 (6H, d, J=6.6 Hz), 1.81 (4H, m), 2.17 (1H, m), 2.38 (2H, d, J=6.8 Hz), 2.57 (4H, m), 2.80 (3H, s), 3.77 (2H, s), 3.81 (2H, s), 7.34 (2H, d, J=8.3 Hz), 7.69 (1H, d, J=8.8 Hz), 7.91 (2H, dt, J=8.4, 1.9 Hz), 7.98 (1H, s), 8.05 (1H, d, J=2.2 Hz), 8.20 (1H, d, J=8.8 Hz), 8.88 (1H, d, J=2.2 Hz). melting point: 153° C. (crystallization solvent: ethyl acetate-isopropyl ether)

Example 318

4-butoxy-N-{8-methyl-3-[(2-methyl-1-pyrrolidinyl)methyl]-7-quinolinyl}benzamide

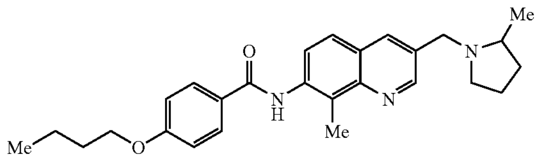

By successively operating in the same manner as in Reference Example 3, Reference Example 4 and Example 1 and using 4-bromo-N-[3-(chloromethyl)-8-methyl-7-quinolinyl]benzamide hydrochloride obtained in Reference Example 49, the title compound was obtained.

$^1$H-NMR ($CDCl_3$) δ: 1.00 (3H, t, J=7.3 Hz), 1.23 (3H, d, J=5.9 Hz), 1.38–2.28 (9H, m), 2.40–2.60 (1H, m), 2.81 (3H, s), 2.85–3.03 (1H, m), 3.38 (1H, d, J=13.4 Hz), 4.05 (2H, t, J=6.4 Hz), 4.20 (1H, d, J=13.4 Hz), 7.01 (2H, d, J=8.8 Hz), 7.71 (1H, d, J=8.8 Hz), 7.87–7.97 (3H, m), 8.07 (1H, br), 8.25 (1H, d, J=8.8 Hz), 8.89 (1H, d, J=2.2 Hz). melting point: 153–156° C. (crystallization solvent: ethyl acetate-isopropyl ether)

Example 319

4-butoxy-N-{8-methyl-3-[1-(1-pyrrolidinyl)ethyl]-7-quinolinyl}benzamide

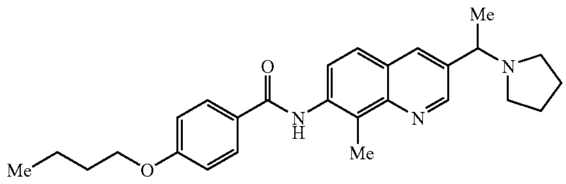

By successively operating in the same manner as in Reference Example 3, Reference Example 4 and Example 1 and using N-[3-(1-chloroethyl)-8-methyl-7-quinolinyl]-4'-fluoro[1,1'-biphenyl]-4-carboxamide obtained in Reference Example 59, the title compound was obtained.

$^1$H-NMR ($CDCl_3$) δ: 1.00 (3H, t, J=7.3 Hz), 1.42–1.92 (11H, m), 2.33–2.51 (2H, m), 2.53–2.70 (2H, m), 2.81 (3H, s), 3.44 (1H, q, J=6.6 Hz), 4.05 (2H, t, J=6.4 Hz), 7.01 (2H, d, J=8.8 Hz), 7.70 (1H, d, J=8.9 Hz), 7.85–7.98 (3H, m), 8.06 (1H, d, J=2.2 Hz), 8.24 (1H, d, J=8.9 Hz), 8.92 (1H, d, J=2.2 Hz). melting point: 136–139° C. (crystallization solvent: isopropyl ether)

Example 320

(+)-4'-fluoro-N-{8-methyl-3-[1-(1-pyrrolidinyl)ethyl]-7-quinolinyl}[1,1'-biphenyl]-4-carboxamide and (−)-4'-fluoro-N-{8-methyl-3-[1-(1-pyrrol-idinyl)ethyl]-7-quinolinyl}[1,1'-biphenyl]-4-carboxamide

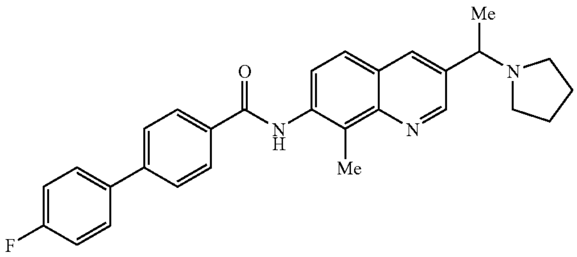

4'-Fluoro-N-{8-methyl-3-[1-(1-pyrrolidinyl)ethyl]-7-quinolinyl}[1,1'-biphenyl]-4-carboxamide obtained in Example 280 was separated using chiral HPLC to give the title compound.

HPLC separation conditions: column, CHIRALCEL OJ 50 mm ID×500 mm L manufactured by DAICEL CHEMICAL INDUSTRIES, LTD.; mobile phase, hexane/ethanol=84/16; flow rate, 60 mL/min; temperature, 30° C.; UV detection, 254 nm. optical purity analysis conditions: column, CHIRALCEL OJ 4.6 mm ID×250 mm L manufactured by DAICEL CHEMICAL INDUSTRIES, LTD.; mobile phase, hexane/ethanol=85/15; flow rate, 0.5 mL/min; temperature, 30° C.; UV detection, 254 nm; optical rotatory power detection, Shodex OR-2.

(+)-4'-fluoro-N-{8-methyl-3-[1-(1-pyrrolidinyl) ethyl]-7-quinolinyl}[1,1'-biphenyl]-4-carboxamide melting point: 198–200° C. (crystallization solvent: isopropyl ether) retention time under analysis conditions: 37.0 min optical purity: >99.9% ee optical rotatory power: wavelength 470 nm, in hexane/ethanol (85/15) solvent, (+)

(−)-4'-fluoro-N-{8-methyl-3-[1-(1-pyrrolidinyl) ethyl]-7-quinolinyl}[1,1'-biphenyl]-4-carboxamide melting point: 198–200° C. (crystallization solvent: isopropyl ether) retention time under analysis conditions: 48.5 min optical purity: 99.6% ee optical rotatory power: wavelength 470 nm, in hexane/ethanol (85/15) solvent, (−)

Example 321

4-butoxy-N-{3-[(2-isobutyl-1-pyrrolidinyl)methyl]-8-methyl-7-quinolinyl}benzamide

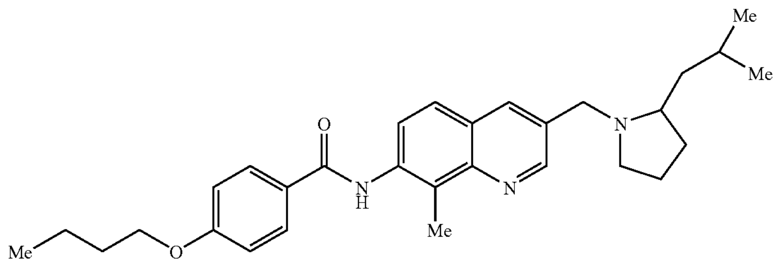

By successively operating in the same manner as in Reference Example 3, Reference Example 4 and Example 1 and using 4-bromo-N-[3-(chloromethyl)-8-methyl-7-quinolinyl]benzamide hydrochloride obtained in Reference Example 49, the title compound was obtained.

$^1$H-NMR ($CDCl_3$) δ: 0.83–1.08 (9H, m), 1.42–2.90 (16H, m), ca.3.1 (1H, br), ca.3.5 (1H, br), 4.06 (2H, t, J=6.4 Hz), ca.4.5 (1H, br), 7.01 (2H, d, J=8.8 Hz), 7.76 (1H, d, J=9.5 Hz), 7.94 (2H, d, J=8.8 Hz), 8.05 (1H, s), 8.30 (1H, d, J=9.2 Hz), 8.51 (1H, br), 8.90 (1H, d, J=2.2 Hz). melting point: 193–196° C. (crystallization solvent: isopropanol-isopropyl ether)

Example 322

(+)-4-butoxy-N-{3-[(2-isobutyl-1-pyrrolidinyl)methyl]-8-methyl-7-quinolinyl}benzamide and (−)-4-butoxy-N-{3-[(2-isobutyl-1-pyrrolidinyl)methyl]-8-methyl-7-quinolinyl}benzamide

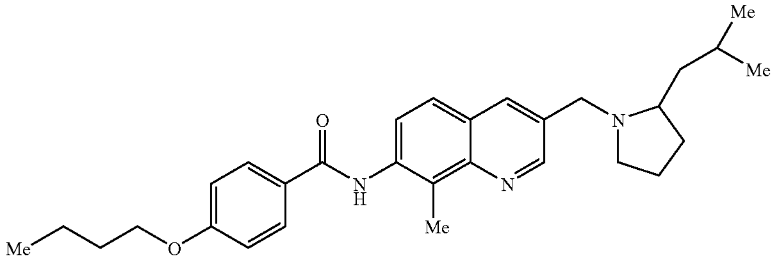

4-Butoxy-N-{3-[(2-isobutyl-1-pyrrolidinyl)methyl]-8-methyl-7-quinolinyl}benzamide obtained in Example 321 was separated by chiral HPLC to give the title compound. HPLC separation conditions: column, CHIRALCEL OJ 50 mm ID×500 mmL manufactured by DAICEL CHEMICAL INDUSTRIES, LTD.; mobile phase, hexane/ethanol=92/8; flow rate, 60 mL/min; temperature, 30° C.; UV detection, 254 nm. optical purity, optical rotatory power analysis conditions: column, CHIRALCEL OJ 4.6 mm ID×250 mL manufactured by DAICEL CHEMICAL INDUSTRIES, LTD.; mobile phase, hexane/ethanol=95/5; flow rate, 1.0 mL/min; temperature, 30° C.; UV detection, 254 nm; optical rotatory power detection, Shodex OR-2.

(+)-4-butoxy-N-{3-[(2-isobutyl-1-pyrrolidinyl)methyl]-8-methyl-7-quinolinyl}benzamide melting point: 128–130° C. (crystallization solvent: isopropyl ether) retention time under analysis conditions: 20.7 min optical purity: 99.9% ee optical rotatory power: wavelength 470 nm, in hexane/ethanol (95/5) solvent, (+)

(−)-4-butoxy-N-{3-[(2-isobutyl-1-pyrrolidinyl)methyl]-8-methyl-7-quinolinyl}benzamide melting point: 128–130° C. (crystallization solvent: isopropyl ether) retention time under analysis conditions: 25.0 min optical purity: 99.8% ee optical rotatory power: wavelength 470 nm, in hexane/ethanol (95/5) solvent, (−)

Example 323

4-(cyclopropylmethoxy)-N-{8-methyl-3-[1-(1-pyrrolidinyl)ethyl]-7-quinolinyl}benzamide

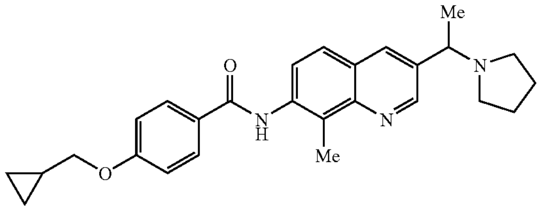

By successively operating in the same manner as in Reference Example 3, Reference Example 4 and Example 1 and using N-[3-(1-chloroethyl)-8-methyl-7-quinolinyl]-4'-fluoro[1,1'-biphenyl]-4-carboxamide obtained in Reference Example 59, the title compound was obtained.

$^1$H-NMR ($CDCl_3$) δ: 0.34–0.45 (2H, m), 0.63–0.76 (2H, m), 1.20–1.43 (1H, m), 1.51 (3H, d, J=6.6 Hz), 1.60–1.90 (4H, m), 2.35–2.50 (2H, m), 2.53–2.70 (2H, m), 2.81 (3H, s), 3.44 (1H, q, J=6.6 Hz), 3.89 (2H, d, J=7.0 Hz), 7.01 (2H, d, J=8.9 Hz), 7.70 (1H, d, J=7.7 Hz), 7.85–7.98 (3H, m), 8.06 (1H, d, J=2.2 Hz), 8.24 (1H, d, J=8.9 Hz), 8.92 (1H, d, J=2.2 Hz). melting point: 162–164° C. (crystallization solvent: isopropyl ether)

Example 324

N-{8-methyl-3-[1-(1-pyrrolidinyl)ethyl]-7-quinolinyl}-4-(2-oxobutyl)benzamide

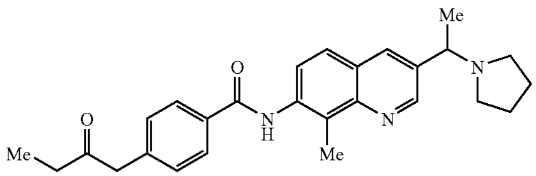

By successively operating in the same manner as in Reference Example 3, Reference Example 4 and Example 1 and using N-[3-(1-chloroethyl)-8-methyl-7-quinolinyl]-4'-fluoro[1,1'-biphenyl]-4-carboxamide obtained in Reference Example 59, the title compound was obtained.

$^1$H-NMR ($CDCl_3$) δ: 1.08 (3H, t, J=7.3 Hz), 1.53 (3H, d, J=6.6 Hz), 1.60–1.92 (4H, m), 2.35–2.74 (6H, m), 2.82 (3H, s), 3.46 (1H, q, J=6.6 Hz), 3.81 (2H, s), 7.38 (2H, d, J=8.4 Hz), 7.71 (1H, d, J=9.0 Hz), 7.87–8.02 (3H, m), 8.08 (1H, d, J=2.2 Hz), 8.23 (1H, d, J=9.0 Hz), 8.93 (1H, d, J=2.2 Hz). melting point: 123–127° C. (crystallization solvent: isopropyl ether)

Example 325

(+)-4'-fluoro-N-{3-[(2-isobutyl-1-pyrrolidinyl)methyl]-8-methyl-7-quinolinyl}[1,1'-biphenyl]-4-carboxamide and (−)-4'-fluoro-N-{3-[(2-isobutyl-1-pyrrolidinyl)methyl]-8-methyl-7-quinolinyl}[1,1'-biphenyl]-4-carboxamide

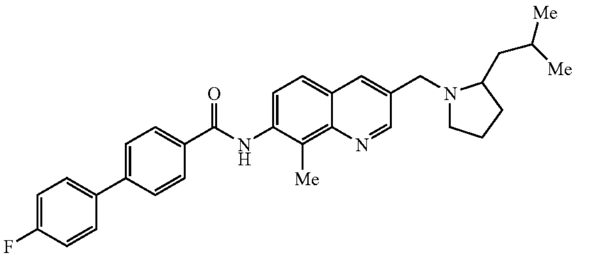

4'-Fluoro-N-{3-[(2-isobutyl-1-pyrrolidinyl)methyl]-8-methyl-7-quinolinyl}[1,1'-biphenyl]-4-carboxamide obtained in Example 283 was separated by chiral HPLC to give the title compound.

HPLC separation conditions: column, CHIRALCEL OJ 50 mm ID×500 mm L manufactured by DAICEL CHEMICAL INDUSTRIES, LTD.; mobile phase, hexane/ethanol=90/10; flow rate, 60 mL/min; temperature, 30° C.; UV detection, 254 nm. optical purity, optical rotatory power analysis conditions: column, CHIRALCEL OJ 4.6 mm ID×250 mm L manufactured by DAICEL CHEMICAL INDUSTRIES, LTD.; mobile phase, hexane/ethanol=85/15; flow rate, 0.5 mL/min; temperature, 30° C.; UV detection, 254 nm; optical rotatory power detection, Shodex OR-2.

(+)-4'-fluoro-N-{3-[(2-isobutyl-1-pyrrolidinyl)methyl]-8-methyl-7-quinolinyl}[1,1'-biphenyl]-4-carboxamide melting point: 192–194° C. (crystallization solvent: isopropyl ether) retention time under analysis conditions: 22.0 min optical purity: >99.9% ee optical rotatory power: wavelength 470 nm, in hexane/ethanol (80/20) solvent, (+)

(−)-4'-fluoro-N-{3-[(2-isobutyl-1-pyrrolidinyl)methyl]-8-methyl-7-quinolinyl}[1,1'-biphenyl]-4-carboxamide melting point: 192–194° C. (crystallization solvent: isopropyl ether) retention time under analysis conditions: 27.9 min optical purity: 99.7% ee optical rotatory power: wavelength 470 nm, in hexane/ethanol (80/20) solvent, (−)

Example 326

4'-chloro-N-(2-methyl-1,2,3,4-tetrahydrobenzo[b][1,6]naphthyridin-7-yl)[1,1'-biphenyl]-4-carboxamide

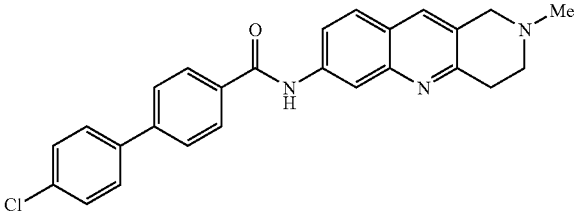

By operating in the same manner as in Example 1 and using 2-methyl-1,2,3,4-tetrahydrobenzo[b][1,6]naphthyridin-7-amine obtained in Reference Example 65, the title compound was obtained.

$^1$H-NMR (DMSO-$d_6$) δ 2.42 (3H, s), 2.81 (2H, t, J=6.0 Hz), 3.10 (2H, t, J=6.0 Hz), 3.71 (2H, s), 7.58 (2H, d, J=8.4 Hz), 7.81–7.95 (7H, m), 8.12 (2H, d, J=8.4 Hz), 8.47 (1H, s), 10.57 (1H, s). FABMS(pos) 428 [M+H]+ melting point: >220° C. (decomp.)(crystallization solvent: ethyl acetate-isopropyl ether)

Example 327

4-bromo-2-fluoro-N-(2-methyl-1,2,3,4-tetrahydrobenzo[b][1,6]naphthyridin-7-yl)benzamide

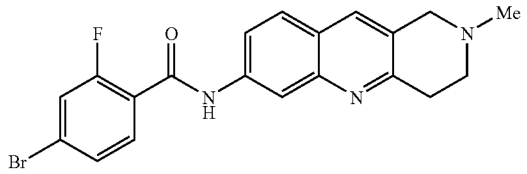

By operating in the same manner as in Example 1 and using 2-methyl-1,2,3,4-tetrahydrobenzo[b][1,6]naphthyridin-7-amine obtained in Reference Example 65, the title compound was obtained.

$^1$H-NMR (DMSO-$d_6$) δ 2.41 (3H, s), 2.78 (2H, t, J=6.0 Hz), 3.09 (2H, t, J=6.0 Hz), 3.68 (2H, s), 7.58 (1H, dd, J=2.1, 8.4 Hz), 7.66–7.85 (4H, m), 7.94 (1H, s), 8.37 (1H, s), 10.73 (1H, s).

Example 328

4'-chloro-3-fluoro-N-(2-methyl-1,2,3,4-tetrahydrobenzo[b][1,6]naphthyridin-7-yl)[1,1'-biphenyl]-4-carboxamide

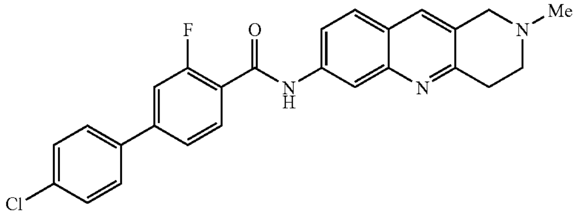

By operating in the same manner as in Example 1 and using 2-methyl-1,2,3,4-tetrahydrobenzo[b][1,6]naphthyridin-7-amine obtained in Reference Example 65, the title compound was obtained.

$^1$H-NMR (DMSO-$d_6$) δ 2.42 (3H, s), 2.80 (2H, t, J=6.0 Hz), 3.09 (2H, t, J=6.0 Hz), 3.70 (2H, s), 7.57 (2H, d, J=8.7 Hz), 7.67–7.85 (7H, m), 7.94 (1H, s), 8.40 (1H, s), 10.72 (1H, s). FABMS(pos) 446 [M+H]+ melting point: >220° C. (decomp.) (crystallization solvent: ethyl acetate-isopropyl ether)

Example 329

4-hydroxy-N-[8-methyl-3-(1-pyrrolidinylmethyl)-7-quinolinyl]benzamide

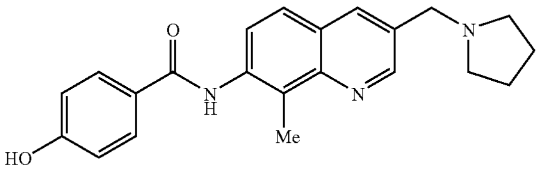

By successively operating in the same manner as in Reference Example 4 and using N-[8-methyl-3-(1-pyrrolidinylmethyl)-7-quinolinyl]acetamide obtained in Example 7, the title compound was obtained. A solution of the obtained oily substance (1.00 g, 4.14 mmol), 4-(chlorocarbonyl)phenyl acetate (905 mg, 4.56 mmol) and triethylamine (0.865 ml, 6.22 mmol) in tetrahydrofuran (20 ml) was stirred for 16 hrs. Ethyl acetate was added to the reaction solution, and the mixture was washed with aqueous potassium carbonate solution and saturated brine, and dried over anhydrous sodium sulfate. The solvent was concentrated under reduced pressure and the obtained residue was purified by alumina column chromatography (eluting solvent; ethyl acetate). To a mixed solution of the obtained solid (1.24 g, 3.07 mmol) in tetrahydrofuran (15 ml)-methanol (15 ml) was added 1N aqueous sodium hydroxide solution and the mixture was stirred at room temperature for 16 hrs. The solvent was evaporated under reduced pressure and the residue was neutralized by adding 1N hydrochloric acid. The resulting precipitate was washed with water, isopropanol and isopropyl ether to give the title compound (631 mg).

$^1$H-NMR (DMSO-$d_6$) δ 1.73 (4H, m), 2.50 (4H, m), 2.63 (3H, s), 3.81 (2H, s), 6.88 (2H, d, J=8.4 Hz), 7.58 (1H, d,

J=8.4 Hz), 7.78 (1H, d, J=8.4 Hz), 7.92 (2H, d, J=8.4 Hz), 8.19 (1H, d, J=1.8 Hz), 8.86 (1H, d, J=1.8 Hz), 9.93 (1H, s), 10.08 (1H, s).

Example 330

4-({[8-methyl-3-(1-pyrrolidinylmethyl)-7-quinolinyl]amino}carbonyl)phenyl propionate

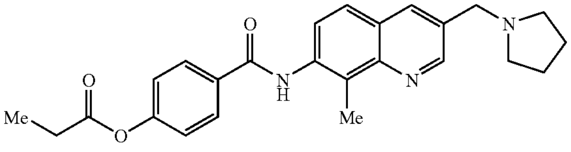

By operating in the same manner as in Example 1 and using 4-hydroxy-N-[8-methyl-3-(1-pyrrolidinylmethyl)-7-quinolinyl]benzamide obtained in Example 329, the title compound was obtained.

$^1$H-NMR (DMSO-$d_6$) δ 1.67 (3H, t, J=7.5 Hz), 1.73 (4H, m), 2.50 (4H, m), 2.65 (5H, m), 3.81 (2H, s), 7.31 (2H, d, J=8.7 Hz), 7.59 (1H, d, J=8.4 Hz), 7.81 (1H, d, J=8.4 Hz), 8.08 (2H, d, J=8.7 Hz), 8.21 (1H, s), 8.88 (1H, s), 10.24 (1H, s). FABMS(pos) 418 [M+H]+ melting point: 146–147° C. (crystallization solvent: ethyl acetate-isopropyl ether)

Example 331

4-({[8-methyl-3-(1-pyrrolidinylmethyl)-7-quinolinyl]amino}carbonyl)phenyl butyrate

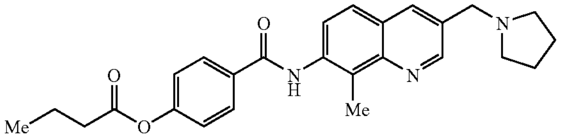

By operating in the same manner as in Example 1 and using 4-hydroxy-N-[8-methyl-3-(1-pyrrolidinylmethyl)-7-quinolinyl]benzamide obtained in Example 329, the title compound was obtained.

$^1$H-NMR (DMSO-$d_6$) δ 1.00 (3H, t, J=7.5 Hz), 1.71 (6H, m), 2.50 (4H, m), 2.59–2.65 (5H, m), 3.81 (2H, s), 7.30 (2H, d, J=9.0 Hz), 7.59 (1H, d, J=9.0 Hz), 7.81 (1H, d, J=9.0 Hz), 8.09 (2H, d, J=9.0 Hz), 8.21 (1H, s), 8.88 (1H, s), 10.24 (1H, s). FABMS(pos) 432 [M+H]+ melting point: 156–158° C. (crystallization solvent: ethyl acetate-isopropyl ether)

Example 332

5-(4-chlorophenyl)-N-[8-methyl-3-(1-pyrrolidinylmethyl)-7-quinolinyl]-5-oxopentanamide

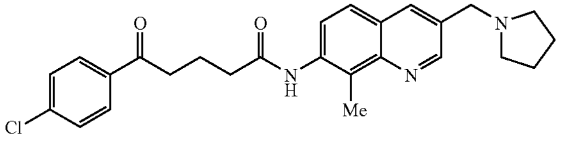

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 1.80 (4H, m), 2.22 (2H, m), 2.56 (6H, m), 2.73 (3H, s), 3.14 (2H, t, J=6.71 Hz) 3.79 (2H, s), 7.42 (2H, d, J=8.55 Hz) 7.46 (1H, s), 7.63 (1H, d, J=8.8 Hz), 7.92 (2H, d, J=8.55 Hz) 8.02 (1H, d, J=1.95 Hz) 8.06 (1H, d, J=9.0 Hz), 8.85 (1H, d, J=1.71 Hz) melting point: 173–174° C. (crystallization solvent: ethyl acetate-isopropyl ether)

Example 333

5-(4-fluorophenyl)-N-[8-methyl-3-(1-pyrrolidinylmethyl)-7-quinolinyl]-5-oxopentanamide

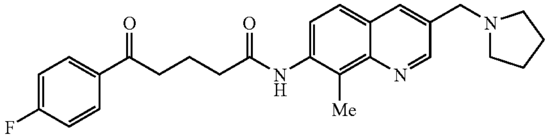

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 1.79 (4H, m), 2.23 (2H, m), 2.57 (6H, m), 2.73 (3H, s), 3.15 (2H, t, J=6.71 Hz) 3.78 (2H, s), 7.12 (2H, t, J=8.67 Hz) 7.48 (1H, s), 7.64 (1H, d, J=8.8 Hz), 8.03 (4H, m), 8.85 (1H, d, J=1.95 Hz) melting point: 170–171° C. (crystallization solvent: ethyl acetate-isopropyl ether)

Example 334

5-(4-fluorophenyl)-N-[8-methyl-3-(1-pyrrolidinylmethyl)-7-quinolinyl]pentanamide

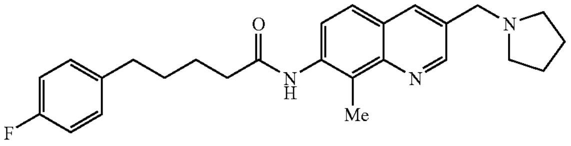

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 1.76 (2H, m), 1.88 (4H, m), 2.04 (3H, m), 2.50 (2H, t, J=6.7 Hz), 2.67 (6H, m), 2.71 (3H, s), 3.91 (2H, s), 6.97 (2H, t, J=8.7 Hz), 7.15 (1H, m), 7.24 (1H, s), 7.67 (1H, d, J=8.8 Hz), 8.10 (1H, d, J=9.1 Hz), 8.16 (1H, s), 8.88 (1H, d, J=1.9 Hz). melting point: 137–138° C. (crystallization solvent: ethyl acetate-isopropyl ether)

Example 335

N-[8-methyl-3-(1-pyrrolidinylmethyl)-7-quinolinyl]-4-(3-oxobutyl)benzamide

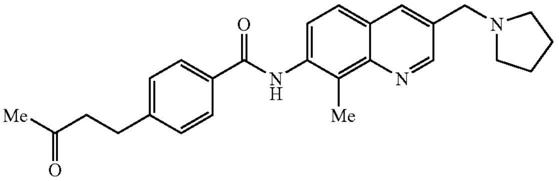

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 1.82 (4H, m), 2.17 (3H, s), 2.56 (4H, m), 2.80 (3H, s), 2.81 (2H, t, J=7.1 Hz), 2.99 (2H, t, J=7.3 Hz), 3.81 (2H, s), 7.34 (2H, d, J=8.1 Hz), 7.69 (1H, d, J=8.8 Hz), 7.87 (2H, ddd, J=8.2, 2.1, 1.9 Hz), 7.94 (1H, s), 8.05 (1H, d, J=2.2 Hz), 8.23 (1H, d, J=8.8 Hz), 8.88 (1H, d, J=2.2 Hz). melting point: 106–108° C. (crystallization solvent: ethyl acetate-isopropyl ether)

Example 336

N-[8-methyl-3-(1-pyrrolidinylmethyl)-7-quinolinyl]-4-(2-oxo-2-tetrahydrofuran-2-ylethyl)benzamide

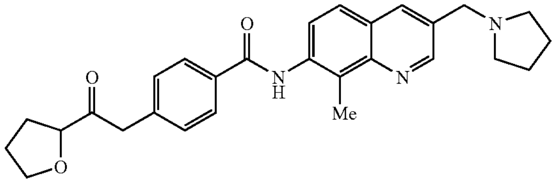

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 1.82 (4H, m), 1.94 (3H, m), 2.20 (1H, m), 2.57 (4H, m), 2.81 (3H, s), 3.81 (2H, s), 3.95 (4H, m), 4.42 (1H, m), 7.37 (2H, d, J=8.3 Hz), 7.70 (1H, d, J=9.0 Hz), 7.91 (2H, dt, J=8.4, 1.9 Hz), 7.95 (1H, s), 8.06 (1H, d, J=2.2 Hz), 8.23 (1H, d, J=9.0 Hz), 8.88 (1H, d, J=2.4 Hz). melting point: 102° C. (crystallization solvent: ethyl acetate-isopropyl ether)

Example 337

N-[8-methyl-3-(1-pyrrolidinylmethyl)-7-quinolinyl]-4-(2-oxo-2-tetrahydrofuran-3-ylethyl)benzamide

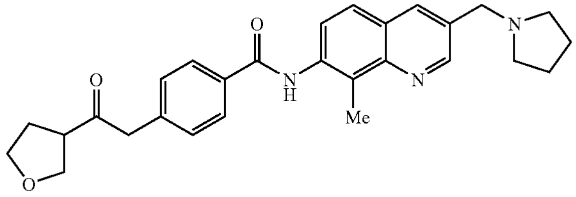

By successively operating in the same manner as in Reference Example 4 and Example 1 and using 4-bromo-N-[8-methyl-3-(1-pyrrolidinylmethyl)-7-quinolinyl]benzamide obtained in Example 93, the title compound was obtained.

$^1$H-NMR ($CDCl_3$) δ: 1.82 (4H, m), 2.12 (2H, m), 2.57 (4H, m), 2.82 (3H, s), 3.82 (2H, s), 3.85 (6H, m), 3.88 (2H, s), 7.37 (2H, d, J=8.4 Hz), 7.71 (1H, d, J=9.2 Hz), 7.94 (2H, d, J=8.4 Hz), 8.07 (1H, d, J=2.2 Hz), 8.23 (1H, d, J=9.2 Hz), 8.90 (1H, d, J=2.2 Hz). melting point: 142–143° C. (crystallization solvent: ethyl acetate-isopropyl ether)

Example 338

N-{8-methyl-3-[(4-methylpiperazin-1-yl)methyl]-7-quinolinyl}-4-(2-oxopentyl)benzamide

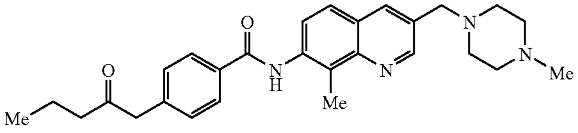

By operating in the same manner as in Example 1 and using 8-methyl-3-[(4-methylpiperazin-1-yl)methyl]-7-quinolinamine obtained in Reference Example 87, the title compound was obtained.

$^1$H-NMR ($CDCl_3$) δ: 0.91 (3H, t, J=7.3 Hz), 1.61 (2H, m), 2.29 (3H, s), 2.48 (2H, t, J=7.3 Hz), 2.51 (8H, m), 2.81 (3H, s), 3.70 (2H, s), 3.79 (2H, s), 7.36 (2H, d, J=8.1 Hz), 7.70 (1H, d, J=8.8 Hz), 7.92 (2H, d, J=8.1 Hz), 7.94 (1H, s), 8.02 (1H, d, J=2.0 Hz), 8.24 (1H, d, J=9.0 Hz), 8.89 (1H, d, J=2.0 Hz). melting point: 177° C. (crystallization solvent: ethyl acetate-isopropyl ether)

Example 339

4-butoxy-2-fluoro-N-{8-methyl-3-[(4-methylpiperazin-1-yl)methyl]-7-quinolinyl}benzamide

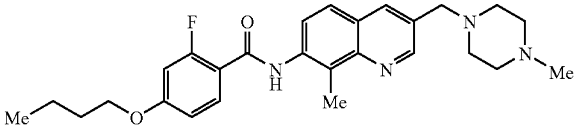

By operating in the same manner as in Example 1 and using 8-methyl-3-[(4-methylpiperazin-1-yl)methyl]-7-quinolinamine obtained in Reference Example 87, the title compound was obtained.

$^1$H-NMR ($CDCl_3$) δ: 1.00 (3H, t, J=7.3 Hz), 1.52 (2H, m), 1.81 (2H, m), 2.29 (3H, s), 2.51 (8H, m), 2.82 (3H, s), 3.69 (2H, s), 4.04 (2H, t, J=6.5 Hz), 6.71 (1H, dd, J=14.7, 2.2 Hz), 6.85 (1H, dd, J=8.8, 2.4 Hz), 7.69 (1H, d, J=8.8 Hz), 8.01 (1H, d, J=2.2 Hz), 8.18 (1H, m), 8.38 (1H, d, J=8.8 Hz), 8.65 (1H, d, J=17.6 Hz), 8.88 (1H, d, J=2.2 Hz). melting point: 155° C. (crystallization solvent: ethyl acetate-isopropyl ether)

Example 340

4-butoxy-N-{8-methyl-3-[(4-methylpiperazin-1-yl)methyl]-7-quinolinyl}benzamide

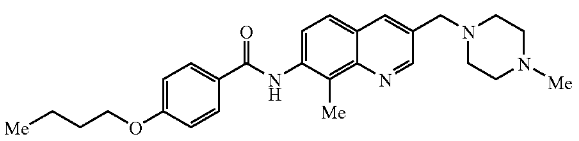

By operating in the same manner as in Example 1 and using 8-methyl-3-[(4-methylpiperazin-1-yl)methyl]-7-quinolinamine obtained in Reference Example 87, the title compound was obtained.

$^1$H-NMR ($CDCl_3$) δ: 1.00 (3H, t, J=7.3 Hz), 1.53 (2H, m), 1.82 (2H, m), 2.29 (3H, s), 2.51 (8H, m), 2.81 (3H, s), 3.69 (2H, s), 4.05 (2H, t, J=6.5 Hz), 7.00 (2H, m), 7.69 (1H, d, J=8.8 Hz), 7.90 (3H, m), 8.02 (1H, d, J=2.2 Hz), 8.26 (1H, d, J=9.0 Hz), 8.88 (1H, d, J=2.2 Hz). melting point: 145° C. (crystallization solvent: ethyl acetate-isopropyl ether)

Example 341

N-{8-methyl-3-[(4-methylpiperazin-1-yl)methyl]-7-quinolinyl}-4-pentylbenzamide

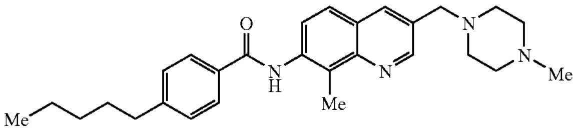

By operating in the same manner as in Example 1 and using 8-methyl-3-[(4-methylpiperazin-1-yl)methyl]-7-quinolinamine obtained in Reference Example 87, the title compound was obtained.

$^1$H-NMR ($CDCl_3$) δ: 0.91 (3H, m), 1.34 (4H, m), 1.66 (2H, m), 2.29 (3H, s), 2.50 (8H, m), 2.70 (2H, m), 2.81 (3H, s), 3.69 (2H, s), 7.33 (2H, d, J=8.6 Hz), 7.70 (1H, d, J=8.8 Hz), 7.87 (2H, m), 7.95 (1H, s), 8.02 (1H, d, J=2.2 Hz), 8.27 (1H, d, J=8.8 Hz), 8.89 (1H, d, J=2.2 Hz). melting-point: 128° C. (crystallization solvent: ethyl acetate-isopropyl ether)

Formulation Example 1

| | | |
|---|---|---|
| (1) | compound obtained in Example 8 | 50 mg |
| (2) | lactose | 34 mg |
| (3) | cornstarch | 10.6 mg |
| (4) | cornstarch (paste) | 5 mg |
| (5) | magnesium stearate | 0.4 mg |
| (6) | carboxymethyl cellulose calcium | 20 mg |
| | total | 120 mg |

According to conventional methods, the above-mentioned (1)–(6) were mixed and punched by a tableting machine to give tablets.

Reference Example 1-1

Amplification of Rat SLC-1 Receptor cDNA by PCR Method Using cDNA Derived from Rat Brain Using poly $(A)^+$ RNA derived from rat brain (Clontech) as a template and a random primer, reverse-transcription reaction was carried out. For the reverse-transcription reaction, a reagent of TaKaRa RNA PCR ver. 2 kit was used. Using this reverse-transcription product as a template and synthetic DNA primers of SEQ Nos:1 and 2, amplification was performed by the PCR method. The synthetic DNA primers were constructed such that the gene in the region to be translated into the receptor protein could be amplified, during which restriction enzyme recognizing sequences of restriction enzyme Sal I and restriction enzyme Spe I were added to the 5' side and 3' side, respectively, so that a base sequence recognized by the restriction enzyme Sal I would be added to the 5' side of the gene and a base sequence recognized by the restriction enzyme Spe I would be added to the 3' side of the gene. The composition of the reaction mixture was cDNA template 5 μl, each synthetic DNA primer 0.4 μM, 0.25 mM dNTPs, pfu (Stratagene) DNA polymerase 0.5 μl and buffer annexed to the enzyme, with the total reaction volume of 50 μl. For amplification cycle, Thermal Cycler (Perkins Elmer) was used. After heating at 94° C. for 60 seconds, a cycle of heating at 94° C. for 60 seconds, at 60° C. for 30 seconds, and at 72° C. for 150 seconds was repeated 35 times, and the mixture was finally reacted at 72° C. for 10 minutes. The amplified product was confirmed by ethidium bromide staining after 0.8% agarose gel electrophoresis.

Reference Example 1-2

Subcloning of PCR Product to Plasmid Vector and Confirmation of Amplified cDNA Sequence by Decoding Base Sequence of Insert cDNA The reaction product after PCR conducted in Reference Example 1-1 was separated using 0.8% low melting point agarose gel and the band was excised with a razor, and subjected to minimization, phenol extraction, phenol-chloroform extraction and ethanol precipitation to recover DNA. According to the direction of PCR-Script™ Amp SK(+) cloning kit (Stratagene), the recovered DNA was subcloned to plasmid vector pCR-Script Amp SK(+). This was introduced into *Escherichia coli* XL-1 Blue (Stratagene) to allow transformation, after which clones containing cDNA insert fragment were selected in an LB agar medium containing ampicillin and X-gal, separated using a sterile toothpick for white clones to give transformant *E. coli* XL-1 Blue/rat SLC-1. The respective clones were cultured overnight in an LB medium containing ampicillin, and using QIA prep8 mini prep (QIAGEN), plasmid DNAs were prepared. A part of the prepared DNAs was cleaved with restriction enzymes Sal I and Spe I to confirm the size of the inserted receptor cDNA fragment. The reaction for determination of the base sequence was carried out using DyeDeoxy Terminator Cycle Sequence Kit (Perkins Elmer), and decoded using a fluorescence automatic DNA sequencer. The sequences of the obtained three clones were analyzed and confirmed to be identical with the gene sequence consisting of a cDNA sequence (Lakaye, B. et al. *Biochim. Biophys. Acta*, Vol. 1401, pp. 216–220 (1998), accession No. AF08650) encoding rat SLC-1 protein (SEQ No:3) whose full length sequence had been reported, a Sal I recognizing sequence added on the 5' side and a Spe I recognizing sequence added on the 3' side (SEQ No:4).

Reference Example 1-3

Preparation of Rat SLC-1 Expression CHO Cell

From a clone of *E. coli* transformed with a plasmid incorporating a gene encoding a full length amino acid sequence of rat brain derived SLC-1 and having a Sal I recognizing sequence added on the 5' side and a Spe I recognizing sequence added on the 3' side, whose sequence was confirmed in Reference Example 1-2, a plasmid was prepared using Plasmid Midi Kit (QIAGEN) and cleaved with restriction enzymes Sal I and Spe I to excise an insert. The insert DNA was recovered by excising, after electrophoresis, from agarose gel with a razor and applying minimization, phenol extraction, phenol-chloroform extraction and ethanol precipitation. This insert DNA was added to animal cell expression vector plasmid pAKKO-111H (vector plasmid identical with pAKKO1.11H described in Hinuma, S. et al. *Biochim. Biophys. Acta*, Vol. 1219, pp. 251–259 (1994)) cleaved with Sal I and Spe I and ligated using T4 ligase (Takara Shuzo Co.) to construct protein expression plasmid pAKKO-SLC-1.

*E. coli* DH5 (TOYOBO) transformed with pAKKO-SLC-1 was cultured and plasmid DNA of pAKKO-SLC-1 was prepared using Plasmid Midi Kit (QIAGEN). This was introduced into CHO dhfr$^-$ cell using CellPhect Transfection Kit (Amersham Pharmacia Biotech) and in accordance with the attached protocol. DNA (10 μg) was prepared into a coprecipitation suspension with calcium phosphate and added into a 10 cm dish inoculated with $5\times10^5$ or $1\times10^6$ CHO dhfr$^-$ cells 24 hours before. The cells were cultured in an MEM α medium containing 10% fetal bovine serum for one day, passaged and cultured in a nucleic acid-free MEM α medium (selection medium) containing 10% dialyzed fetal bovine serum. 56 clones of transformed cell colonies, which were SLC-1 expression CHO cells grown in the selection medium, were selected.

Reference Example 1-4

Selection of CHO/SLC-1 Cell Line with High Expression Amount of Full Length Rat SLC-1 Receptor Protein mRNA The expression amount of full length rat SLC-1 receptor protein mRNA by 56 clones of CHO/SLC-1 cell line established in Reference Example 1-3 was measured as in the following using Cytostar T Plate (Amersham Pharmacia Biotech) and in accordance with the attached protocol. Each clone of the CHO/SLC-1 cell line was inoculated to each well of Cytostar T Plate at $2.5\times10^4$, cultured for 24 hours and fixed with 10% formalin. After 0.25% Triton X-100 was added to each well to enhance permeability of the cells, riboprobe of $^{35}$S labeled SEQ No:5 was added for hybridization. RNase A (20 mg/ml) was added to each well to digest free riboprobe. The plate was washed thoroughly and the radioactivity of the hybridized riboprobe was measured on Topcounter. The cell strain having high radioactivity showed higher expression amount of mRNA. Of the three clones showing high mRNA expression amount, particularly clone No. 44 was used mainly.

Reference Example 1-5

Isolation of Plasmid Containing Human SLC-1 cDNA

According to the manual attached to Genetrapper cDNA positive selection system (GIBCOBRL) and using phage F1 endonuclease, nick was inserted into cDNA derived from human fetal brain library (SUPERSCRIPT™ cDNA Library; GIBCOBRL) and digested with *Escherichia coli* exonuclease III to prepare a single strand cDNA derived from human fetal brain library.

Using Terminal Deoxynucleotidyl Transferase, biotin-14-dCTP was added to the 3' terminal of the synthetic oligonucleotide (corresponding to 1434–1451 of accession No. U71092) of SEQ No:6 prepared based on the report of Kolakowski Jr. et al. (Kolakowski Jr., et al (1996) *FEBS Lett*. Vol. 398, pp. 253–258), whereby biotinylated oligonucleotide was prepared. The composition of the reaction mixture and reaction time followed the manual.

Single strand cDNA library (4 μg) derived from human fetal brain was kept at 95° C. for 1 min and rapidly cooled on ice. Biotinylated oligonucleotide (20 ng) was added and the mixture was hybridized in the accompanying hybridization buffer at 37° C. for 1 hr. Streptavidin beads were added and single strand cDNA derived from human fetal brain hybridized to biotinylated oligonucleotide was isolated using MAGNA-SEP Magnetic Particle Separator (GIBCOBRL). Using synthetic oligonucleotide (50 ng, corresponding to 1011–1028 of accession No. U71092) of SEQ No:7 prepared according to the report of Kolakowski Jr. et al. (Kolakowski Jr., et al (1996) *FEBS Lett*. Vol. 398, pp. 253–258) as a primer, a complementary chain was synthesized according to the manual to give a double strand plasmid.

Reference Example 1-6

Determination of Base Sequence of Plasmid Containing Isolated Human SLC-1 cDNA

The plasmid obtained in Reference Example 1-5 was introduced into ELECTROMAX™ DH10B™ Cells by electroporation method to allow transformation, after which clones containing cDNA insert fragment were selected in an LB agar medium containing ampicillin and X-gal and separated using a sterile toothpick for white clones to give transformant *E. coli* DH10B/hSLC-1. The respective clones were cultured overnight in an LB medium containing ampi cillin, and using QIA prep8 mini prep (QIAGEN), the plasmid DNA was purified. The reaction for determination of the base sequence was carried out using DyeDeoxy Terminator Cycle Sequence Kit (Perkins Elmer), and decoded using a fluorescence automatic DNA sequencer. As a result, the sequence depicted in SEQ No:8 was obtained. The amino acid sequence (SEQ No:9) encoded by the obtained base sequence was different from the human SLC-1 amino acid sequence as the sequence deduced from rat SLC-1 based on the human chromosomal DNA sequence (accession number:Z86090) containing the sequence of human SLC-1, in a report by Lakaye et al. (Lakaye, B. et al. (1998) *Biochem. Biophys. Acta*, vol. 1401, pp. 216–220) in that the presence of the initiating codon ATG on mRNA was indicated at 69 and 64 amino acids further upstream of the deduced sequence. A transformant *Escherichia coli* DH10B/phSLC1L8 obtained using a plasmid containing DNA encoding this sequence was deposited at IFO.

Reference Example 1-7

Amplification of Human SLC-1cDNA by PCR Method Using cDNA Derived from Human Fetal Brain Using, as a template, the plasmid containing human SLC-1DNA sequence cloned by the gene-trap method, synthetic DNA primers of SEQ Nos:10 and 11 and synthetic DNA primers of SEQ Nos:12 and 13, amplification was conducted by the PCR method. The amplified DNA of the former was named human SLC-1 (S) and the amplified DNA of the latter was named human SLC-1 (L). The synthetic DNA primers were constructed such that the gene of the region to be translated into the receptor protein was amplified, during which restriction enzyme recognizing sequences of restriction enzyme Sal I and restriction enzyme Spe I were added to the 5' side and 3' side, respectively, so that a base sequence recognized by the restriction enzyme Sal I would be added to the 5' side of the gene and a base sequence recognized by the restriction enzyme Spe I would be added to the 3' side of the gene. The composition of the reaction mixture for human SLC-1 (S) amplification was plasmid template (5 μl) containing human SLC-1 DNA sequence, each synthetic DNA primer (0.4 μM), dNTPs(0.2 mM), pfuDNA polymerase (0.5 μl) and buffer annexed to the enzyme, with the total reaction volume of 50 μl. For amplification cycle, Thermal Cycler (Perkins Elmer) was used. After heating at 94° C. for 60 seconds, a cycle of heating at 94° C. for 60 seconds, at 57° C. for 60 seconds, and at 72° C. for 150 seconds was repeated 25 times, and the mixture was finally incubated at 72° C. for 10 minutes. The composition of the reaction mixture for human SLC-1 (L) amplification was plasmid template (5 μl) containing human SLC-1 DNA sequence, each synthetic DNA primer (0.4 μM), dNTPs (0.2 mM), pfuDNA polymerase (0.5 μl) and buffer annexed to the enzyme, with the total reaction volume of 50 μl. For amplification cycle, Thermal Cycler (Perkins Elmer) was used. After heating at 94° C. for 60 seconds, a cycle of heating at 94° C. for 60 seconds, at 60° C. for 60 seconds, and at 72° C. for 3 min was repeated times, and the mixture was finally incubated at 72° C. for 10 minutes. The amplified product was confirmed by ethidium bromide staining after 0.8% agarose gel electrophoresis.

Reference Example 1-8

Subcloning of PCR Product to Plasmid Vector and Confirmation of Amplified cDNA Sequence by Decoding Base Sequence of Insert cDNA The reaction product after PCR conducted in Reference Example 1-7 was separated using 0.8% low melting point agarose gel and the band region was excised with a razor, and subjected to minimization, phenol extraction, phenol-chloroform extraction and ethanol precipitation to recover DNA. According to the direction of PCR-Script™ Amp SK($^+$) cloning kit (Stratagene), the recovered DNA was subcloned to plasmid vector pCR-Script Amp SK($^+$). This was introduced into *Escherichia coli* DH5 α competent cell (TOYOBO) to allow transformation, after which clones containing cDNA insert fragment were selected in an LB agar medium containing ampicillin and X-gal, separated using a sterile toothpick for white clones to give transformant *E. coli* DH5 α/hSLC-1(S) of human SLC-1 (S) and transformant *E. coli* DH5 α/hSLC-1(L) of human SLC-1 (L). The respective clones were cultured overnight in an LB medium containing ampicillin, and using QIA prep8 mini prep (QIAGEN), the plasmid DNA was prepared. A part of the prepared DNA was cleaved with restriction enzymes Sal I and Spe I to confirm the size of the inserted receptor cDNA fragment. The reaction for determination of the base sequence was carried out using DyeDeoxy Terminator Cycle Sequence Kit (Perkins Elmer), and decoded using a fluorescence automatic DNA sequencer. The sequences of the obtained clones were respectively identical with the DNA sequence (SEQ No:14) to be amplified using synthetic DNA primers of SEQ Nos:10 and 11 and DNA sequence (SEQ No:15) to be amplified using synthetic DNA primers of SEQ Nos: 12 and 13, with human SLC-1 gene as a template.

Reference Example 1-9

Preparation of Human SLC-1 (S) Expression CHO Cell and Human SLC-1 (L) Expression CHO Cell From a clone of *E. coli* transformed with a plasmid incorporating human SLC-1 (S) and human SLC-1(L), whose sequences were confirmed in Reference Example 1-8, a plasmid was prepared using Plasmid Midi Kit (QIAGEN) and cleaved with restriction enzymes Sal I and Spe I to excise an insert. The insert DNA was recovered by cutting out, after electrophoresis, from agarose gel with a razor and applying minimization, phenol extraction, phenol-chloroform extraction and ethanol precipitation. This insert DNA was added to animal cell expression vector plasmid pAKKO-111H (vector plasmid identical with pAKKO1.11H described in Hinuma, S. et al. *Biochim. Biophys. Acta*, Vol. 1219, pp. 251–259 (1994)) cleaved with Sal I and Spe I and ligated using T4 ligase (Takara Shuzo Co.) to respectively construct protein expression plasmids pAKKO-hSLC-1 (S) and PAKKO-hSLC-1 (L)

*E. coli* DH5 α (TOYOBO) transformed with pAKKO-hSLC-1(S) and pAKKO-hSLC-1(L) was cultured and, using Plasmid Midi Kit (QIAGEN), plasmid DNAs of pAKKO-hSLC-1(S) and pAKKO-hSLC-1(L) were prepared. These were introduced into CHO dhfr$^-$ cells using CellPhect Transfection Kit (Amersham Pharmacia Biotech) in accordance with the attached protocol. DNA (10 μg) was prepared into a coprecipitation suspension with calcium phosphate and added into a 10 cm dish inoculated with $5\times10^5$ or $1\times10^6$ CHO dhfr$^-$ cells 24 hours before. The cells were cultured in an MEM α medium containing 10% fetal bovine serum for one day, passaged and cultured in a nucleic acid-free MEM α medium (selection medium) containing 10% dialyzed fetal bovine serum. 56 clones of transformed cell colonies, which were human SLC-1(S) gene introduced CHO cells, and 61 clones of transformed cell colonies, which were human SLC-1 (L) gene introduced CHO cells, grew in the selection medium and were selected.

Reference Example 1-10

Selection of Gene Introduced Cell Line with High Expression Amount of Human SLC-1 (S) mRNA and Human SLC-1 (L) mRNA The expression amount of mRNA of 56 clones of CHO/hSLC-1(S) cell line and 61 clones of CHO/hSLC-1(L) cell line established in Reference Example 1-9 was measured as in the following using Cytostar T Plate (Amersham Pharmacia Biotech) and in accordance with the attached protocol. Each clone of the CHO/hSLC-1(S) cell line and CHO/hSLC-1(L) cell line was inoculated to each well of Cytostar T Plate at $2.5\times10^4$, cultured for 24 hours and fixed with 10% formalin. After adding 0.25% Triton X-100 to each well to enhance permeability of the cells, riboprobe of $^{35}S$ labeled SEQ No:16 was added for hybridization. RNase A (20 mg/ml) was added to each well to digest free riboprobe. The plate was washed thoroughly and the radioactivity of the hybridized riboprobe was measured on Topcounter. The cell strain having high radioactivity showed higher expression amount of mRNA. Of the 7 clones showing high mRNA expression amount, particularly clone No. 57 was used mainly.

Experimental Example 1

Determination of Antagonistic Activity of Test Compound Using GTP γ S Binding Assay Using human SLC-1 expression CHO cell clone 57 obtained in Reference Example 1-10 and rat SLC-1 expression CHO cell clone 44 obtained in Reference Example 1-4, membrane fractions were prepared by the following method. In phosphate buffered saline (pH 7.4) supplemented with 5 mM EDTA (ethylenediamine tetraacetic acid) were suspended human and rat SLC-1 expression CHO cells ($1\times10^8$) and centrifuged. Homogenate buffer (10 ml, 10 mM $NaHCO_3$, 5 mM EDTA, pH 7.5) was added to the pellets of the cells and, using Polytron Homogeniser, the mixture was homogenated. The supernatant obtained after centrifugation at 400×g for 15 min was further centrifuged at 100,000×g for 1 hr to give precipitate of the membrane fraction. The precipitate was suspended in 2 ml of an assay buffer [50 mM Tris-HCl (pH 7.5), 1 mM EDTA, 0.1% BSA (bovine serum albumin), 10 mM $MgCl_2$, 100 mM NaCl, 1 μM GDP (guanosine 5'-diphosphate), 0.25 mM PMSF (phenylmethylsulfonylfluoride), 1 mg/ml pepstatin, 20 mg/ml leupeptin, 10 mg/ml phosphoramidon] and centrifuged at 100,000×g for 1 hr. The membrane fraction recovered as precipitate was suspended again in 20 ml of an assay buffer, and after dispensing, preserved at −80° C. and used upon thawing each time when in use.

The antagonistic activity of the test compound was determined as follows. The SLC-1 expression CHO cell membrane fraction (171 μl) diluted with an assay buffer was dispensed to a polypropylene 96 well plate and $3\times\ ^{-10}$ M MCH (2 μl) diluted with DMSO solution, test compound solution (2 μl) diluted to various concentrations and [$^{35}S$]-Guanosine5'-(γ-thio)triphosphate (25 μl, Daiichi Pure Chemicals Co., Ltd.) were respectively added (cell membrane final concentration: 20 μg/ml, [$^{35}S$]-Guanosine 5'-(γ-thio)triphosphate final concentration: 0.33 nM). The reaction mixture was reacted at 25° C. for 1 hr with stirring, suction filtered with a glass filter (GF-C) and washed 3 times with a wash solution (300 μl, 50 mM Tris-HCl buffer, pH 7.5). Liquid scintillator (50 ml) was added to the glass filter and the residual radioactivity was determined by a liquid scintillation counter.

Binding inhibition (%)=(radioactivity upon addition of compound and MCH−radioactivity upon addition of DMSO solution)/(radioactivity upon addition of MCH−radioactivity upon addition of DMSO solution)×100

From the binding inhibition (%), $IC_{50}$ of the compound was calculated. The results are shown in the following.

| Compound No. | Inhibitory activity ($IC_{50}$: nM) |
|---|---|
| Example 8 | 6 |

Experimental Example 2

Evaluation of Antidepressive Action by Forced Swim Test

By performing a forced swim test using SD (Sprague Dawley) rats (seven-week-old, male, body weight 233.3–266.9 g, purchased from Japan Clea), the antidepressive action of the compound of the present invention was evaluated.

First, a suspension of the compound of Example 19 in 0.5% methyl cellulose was orally administered to SD rats (n=10) (compound dose: 3 mg/kg body weight). Thirty minutes later, the rats were placed in a pipe (diameter 21 cm, height 50 cm) made of Plexiglass (trade name, made by Rohm & Haas, U.S.A.) containing tap water (water temperature 25±2° C., 30 cm deep). Immobility time of the rats for five minutes thereafter was measured using a digital video camera.

In addition, 0.5% methyl cellulose suspension without the compound was orally administered to SD rats (n=10), and the rats were subjected the forced swim test in the same manner as above and taken as a control group.

As a result, the immobility time (seconds, mean±standard deviation) of the rats of the compound administration group and control group was 15.93±5.62 and 30.86±8.71, respectively, and the immobility time was shortened in the compound administration group. In other words, it was clarified that the compound of the present invention has a superior antidepressive action.

INDUSTRIAL APPLICABILITY

The compound of the present invention has a superior MCH receptor antagonistic action and is useful as an agent for the prophylaxis or treatment of obesity and the like.

The invention claimed is:

1. A compound represented by the formula:

(I)

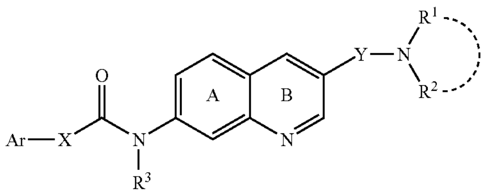

wherein

Ar is a cyclic group optionally having substituent(s);

X is a bond or a spacer having a main chain of 1 to 6 atoms;

$R^1$ and $R^2$ are the same or different and each is a hydrogen atom or a hydrocarbon group optionally having substituent(s), or $R^1$ and $R^2$ may form, together with the adjacent nitrogen atom, a nitrogen-containing heterocycle optionally having substituent(s);

Y is a $C_1$–$C_6$ alkylene;

$R^3$ is a hydrogen atom or a hydrocarbon group optionally having substituent(s); and ring A and ring B may further have substituent(s), and when ring B further has a substituent, the substituent may be linked to $R^1$ to form a ring, or a salt thereof or a prodrug thereof.

2. The compound of claim 1, wherein X is a bond and the substituent that ring B may further have does not link with $R^1$.

3. The compound of claim 1, wherein Ar is a group represented by the formula: $Ar^2$—$Ar^1$— wherein $Ar^1$ is a cyclic group optionally having substituent(s) and $A^2$ is an aromatic ring group optionally having substituent(s).

4. The compound of claim 3, wherein the cyclic group for $Ar^1$ is a phenyl, a 5- or 6-membered aromatic heterocyclic group or a 5- to 8-membered monocyclic non-aromatic heterocyclic group.

5. The compound of claim 3, wherein the aromatic ring group for $Ar^2$ is a phenyl or a 5- or 6-membered aromatic heterocyclic group.

6. The compound of claim 1, wherein X is a bond.

7. The compound of claim 1, wherein $R^1$ and $R^2$ form, together with the adjacent nitrogen atom, a nitrogen-containing heterocycle optionally having substituent(s).

8. The compound of claim 7, wherein the nitrogen-containing heterocycle is azetidine, morpholine, piperidine, piperazine, pyrrolidine, hexamethyleneimine, 1,3-thiazolidine, 1H-imidazole, 4,5-dihydro-1H-imidazole, 2,3-dihydroindole, 1,2,3,4-tetrahydroquinoline or 1,2,3,4-tetrahydroisoquinoline.

9. The compound of claim 1, wherein Y is a $C_{1-3}$ alkylene.

10. The compound of claim 1, wherein $R^3$ is a hydrogen atom.

11. The compound of claim 1, wherein the substituent that the ring A and the ring B may further have is a halogen atom, an optionally halogenated $C_{1-6}$ alkyl or an optionally halogenated $C_{1-6}$ alkoxy.

12. The compound of claim 1, which is 4'-fluoro-N-[8-methyl-3-(1-pyrrolidinylmethyl)-7-quinolinyl][1,1'-biphenyl]-4-carboxamide;

N-[6-fluoro-3-(1-pyrrolidinylmethyl)-7-quinolinyl]-4'-methoxy[1,1'-biphenyl]-4-carboxamide;

6-(4-methoxyphenyl)-N-[8-methyl-3-(1-pyrrolidinylmethyl)-7-quinolinyl]nicotinamide;

3-fluoro-4'-methoxy-N-[8-methyl-3-(1-pyrrolidinylmethyl)-7-quinolinyl][1,1'-biphenyl]-4-carboxamide;

4-(cyclopropylmethoxy)-N-[8-methyl-3-(1-pyrrolidinylmethyl)-7-quinolinyl]benzamide;

N-[3-(1-azepanylmethyl)-8-methyl-7-quinolinyl]-4-(2-oxopentyl)benzamide;

4-(cyclopropylmethoxy)-N-{8-methyl-3-[1-(1-pyrrolidinyl)ethyl]-7-quinolinyl}benzamide;

or a salt thereof.

13. A pharmaceutical composition comprising the compound of claim 1.

14. A method for producing the compound of claim 1 or a salt thereof or a prodrug thereof, which comprises reacting a compound represented by the formula: Ar—X—COOH wherein Ar and X are as defined in claim 1, or a salt thereof or a reactive derivative thereof with a compound represented by the formula:

(III)

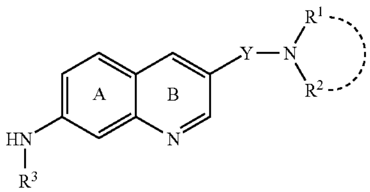

wherein the symbols in the formula are as defined in claim 1, or a salt thereof.

15. A compound represented by the formula (III)

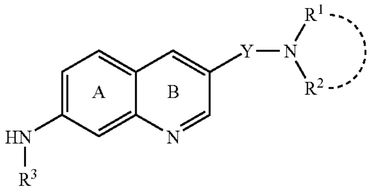

wherein the symbols in the formula are as defined in claim 1, or a salt thereof.

* * * * *